US006589779B1

(12) United States Patent
McDevitt et al.

(10) Patent No.: US 6,589,779 B1
(45) Date of Patent: Jul. 8, 2003

(54) GENERAL SIGNALING PROTOCOL FOR CHEMICAL RECEPTORS IN IMMOBILIZED MATRICES

(75) Inventors: John T. McDevitt, Austin, TX (US);
Eric V. Anslyn, Austin, TX (US);
Jason B. Shear, Austin, TX (US);
Dean P. Neikirk, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/616,482

(22) Filed: Jul. 14, 2000

Related U.S. Application Data
(60) Provisional application No. 60/144,436, filed on Jul. 16, 1999, provisional application No. 60/144,435, filed on Jul. 16, 1999, and provisional application No. 60/144,126, filed on Jul. 16, 1999.

(51) Int. Cl.[7] .................................................. C12M 1/34
(52) U.S. Cl. ................................ 435/288.7; 435/287.2
(58) Field of Search ........................... 435/287.1, 287.2, 435/288.7

(56) References Cited

U.S. PATENT DOCUMENTS

| | | | |
|---|---|---|---|
| 3,709,868 A | 1/1973 | Spector | 260/121 |
| 3,843,696 A | 10/1974 | Wagner et al. | 260/404 |
| 3,856,469 A | 12/1974 | Schneider et al. | |
| 3,876,504 A | 4/1975 | Koffler | |
| 3,964,974 A | 6/1976 | Banauch et al. | |
| 4,245,041 A | 1/1981 | Denney | 435/15 |
| 4,294,817 A | 10/1981 | Burgett | 424/8 |
| 4,378,429 A | 3/1983 | Modrovich | 435/11 |
| 4,567,149 A | 1/1986 | Sell et al. | 436/513 |
| 4,683,195 A | 7/1987 | Mullis et al. | 435/6 |
| 4,683,202 A | 7/1987 | Mullis | 435/91 |
| 4,795,698 A | 1/1989 | Owen et al. | 435/4 |
| 4,813,277 A | 3/1989 | Miller et al. | 73/49.2 |
| 4,925,800 A | 5/1990 | Kovacs et al. | 435/240.27 |

(List continued on next page.)

FOREIGN PATENT DOCUMENTS

| | | |
|---|---|---|
| EP | 0 518 557 A2 | 12/1992 |
| EP | 439182 | 4/1996 |
| GB | 2 315 131 A | 1/1998 |
| WO | 90/01069 | 2/1990 |
| WO | 92/0880 | 1/1992 |
| WO | 98/17383 A1 | 4/1998 |
| WO | WO-98533300 | * 11/1998 |
| WO | WO-9918434 | * 4/1999 |
| WO | 00/04372 | 1/2000 |

OTHER PUBLICATIONS

Cho et al., "An Unnatural Biopolymer," *Science*, 1993, 261, p. 1303–1305.

Lauritzen et al., "Peptide Dot Immunoassay and Iimmuno–blotting: Electroblotting from Aluminum Thin–layer Chromatography Plates and Isoelectric Focusing Gels to Activated Nitrocellulose," *Electrophoresis*, 1993, 14, p. 852–859.

(List continued on next page.)

*Primary Examiner*—David A. Redding
(74) *Attorney, Agent, or Firm*—Meyertons, Hood, Kivlin, Kowert & Goetzel, P.C.; Eric B. Meyertons

(57) ABSTRACT

A system for the rapid characterization of multi-analyte fluids, in one embodiment, includes a light source, a sensor array, and a detector. The sensor array is formed from a supporting member into which a plurality of cavities may be formed. A series of chemically sensitive particles are, in one embodiment positioned within the cavities. The particles may be configured to produce a signal when a receptor coupled to the particle interacts with the analyte. Using pattern recognition techniques, the analytes within a multi-analyte fluid may be characterized.

45 Claims, 69 Drawing Sheets

U.S. PATENT DOCUMENTS

| | | | | |
|---|---|---|---|---|
| 4,965,188 | A | 10/1990 | Mullis et al. | 435/6 |
| 5,071,076 | A | 12/1991 | Chagnon et al. | 241/21 |
| 5,108,933 | A | 4/1992 | Liberti et al. | 436/501 |
| 5,126,276 | A | 6/1992 | Fish et al. | 436/531 |
| 5,130,238 | A | 7/1992 | Malek et al. | 435/91 |
| 5,137,833 | A | 8/1992 | Russell | 436/94 |
| 5,156,810 | A | 10/1992 | Ribi | 422/82.01 |
| 5,156,972 | A | 10/1992 | Issachar | 435/288 |
| 5,168,044 | A | 12/1992 | Joyce et al. | 435/7.24 |
| 5,223,393 | A | 6/1993 | Khanna et al. | 435/6 |
| 5,235,028 | A | 8/1993 | Barany et al. | 528/335 |
| 5,248,742 | A | 9/1993 | McGarry et al. | 525/531 |
| 5,252,294 | A | 10/1993 | Kroy et al. | 422/102 |
| 5,391,272 | A | 2/1995 | O'Daly et al. | 204/153.12 |
| 5,491,097 | A | 2/1996 | Ribi et al. | 436/518 |
| 5,563,042 | A | 10/1996 | Phillips et al. | 435/14 |
| 5,583,054 | A | 12/1996 | Ito et al. | 436/523 |
| 5,616,790 | A | 4/1997 | Arnold et al. | 562/444 |
| 5,631,130 | A | 5/1997 | Leckie et al. | 435/6 |
| 5,690,807 | A | 11/1997 | Clark, Jr. et al. | 205/655 |
| 5,714,122 | A | 2/1998 | Bretscher et al. | 422/82.07 |
| 5,747,349 | A | 5/1998 | Van Den Engh et al. | 436/526 |
| 5,773,307 | A | 6/1998 | Colin et al. | 436/526 |
| 5,788,814 | A | 8/1998 | Sun et al. | 204/297 R |
| 5,827,748 | A | 10/1998 | Golden | 436/527 |
| 5,843,767 | A | 12/1998 | Beattie | 435/287.1 |
| 5,846,396 | A | 12/1998 | Zanzucchi et al. | 204/601 |
| 5,846,708 | A | 12/1998 | Hollis et al. | 435/6 |
| 5,854,141 | A | 12/1998 | Cronin et al. | 438/763 |
| 5,856,174 | A | 1/1999 | Lipshutz et al. | 435/286.5 |
| 5,869,241 | A | 2/1999 | Edwards et al. | 435/6 |
| 5,872,170 | A | 2/1999 | Mine et al. | 524/440 |
| 5,872,623 | A | 2/1999 | Stabile et al. | 356/73 |
| 5,891,656 | A | 4/1999 | Zarling et al. | 435/792 |
| 5,942,443 | A | 8/1999 | Parce et al. | 436/514 |
| 5,965,590 | A | 10/1999 | Rossignol | 514/371 |
| 5,980,704 | A | 11/1999 | Cherukuri et al. | 204/263 |
| 5,981,297 | A | 11/1999 | Baselt | 436/514 |
| 5,992,820 | A | 11/1999 | Fare et al. | 251/129.01 |
| 6,008,031 | A | 12/1999 | Modrich et al. | 435/200 |
| 6,013,440 | A | 1/2000 | Lipshutz et al. | 435/6 |
| 6,045,579 | A | 4/2000 | Hochshuler et al. | 623/17 |
| 6,063,581 | A | 5/2000 | Sundrehagen | 435/7.1 |
| 6,083,761 | A | 7/2000 | Kedar et al. | 436/178 |
| 6,083,763 | A | 7/2000 | Balch | 436/518 |
| 6,127,139 | A | 10/2000 | Te Koppele et al. | 435/24 |
| 6,151,973 | A | 11/2000 | Geysen et al. | 43/865.8 |
| 6,210,910 | B1 | 4/2001 | Walt et al. | 435/7.32 |
| 6,245,296 | B1 | 6/2001 | Ligler et al. | 422/57 |
| 6,288,220 | B1 | 9/2001 | Kambara et al. | 536/24.31 |
| 6,331,441 | B1 | 12/2001 | Balch et al. | 436/518 |

OTHER PUBLICATIONS

Schultz et al., "Direct Observation of Ligand Colocalization on Individual Receptor Molecules," *Biophysical Journal,* 1998, 74.

Adler, M; Nicholson, J.D.; Hackley, B.E., Jr. "Efficacy of a novel metalloprotease inhibitor on botulinum neurotoxin B activity" FEBS Lett., 1998, 429, 234–238.

James, T.D.; Sandanayake, K.R.A.S.; Iguchi, R.; Shinkai, S.J. Am. Chem. Soc. 1995, 117, 8982–8987.

Murukami, H.; Nagasaki, T.; Hamachi, I.; Shinkai, S. Tetrahedron Lett., 1993, 34, 6273–6276.

Shinkai, S.; Tsukagohsi, K.; Ishikawa, Y.; Kunitake, T.J. Chem. Soc. Chem. Commun. 1991, 1039–1041.

Kondo, K.; Shiomi, Y.; Saisho, M.; Harada, T.; Shinkai, S. Tetrahedron. 1992, 48, 8239–8252.

Shiomi, Y.; Saisho, M.; Tsukagoshi, K.; Shinkai, S.J. Chem. Soc. Perkin Trans I 1993, 2111–2117.

Deng, G.; James, T.D.; Shinkai, S.J. Am. Chem. Soc. 1994, 116, 4567–4572.

James, T.D.; Harada, T.; Shinkai, S.J. Chem. Soc. Chem. Commun. 1993, 857–860.

James T. D.; Murata, K.; Harada, T.; Ueda, K.; Shinkai, S.Chem. Lett. 1994, 273–276.

Ludwig, R.; Harada, T.; Ueda, K.; James, T.D.; Shinkai, S.J., Chem. Soc. Perkin Trans 2. 1994, 697–702.

Sandanayake, K.R.A.S.; Shinkai, S.J. Chem. Soc., Chem. Commun. 1994, 1083–1084.

Nagasaki, T.; Shinmori, H.; Shinkai, S. Tetrahedron Lett. 1994, 35, 2201–2204.

Murakami, H.; Nagasaki, T.; Hamachi, I.; Shinkai, S., J. Chem. Soc. Perkin Trans 2. 1994, 975–981.

Nakashima, K.; Shinkai, S,.Chem. Lett. 1994, 1267–1270.

Sandanayake, K.R.A.S.; Nakashima, K.; Shinkai, S.J., Chem. Soc.,Chem. Commun. 1994, 1621–1622.

James, T.D.; Sandanayake, K.R.A.S.; Shinkai, S.,J. Chem. Soc., Chem. Commun. 1994, 477–478.

James T.D.; Sandanayake, K.R.A.S.; Shinkai, S.,Angew. Chem., Int. Ed. Eng. 1994, 33, 2207–2209.

James T.D.; Sandanayake, K.R.A.S.; Shinkai, S. Nature, 1995, 374, 345–347.

Förster, Th. Transfer Mechanisms of Electronic Excitation;, Discuss. Faraday Soc., 1959, 27, 7–17.

Khanna, P.L., Ullman, E.F. "4', 5'—Dimethoxyl–6–carboxyfluorescein; A novel dipoledipole coupled fluorescence energy transfer acceptor useful for fluorescence immunoassays", Anal. Biochem. 1980, 108, 156–161.

Morrison, L.E. "Time resolved Detection of Energy Transfer: Theory and Application to Immunoassays", Anal. Biochem. 1988, 174, 101–120.

Schmidt, J.J.; Stafford, R.G.; Bostian, K.A.; "Type A botulinum neurotoxin proteolytic activity: development of competitive inhibitors and implicatins for substrate specificity at the $S_1$' binding subsite", FEBS Lett., 1998, 435, 61–64.

Shone, C.C.; Roberts, A.K., "Peptide substrate specificity and properties of the zincendopetidase activity of botulinum type B neurotoxin,", Eur. J. Biochem., 1994, 225, 263–270.

Soleihac, J.–M.; Cornille, F.; Martin, L.; Lenoir, C.; Fournie–Zaluski, M.–C.; Roques, B.P. A sensitive and rapid fluorescence–based assay for determination of tetnus toxin peptidase activity: Anal. Biochem., 1996, 241, 120–127.

Stimpson, D.I.; Hoijer, J.V.; Hsieh, WT.; Jou, C.; Gordon, J.; Theriault, T.; Gamble, R.; Baldeschwieler, J.D.; Proc. Natl. Acad. Sci. USA 1995, 92, 6379–6383.

Niikura, K.; Metzger, A.; Anslyn, E.V., "A Sensing Ensemble with Selectivity for Iositol Triphosphate", J. Am. Chem. Soc., 1998, 120, 8533–8534.

Kaiser, E.; Colescott, R.L.; Bossinger, C.D.; Cook, P.I.; "Color Test for Detection of Free Terminal Amino Groups in the Solid–Phase Synthesis of Peptides", Anal. Biochem., 1970, 34, 595–598.

Hamasaki, K.; Ikeda, H.; Nakamura, A.; Ueno, A.; Toda, F.: Suzuki, I.; Osa, T. "Fluorescent Sensors of Molecular Recognition. Modified Cyclodextrins Capable of Exhibiting Guest–Responsive Twisted Intramolecular Charge Transfer Fluorescence", J. Am. Chem. Soc., 1993, 115, 5035–5040. And reference 5 therein.

Youil R; Kemper, B; Cotton, RGH, "Detection of 81 of 81 Known Mouse Beta–Globin Promoter Mutations with T4 Endonuclease–VII–The EMC Method", Genomics, 1996, 32, 431–5.

Pabo and Sauer, 1992, Annu. Rev. Biochem, 61, 1053–1095.

Harrison, 1991, Nature, 353, 715–719.

Klug A., Gene 1993, 135–83–92.

Hsu, I.C.; Yang, Q.P.; Kahng, M.W.; Xu, J.F.; "Detection of DNA Point Mutations with DNA Mismatch Repaire Enzymes", Carcinogenesis, 1994, 15, 1657–1662.

Saiki, et al., Science, 1985, 230, 1350–1354.

Mullis, et al., Cold Springs Harbor Symp. Quant. Biol., 1986, 51, 263–273.

Mullis K.B.; and Faloona, F.A., Methods Enzymol., 1987, 155, 335–350.

Barany, F.PCR Methods and Applications, 1991, 1, 5–16.

Wu D.Y.; Wallace, R.B., Genomics, 1989, 4:560–569.

Barany, F., Proc. Natl. Acad. Sci. USA, 1991, 88,189–193.

Kwoh, et al., Proc. Natl. Acad. Sci., USA, 1989, 86,1173–1177.

Guatelli, et al., Proc. Natl. Acad, Sci., 1990, USA, 87,1874–1878.

Goldrick, M.M.; Kimball, G.R.; Liu, Q.: Martin, L.A.; Sommer, S.S.: Tseng, J.Y.H.; "Nirca™–A Rapid Robust Method for Screening for Unknown Point Mutations", Bio-Techniques, 1996, 21, 106–112.

* cited by examiner

Peptides

Nucleotides

Polythioureas

Polyguanidiniums

| RESIN: pH | Ion | Blank | Alizarin | o-Cresol-phthalein | Fluorescein | Alizarin-Ce³⁺ complex |
|---|---|---|---|---|---|---|
| 2 | none | | | | | |
| 2 | Ca²⁺ | | | | | |
| 7 | none | | | | | |
| 7 | Ca²⁺ | | | | | |
| 7 | F⁻ | | | | | |
| 12 | none | | | | | |
| 12 | Ca²⁺ | | | | | |
| 12 | F⁻ | | | | | |

FIG. 16

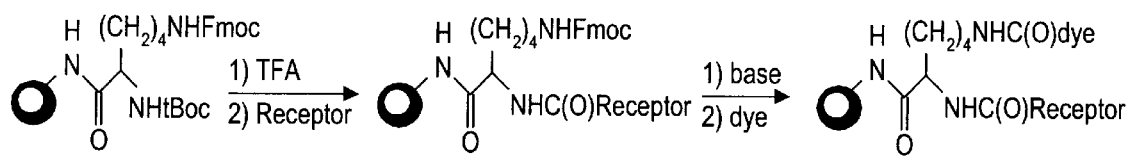
FIG. 45D
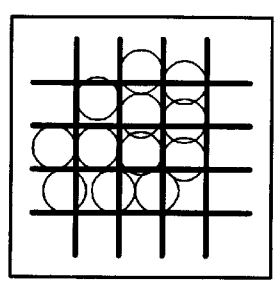
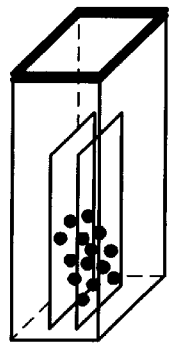
FIG. 46A　　　FIG. 46B green to brown blue to black red to purple yellow to orange yellow to red to blue

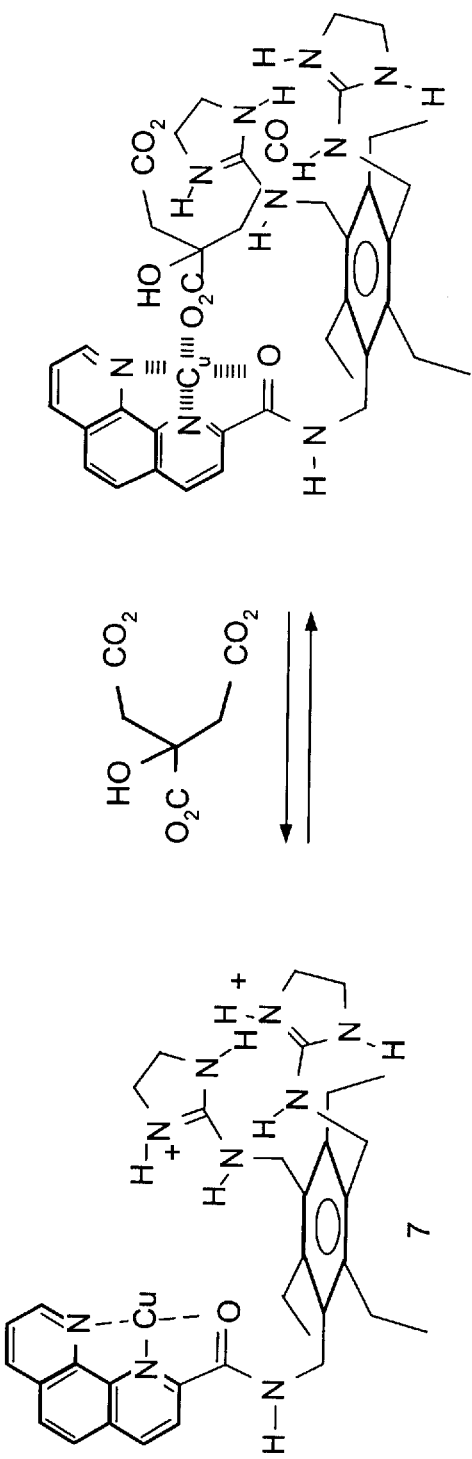
FIG. 53
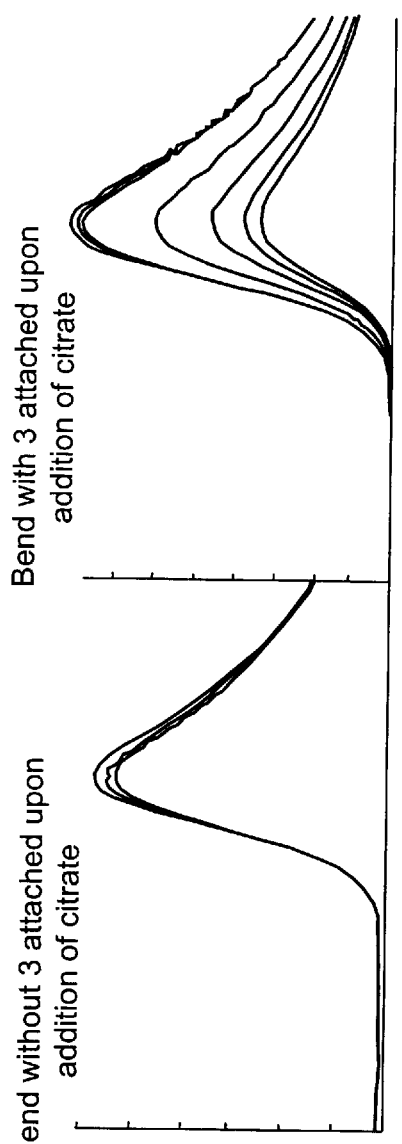
FIG. 54
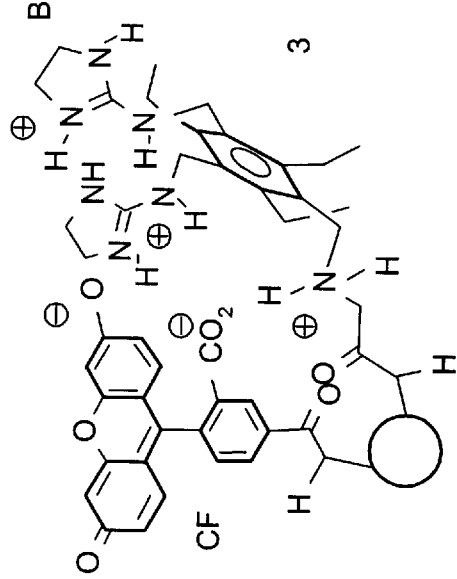

GENERAL SIGNALING PROTOCOL FOR CHEMICAL RECEPTORS IN IMMOBILIZED MATRICES

This application claims priority to U.S. Provisional Application No. 60/144,436 entitled "DETECTION SYSTEM BASED ON AN ANALYTE REACTIVE PARTICLE," filed Jul. 16, 1999, U.S. Provisional Application No. 60/144,435 entitled "GENERAL SIGNALING PROTOCOLS FOR CHEMICAL RECEPTORS IN IMMOBILIZED MATRICES," filed Jul. 16, 1999, and U.S. Provisional Application No. 60/144,126 entitled "METHOD AND APPARATUS FOR THE DELIVERY OF SAMPLES TO A CHEMICAL SENSOR ARRAY," filed Jul. 16, 1999.

STATEMENT REGARDING FEDERALLY SPONSORED RESEARCH OR DEVELOPMENT

Research leading to this invention was federally supported, in part, by grant No. 1R01GM57306-01 entitled "The Development of an Electronic Tongue" from the National Institute of Health and the U.S. Government has certain rights to this invention.

BACKGROUND OF THE INVENTION

1. Field of the Invention

The present invention relates to a method and device for the detection of analytes in a fluid. More particularly, the invention relates to the development of a sensor array system capable of discriminating mixtures of analytes, toxins, and/or bacteria in medical, food/beverage, and environmental solutions.

2. Brief Description of the Related Art

The development of smart sensors capable of discriminating different analytes, toxins, and bacteria has become increasingly important for clinical, environmental, health and safety, remote sensing, military, food/beverage and chemical processing applications. Although many sensors capable of high sensitivity and high selectivity detection have been fashioned for single analyte detection, only in a few selected cases have array sensors been prepared which display solution phase multi-analyte detection capabilities. The advantages of such array systems are their utility for the analysis of multiple analytes and their ability to be "trained" to respond to new stimuli. Such on site adaptive analysis capabilities afforded by the array structures make their utilization promising for a variety of future applications. Array based sensors displaying the capacity to sense and identify complex vapors have been demonstrated recently using a number of distinct transduction schemes. For example, functional sensors based on Surface Acoustic Wave (SAW), tin oxide ($SnO_2$) sensors, conductive organic polymers, and carbon black/polymer composites have been fashioned. The use of tin oxide sensors, for example, is described in U.S. Pat. No. 5,654,497 to Hoffheins et al. These sensors display the capacity to identify and discriminate between a variety of organic vapors by virtue of small site-to-site differences in response characteristics. Pattern recognition of the overall fingerprint response for the array serves as the basis for an olfaction-like detection of the vapor phase analyte species. Indeed, several commercial "electronic noses" have been developed recently. Most of the well established sensing elements are based on $SnO_2$ arrays which have been derivatized so as to yield chemically distinct response properties. Arrays based on SAW crystals yield extremely sensitive responses to vapor, however, engineering challenges have prevented the creation of large SAW arrays having multiple sensor sites. To our knowledge, the largest SAW device reported to date possesses only 12 sensor elements. Additionally, limited chemical diversity and the lack of understanding of the molecular features of such systems makes their expansion into more complex analysis difficult.

Other structures have been developed that are capable of identifying and discriminating volatile organic molecules. One structure involves a series of conductive polymer layers deposited onto metal contacting layers. When these sensors are exposed to volatile reagents, some of the volatile reagents adsorb into the polymer layers, leading to small changes in the electrical resistance of these layers. It is the small differences in the behavior of the various sites that allows for a discrimination, identification, and quantification of the vapors. The detection process takes only a few seconds, and sensitivities of part-per-billion can be achieved with this relatively simple approach. This "electronic nose" system is described in U.S. Pat. No. 5,698,089 to Lewis et al. which is incorporated herein by reference as if set forth herein.

Although the above described electronic nose provides an impressive capability for monitoring volatile reagents, the system possesses a number of undesirable characteristics that warrant the development of alternative sensor array systems. For example, the electronic nose can be used only for the identification of volatile reagents. For many environmental, military, medical, and commercial applications, the identification and quantification of analytes present in liquid or solid-phase samples is necessary. Moreover, the electronic nose systems are expensive (e.g., the Aromascan system costs about $50,000/unit) and bulky ($\geq 1$ $ft^3$). Furthermore, the functional elements for the currently available electronic nose are composed of conductive polymer systems which possess little chemical selectivity for many of the analytes which are of interest to the military and civilian communities.

One of the most commonly employed sensing techniques has exploited colloidal polymer microspheres for latex agglutination tests (LATs) in clinical analysis. Commercially available LATs for more than 60 analytes are used routinely for the detection of infectious-diseases, illegal drugs, and early pregnancy tests. The vast majority of these types of sensors operate on the principle of agglutination of latex particles (polymer microspheres) which occurs when the antibody-derivatized microspheres become effectively "cross-linked" by a foreign antigen resulting in the attachment to, or the inability to pass through a filter. The dye-doped microspheres are then detected calorimetrically upon removal of the antigen carrying solution. However, the LATs lack the ability to be utilized for multiple, real time analyte detection schemes as the nature of the response intrinsically depends on a cooperative effect of the entire collection of microspheres.

Similar to the electronic nose, array sensors that have shown great analytical promise are those based on the "DNA on a chip" technology. These devices possess a high density of DNA hybridization sites that are affixed in a two-dimensional pattern on a planar substrate. To generate nucleotide sequence information, a pattern is created from unknown DNA fragments binding to various hybridization sites. Both radiochemical and optical methods have provided excellent detection limits for analysis of limited quantities of DNA. (Stimpson, D. I.; Hoijer, J. V.; Hsieh, W.; Jou, C.; Gardon, J.; Theriault, T.; Gamble, R.; Baldeschwieler, J. D. Proc. Natl. Acad. Sci. USA 1995, 92, 6379). Although quite promising for the detection of DNA fragments, these arrays are generally not designed for non-DNA molecules, and accordingly show very little sensitivity to smaller organic molecules. Many of the target molecules of interest to civilian and military communities, however, do not possess DNA components. Thus, the need for a flexible, non-DNA based sensor is still desired. Moreover, while a number of prototype DNA chips containing up to a few thousand different nucleic acid probes have been described, the existing technologies tend to be difficult to expand to a practical size. As a result, DNA chips may be prohibitively expensive for practical uses.

Systems for analyzing fluid samples using an array formed of heterogeneous, semi-selective thin films which function as sensing receptor units are described in U.S. Pat. Nos. 6,023,540; 5,814,524; 5,700,897; 5,512,490; 5,480,723; 5,252,494; 5,250,264; 5,244,813; 5,244,636; and 5,143,853 which are incorporated herein by reference as if set forth herein. These systems appears to describe the use of covalently attached polymeric "cones" which are grown via photopolymerization onto the distal face of fiber optic bundles. These sensor probes appear to be designed with the goal of obtaining unique, continuous, and reproducible responses from small localized regions of dye-doped polymer. The polymer appears to serve as a solid support for indicator molecules that provide information about test solutions through changes in optical properties. These polymer supported sensors have been used for the detection of analytes such as pH, metals, and specific biological entities. Methods for manufacturing large numbers of reproducible sensors, however, has yet to be developed. Moreover, no methods for acquisitions of data streams in a simultaneous manner are commercially available with this system. Optical alignment issues may also be problematic for these systems.

A method of rapid sample analysis for use in the diagnostic microbiology field is also desirable. The techniques now used for rapid microbiology diagnostics detect either antigens or nucleic acids. Rapid antigen testing is based on the use of antibodies to recognize either the single cell organism or the presence of infected cell material. Inherent to this approach is the need to obtain and characterize the binding of the antibody to unique structures on the organism being tested. Since the identification and isolation of the appropriate antibodies is time consuming, these techniques are limited to a single agent per testing module and there is no opportunity to evaluate the amount of agent present.

Most antibody methods are relatively insensitive and require the presence of $10^5$ to $10^7$ organisms. The response time of antibody-antigen reactions in diagnostic tests of this type ranges from 10 to 120 minutes, depending on the method of detection. The fastest methods are generally agglutination reactions, but these methods are less sensitive due to difficulties in visual interpretation of the reactions. Approaches with slower reaction times include antigen recognition by antibody conjugated to either an enzyme or chromophore. These test types tend to be more sensitive, especially when spectrophotometric methods are used to determine if an antigen-antibody reaction has occurred. These detection schemes do not, however, appear to allow the simultaneous detection of multiple analytes on a single detector platform.

The alternative to antigen detection is the detection of nucleic acids. An approach for diagnostic testing with nucleic acids uses hybridization to target unique regions of the target organism. These techniques require fewer organisms ($10^3$ to $10^5$), but require about five hours to complete. As with antibody-antigen reactions this approach has not been developed for the simultaneous detection of multiple analytes.

The most recent improvement in the detection of microorganisms has been the use of nucleic acid amplification. Nucleic acid amplification tests have been developed that generate both qualitative and quantitative data. However, the current limitations of these testing methods are related to delays caused by specimen preparation, amplification, and detection. Currently, the standard assays require about five hours to complete. The ability to complete much faster detection for a variety of microorganisms would be of tremendous importance to military intelligence, national safety, medical, environmental, and food areas.

It is therefore desirable that new sensors capable of discriminating different analytes, toxins, and bacteria be developed for medical/clinical diagnostic, environmental, health and safety, remote sensing, military, food/beverage, and chemical processing applications. It is further desired that the sensing system be adaptable to the simultaneous detection of a variety of analytes to improve throughput during various chemical and biological analytical procedures.

SUMMARY OF THE INVENTION

Herein we describe a system and method for the analysis of a fluid containing one or more analytes. The system may be used for either liquid or gaseous fluids. The system, in some embodiments, may generate patterns that are diagnostic for both the individual analytes and mixtures of the analytes. The system in some embodiments, is made of a plurality of chemically sensitive particles, formed in an ordered array, capable of simultaneously detecting many different Kinds of analytes rapidly. An aspect of the system is that the array may be formed using a microfabrication process, thus allowing the system to be manufactured in an inexpensive manner.

In an embodiment of a system for detecting analytes, the system, in some embodiments, includes a light source, a sensor array, and a detector. The sensor array, in some embodiments, is formed of a supporting member which is configured to hold a variety of chemically sensitive particles (herein referred to as "particles") in an ordered array. The particles are, in some embodiments, elements which will create a detectable signal in the presence of an analyte. The particles may produce optical (e.g., absorbance or reflectance) or fluorescence/phosphorescent signals upon exposure to an analyte. Examples of particles include, but are not limited to functionalized polymeric beads, agarous beads, dextrose beads, polyacrylamide beads, control pore glass beads, metal oxides particles (e.g., silicon dioxide ($SiO_2$) or aluminum oxides ($Al_2O_3$)), polymer thin films, metal quantum particles (e.g., silver, gold, platinum, etc.), and semiconductor quantum particles (e.g., Si, Ge, GaAs, etc.). A detector (e.g., a charge-coupled device "CCD") in one embodiment is positioned below the sensor array to allow for the data acquisition. In another embodiment, the detector may be positioned above the sensor array to allow for data acquisition from reflectance of the light off of the particles.

Light originating from the light source may pass through the sensor array and out through the bottom side of the sensor array. Light modulated by the particles may pass through the sensor array and onto the proximally spaced detector. Evaluation of the optical changes may be completed by visual inspection or by use of a CCD detector by itself or in combination with an optical microscope. A microprocessor may be coupled to the CCD detector or the microscope. A fluid delivery system may be coupled to the supporting member of the sensor array. The fluid delivery system, in some embodiments, is configured to introduce samples into and out of the sensor array.

In an embodiment, the sensor array system includes an array of particles. The particles may include a receptor molecule coupled to a polymeric bead. The receptors, in some embodiments, are chosen for interacting with analytes. This interaction may take the form of a binding/association of the receptors with the analytes. The supporting member may be made of any material capable of supporting the particles, while allowing the passage of the appropriate wavelengths of light. The supporting member may include a plurality of cavities. The cavities may be formed such that at least one particle is substantially contained within the cavity.

In an embodiment, the optical detector may be integrated within the bottom of the supporting member, rather than using a separate detecting device. The optical detectors may be coupled to a microprocessor to allow evaluation of fluids without the use of separate detecting components. Additionally, a fluid delivery system may also be incorporated into the supporting member. Integration of detectors and a fluid delivery system into the supporting member may allow the formation of a compact and portable analyte sensing system.

A high sensitivity CCD array may be used to measure changes in optical characteristics which occur upon binding of the biological/chemical agents. The CCD arrays may be interfaced with filters, light sources, fluid delivery and micromachined particle receptacles, so as to create a functional sensor array. Data acquisition and handling may be performed with existing CCD technology. CCD detectors may be configured to measure white light, ultraviolet light or fluorescence. Other detectors such as photomultiplier tubes, charge induction devices, photo diodes, photodiode arrays, and microchannel plates may also be used.

A particle, in some embodiments, possess both the ability to bind the analyte of interest and to create a modulated signal. The particle may include receptor molecules which posses the ability to bind the analyte of interest and to create a modulated signal. Alternatively, the particle may include receptor molecules and indicators. The receptor molecule may posses the ability to bind to an analyte o f interest. Upon binding the analyte of interest, the receptor molecule may cause the indicator molecule to produce the modulated signal. The receptor molecules may be naturally occurring or synthetic receptors formed by rational design or combinatorial methods. Some examples of natural receptors include, but are not limited to, DNA, RNA, proteins, enzymes, oligopeptides, antigens, and antibodies. Either natural or synthetic receptors may be chosen for their ability to bind to the analyte molecules in a specific manner.

In one embodiment, a naturally occurring or synthetic receptor is bound to a polymeric bead in order to create the particle. The particle, in some embodiments, is capable of both binding the analyte(s) of interest and creating a detectable signal. In some embodiments, the particle will create an optical signal when bound to an analyte of interest.

A variety of natural and synthetic receptors may be used. The synthetic receptors may come from a variety of classes including, but not limited to, polynucleotides (e.g., aptamers), peptides (e.g., enzymes and antibodies), synthetic receptors, polymeric unnatural biopolymers (e.g., polythioureas, polyguanidiniums), and imprinted polymers. Polynucleotides are relatively small fragments of DNA which may be derived by sequentially building the DNA sequence. Peptides include natural peptides such as antibodies or enzymes or may be synthesized from amino acids. Unnatural biopolymers are chemical structure which are based on natural biopolymers, but which are built from unnatural linking units. For example, polythioureas and polyguanidiniums have a structure similar to peptides, but may be synthesized from diamines (i.e., compounds which include at least two amine functional groups) rather than amino acids. Synthetic receptors are designed organic or inorganic structures capable of binding various analytes.

In an embodiment, a large number of chemical/biological agents of interest to the military and civilian communities may be sensed readily by the described array sensors. Bacteria may also be detected using a similar system. To detect, sense, and identify intact bacteria, the cell surface of one bacteria may be differentiated from other bacteria, or genomic material may be detected using oligonucleic receptors. One method of accomplishing this differentiation is to target cell surface oligosaccharides (i.e., sugar residues). The use of synthetic receptors which are specific for oligosaccharides may be used to determine the presence of specific bacteria by analyzing for cell surface oligosaccharides.

In one embodiment, a receptor may be coupled to a polymeric resin. The receptor may undergo a chemical reaction in the presence of an analyte such that a signal is produced. Indicators may be coupled to the receptor or the polymeric bead. The chemical reaction of the analyte with the receptor may cause a change in the local microenvironment of the indicator to alter the spectroscopic properties of the indicator. This signal may be produced using a variety of signalling protocols. Such protocols may include absorbance, fluorescence resonance energy transfer, and/or fluorescence quenching. Receptor-analyte combination may include, but are not limited to, peptides-proteases, polynucleotides-nucleases, and oligosaccharides-oligosaccharide cleaving agents.

In one embodiment, a receptor and an indicator may be coupled to a polymeric resin. The receptor may undergo a conformational change in the presence of an analyte such that a change in the local microenvironment of the indicator occurs. This change may alter the spectroscopic properties of the indicator. The interaction of the receptor with the indicator may be produce a variety of different signals depending on the signalling protocol used. Such protocols may include absorbance, fluorescence resonance energy transfer, and/or fluorescence quenching.

In an embodiment, the sensor array system includes an array of particles. The particles may include a receptor molecule coupled to a polymeric bead. The receptors, in some embodiments, are chosen for interacting with analytes. This interaction may take the form of a binding/association of the receptors with the analytes. The supporting member may be made of any material capable of supporting the particles, while allowing the passage of the appropriate wavelengths of light. The supporting member may include a plurality of cavities. The cavities may be formed such that at least one particle is substantially contained within the cavity. A vacuum may be coupled to the cavities. The vacuum may be applied to the entire sensor array. Alternatively, a vacuum apparatus may be coupled to the cavities to provide a vacuum to the cavities. A vacuum apparatus is any device capable of creating a pressure differential to cause fluid movement. The vacuum apparatus may apply a pulling force to any fluids within the cavity. The vacuum apparatus may pull the fluid through the cavity. Examples of vacuum apparatuss include pre-sealed vacuum chamber, vacuum pumps, vacuum lines, or aspirator-type pumps.

BRIEF DESCRIPTION OF THE DRAWINGS

The above brief description as well as further objects, features and advantages of the methods and apparatus of the present invention will be more fully appreciated by reference to the following detailed description of presently preferred but nonetheless illustrative embodiments in accordance with the present invention when taken in conjunction with the accompanying drawings in which:

FIG. 16 depicts the color responses of a variety of sensing particles to solutions of $Ca^{+2}$ and various pH levels;

FIG. 45D depicts the attachment of differentially protected lysine to a bead;

FIGS. 46A–B depicts a system for measuring the absorbance or emission of a sensing particle;

FIG. 53 depicts a scheme wherein a signal of apo-7 to citrate is triggered by Cu(II) binding;

FIG. 54 depicts the response of receptor 3 and 5-carboxyfluoroscein on a resin bead to the addition of citrate;

DETAILED DESCRIPTION OF PREFERRED EMBODIMENTS

Herein we describe a system and method for the simultaneous analysis of a fluid containing multiple analytes. The system may be used for either liquid or gaseous fluids. The system may generate patterns that are diagnostic for both individual analytes and mixtures of the analytes. The system, in some embodiments, is made of a combination of chemically sensitive particles, formed in an ordered array, capable of simultaneously detecting many different kinds of analytes rapidly. An aspect of the system is that the array may be formed using a microfabrication process, thus allowing the system to be manufactured in an inexpensive manner.

SYSTEM FOR ANALYSIS OF ANALYTES

Figure 1:
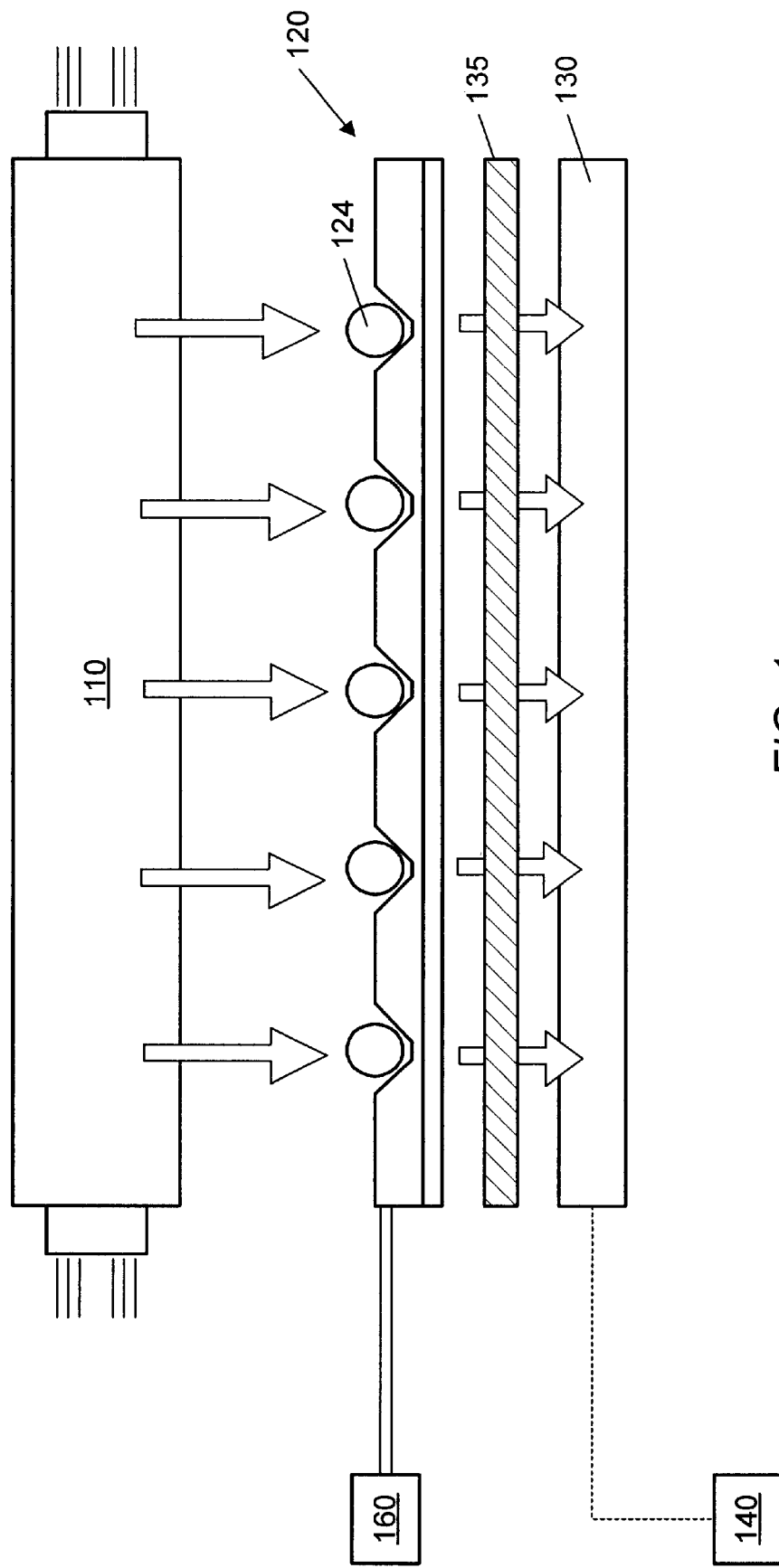
FIG. 1 depicts a schematic of an analyte detection system.

Shown in FIG. 1 is an embodiment of a system for detecting analytes in a fluid. The system, in some embodiments, includes a light source 110, a sensor array 120 and a detector 130. The light source 110 may be a white light source or light emitting diodes (LED). In one embodiment, light source 110 may be a blue light emitting diode (LED) for use in systems relying on changes in fluorescence signals. For colorimetric (e.g., absorbance) based systems, a white light source may be used. The sensor array 120, in some embodiments, is formed of a supporting member which is configured to hold a variety of particles 124. A detecting device 130 (e.g., a charge-coupled device "CCD") may be positioned below the sensor array to allow for data acquisition. In another embodiment, the detecting device 130 may be positioned above the sensor array.

Light originating from the light source 110, in some embodiments, passes through the sensor array 120 and out through the bottom side of the sensor array. The supporting member and the particles together, in some embodiments, provide an assembly whose optical properties are well matched for spectral analyses. Thus, light modulated by the particles may pass through the sensor array and onto the proximally spaced detector 130. Evaluation of the optical changes may be completed by visual inspection (e.g., with a microscope) or by use of a microprocessor 140 coupled to the detector. For fluorescence measurements, a filter 135 may be placed between supporting member 122 and detector 130 to remove the excitation wavelength. A fluid delivery system 160 may be coupled to the supporting member. The fluid delivery system 160 may be configured to introduce samples into and out of the sensor array.

In an embodiment, the sensor array system includes an array of particles. Upon the surface and within the interior region of the particles are, in some embodiments, located a variety of receptors for interacting with analytes. The supporting member, in some embodiments, is used to localize these particles as well as to serve as a microenvironment in which the chemical assays can be performed. For the chemical/biological agent sensor arrays, the particles used for analysis are about 0.05–500 microns in diameter, and may actually change size (e.g., swell or shrink) when the chemical environment changes. Typically, these changes occur when the array system is exposed to the fluid stream which includes the analytes. For example, a fluid stream which comprises a non-polar solvent, may cause non-polar particles to change in volume when the particles are exposed to the solvent. To accommodate these changes, it is preferred that the supporting member consist of an array of cavities which serve as micro test-tubes.

The supporting member may be made of any material capable of supporting the particles, while allowing the passage of the appropriate wavelength of light. The supporting member is also made of a material substantially impervious to the fluid in which the analyte is present. A variety of materials may be used including plastics, glass, silicon based materials (e.g., silicon, silicon dioxide, silicon nitride, etc.) and metals. In one embodiment, the supporting member includes a plurality of cavities. The cavities may be formed such that at least one particle is substantially contained within the cavity. Alternatively, a plurality of particles may be contained within a single cavity.

In an embodiment, the supporting member may consist of a strip of plastic which is substantially transparent to the wavelength of light necessary for detection. A series of cavities may be formed within the strip. The cavities may be configured to hold at least one particle. The particles may be contained within the strip by a transparent cover which is configured to allow passage of the analyte containing fluid into the cavities.

Figure 2:
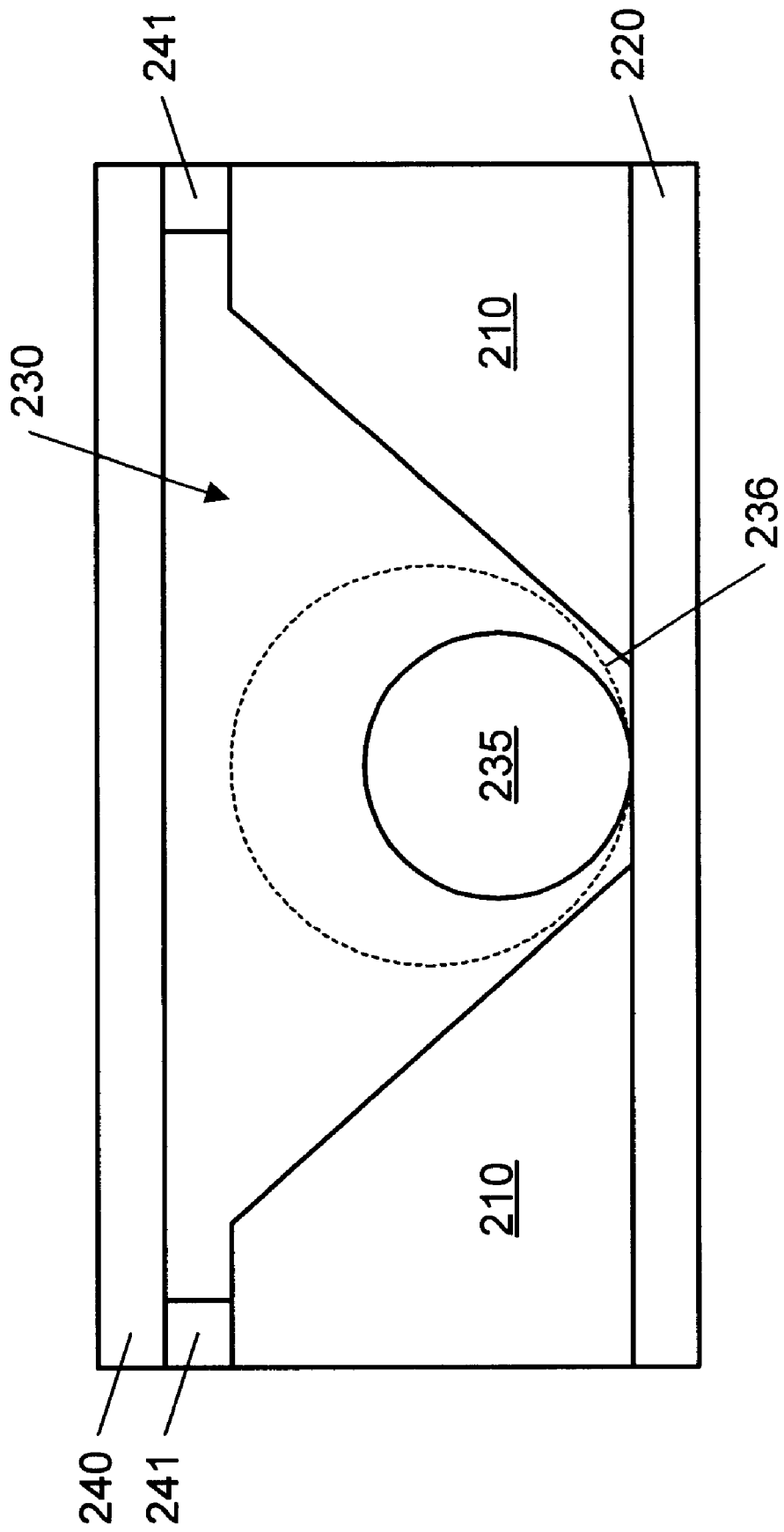
FIG. 2 depicts a particle disposed in a cavity.

In another embodiment, the supporting member may be formed using a silicon wafer as depicted in FIG. 2. The silicon wafer 210 may include a substantially transparent layer 220 formed on the bottom surface of the wafer. The cavities 230, in one embodiment, are formed by an anisotropic etch process of the silicon wafer. In one embodiment, anisotropic etching of the silicon wafer is accomplished using a wet hydroxide etch. Photolithographic techniques may be used to define the locations of the cavities. The cavities may be formed such that the sidewalls of the cavities are substantially tapered at an angle of between about 50 to 60 degrees. Formation of such angled cavities may be accomplished by wet anisotropic etching of <100> silicon. The term "<100> silicon" refers to the crystal orientation of the silicon wafer. Other types of silicon, (e.g., <110> and <111> silicon) may lead to steeper angled sidewalls. For example, <111>silicon may lead to sidewalls formed at about 90 degrees. The angled sides of the cavities in some embodiments, serve as "mirror layers" which may improve the light collection efficiency of the cavities. The etch process may be controlled so that the formed cavities extend through the silicon wafer to the upper surface of transparent layer 220. While depicted as pyramidal, the cavities may be formed in a number of shapes including but not limited to, spherical, oval, cubic, or rectangular. An advantage to using a silicon wafer for the support member, is that the silicon material is substantially opaque to the light produced from the light source. Thus, the light may be inhibited from passing from one cavity to adjacent cavities. In this manner, light from one cavity may be inhibited from influencing the spectroscopic changes produced in an adjacent cavity.

The silicon wafer, in some embodiments, has an area of approximately 1 cm$^2$ to about 100 cm$^2$ and includes about $10^1$ to about $10^6$ cavities. In an embodiment, about 100 cavities are formed in a ten by ten matrix. The center to center distance between the cavities, in some embodiments, is about 500 microns. Each of the cavities may include at least one particle.

The transparent layer 220 may serve as a window, allowing light of a variety of wavelengths to pass through the cavities 230 and to the detector. Additionally, the transparent layer may serve as a platform onto which the individual particles 235 may be positioned. The transparent layer may be formed of silicon dioxide ($SiO_2$), silicon nitride ($Si_3N_4$) or silicon dioxide/silicon nitride multi-layer stacks. The transparent layer, in some embodiments, is deposited onto the silicon wafer prior to the formation of the cavities.

The cavities 230 may be sized to substantially contain a particle 235. The cavities are, in some embodiments, larger than a particle. The cavities are, in some embodiments, sized to allow facile placement and removal of the particle within the cavities. The cavity may be substantially larger than the particle, thus allowing the particle to swell during use. For example, a particle may have a size as depicted in FIG. 2 by particle 235. During use, contact with a fluid (e.g., a solvent) may cause the particle to swell, for example, to a size depicted as circle 236. In some embodiments, the cavity is sized to allow such swelling of the particle during use. A particle may be positioned at the bottom of a cavity using, e.g., a micromanipulator. After a particle has been placed within the cavity, a transparent cover plate 240 may be placed on top of the supporting member to keep the particle in place.

When forming an array which includes a plurality of particles, the particles may be placed in the array in an ordered fashion using the micromanipulator. In this manner, a ordered array having a predefined configuration of particles may be formed. Alternatively, the particles may be randomly placed within the cavities. The array may subsequently undergo a calibration test to determine the identity of the particle at any specified location in the supporting member.

The transparent cover plate 240, in some embodiments, is coupled to the upper surface of the silicon wafer 220 such that the particles are inhibited from becoming dislodged from the cavity. The transparent cover plate, in some embodiments, is positioned a fixed distance above the silicon wafer, as depicted in FIG. 2, to keep the particle in place, while allowing the entrance of fluids into the cavities. The transparent cover plate, in some embodiments, is positioned at a distance above the substrate which is substantially less than a width of the particle. The transparent cover plate may be made of any material which is substantially transparent to the wavelength of light being utilized by the detector. The transparent cover plate may be made of plastic, glass, quartz, or silicon dioxide/silicon nitride.

In one embodiment, the transparent cover plate 240 is a thin sheet of glass (e.g., a microscope slide cover slip). The slide may be positioned a fixed distance above the silicon wafer. Support structures 241 (See FIG. 2) may be placed upon the silicon wafer 210 to position the transparent cover plate 240. The support structures may be formed from a polymer or a silicon based material. In another embodiment, a polymeric substrate is coupled to the silicon wafer to form the support structures 241 for the transparent cover plate 240. In an embodiment, a plastic material with an adhesive backing (e.g., cellophane tape) is positioned on the silicon wafer 210. After the support structures 241 are placed on the wafer, the transparent cover plate 240 is placed upon the support structures. The support structures inhibit the transparent cover sheet from contacting the silicon wafer 210. In this manner, a channel is formed between the silicon wafer and the transparent cover plate, which allow the fluid to pass into the cavity, while inhibiting displacement of the particle by the fluid.

Figure 3:
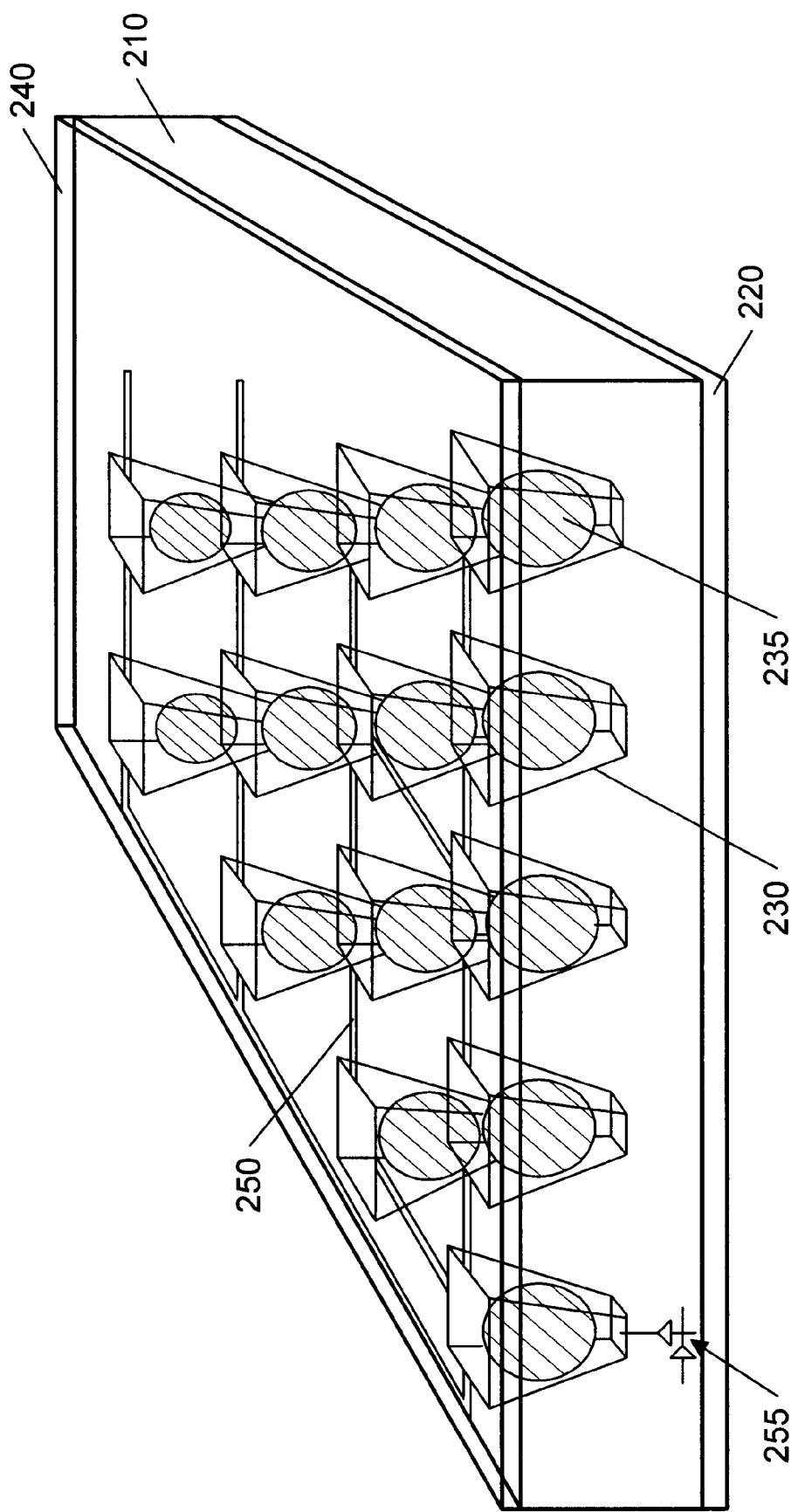
FIG. 3 depicts a sensor array.

In another embodiment, the transparent cover plate 240 may be fastened to the upper surface of the silicon wafer, as depicted in FIG. 3. In this embodiment, the fluid may be inhibited from entering the cavities 230 by the transparent cover plate 240. To allow passage of the fluid into the cavities, a number of channels 250 may be formed in the silicon wafer. The channels, in one embodiment, are oriented to allow passage of the fluid into substantially all of the cavities. When contacted with the fluid, the particles may swell to a size which may plug the channels. To prevent this plugging, the channels may be formed near the upper portion of the cavities, as depicted in FIG. 3. The channels, in one embodiment, are formed using standard photolithographic masking to define the regions where the trenches are to be formed, followed by the use of standard etching techniques. A depth of the cavity may be such that the particle resides substantially below the position of the channel. In this way, the plugging of the channels due to swelling of the particle may be prevented.

The inner surfaces of the cavities may be coated with a material to aid the positioning of the particles within the cavities. In one embodiment, a thin layer of gold or silver may be used to line the inner surface of the cavities. The gold or silver layer may act as an anchoring surface to anchor particles (e.g., via alkylthiol bonding). In addition, the gold or silver layer may also increase the reflectivity of the inner surface of the cavities. The increased reflectance of the surface may enhance the analyte detection sensitivity of the system. Alternatively, polymer layers and self-assembled monolayers formed upon the inner surface of the cavities may be used to control the particle adhesion interactions. Additional chemical anchoring methods may be used for silicon surfaces such as those based on siloxane type reagents, which may be attached to Si—OH functionalities. Similarly, monomeric and polymeric reagents attached to an interior region of the cavities can be used to alter the local wetting characteristics of the cavities. This type of methodology can be used to anchor the particles as well as to alter the fluid delivery characteristics of the cavity. Furthermore, amplification of the signals for the analytes may be accomplished with this type of strategy by causing preconcentration of appropriate analytes in the appropriate type of chemical environment.

In another embodiment, the optical detector may be integrated within the bottom transparent layer 220 of the supporting member, rather than using a separate detecting device. The optical detectors may be formed using a semiconductor-based photodetector 255. The optical detectors may be coupled to a microprocessor to allow evaluation of fluids without the use of separate detecting components. Additionally, the fluid delivery system may also be incorporated into the supporting member. Micro-pumps and micro-valves may also be incorporated into the silicon wafer to aid passage of the fluid through the cavities. Integration of detectors and a fluid delivery system into the supporting member may allow the formation of a compact and portable analyte sensing system. Optical filters may also be integrated into the bottom membrane of the cavities. These filters may prevent short wavelength excitation from producing "false" signals in the optical detection system (e.g., a CCD detector array) during fluorescence measurements.

A sensing cavity may be formed on the bottom surface of the support substrate. An example of a sensing cavity that may be used is a Fabry-Perot type cavity. Fabry-Perot cavity-based sensors may be used to detect changes in optical path length induced by either a change in the refractive index or a change in physical length of the cavity. Using micromachining techniques, Fabry-Perot sensors may be formed on the bottom surface of the cavity.

Figure 4A:
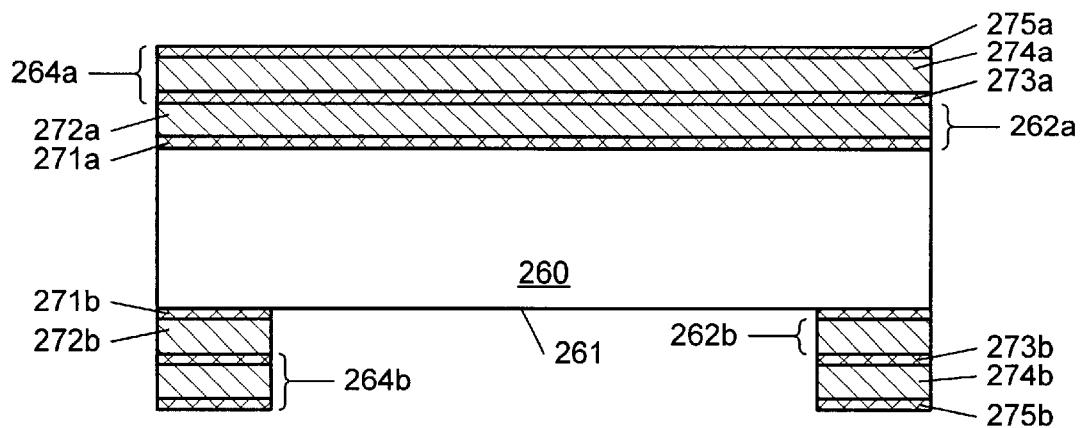
FIGS. 4A–F depict the formation of a Fabry-Perot cavity on the back of a sensor array.

FIGS. 4A–F depict a sequence of processing steps for the formation of a cavity and a planar top diaphragm Fabry-Perot sensor on the bottom surface of a silicon based supporting member. A sacrificial barrier layer 262a/b is deposited upon both sides of a silicon supporting member 260. The silicon supporting member 260 may be a double-side polished silicon wafer having a thickness ranging from about 100 µm to about 500 µm, preferably from about 200 µm to about 400 µm, and more preferably of about 300 µm. The barrier layer 262a/b may be composed of silicon dioxide, silicon nitride, or silicon oxynitride. In one embodiment, the barrier layer 262a/b is composed of a stack of dielectric materials. As depicted in FIG. 4A, the barrier layer 262a/b is composed of a stack of dielectric materials which includes a silicon nitride layer 271a/b and a silicon dioxide layer 272a/b. Both layers may be deposited using a low pressure chemical vapor deposition ("LPCVD") process. Silicon nitride may be deposited using an LPCVD reactor by reaction of ammonia ($NH_3$) and dichlorosilane ($SiCl_2H_2$) at a gas flow rate of about 3.5:1, a temperature of about 800° C., and a pressure of about 220 mTorr. The silicon nitride layer 271a/b is deposited to a thickness in the range from about 100 Å to about 500 Å, preferably from 200 Å to about 400 Å, and more preferably of about 300 Å. Silicon dioxide is may be deposited using an LPCVD reactor by reaction of silane ($SiH_4$) and oxygen ($O_2$) at a gas flow rate of about 3:4, a temperature of about 450° C., and a pressure of about 110 mTorr. The silicon dioxide layer 272a/b is deposited to a thickness in the range from about 3000 Å to about 7000 Å, preferably from 4000 Å to about 6000 Å, and more preferably of about 5000 Å. The front face silicon dioxide layer 272a, in one embodiment, acts as the main barrier layer. The underlying silicon nitride layer 271a acts as an intermediate barrier layer to inhibit overetching of the main barrier layer during subsequent KOH wet anisotropic etching steps.

A bottom diaphragm layer 264a/b is deposited upon the barrier layer 262a/b on both sides of the supporting member 260. The bottom diaphragm layer 264a/b may be composed of silicon nitride, silicon dioxide, or silicon oxynitride. In one embodiment, the bottom diaphragm layer 264a/b is composed of a stack of dielectric materials. As depicted in FIG. 4A, the bottom diaphragm layer 264a/b is composed of a stack of dielectric materials which includes a pair of silicon nitride layers 273a/b and 275a/b surrounding a silicon dioxide layer 274a/b. All of the layers may be deposited using an LPCVD process. The silicon nitride layers 273a/b and 275a/b have a thickness in the range from about 500 Å to about 1000 Å, preferably from 700 Å to about 800 Å, and more preferably of about 750 Å. The silicon dioxide layer 274a/b has a thickness in the range from about 3000 Å to about 7000 Å, preferably from 4000 Å to about 6000 Å, and more preferably of about 4500 Å.

Figure 4B:
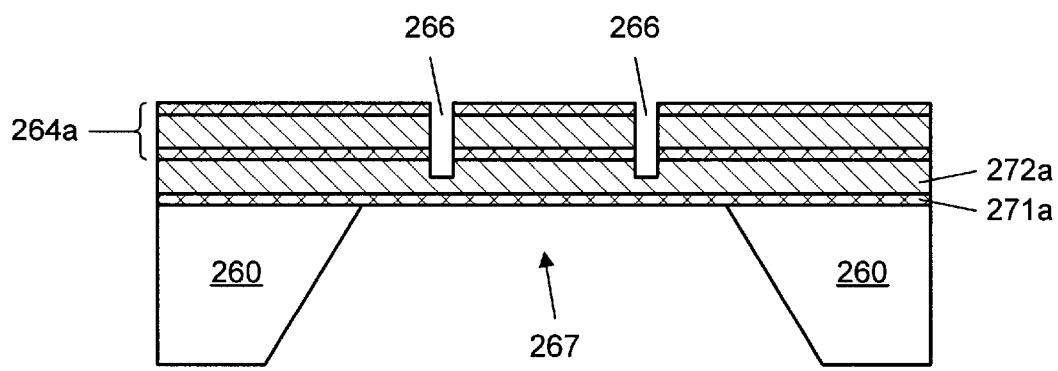

A cavity which will hold the particle may now be formed in the supporting member 260. The bottom diaphragm layer 264b and the barrier layer 262b formed on the back side 261 of the silicon supporting member 260 are patterned and etched using standard photolithographic techniques. In one embodiment, the layers are subjected to a plasma etch process. The plasma etching of silicon dioxide and silicon nitride may be performed using a mixture of carbontetrafluoride ($CF_4$) and oxygen ($O_2$). The patterned back side layers 262b and 264b may be used as a mask for anisotropic etching of the silicon supporting member 260. The silicon supporting member 260, in one embodiment, is anisotropically etched with a 40% potassium hydroxide ("KOH") solution at 80° C. to form the cavity. The etch is stopped when the front side silicon nitride layer 271a is reached, as depicted in FIG. 4B. The silicon nitride layer 271a inhibits etching of the main barrier layer 272a during this etch process. The cavity 267 may be formed extending through the supporting member 260. After formation of the cavity, the remaining portions of the back side barrier layer 262b and the diaphragm layer 264b may be removed.

Etch windows 266 are formed through the bottom diaphragm layer 264a on the front side of the wafer. A masking layer (not shown) is formed over the bottom diaphragm layer 264a and patterned using standard photolithographic techniques. Using the masking layer, etch windows 266 may be formed using a plasma etch. The plasma etching of silicon dioxide and silicon nitride may be performed using a mixture of carbontetrafluoride ($CF_4$) and oxygen ($O_2$). The etching is continued through the bottom diaphragm layer 264a and partially into the barrier layer 262a. In one embodiment, the etching is stopped at approximately half the thickness of the barrier layer 262a. Thus, when the barrier layer 262a is subsequently removed the etch windows 266 will extend through the bottom diaphragm layer 264a, communicating with the cavity 267. By stopping the etching at a midpoint of the barrier layer, voids or discontinuities may be reduced since the bottom diaphragm is still continuous due to the remaining barrier layer.

Figure 4C:
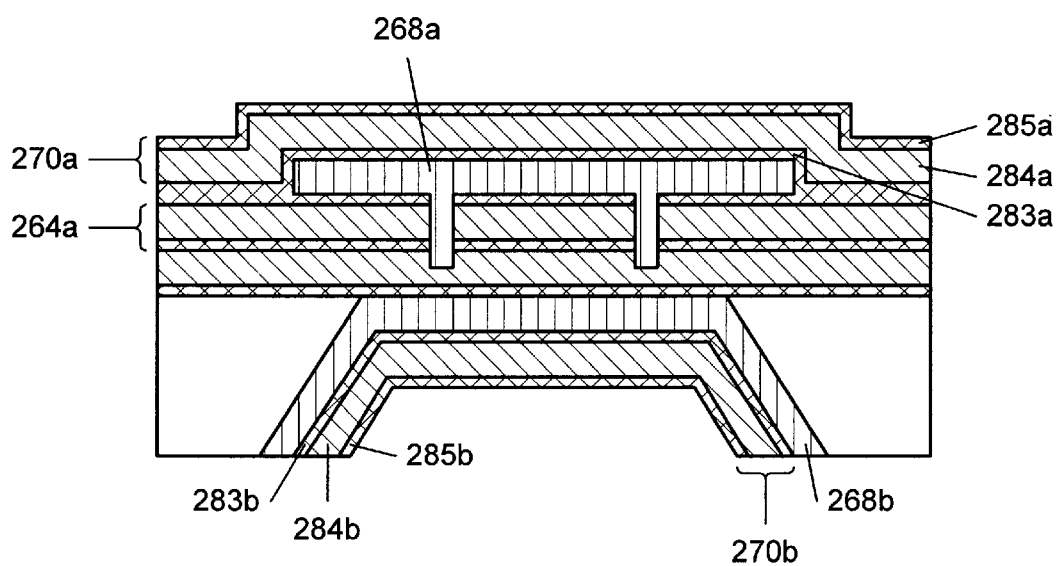

After the etch windows 266 are formed, a sacrificial spacer layer 268a/b is deposited upon the bottom diaphragm layer 264a and within cavity 267, as depicted in FIG. 4C. The spacer layer may be formed from LPCVD polysilicon. In one embodiment, the front side deposited spacer layer 268a will also at least partially fill the etch windows 266. Polysilicon may be deposited using an LPCVD reactor using silane ($SiH_4$) at a temperature of about 650° C. The spacer layer 268a/b is deposited to a thickness in the range from about 4000 Å to about 10,000 Å, preferably from 6000 Å to about 8000 Å, and more preferably of about 7000 Å. The preferred thickness of the spacer layer 268a is dependent on the desired thickness of the internal air cavity of the Fabry-Perot detector. For example, if a Fabry-Perot detector which is to include a 7000 Å air cavity between the top and bottom diaphragm layer is desired, a spacer layer having a thickness of about 7000 Å would be formed. After the spacer layer has been deposited, a masking layer for etching the spacer layer 268a (not shown) is used to define the etch regions of the spacer layer 268a. The etching may be performed using a composition of nitric acid ($HNO_3$), water, and hydrogen fluoride (HF) in a ratio of 25:13:1, respectively, by volume. The lateral size of the subsequently formed cavity is determined by the masking pattern used to define the etch regions of the spacer layer 268a.

After the spacer layer 268a has been etched, the top diaphragm layer 270a/b is formed. The top diaphragm 270a/b, in one embodiment, is deposited upon the spacer layer 268a/b on both sides of the supporting member. The top diaphragm 270a/b may be composed of silicon nitride, silicon dioxide, or silicon oxynitride. In one embodiment, the top diaphragm 270a/b is composed of a stack of dielectric materials. As depicted in FIG. 4C, the top diaphragm 270a/b is composed of a stack of dielectric materials which includes a pair of silicon nitride layers 283a/b and 285a/b surrounding a silicon dioxide layer 284a/b. All of the layers may be deposited using an LPCVD process. The silicon nitride layers 283a/b and 285a/b have a thickness in the range from about 1000 Å to about 2000 Å, preferably from 1200 Å to about 1700 Å, and more preferably of about 1500 Å. The silicon dioxide layer 284a/b has a thickness in the range from about 5000 Å to about 15,500 Å, preferably from 7500 Å to about 12,000 Å, and more preferably of about 10,500 Å.

Figure 4D:
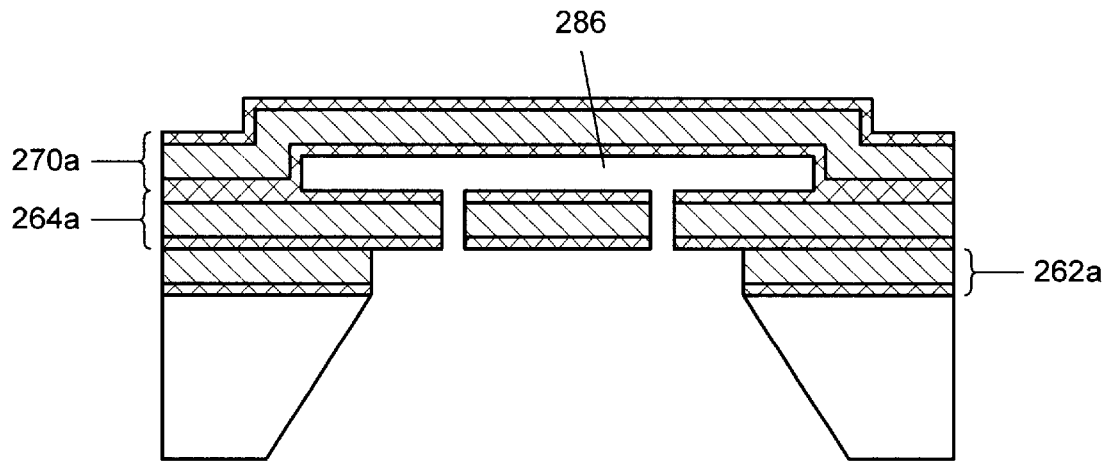

After depositing the top diaphragm 270a/b, all of the layers stacked on the bottom face of the supporting member (e.g., layers 268b, 283b, 284b, and 285b) are removed by multiple wet and plasma etching steps, as depicted in FIG. 4D. After these layers are removed, the now exposed portions of the barrier layer 262a are also removed. This exposes the spacer layer 268a which is present in the etch windows 266. The spacer layer 268 may be removed from between the top diaphragm 270a and the bottom diaphragm 264a by a wet etch using a KOH solution, as depicted in FIG. 4D. Removal of the spacer material 268a, forms a cavity 286 between the top diaphragm layer 270a and the bottom diaphragm layer 264a. After removal of the spacer material, the cavity 286 may be washed using deionized water, followed by isopropyl alcohol to clean out any remaining etching solution.

Figure 4E:
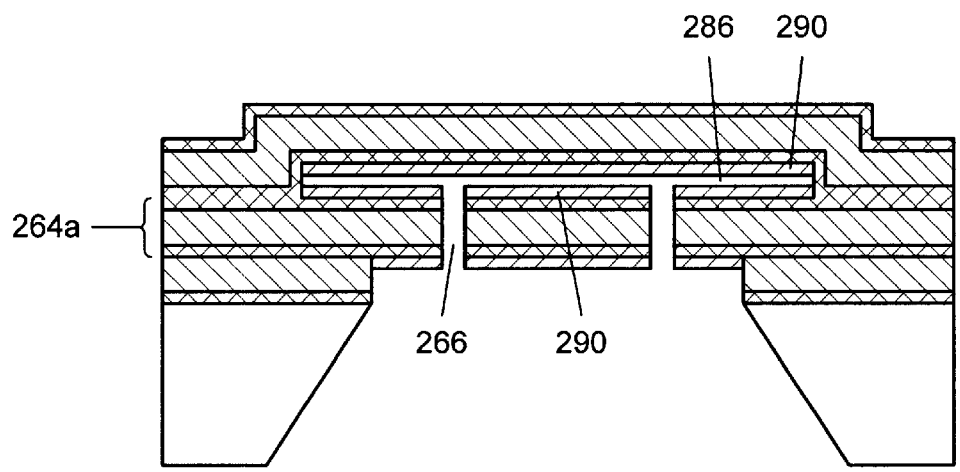

The cavity 286 of the Fabry-Perot sensor may be filled with a sensing substrate 290, as depicted in FIG. 4E. To coat the cavity 286 with a sensing substrate 290, the sensing substrate may be dissolved in a solvent. A solution of the sensing substrate is applied to the supporting member 260. The solution is believed to rapidly enter the cavity 286 through the etched windows 266 in the bottom diaphragm 264a, aided in part by capillary action. As the solvent evaporates, a thin film of the sensing substrate 290 coats the inner walls of the cavity 286, as well as the outer surface of the bottom diaphragm 264a. By repeated treatment of the supporting member with the solution of the sensing substrate, the thickness of the sensing substrate may be varied.

In one embodiment, the sensing substrate 290 is poly(3-dodecylthiophene) whose optical properties change in response to changes in oxidation states. The sensing substrate poly(3-dodecylthiophene) may be dissolved in a solvent such as chloroform or xylene. In one embodiment, a concentration of about 0.1 g of poly(3-dodecylthiophene)/mL is used. Application of the solution of poly(3-dodecylthiophene) to the supporting member causes a thin film of poly(3-dodecylthiophene) to be formed on the inner surface of the cavity.

Figure 4F:
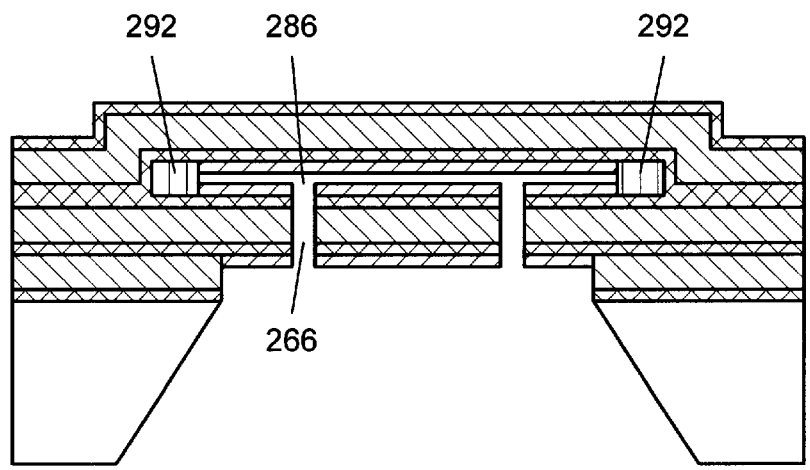

In some instances, the sensing substrate, when deposited within a cavity of a Fabry-Perot type detector, may cause stress in the top diaphragm of the detector. It is believed that when a sensing polymer coats a planar top diaphragm, extra residual stress on the top diaphragm causes the diaphragm to become deflected toward the bottom diaphragm. If the deflection becomes to severe, sticking between the top and bottom diaphragms may occur. In one embodiment, this stress may be relieved by the use of supporting members 292 formed within the cavity 286, as depicted in FIG. 4F. The supporting members 292 may be formed without any extra processing steps to the above described process flow. The formation of supporting members may be accomplished by deliberately leaving a portion of the spacer layer within the cavity. This may be accomplished by underetching the spacer layer (e.g., terminating the etch process before the entire etch process is finished). The remaining spacer will behave as a support member to reduce the deflection of the top diaphragm member. The size and shape of the support members may be adjusted by altering the etch time of the spacer layer, or adjusting the shape of the etch windows 266.

In another embodiment, a high sensitivity CCD array may be used to measure changes in optical characteristics which occur upon binding of the biological/chemical agents. The CCD arrays may be interfaced with filters, light sources, fluid delivery and micromachined particle receptacles, so as to create a functional sensor array. Data acquisition and handling may be performed with existing CCD technology. Data streams (e.g., red, green, blue for colorimetric assays; gray intensity for fluorescence assays) may be transferred from the CCD to a computer via a data acquisition board. Current CCDs may allow for read-out rates of $10^5$ pixels per second. Thus, the entire array of particles may be evaluated hundreds of times per second allowing for studies of the dynamics of the various host-guest interaction rates as well as the analyte/polymer diffusional characteristics. Evaluation of this data may offer a method of identifying and quantifying the chemical/biological composition of the test samples. CCD detectors may be configured to measure white light, ultraviolet light or fluorescence. Other detectors such as photomultiplier tubes, charge induction devices, photodiode, photodiode arrays, and microchannel plates may also be used. It should be understood that while the detector is depicted as being positioned under the supporting member, the detector may also be positioned above the supporting member. It should also be understood that the detector typically includes a sensing element for detecting the spectroscopic events and a component for displaying the detected events. The display component may be physically separated from the sensing element. The sensing element may be positioned above or below the sensor array while the display component is positioned close to a user.

In one embodiment, a CCD detector may be used to record color changes of the chemical sensitive particles during analysis. As depicted in FIG. 1, a CCD detector 130 may be placed beneath the supporting member 120. The light transmitted through the cavities is captured and analyzed by the CCD detector. In one embodiment, the light is broken down into three color components, red, green and blue. To simplify the data, each color is recorded using 8 bits of data. Thus, the data for each of the colors will appear as a value between 0 and 255. The color of each chemical sensitive element may be represented as a red, blue and green value. For example, a blank particle (i.e., a particle which does not include a receptor) will typically appear white. For example, when broken down into the red, green and blue components, it is found that a typical blank particle exhibits a red value of about 253, a green value of about 250, and a blue value of about 222. This signifies that a blank particle does not significantly absorb red, green or blue light. When a particle with a receptor is scanned, the particle may exhibit a color change, due to absorbance by the receptor. For example, it was found that when a particle which includes a 5-carboxyfluorescein receptor is subjected to white light, the particle shows a strong absorbance of blue light. The CCD detector values for the 5-carboxyfluorescein particle exhibits a red value of about 254, a green value of about 218, and a blue value of about 57. The decrease in transmittance of blue light is believed to be due to the absorbance of blue light by the 5-carboxyfluorescein. In this manner, the color changes of a particle may be quantitatively characterized. An advantage of using a CCD detector to monitor the color changes is that color changes which may not be noticeable to the human eye may now be detected.

The support array may be configured to allow a variety of detection modes to be practiced. In one embodiment, a light source is used to generate light which is directed toward the particles. The particles may absorb a portion of the light as the light illuminates the particles. The light then reaches the detector, reduced in intensity by the absorbance of the particles. The detector may be configure to measure the reduction in light intensity (i.e., the absorbance) due to the particles. In another embodiment, the detector may be placed above the supporting member. The detector may be configured to measure the amount of light reflected off of the particles. The absorbance of light by the particles is manifested by a reduction in the amount of light being reflected from the cavity. The light source in either embodiment may be a white light source or a fluorescent light source.

CHEMICALLY SENSITIVE PARTICLES

A particle, in some embodiments, possess both the ability to bind the analyte of interest and to create a modulated signal. The particle may include receptor molecules which posses the ability to bind the analyte of interest and to create a modulated signal. Alternatively, the particle may include receptor molecules and indicators. The receptor molecule may posses the ability to bind to an analyte of interest. Upon binding the analyte of interest, the receptor molecule may cause the indicator molecule to produce the modulated signal. The receptor molecules may be naturally occurring or synthetic receptors formed by rational design or combinatorial methods. Some examples of natural receptors include, but are not limited to, DNA, RNA, proteins, enzymes, oligopeptides, antigens, and antibodies. Either natural or synthetic receptors may be chosen for their ability to bind to the analyte molecules in a specific manner. The forces which drive association/recognition between molecules include the hydrophobic effect, anion-cation attraction, and hydrogen bonding. The relative strengths of these forces depend upon factors such as the solvent dielectric properties, the shape of the host molecule, and how it complements the guest. Upon host-guest association, attractive interactions occur and the molecules stick together. The most widely used analogy for this chemical interaction is that of a "lock and key". The fit of the key molecule (the guest) into the lock (the host) is a molecular recognition event.

A naturally occurring or synthetic receptor may be bound to a polymeric resin in order to create the particle. The polymeric resin may be made from a variety of polymers including, but not limited to, agarous, dextrose, acrylamide, control pore glass beads, polystyrene-polyethylene glycol resin, polystyrene-divinyl benzene resin, formylpolystyrene resin, trityl-polystyrene resin, acetyl polystyrene resin, chloroacetyl polystyrene resin, aminomethyl polystyrene-divinylbenzene resin, carboxypolystyrene resin, chloromethylated polystyrene-divinylbenzene resin, hydroxymethyl polystyrene-divinylbenzene resin, 2-chlorotrityl chloride polystyrene resin, 4-benzyloxy-2'4'-dimethoxybenzhydrol resin (Rink Acid resin), triphenyl methanol polystyrene resin, diphenylmethanol resin, benzhydrol resin, succinimidyl carbonate resin, p-nitrophenyl carbonate resin, imidazole carbonate resin, polyacrylamide resin, 4-sulfamylbenzoyl-4'-methylbenzhydrylamine-resin (Safety-catch resin), 2-amino-2-(2'-nitrophenyl) propionic acid-aminomethyl resin (ANP Resin), p-benzyloxybenzyl alcohol-divinylbenzene resin (Wang resin), p-methylbenzhydrylamine-divinylbenzene resin (MBHA resin), Fmoc-2,4-dimethoxy-4'-(carboxymethyloxy)-benzhydrylamine linked to resin (Knorr resin), 4-(2',4'-Dimethoxyphenyl-Fmoc-aminomethyl)-phenoxy resin (Rink resin), 4-hydroxymethyl-benzoyl-4'-methylbenzhydrylamine resin (HMBA-MBHA Resin), p-nitrobenzophenone oxime resin (Kaiser oxime resin), and amino-2,4-dimethoxy-4'-(carboxymethyloxy)-benzhydrylamine handle linked to 2-chlorotrityl resin (Knorr-2-chlorotrityl resin). In one embodiment, the material used to form the polymeric resin is compatible with the solvent in which the analyte is dissolved. For example, polystyrene-divinyl benzene resin will swell within non-polar solvents, but does not significantly swell within polar solvents. Thus, polystyrene-divinyl benzene resin may be used for the analysis of analytes within non-polar solvents. Alternatively, polystyrene-polyethylene glycol resin will swell with polar solvents such as water. Polystyrene-polyethylene glycol resin may be useful for the analysis of aqueous fluids.

Figure 5:
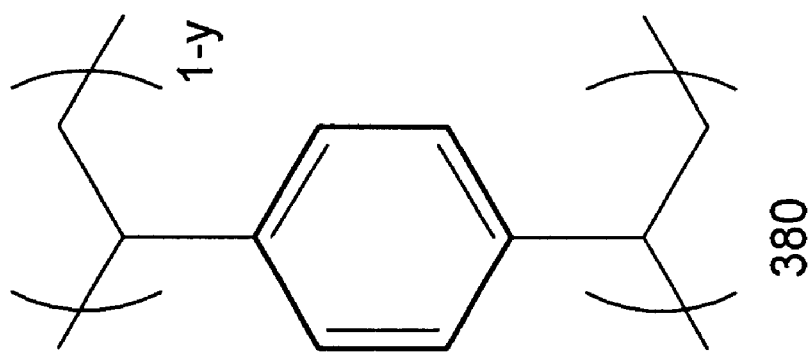
FIG. 5 depicts the chemical constituents of a particle.
Figure 5:
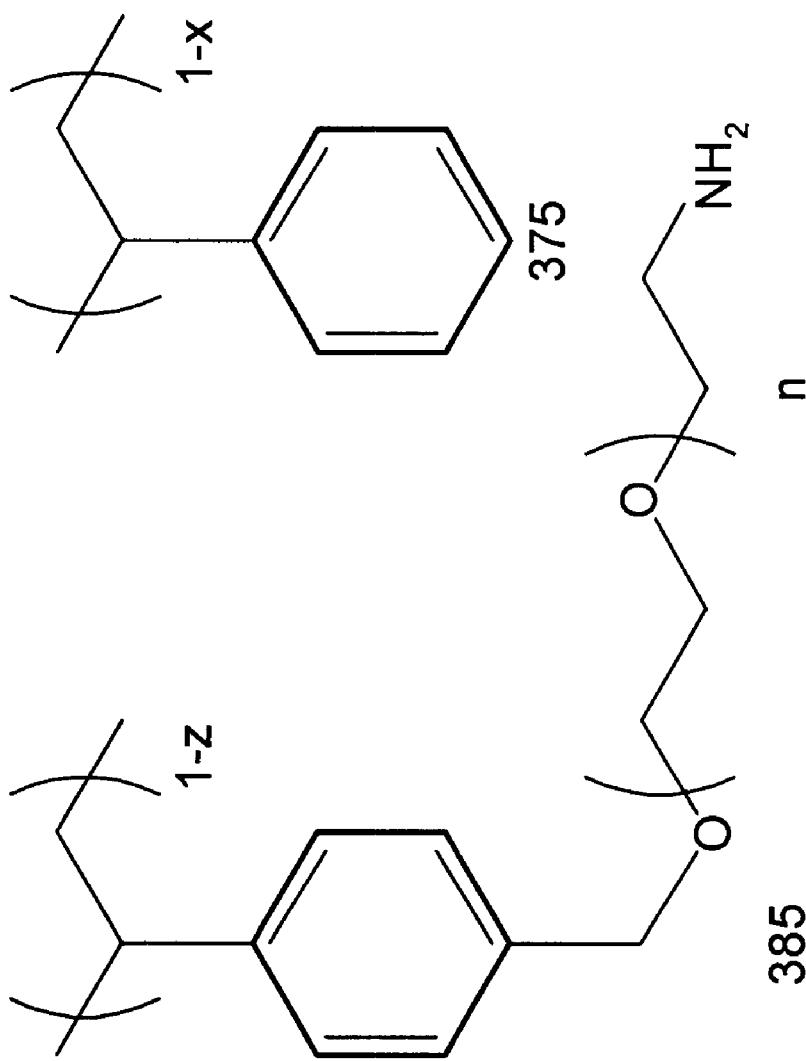

In one embodiment, a polystyrene-polyethylene glycol-divinyl benzene material is used to form the polymeric resin. The polystyrene-polyethylene glycol-divinyl benzene resin is formed from a mixture of polystyrene 375, divinyl benzene 380 and polystyrene-polyethylene glycol 385, see FIG. 5. The polyethylene glycol portion of the polystyrene-polyethylene glycol 385, in one embodiment, may be terminated with an amine. The amine serves as a chemical handle to anchor both receptors and indicator dyes. Other chemical functional groups may be positioned at the terminal end of the polyethylene glycol to allow appropriate coupling of the polymeric resin to the receptor molecules or indicators.

The chemically sensitive particle, in one embodiment, is capable of both binding the analyte(s) of interest and creating a detectable signal. In one embodiment, the particle will create an optical signal when bound to an analyte of interest. The use of such a polymeric bound receptors offers advantages both in terms of cost and configurability. Instead of having to synthesize or attach a receptor directly to a supporting member, the polymeric bound receptors may be synthesized en masse and distributed to multiple different supporting members. This allows the cost of the sensor array, a major hurdle to the development of mass-produced environmental probes and medical diagnostics, to be reduced. Additionally, sensor arrays which incorporate polymeric bound receptors may be reconfigured much more quickly than array systems in which the receptor is attached directly tot he supporting member. For example, if a new variant of a pathogen or a pathogen that contains a genetically engineered protein is a threat, then a new sensor array system may be readily created to detect these modified analytes by simply adding new sensor elements (e.g., polymeric bound receptors) to a previously formed supporting member.

Figure 6:
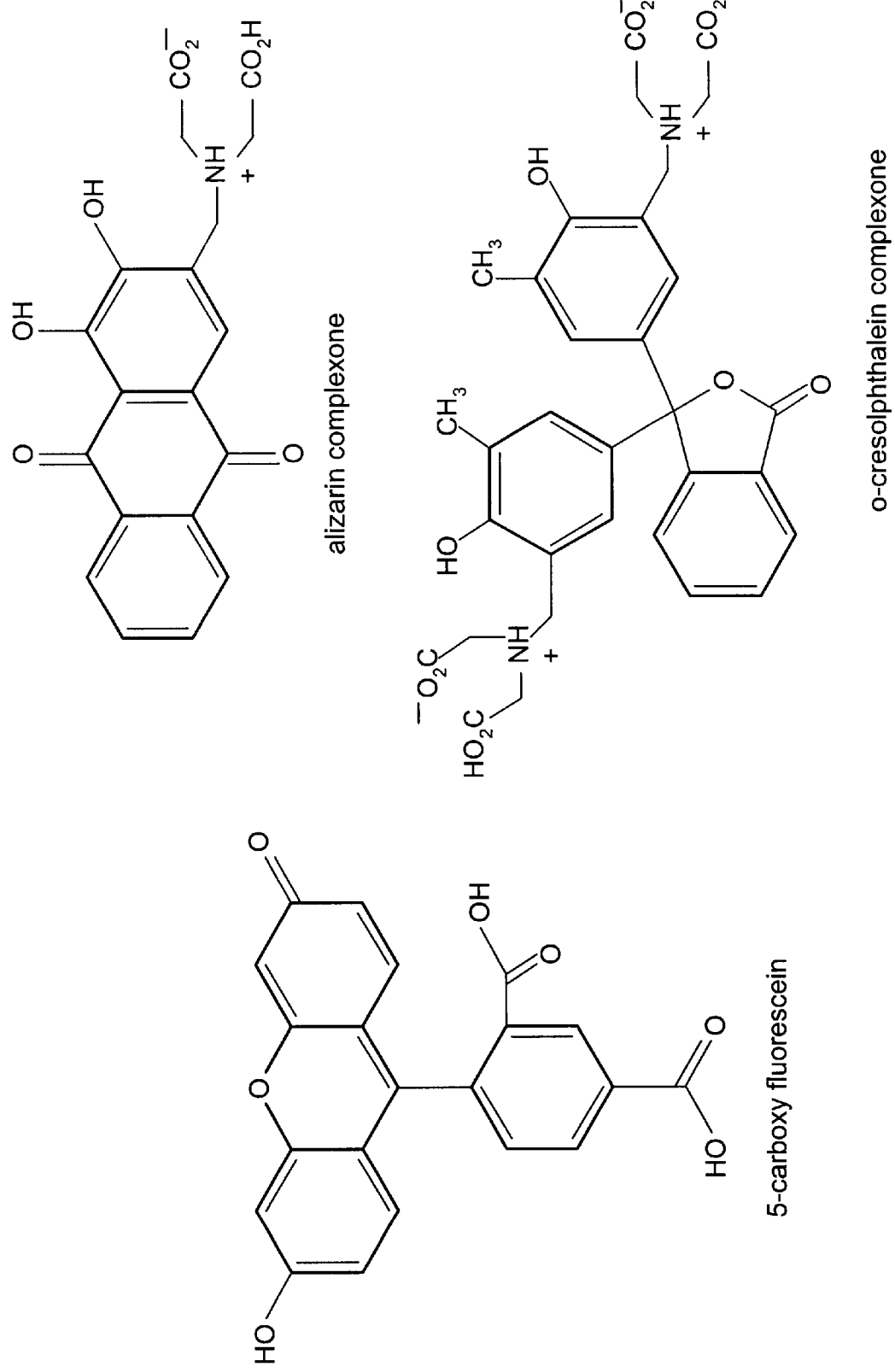
FIG. 6 depicts the chemical formulas of some receptor compounds.

In one embodiment, a receptor, which is sensitive to changes in the pH of a fluid sample is bound to a polymeric resin to create a particle. That is, the receptor is sensitive to the concentration of hydrogen cations, ($H^+$). The receptor in this case is typically sensitive to the concentration of $H^+$ in a fluid solution. The analyte of interest may therefore be $H^+$. There are many types of molecules which undergo a color change when the pH of the fluid is changed. For example, many types of dyes undergo significant color changes as the pH of the fluid medium is altered. Examples of receptors which may be used to monitor the pH of a fluid sample include 5-carboxyfluorescein and alizarin complexone, depicted in FIG. 6. Each of these receptors undergoes significant color changes as the pH of the fluid is altered. 5-carboxyfluorescein undergoes a change from yellow to orange as the pH of the fluid is increased. Alizarin complexone undergoes two color changes, first from yellow to red, then from red to blue as the pH of the fluid increases. By monitoring the change in color caused by dyes attached to a polymeric particle, the pH of a solution may be qualitatively and, with the use of a detector (e.g., a CCD detector), quantitatively monitored.

In another embodiment, a receptor which is sensitive to presence of metal cations is bound to a polymeric particle to create a particle. The receptor in this case is typically sensitive to the concentration of one or more metal cations present in a fluid solution. In general, colored molecules which will bind cations may be used to determine the presence of a metal cation in a fluid solution. Examples of receptors which may be used to monitor the presence of cations in a fluid sample include alizarin complexone and o-cresolphthalein complexone, see FIG. 6. Each of these receptors undergoes significant color changes as the concentration of a specific metal ion in the fluid is altered. Alizarin complexone is particularly sensitive to lanthanum ions. In the absence of lanthanum, alizarin complexone will exhibit a yellow color. As the concentration of lanthanum is increased, alizarin complexone will change to a red color. o-Cresolphthalein complexone is particularly sensitive to calcium ions. In the absence of calcium, o-cresolphthalein complexone is colorless. As the concentration of calcium is increased, o-cresolphthalein complexone will change to a blue color. By monitoring the change in color of metal cation sensitive receptors attached to a polymeric particle, the presence of a specific metal ion may be qualitatively and, with the use of a detector (e.g., a CCD detector), quantitatively monitored.

Figure 7:
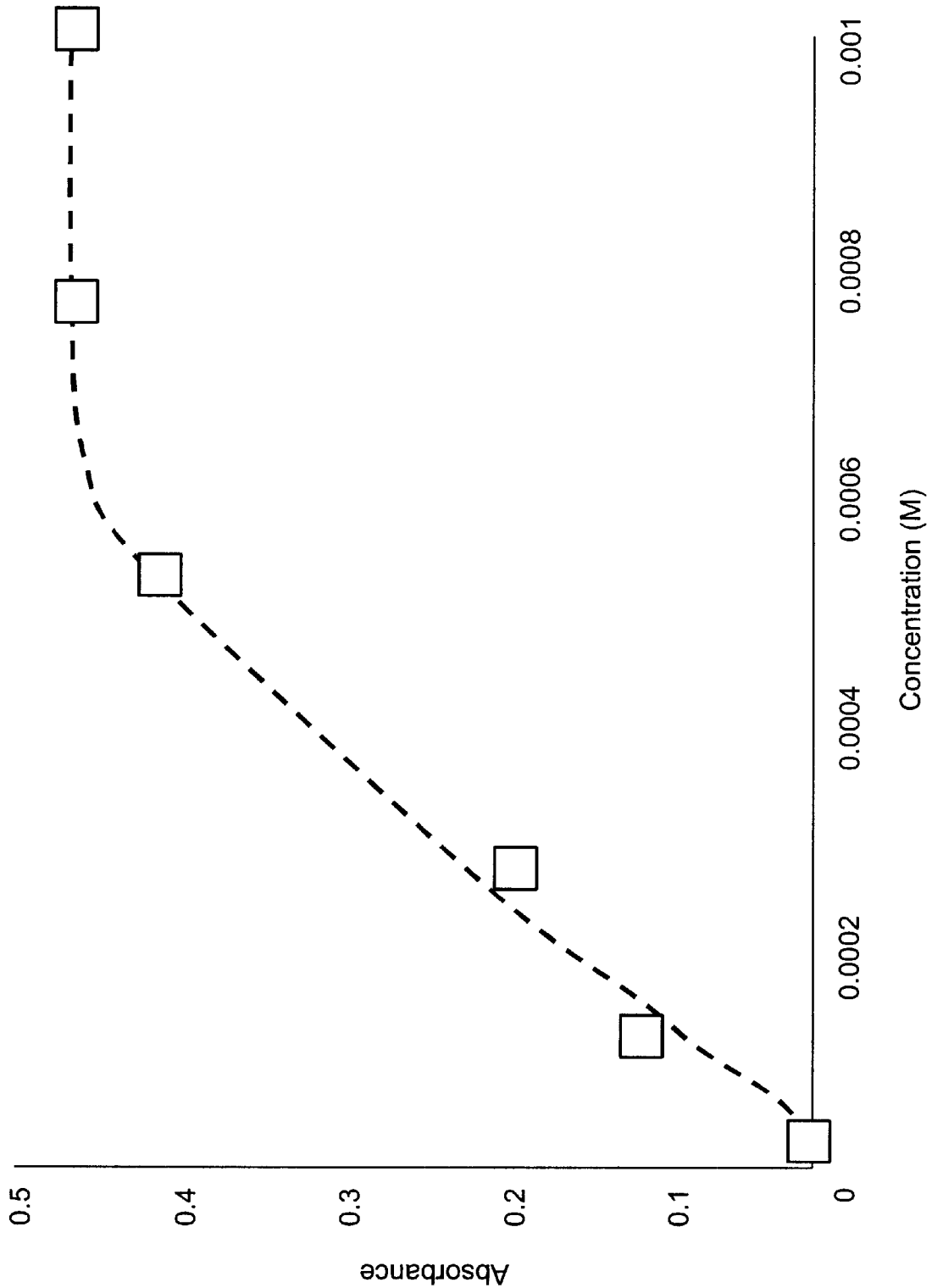
FIG. 7 depicts a plot of the absorbance of green light vs. concentration of calcium ($Ca^{+2}$) for a particle which includes an o-cresolphthalein complexone receptor.

Referring to FIG. 7, a graph of the absorbance of green light vs. concentration of calcium ($Ca^{+2}$) is depicted for a particle which includes an o-cresolphthalein complexone receptor. As the concentration of calcium is increased, the absorbance of green light increases in a linear manner up to a concentration of about 0.0006 M. A concentration of 0.0006 M is the solubility limit of calcium in the fluid, thus no significant change in absorbance is noted after this point. The linear relationship between concentration and absorbance allows the concentration of calcium to be determined by measuring the absorbance of the fluid sample.

In one embodiment, a detectable signal may be caused by the altering of the physical properties of an indicator ligand bound to the receptor or the polymeric resin. In one embodiment, two different indicators are attached to a receptor or the polymeric resin. When an analyte is captured by the receptor, the physical distance between the two indicators may be altered such that a change in the spectroscopic properties of the indicators is produced. A variety of fluorescent and phosphorescent indicators may be used for this sensing scheme. This process, known as Forster energy transfer, is extremely sensitive to small changes in the distance between the indicator molecules.

Figure 8:
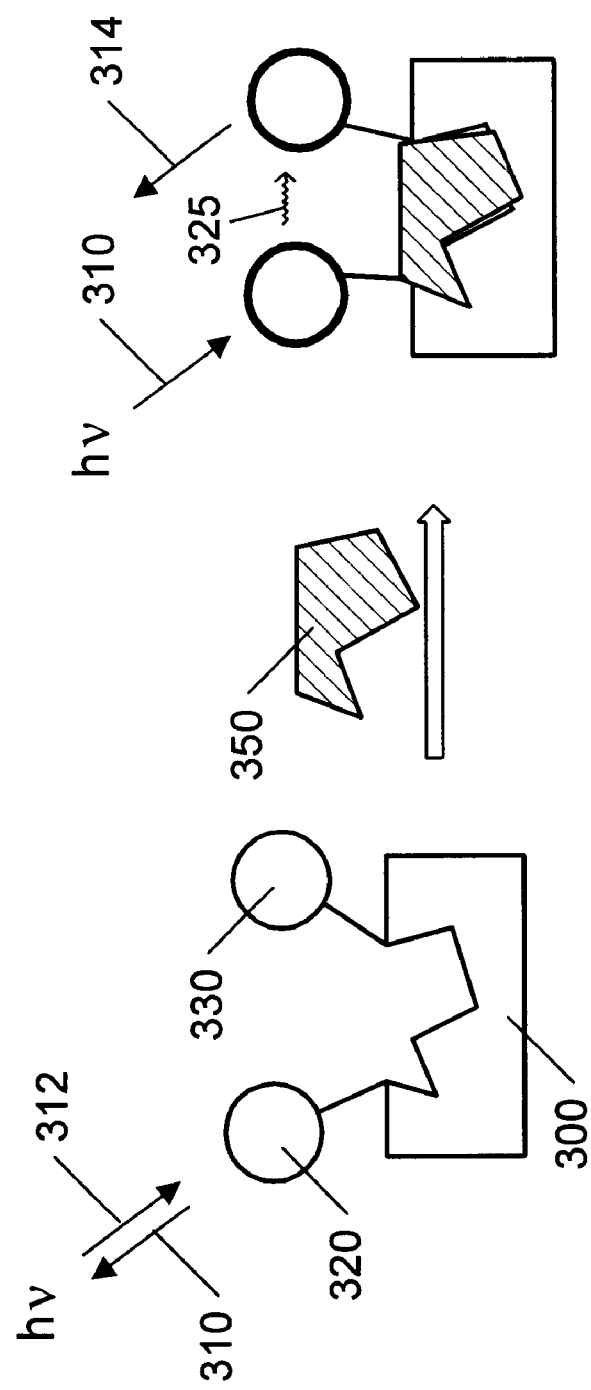
FIG. 8 depicts a schematic view of the transfer of energy from a first indicator to a second indicator in the presence of an analyte.

For example, a first fluorescent indicator 320 (e.g., a fluorescein derivative) and a second fluorescent indictor 330 (e.g., a rhodamine derivative) may be attached to a receptor 300, as depicted in FIG. 8. When no analyte is present short wavelength excitation 310 may excite the first fluorescent indicator 320, which fluoresces as indicated by 312. The short wavelength excitation, however, may cause little or no fluorescence of the second fluorescent indicator 330. After binding of analyte 350 to the receptor, a structural change in the receptor molecule may bring the first and second fluorescent indicators closer to each other. This change in intermolecular distance may allow the excited first indicator 320 to transfer a portion of its fluorescent energy 325 to the second fluorescent indicator 330. This transfer in energy may be measured by either a drop in energy of the fluorescence of the first indicator molecule 320, or the detection of increased fluorescence 314 by the second indicator molecule 330.

Alternatively, the first and second fluorescent indicators may initially be positioned such that short wavelength excitation, may cause fluorescence of both the first and second fluorescent indicators, as described above. After binding of analyte 350 to the receptor, a structural change in the receptor molecule may cause the first and second fluorescent indicators to move further apart. This change in intermolecular distance may inhibit the transfer of fluorescent energy from the first indicator 320 to the second fluorescent indicator 330. This change in the transfer of energy may be measured by either a drop in energy of the fluorescence of the second indicator molecule 330, or the detection of increased fluorescence by the first indicator molecule 320.

In another embodiment, an indicator ligand may be preloaded onto the receptor. An analyte may then displace the indicator ligand to produce a change in the spectroscopic properties of the particles. In this case, the initial background absorbance is relatively large and decreases when the analyte is present. The indicator ligand, in one embodiment, has a variety of spectroscopic properties which may be measured. These spectroscopic properties include, but are not limited to, ultraviolet absorption, visible absorption, infrared absorption, fluorescence, and magnetic resonance. In one embodiment, the indicator is a dye having either a strong fluorescence, a strong ultraviolet absorption, a strong visible absorption, or a combination of these physical properties. Examples of indicators include, but are not limited to, carboxyfluorescein, ethidium bromide, 7-dimethylamino-4-methylcoumarin, 7-diethylamino-4-methylcoumarin, eosin, erythrosin, fluorescein, Oregon Green 488, pyrene, Rhodamine Red, tetramethylrhodamine, Texas Red, Methyl Violet, Crystal Violet, Ethyl Violet, Malachite green, Methyl Green, Alizarin Red S, Methyl Red, Neutral Red, o-cresolsulfonephthalein, o-cresolphthalein, phenolphthalein, Acridine Orange, B-naphthol, coumarin, and α-naphthionic acid. When the indicator is mixed with the receptor, the receptor and indicator interact with each other such that the above mentioned spectroscopic properties of the indicator, as well as other spectroscopic properties may be altered. The nature of this interaction may be a binding interaction, wherein the indicator and receptor are attracted to each other with a sufficient force to allow the newly formed receptor-indicator complex to function as a single unit. The binding of the indicator and receptor to each other may take the form of a covalent bond, an ionic bond, a hydrogen bond, a van der Waals interaction, or a combination of these bonds.

The indicator may be chosen such that the binding strength of the indicator to the receptor is less than the binding strength of the analyte to the receptor. Thus, in the presence of an analyte, the binding of the indicator with the receptor may be disrupted, releasing the indicator from the receptor. When released, the physical properties of the indicator may be altered from those it exhibited when bound to the receptor. The indicator may revert back to its original structure, thus regaining its original physical properties. For example, if a fluorescent indicator is attached to a particle that includes a receptor, the fluorescence of the particle may be strong before treatment with an analyte containing fluid. When the analyte interacts with the particle, the fluorescent indicator may be released. Release of the indicator may cause a decrease in the fluorescence of the particle, since the particle now has less indicator molecules associated with it.

Figure 9:
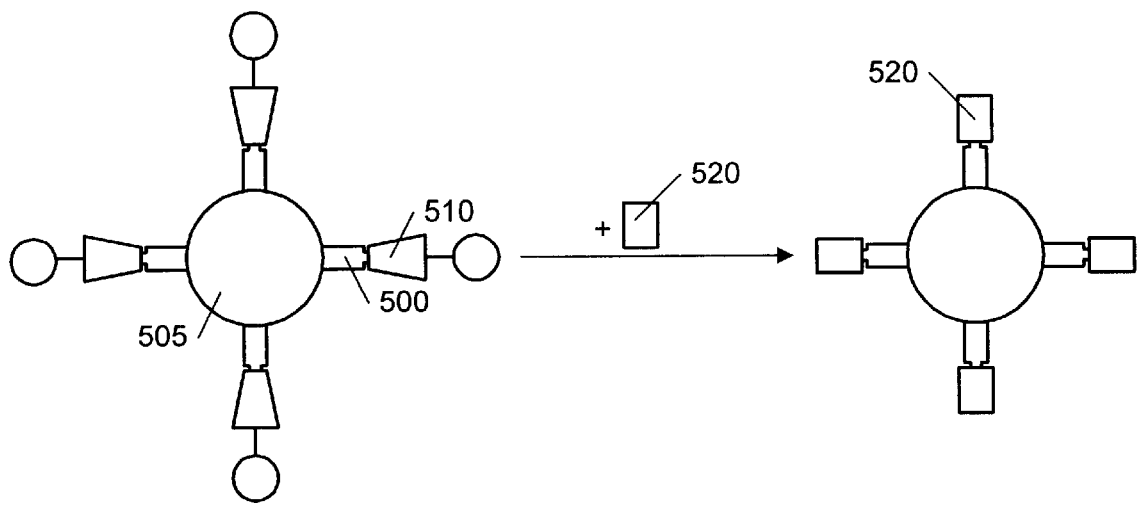
FIG. 9 depicts a schematic of the interaction of a sugar molecule with a boronic acid based receptor.
Figure 9:
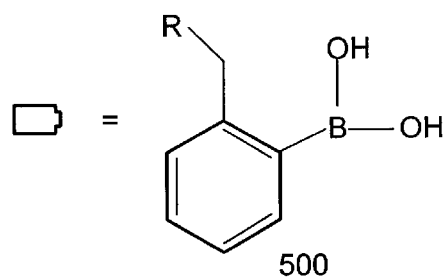
Figure 9:
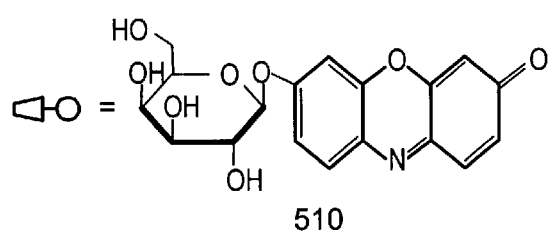
Figure 9:
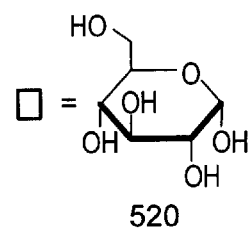

An example of this type of system is illustrated by the use of a boronic acid substituted resin 505 as a particle. Prior to testing, the boronic acid substituted resin 505 is treated with a sugar 510 which is tagged with an indicator (e.g., resorufin) as depicted in FIG. 9. The sugar 510 binds to the boronic acid receptor 500 imparting a color change to the boronic substituted resin 505 (yellow for the resorufin tagged sugar). When the boronic acid resin 505 is treated with a fluid sample which includes a sugar 520, the tagged sugar 510 may be displaced, causing a decrease in the amount of color produced by the boronic acid substituted resin 505. This decrease may be qualitatively or, with the use of a detector (e.g., a CCD detector), quantitatively monitored.

In another embodiment, a designed synthetic receptor may be used. In one embodiment, a polycarboxylic acid receptor may be attached to a polymeric resin. The polycarboxylic receptors are discussed in U.S. patent application Ser. No. 08/950,712 which is incorporated herein by reference.

In an embodiment, the analyte molecules in the fluid may be pretreated with an indicator ligand. Pretreatment may involve covalent attachment of an indicator ligand to the analyte molecule. After the indicator has been attached to the analyte, the fluid may be passed over the sensing particles. Interaction of the receptors on the sensing particles with the analytes may remove the analytes from the solution. Since the analytes include an indicator, the spectroscopic properties of the indicator may be passed onto the particle. By analyzing the physical properties of the sensing particles after passage of an analyte stream, the presence and concentration of an analyte may be determined.

For example, the analytes within a fluid may be derivatized with a fluorescent tag before introducing the stream to the particles. As analyte molecules are adsorbed by the particles, the fluorescence of the particles may increase. The presence of a fluorescent signal may be used to determine the presence of a specific analyte. Additionally, the strength of the fluorescence may be used to determine the amount of analyte within the stream.

RECEPTORS

Figure 10:
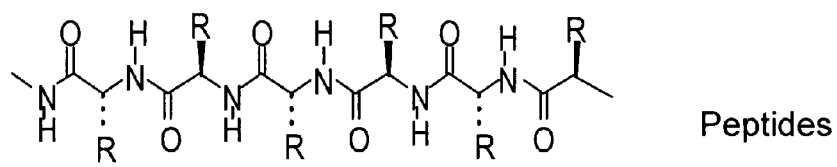
FIG. 10 depicts various synthetic receptors.
Figure 10:
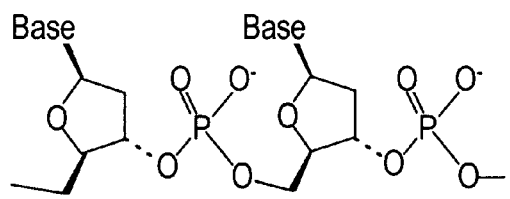
Figure 10:
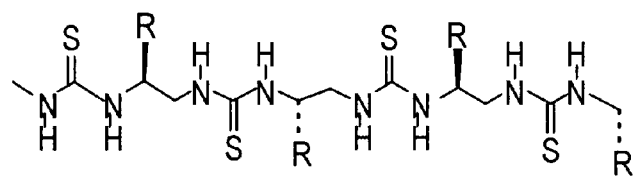
Figure 10:
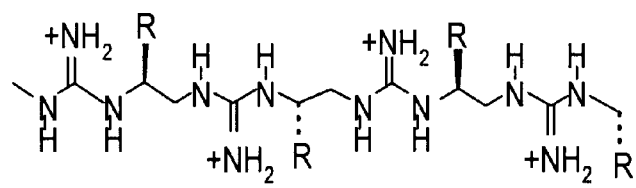

A variety of natural and synthetic receptors may be used. The synthetic receptors may come from a variety of classes including, but not limited to, polynucleotides (e.g., aptamers), peptides (e.g., enzymes and antibodies), synthetic receptors, polymeric unnatural biopolymers (e.g., polythioureas, polyguanidiniums), and imprinted polymers., some of which are generally depicted in FIG. 10. Natural based synthetic receptors include receptors which are structurally similar to naturally occurring molecules. Polynucleotides are relatively small fragments of DNA which may be derived by sequentially building the DNA sequence. Peptides may be synthesized from amino acids. Unnatural biopolymers are chemical structure which are based on natural biopolymers, but which are built from unnatural linking units. Unnatural biopolymers such as polythioureas and polyguanidiniums may be synthesized from diamines (i.e., compounds which include at least two amine functional groups). These molecules are structurally similar to naturally occurring receptors, (e.g., peptides). Some diamines may, in turn, be synthesized from amino acids. The use of amino acids as the building blocks for these compounds allow a wide variety of molecular recognition units to be devised. For example, the twenty natural amino acids have side chains that possess hydrophobic residues, cationic and anionic residues, as well as hydrogen bonding groups. These side chains may provide a good chemical match to bind a large number of targets, from small molecules to large oligosaccharides. Amino acid based peptides, polythioureas, and polyguanidiniums are depicted in FIG. 10.

Figure 11:
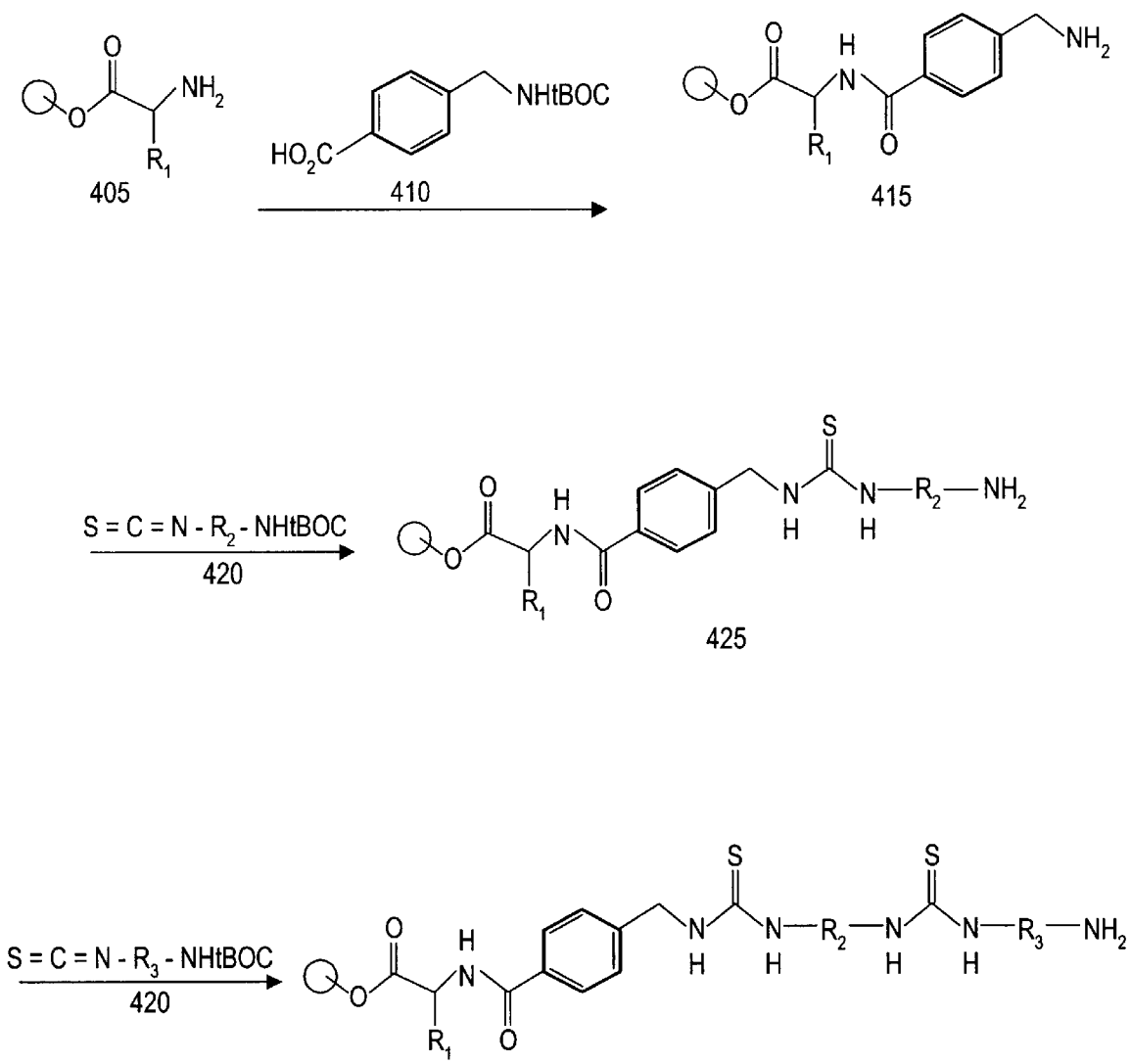
FIG. 11 depicts a synthetic pathway for the synthesis of polythioureas.

Techniques for the building of DNA fragments and polypeptide fragments on a polymer particle are well known. Techniques for the immobilization of naturally occurring antibodies and enzymes on a polymeric resin are also well known. The synthesis of polythioureas upon a resin particle may be accomplished by the synthetic pathway depicted in FIG. 11. The procedure may begin by deprotection of the terminal tBoc protecting group on an amino acid coupled to a polymeric particle. Removal of the protecting group is followed by coupling of the rigid spacer 410 to the resulting amine 405 using diisopropylcarbodiimide (DIC) and 1-hydroxybenzotriazole hydrate (HOBT). The spacer group may inhibit formation of a thiazolone by reaction of the first amino acids with subsequently formed thioureas. After the spacer group is coupled to the amino acid, another tBoc deprotection is performed to remove the spacer protecting group, giving the amine 415. At this point, monomer may be added incrementally to the growing chain, each time followed by a tBoc deprotection. The addition of a derivative of the diamine 420 (e.g., an isothiocyanate) to amine 415 gives the mono-thiourea 425. The addition of a second thiourea substituent is also depicted. After the addition of the desired number of monomers, a solution of benzylisothiocyanate or acetic anhydride may be added to cap any remaining amines on the growing oligomers. Between 1 to 20 thioureas groups may be formed to produce a synthetic polythiourea receptor.

Figure 12:
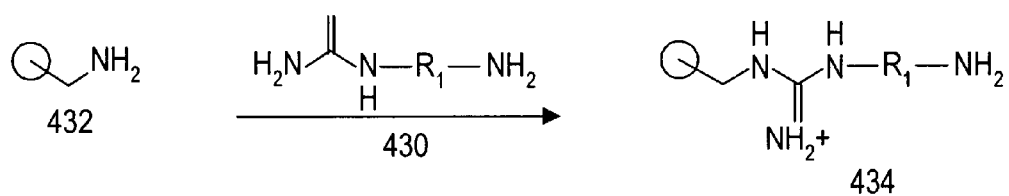
FIG. 12 depicts a synthetic pathway for the synthesis of polyguanidiniums.
Figure 12:
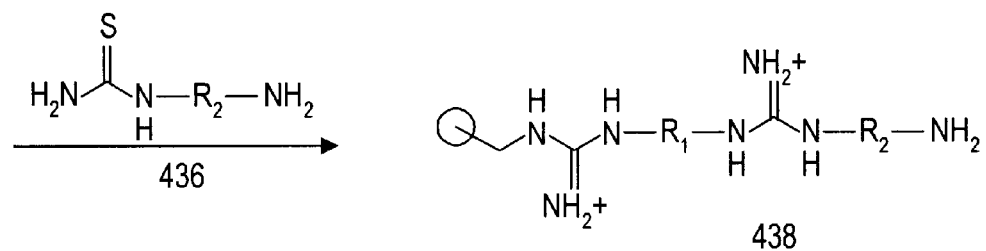
Figure 12:
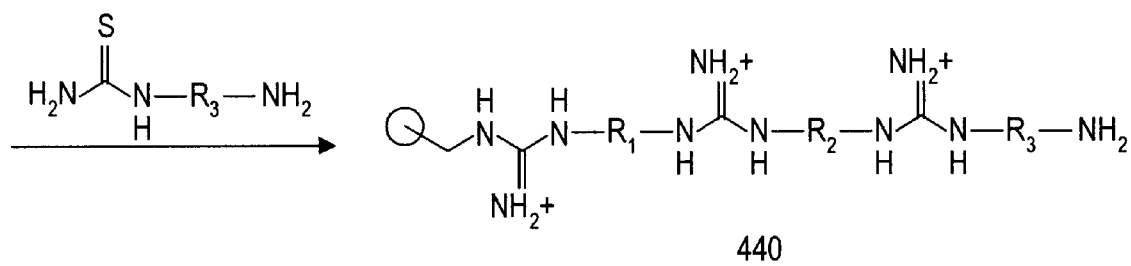

The synthesis of polyguanidiniums may be accomplished as depicted in FIG. 12. In order to incorporate these guanidinium groups into the receptor, the coupling of a thiourea with a terminal amine in the presence of Mukaiyama's reagent may be utilized. The coupling of the first thiourea diamine 430 with an amino group of a polymeric particle gives the mono-guanidinium 434. Coupling of the resulting mono-guanidinium with a second thiourea diamine 436 gives a di-guanidinium 438. Further coupling may create a tri-guanidinium 440. Between 1 to 20 guanidinium groups may be formed to produce a synthetic polyguanidinium receptor.

Figure 13:
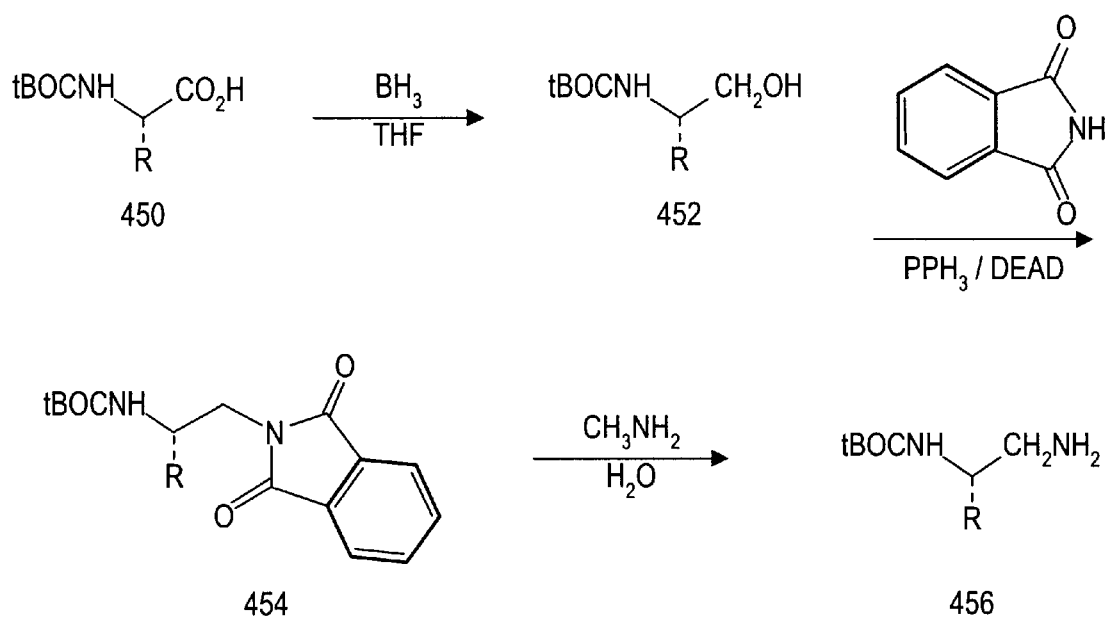
FIG. 13 depicts a synthetic pathway for the synthesis of diamines from amino acids.

The above described methods for making polythioureas and polyguanidiniums are based on the incorporation of diamines (i.e., molecules which include at least two amine functional groups) into the oligomenrc receptor. The method may be general for any compound having at least two amino groups. In one embodiment, the diamine may be derived from amino acids. A method for forming diamines from amino acids is shown in FIG. 13. Treatment of a protected amino acid 450 with borane-THF reduces the carboxylic acid portion of the amino acid to the primary alcohol 452. The primary alcohol is treated with phthalimide under Mitsunobu conditions ($PPh_3$/DEAD). The resulting compound 454 is treated with aqueous methylamine to form the desired monoprotected diamine 456. The process may be accomplished such that the enantiomeric purity of the starting amino acid is maintained. Any natural or synthetic amino acid may be used in the above described method.

The three coupling strategies used to form the respective functional groups may be completely compatible with each other. The capability to mix linking groups (amides, thioureas, and guanidiniums) as well as the side chains (hydrophobic, cationic, anionic, and hydrogen bonding) may allow the creation of a diversity in the oligomers that is beyond the diversity of receptors typically found with natural biological receptors. Thus, we may produce ultrasensitive and ultra-selective receptors which exhibit interactions for specific toxins, bacteria, and environmental chemicals. Additionally, these synthetic schemes may be used to build combinatorial libraries of particles for use in the sensor array.

In an embodiment, the indicator ligand may be incorporated into synthetic receptors during the synthesis of the receptors. The ligand may be incorporated into a monomeric unit, such as a diamine, that is used during the synthesis of the receptor. In this manner, the indicator may be covalently attached to the receptor in a controlled position. By placing the indicator within the receptor during the synthesis of the receptor, the positioning of the indicator ligand within the receptor may be controlled. This control may be difficult to achieve after synthesis of the receptor is completed.

Figure 14:
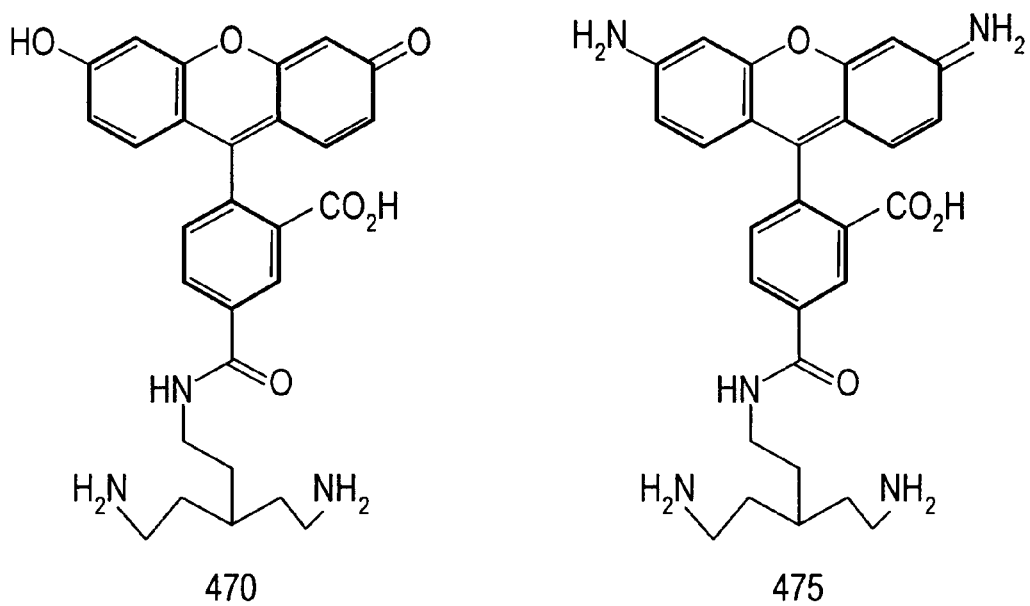
FIG. 14 depicts fluorescent diamino monomers.

In one embodiment, a fluorescent group may be incorporated into a diamine monomer for use in the synthetic sequences. Examples of monomeric units which may be used for the synthesis of a receptor are depicted in FIG. 14. The depicted monomers include fluorescent indicator groups. After synthesis, the interaction of the receptor with the analyte may induce changes in the spectroscopic properties of the molecule. Typically, hydrogen bonding or ionic substituents on the fluorescent monomer involved in analyte binding have the capacity to change the electron density and/or rigidity of the fluorescent ring system, thereby causing observable changes in the spectroscopic properties of the indicator. For fluorescent indicators such changes may be exhibited as changes in the fluorescence quantum yield, maximum excitation wavelength, and/or maximum emission wavelength. This approach does not require the dissociation of a preloaded fluorescent ligand, which may be limited in response time by $k_{(off)}$. While fluorescent ligands are shown here, it is to be understood that a variety of other ligand may be used including colorimetric ligands.

In another embodiment, two fluorescent monomers for signaling may be used for the synthesis of the receptor. For example, compound 470 (a derivative of fluorescein) and compound 475 (a derivative of rhodamine), depicted in FIG. 14, may both be incorporated into a synthetic receptor. Compound 470 contains a common colorimetric/fluorescent probe that will, in some embodiments, send out a modulated signal upon analyte binding. The modulation may be due to resonance energy transfer to compound 475. When an analyte binds to the receptor, structural changes in the receptor may alter the distance between monomeric units 470 and 475. It is well known that excitation of fluorescein can result in emission from rhodamine when these molecules are oriented correctly. The efficiency of resonance energy transfer from monomers 470 to 475 will depend strongly upon the presence of analyte binding; thus, measurement of rhodamine fluorescence intensity (at a substantially longer wavelength than fluorescein fluorescence) may serve as an indicator of analyte binding. To greatly improve the likelihood of a modulatory fluorescein-rhodamine interaction, multiple rhodamine tags may be attached at different sites along a receptor molecule without substantially increasing background rhodamine fluorescence (only rhodamine very close to fluorescein will yield appreciable signal). This methodology may be applied to a number of alternate fluorescent pairs.

In an embodiment, a large number of chemical/biological agents of interest to the military and civilian communities may be sensed readily by the described array sensors including both small and medium size molecules. For example, it is known that nerve gases typically produce phosphate structures upon hydrolysis in water. The presence of molecules which contain phosphate functional groups may be detected using polyguanidiniums. Nerve gases which have contaminated water sources may be detected by the use of the polyguanidinium receptors described above.

In order to identify, sense, and quantitate the presence of various bacteria using the proposed micro-machined sensor, two strategies may be used. First, small molecule recognition and detection may be exploited. Since each bacteria possesses a unique and distinctive concentration of the various cellular molecules, such as DNA, proteins, metabolites, and sugars, the fingerprint (i.e., the concentration and types of DNA, proteins, metabolites, and sugars) of each organism is expected to be unique. Hence, the analytes obtained from whole bacteria or broken down bacteria may be used to determine the presence of specific bacteria. A series of receptors specific for DNA molecules, proteins, metabolites, and sugars may be incorporated into an array. A solution containing bacteria, or more preferably broken down bacteria, may be passed over the array of particles. The individual cellular components of the bacteria may interact in a different manner with each of the particles. This interaction will provide a pattern within the array which may be unique for the individual bacteria. In this manner, the presence of bacteria within a fluid may be determined.

In another embodiment, bacteria may be detected as whole entities, as found in ground water, aerosols, or blood. To detect, sense, and identify intact bacteria, the cell surface of one bacteria may be differentiated from other bacteria. One method of accomplishing this differentiation is to target cell surface oligosaccharides (i.e. sugar residues). Each bacterial class (gram negative, gram positive, etc.) displays a different oligosaccharide on their cell, surfaces. The oligosaccharide, which is the code that is read by other cells giving an identification of the cell, is part of the cell-cell recognition and communication process. The use of synthetic receptors which are specific for oligosaccharides may be used to determine the presence of specific bacteria by analyzing for the cell surface oligosaccharides.

In another embodiment, the sensor array may be used to optimize which receptor molecules should be used for a specific analyte. An array of receptors may be placed within the cavities of the supporting member and a stream containing an analyte may be passed over the array. The reaction of each portion of the sensing array to the known analyte may be analyzed and the optimal receptor determined by determining which particle, and therefore which receptor, exhibits the strongest reaction toward the analyte. In this manner, a large number of potential receptors may be rapidly scanned. The optimal receptor may then be incorporated into a system used for the detection of the specific analyte in a mixture of analytes.

It should be emphasized that although some particles may be purposefully designed to bind to important species (biological agents, toxins, nerve gasses, etc.), most structures will possess nonspecific receptor groups. One of the advantages associated with the proposed sensor array is the capacity to standardize each array of particles via exposure to various analytes, followed by storage of the patterns which arise from interaction of the analytes with the particles. Therefore, there may not be a need to know the identity of the actual receptor on each particle. Only the characteristic pattern for each array of particles is important. In fact, for many applications it may be less time consuming to place the various particles into their respective holders without taking precautions to characterize the location associated with the specific particles. When used in this manner, each individual sensor array may require standardization for the type of analyte to be studied.

On-site calibration for new or unknown toxins may also be possible with this type of array. Upon complexation of an analyte, the local microenvironment of each indicator may change, resulting in a modulation of the light absorption and/or emission properties. The use of standard pattern recognition algorithms completed on a computer platform may serves as the intelligence factor for the analysis. The "fingerprint" like response evoked from the simultaneous interactions occurring at multiple sites within the substrate may be used to identify the species present in unknown samples.

The above described sensor array system offers a number of distinct advantages over exiting technologies. One advantage is that "real time" detection of analytes may be performed. Another advantage is that the simultaneous detection of multiple analytes may be realized. Yet another advantage is that the sensor array system allows the use of synthetic reagents as well as biologically produced reagents. Synthetic reagents typically have superior sensitivity and specificity toward analytes when compared to the biological reagents. Yet another advantage is that the sensor array system may be readily modified by simply changing the particles which are placed within the sensor array. This interchangability may also reduce production costs.

EXAMPLES

1. The Determination of pH Using a Chemically Sensitive Particle

Figure 15:
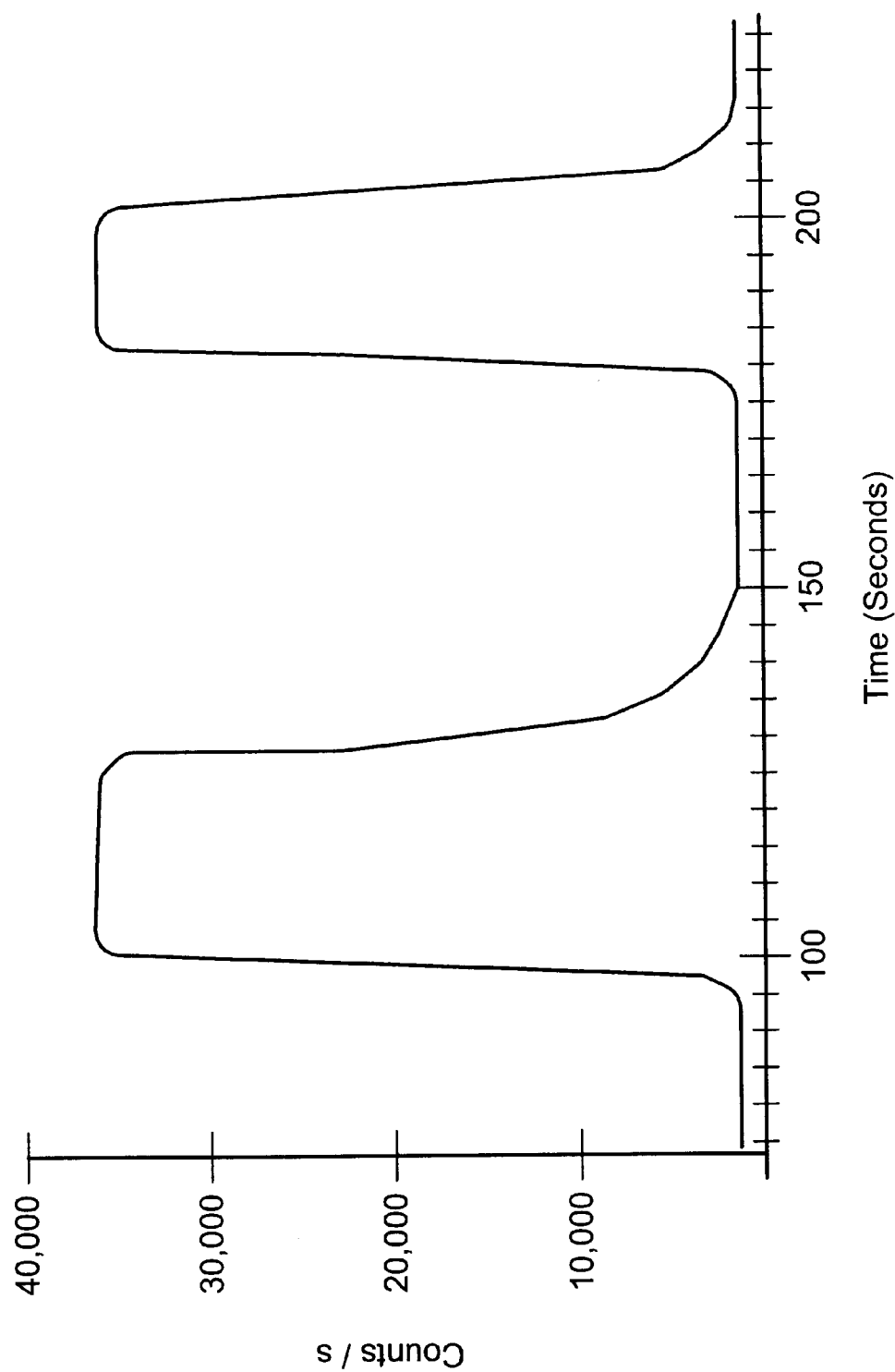
FIG. 15 depicts a plot of counts/sec. (i.e., intensity) vs. time as the pH of a solution surrounding a particle coupled to o-cresolphthalein is cycled from acidic to basic conditions.

Shown in FIG. 15 is the magnitude of the optical signal transmitted through a single polymer particle derivatized with o-cresolphthalein. Here, a filter is used to focus the analysis on those wavelengths which the dye absorbs most strongly (i.e., about 550 nm). Data is provided for the particle as the pH is cycled between acid and basic environments. In acidic media (i.e., at times of 100–150 seconds and 180–210 seconds), the particle is clear and the system yields large signals (up to greater than 300,000 counts) at the optical detector. Between times of 0–100 and 150–180 seconds, the solution was made basic. Upon raising the pH (i.e., making the solution more basic), the particle turns purple in color and the transmitted green light is greatly diminished. Large signal reductions are recorded under such circumstances. The evolution of the signal changes show that the response time is quite rapid, on the order of 10 seconds. Furthermore, the behavior is highly reproducible.

2. The Simultaneous Detection of $Ca^{+2}$, $Ce^{+3}$, and pH by a Sensor Array System The synthesis of four different particles was accomplished by coupling a variety of indictor ligands to a polyethylene glycol-polystyrene ("PEG-PS") resin particle. The PEG-PS resin particles were obtained from Novabiochem Corp., La Jolla, Calif. The particles have an average diameter of about 130 $\mu$m when dry and about 250 $\mu$m when wet. The indicator ligands of fluorescein, o-cresolphthalein complexone, and alizarin complexone were each attached to PEG-PS resin particles using a dicyclohexylcarbodiimide (DCC) coupling between a terminal resin bound amine and a carboxylic acid on the indicator ligand.

These synthetic receptors, localized on the PEG-PS resin to create sensing particles, were positioned within micromachined wells formed in silicon/silicon nitride wafers, thus confining the particles to individually addressable positions on a multicomponent chip. These wells were sized to hold the particles in both swollen and unswollen states. Rapid introduction of the test fluids can be accomplished using these structures while allowing spectrophotometric assays to probe for the presence of analytes. For the identification and quantification of analyte species, changes in the light absorption and light emission properties of the immobilized resin particles can be exploited, although only identification based upon absorption properties are discussed here. Upon exposure to analytes, color changes for the particles were found to be 90% complete within one minute of exposure, although typically only seconds were required. To make the analysis of the calorimetric changes efficient, rapid, and sensitive, a charge-coupled-device (CCD) was directly interfaced with the sensor array. Thus, data streams composed of red, green, and blue (RGB) light intensities were acquired and processed for each of the individual particle elements. The red, blue, and green responses of the particles to various solutions are graphically depicted in FIG. 16.

The true power of the described bead sensor array occurs when simultaneous evaluation of multiple chemically distinct bead structures is completed. A demonstration of the capacity of five different beads is provided in FIG. 16. In this case, blank, alizarin, o-cresolphthalein, fluorescein, and alizarin-Ce3+ complex derivatized beads serve as a matrix for subtle differentiation of chemical environments. The blank bead is simply a polystyrene sphere with no chemical derivatization. The bead derivatized with o-cresolphthalein responds to Ca+2 at pHs values around 10.0. The binding of calcium is noted from the large green color attenuation noted for this dye while exposed to the cation. Similarly, the fluorescein derivatized bead acts as a pH sensor. At pHs below 7.4 it is light yellow, but at higher pHs it turns dark orange. Interesting, the alizarin complexone plays three distinct roles. First, it acts as a proton sensor yielding a yellow color at pHs below 4.5, orange is noted at pHs between 4.5 and 11.5, and at pHs above 11.5 a blue hue is observed. Second, it functions as a sensor for lanthanum ions at lower pHs by turning yellow to orange. Third, the combination of both fluoride and lanthanum ions results in yellow/orange coloration.

The analysis of solutions containing various amount of $Ca^{+2}$ or $F^-$ at various pH levels was performed using alizarin complexone, o-cresolphthalein complexone, 5-carboxy fluorescein, and alizarin-$Ce^{3+}$ complex. A blank particle in which the terminal amines of a PEG-PS resin particle have been acylated was also used. In this example, the presence of $Ca^{+2}$ (0.1 M $Ca(NO_3)_2$) was analyzed under conditions of varying pH. The pH was varied to values of 2, 7, and 12, all buffered by a mixture of 0.04 M phosphate, 0.04 M acetate, and 0.04 M borate. The RGB patterns for each sensor element in all environments were measured. The bead derivatized with o-cresolphthalein responds to $Ca^{+2}$ at pH values around 12. Similarly, the 5-carboxy fluorescein derivatized bead acts as a pH sensor. At pHs below 7.4 it is light yellow, but at higher pHs it turns dark orange. Interesting, the alizarin complexone plays three distinct roles. First, it acts as a proton sensor yielding a yellow color at pHs below 4.5, orange is noted at pHs between 4.5 and 11.5, and at pHs above 11.5 a blue hue is observed. Second, it functions as a sensor for lanthanum ions at lower pHs by turning yellow to orange. Third, the combination of both fluoride and lanthanum ions results in yellow/orange coloration.

This example demonstrates a number of important factors related to the design, testing, and functionality of micromachined array sensors for solution analyses. First, derivatization of polymer particles with both colorimetric and fluorescent dyes was completed. These structures were shown to respond to pH and $Ca^{2+}$. Second, response times well under 1 minute were found. Third, micromachined arrays suitable both for confinement of particles, as well as optical characterization of the particles, have been prepared. Fourth, integration of the test bed arrays with commercially available CCD detectors has been accomplished. Finally, simultaneous detection of several analytes in a mixture was made possible by analysis of the RGB color patterns created by the sensor array.

3. The Detection of Sugar Molecules Using a Boronic Acid Based Receptor

A series of receptors were prepared with functionalities that associate strongly with sugar molecules, as depicted in FIG. 9. In this case, a boronic acid sugar receptor 500 was utilized to demonstrate the functionality of a new type of sensing scheme in which competitive displacement of a resorufin derivatized galactose sugar molecule was used to assess the presence (or lack thereof) of other sugar molecules. The boronic acid receptor 500 was formed via a substitution reaction of a benzylic bromide. The boronic acid receptor was attached to a polyethylene glycol-polystyrene ("PEG-PS") resin particle at the "R" position. Initially, the boronic acid derivatized particle was loaded with resorufin derivatized galactose 510. Upon exposure of the particle to a solution containing glucose 520, the resorufin derivatized galactose molecules 510 are displaced from the particle receptor sites. Visual inspection of the optical photographs taken before and after exposure to the sugar solution show that the boron substituted resin is capable of sequestering sugar molecules from an aqueous solution. Moreover, the subsequent exposure of the colored particles to a solution of a non-tagged sugar (e.g., glucose) leads to a displacement of the bound colored sugar reporter molecule. Displacement of this molecule leads to a change in the color of the particle. The sugar sensor turns from dark orange to yellow in solutions containing glucose. The particles were also tested in conditions of varying pH. It was noted that the color of the particles changes from dark orange to yellow as the pH is varied from low pH to high pH.

FURTHER IMPROVEMENTS

1. System Improvements

Figure 17:
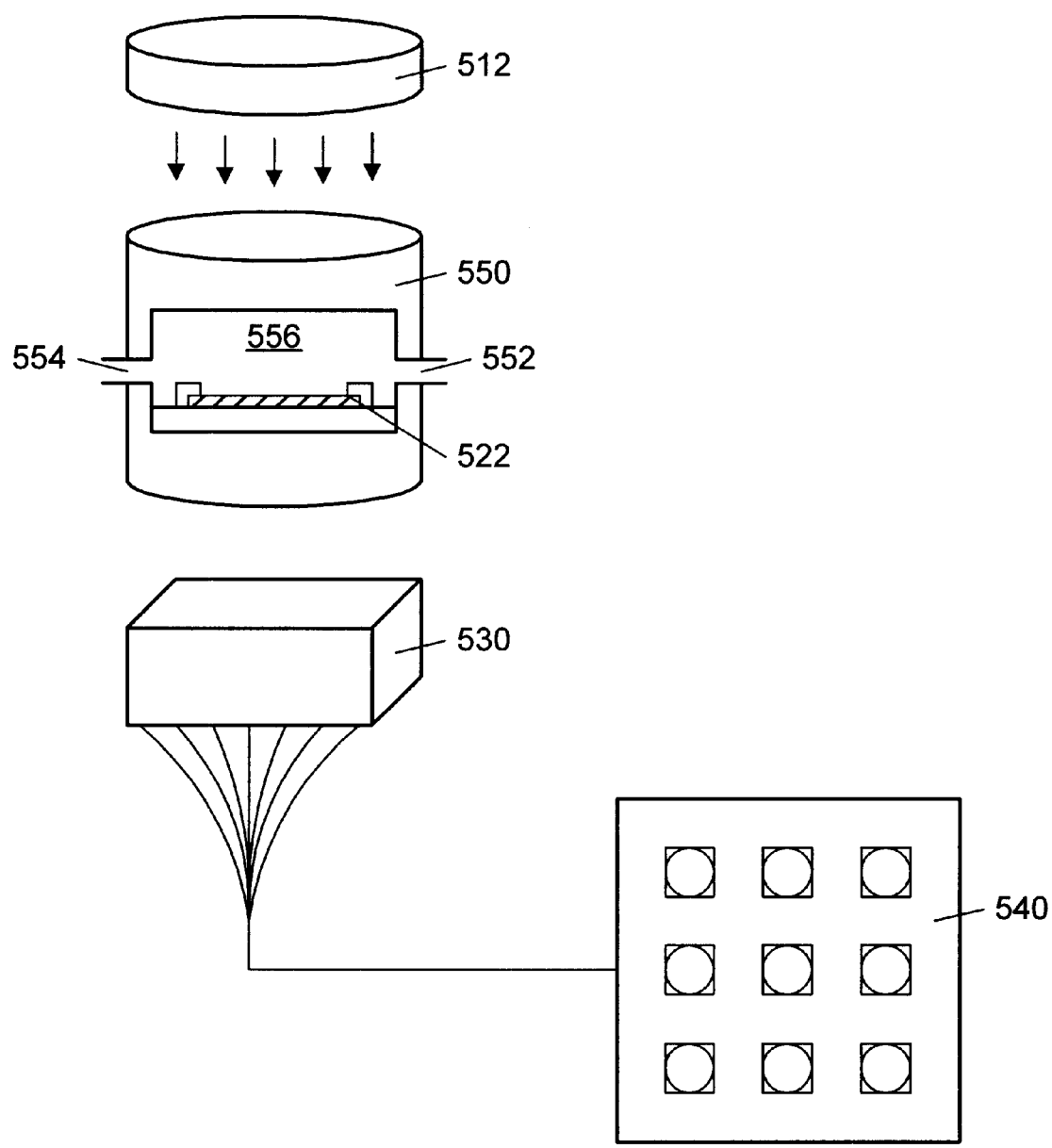
FIG. 17 depicts an analyte detection system which includes a sensor array disposed within a chamber.

Shown in FIG. 17 is an embodiment of a system for detecting analytes in a fluid. In one embodiment, the system includes a light source 512, a sensor array 522, a chamber 550 for supporting the sensor array and a detector 530. The sensor array 522 may include a supporting member which is configured to hold a variety of particles. In one embodiment, light originating from the light source 512 passes through the sensor array 522 and out through the bottom side of the sensor array. Light modulated by the particles may be detected by a proximally spaced detector 530. While depicted as being positioned below the sensor array, it should be understood that the detector may be positioned above the sensor array for reflectance measurements. Evaluation of the optical changes may be completed by visual inspection (e.g., by eye, or with the aid of a microscope) or by use of a microprocessor 540 coupled to the detector.

In this embodiment, the sensor array 522 is positioned within a chamber 550. The chamber 550, may be configured to allow a fluid stream to pass through the chamber such that the fluid stream interacts with the sensor array 522. The chamber may be constructed of glass (e.g, borosilicate glass or quartz) or a plastic material which is transparent to a portion of the light from the light source. If a plastic material is used, the plastic material should also be substantially unreactive toward the fluid. Examples of plastic materials which may be used to form the chamber include, but are not limited to, acrylic resins, polycarbonates, polyester resins, polyethylenes, polyimides, polyvinyl polymers (e.g., polyvinyl chloride, polyvinyl acetate, polyvinyl dichloride, polyvinyl fluoride, etc.), polystyrenes, polypropylenes, polytetrafluoroethylenes, and polyurethanes. An example of such a chamber is a Sykes-Moore chamber, which is commercially available from Bellco Glass, Inc., in New Jersey. Chamber 550, in one embodiment, includes a fluid inlet port 552 and a fluid outlet port 554. The fluid inlet 552 and outlet 554 ports are configured to allow a fluid stream to pass into the interior 556 of the chamber during use. The inlet and outlet ports may be configured to allow facile placement of a conduit for transferring the fluid to the chamber. In one embodiment, the ports may be hollow conduits. The hollow conduits may be configured to have an outer diameter which is substantially equal to the inner diameter of a tube for transferring the fluid to or away from the chamber. For example, if a plastic or rubber tube is used for the transfer of the fluid, the internal diameter of the plastic tube is substantially equal to the outer diameter of the inlet and outlet ports.

In another embodiment, the inlet and outlet ports may be Luer lock style connectors. Preferably, the inlet and outlet ports are female Luer lock connectors. The use of female Luer lock connectors will allow the fluid to be introduced via a syringe. Typically, syringes include a male Luer lock connector at the dispensing end of the syringe. For the introduction of liquid samples, the use of Luer lock connectors may allow samples to be transferred directly from a syringe to the chamber 550. Luer lock connectors may also allow plastic or rubber tubing to be connected to the chamber using Luer lock tubing connectors.

The chamber may be configured to allow the passage of a fluid sample to be substantially confined to the interior 556 of the chamber. By confining the fluid to a small interior volume, the amount of fluid required for an analysis may be minimized. The interior volume may be specifically modified for the desired application. For example, for the analysis of small volumes of fluid samples, the chamber may be designed to have a small interior chamber, thus reducing the amount of fluid needed to fill the chamber. For larger samples, a larger interior chamber may be used. Larger chambers may allow a faster throughput of the fluid during use.

Figure 18:
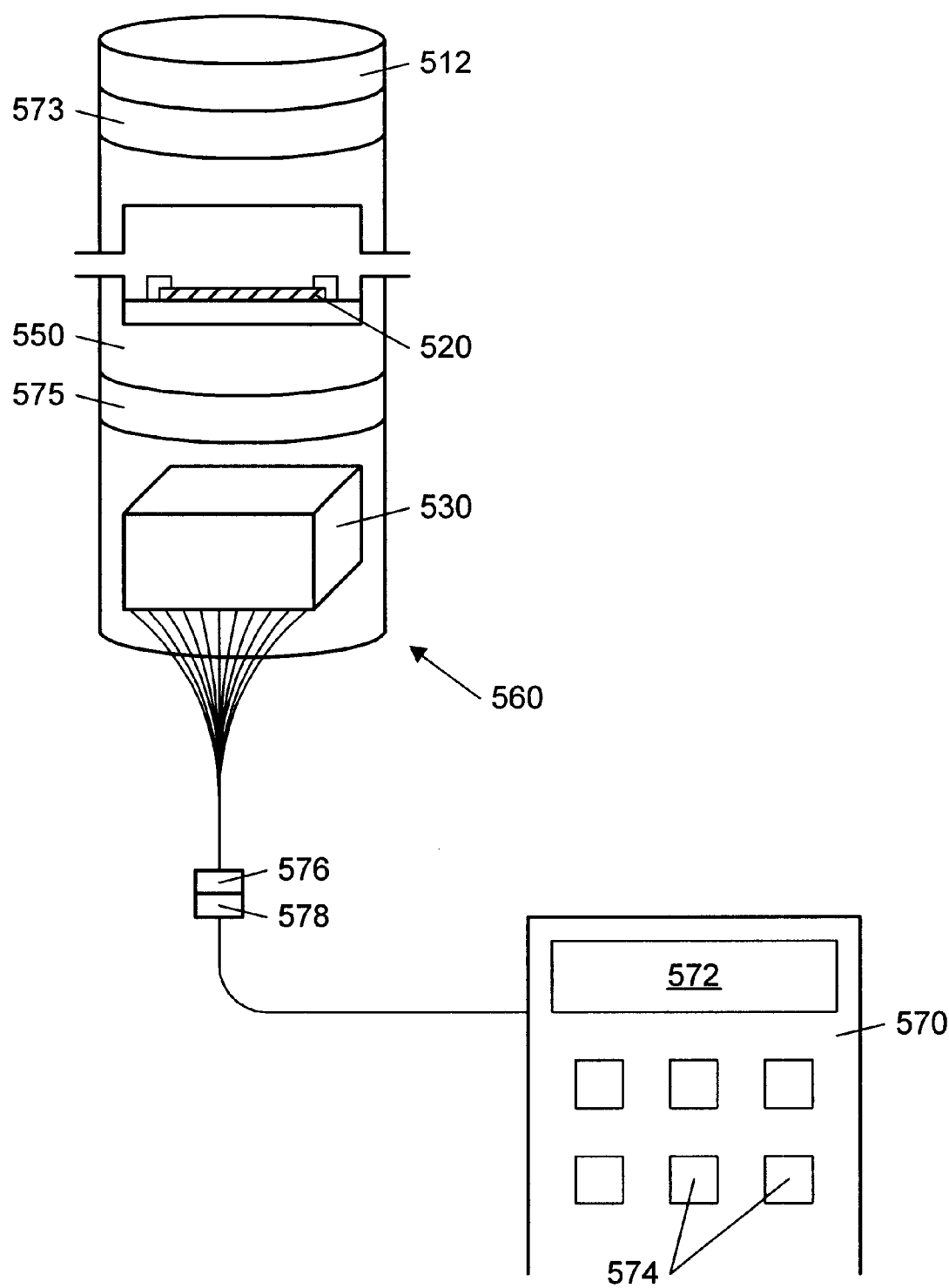
FIG. 18 depicts an integrated analyte detection system.

In another embodiment, depicted in FIG. 18, a system for detecting analytes in a fluid includes a light source 512, a sensor array 520, a chamber 550 for supporting the sensor array and a detector 530, all enclosed within a detection system enclosure 560. As described above, the a sensor array 520 is preferably formed of a supporting member, which is configured to hold a variety of particles. Thus, in a single enclosure, all of the components of an analyte detection system are included.

The formation of an analyte detection system in a single enclosure may allow the formation of a portable detection system. For example, a small controller 570 may be coupled to the analyte detection system. The controller 570 may be configured to interact with the detector and display the results from the analysis. In one embodiment, the controller includes a display device 572 for displaying information to a user. The controller may also include input devices 574 (e.g., buttons) to allow the user to control the operation of the analyte detection system. For example, the controller may control the operation of the light source 512 and the operation of the detector 530.

The detection system enclosure 560, may be interchangeable with the controller. Coupling members 576 and 578 may be used to remove the detection system enclosure 560 from the controller 570. A second detection system enclosure may be readily coupled to the controller using coupling members 576 and 578. In this manner, a variety of different types of analytes may be detecting using a variety of different detection system enclosures. Each of the detection system enclosures may include different sensor arrays mounted within their chambers. Instead of having to exchange the sensor array for different types of analysis, the entire detection system enclosure may be exchanged. This may prove advantageous, when a variety of detection schemes are used. For example a first detection system enclosure may be configured for white light applications. The first detection system enclosure may include a white light source, a sensor that includes particles that produce a visible light response in the presence of an analyte, and a detector sensitive to white light. A second detection system enclosure may be configured for fluorescent applications, including a fluorescent light source, a sensor array which includes particles which produce a fluorescent response on the presence of an analyte, and a fluorescent detector. The second detection system enclosure may also include other components necessary for producing a proper detection system. For example, the second detection system may also include a filter for preventing short wavelength excitation from producing "false" signals in the optical detection system during fluorescence measurements. A user need only select the proper detection system enclosure for the detection of the desired analyte. Since each detection system enclosure includes many of the required components, a user does not have to make light source selections, sensor array selections or detector arrangement selections to produce a viable detection system.

In another embodiment, the individual components of the system may be interchangeable. The system may include coupling members 573 and 575 that allow the light source and the detector, respectively, to be removed from the chamber 550. This may allow a more modular design of the system. For example, an analysis may be first performed with a white light source to give data corresponding to an absorbance/reflectance analysis. After this analysis is performed the light source may be changed to a ultraviolet light source to allow ultraviolet analysis of the particles. Since the particles have already been treated with the fluid, the analysis may be preformed without further treatment of the particles with a fluid. In this manner a variety of tests may be performed using a single sensor array.

In one embodiment, the supporting member is made of any material capable of supporting the particles, while allowing the passage of the appropriate wavelength of light. The supporting member may also be made of a material substantially impervious to the fluid in which the analyte is present. A variety of materials may be used including plastics (e.g., photoresist materials, acrylic polymers, carbonate polymers, etc.), glass, silicon based materials (e.g., silicon, silicon dioxide, silicon nitride, etc.) and metals. In one embodiment, the supporting member includes a plurality of cavities. The cavities are preferably formed such that at least one particle is substantially contained within the cavity. Alternatively, a plurality of particles may be contained within a single cavity.

Figure 19:
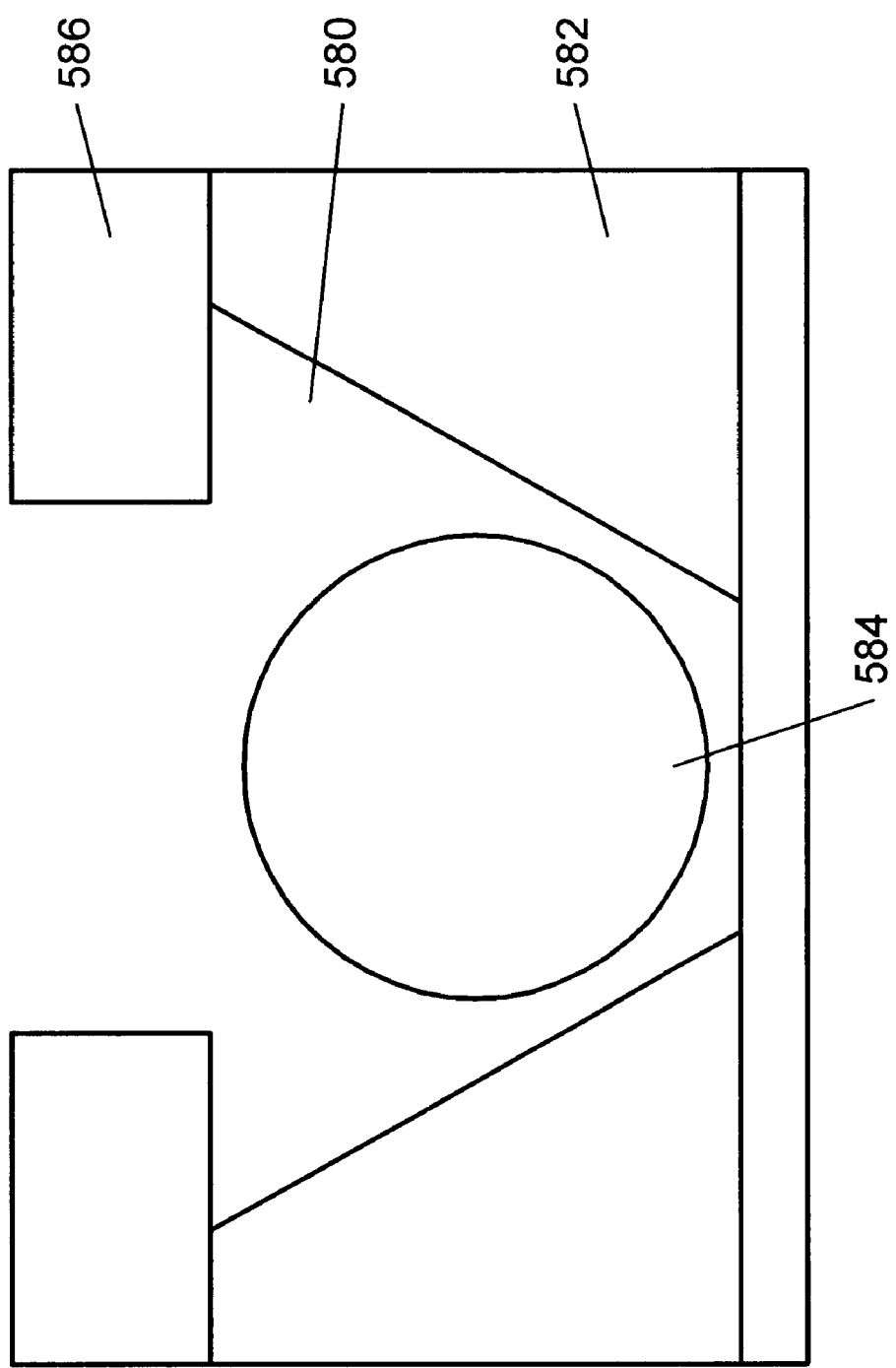
FIG. 19 depicts a cross-sectional view of a cavity covered by a mesh cover.
Figure 20:
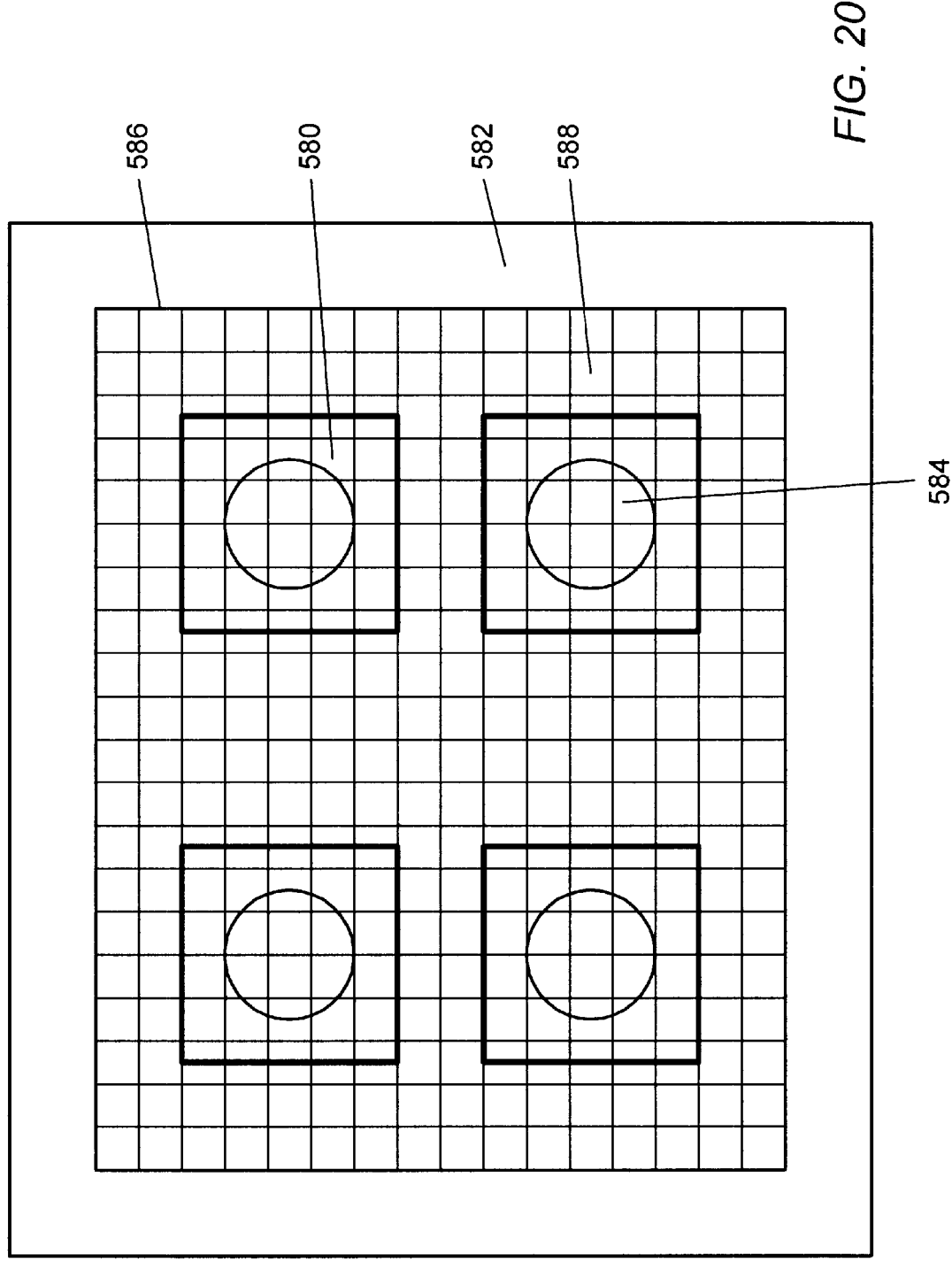
FIG. 20 depicts a top view of a cavity covered by a mesh cover.

In some embodiments, it will be necessary to pass liquids over the sensor array. The dynamic motion of liquids across the sensor array may lead to displacement of the particles from the cavities. In another embodiment, the particles are preferably held within cavities formed in a supporting member by the use of a transmission electron microscope ("TEM") grid. As depicted in FIG. 19, a cavity 580 is formed in a supporting member 582. After placement of a particle 584 within the cavity, a TEM grid 586 may be placed atop the supporting member 582 and secured into position. TEM grids and adhesives for securing TEM grids to a support are commercially available from Ted Pella, Inc., Redding, Calif. The TEM grid 586 may be made from a number of materials including, but not limited to, copper, nickel, gold, silver, aluminum, molybdenum, titanium, nylon, beryllium, carbon, and beryllium-copper. The mesh structure of the TEM grid may allow solution access as well as optical access to the particles that are placed in the cavities. FIG. 20 further depicts a top view of a sensor array with a TEM grid 586 formed upon the upper surface of the supporting member 582. The TEM grid 586 may be placed on the upper surface of the supporting member, trapping particles 584 within the cavities 580. As depicted, the openings 588 in the TEM grid 586 may be sized to hold the particles 584 within the cavities 580, while allowing fluid and optical access to cavities 580.

In another embodiment, a sensor array includes a supporting member configured to support the particles, while allowing the passage of the appropriate wavelength of light to the particle. The supporting member, in one embodiment, includes a plurality of cavities. The cavities may be formed such that at least one particle is substantially contained within the cavity. The supporting member may be configured to substantially inhibit the displacement of the particles from the cavities during use. The supporting member may also be configured to allow the passage of the fluid through cavities, e.g., the fluid may flow from the top surface of the supporting member, past the particle, and out the bottom surface of the supporting member. This may increase the contact time between the particle and the fluid.

Figure 21A:
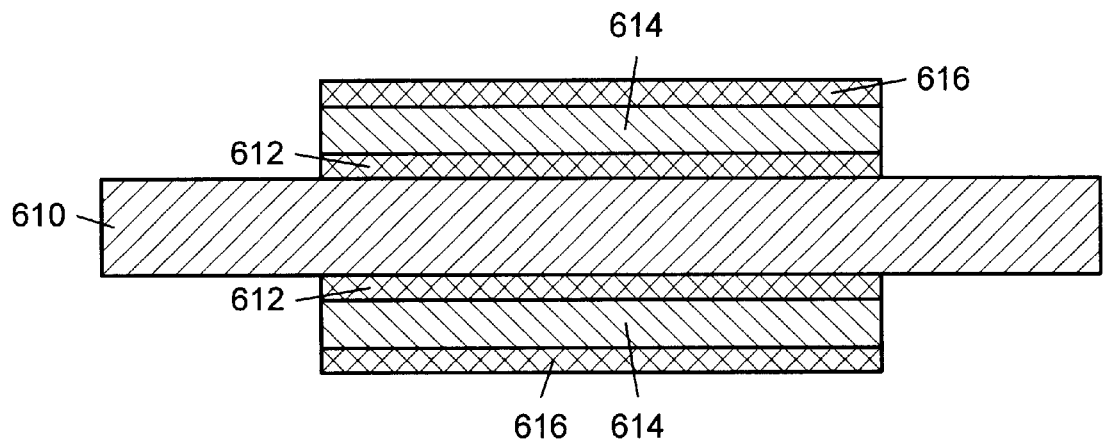
FIGS. 21A–G depict a cross-sectional view of a series of processing steps for the formation of a sensor array which includes a removable top and bottom cover.

FIGS. 21A–G depict a sequence of processing steps for the formation of a silicon based supporting member which includes a removable top cover and bottom cover. The removable top cover may be configured to allow fluids to pass through the top cover and into the cavity. The removable bottom cover may also be configured to allow the fluid to pass through the bottom cover and out of the cavity. As depicted in FIG. 21A, a series of layers may be deposited upon both sides of a silicon substrate 610. First removable layers 612 may be deposited upon the silicon substrate. The removable layers 612 may be silicon dioxide, silicon nitride, or photoresist material. In one embodiment, a layer of silicon dioxide is deposited upon both surfaces of the silicon substrate 610. Upon these removable layers, covers 614 may be formed. In one embodiment, covers 614 are formed from a material that differs from the material used to form the removable layers 612 and which is substantially transparent to the light source of a detection system. For example, if the removable layers 612 are formed from silicon dioxide, the cover may be formed from silicon nitride. Second removable layers 616 may be formed upon the covers 614. Second removable layers 616 may be formed from a material that differs from the material used to form the covers 614. Second removable layers 616 may be formed from a material similar to the material used to form the first removable layers 612. In one embodiment, first and second removable layers 612 and 616 are formed from silicon dioxide and covers 614 are formed from silicon nitride. The layers are patterned and etched using standard photolithographic techniques. In one embodiment, the remaining portions of the layers are substantially aligned in the position where the cavities are to be formed in the silicon substrate 610.

Figure 21B:
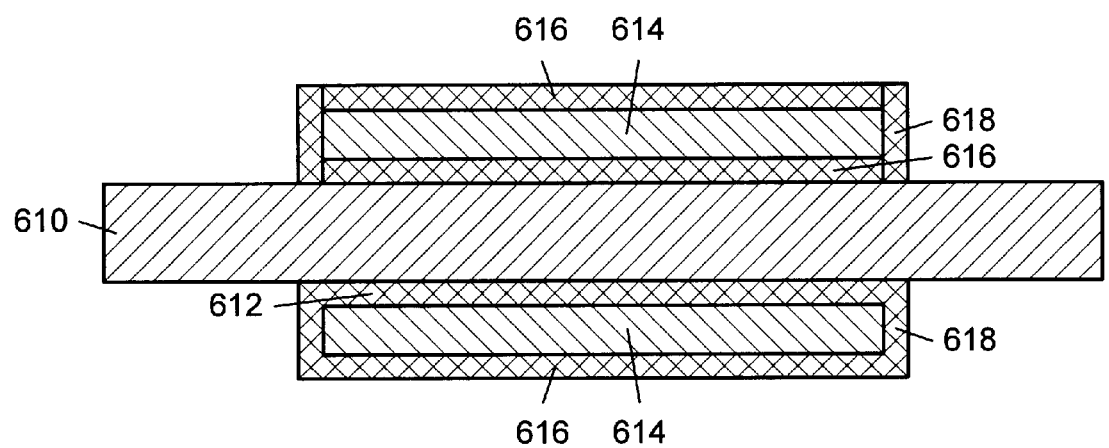

After the layers have been etched, spacer structures may be formed on the sidewalls of the first removable layers 612, the covers 614, and the second removable layers 616, as depicted in FIG. 21B. The spacer structures may be formed from the same material used to form the second removable layers 616. In one embodiment, depositing a spacer layer of the appropriate material and subjecting the material to an anisotropic etch may form the spacer structures. An anisotropic etch, such as a plasma etch, employs both physical and chemical removal mechanisms. Ions are typically bombarded at an angle substantially perpendicular to the semiconductor substrate upper surface. This causes substantially horizontal surfaces to be removed faster than substantially vertical surfaces. During this etching procedure the spacer layers are preferably removed such that the only regions of the spacer layers that remain may be those regions near substantially vertical surfaces, e.g., spacer structures 618.

Figure 21C:
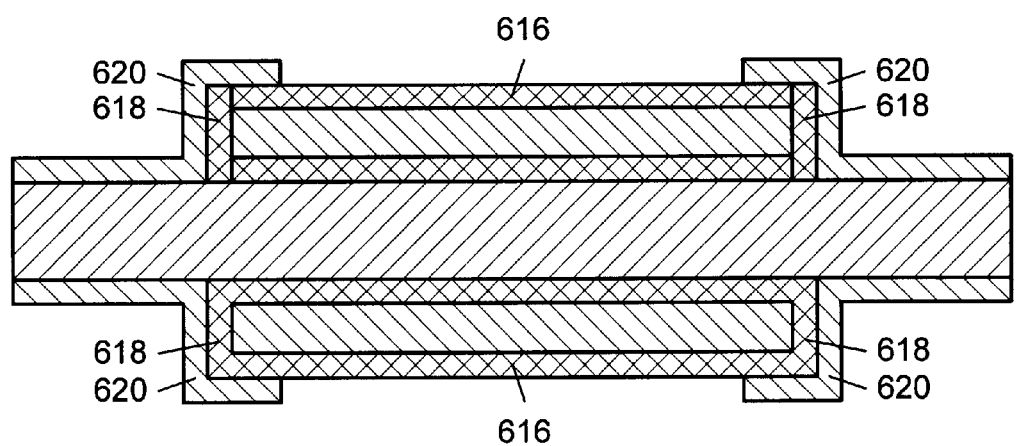

After formation of the spacer structures 618, cover support structures 620, depicted in FIG. 21C, may be formed. The cover support structures may be initially formed by depositing a support structure layer upon the second removable layer 616 and spacer structures 618. The support structure layer is then patterned and etched, using standard photolithography, to form the support structures 620. In one embodiment, the support structures are formed from a material that differs from the removable layers material. In one embodiment, the removable layers may be formed from silicon dioxide while the support structures and covers may be formed from silicon nitride.

Figure 21D:
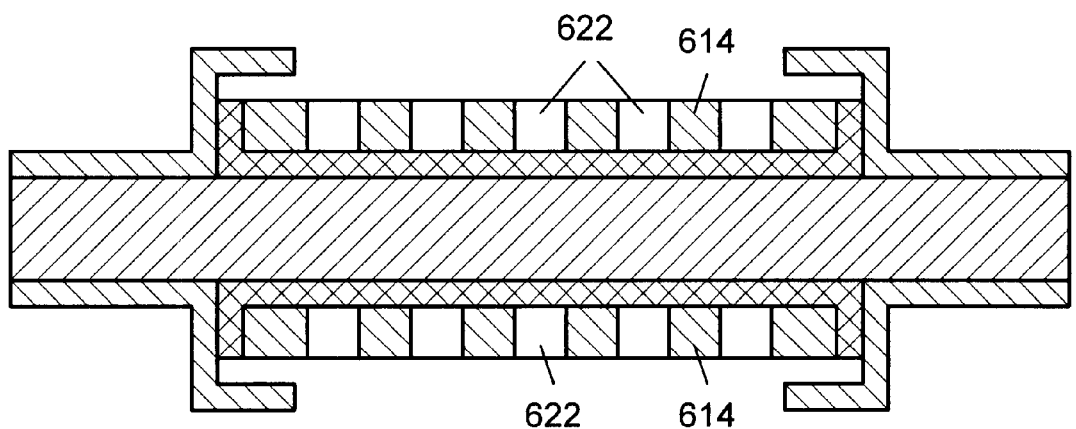

Turning to FIG. 21D, the second removable layers 616 and an upper portion of the spacer structures 618 are preferably removed using a wet etch process. Removal of the second removable layers leaves the top surface of the covers 614 exposed. This allows the covers to be patterned and etched such that openings 622 are formed extending through the covers. These openings 622 may be formed in the covers 614 to allow the passage of fluid through the cover layers. In one embodiment, the openings 622 are formed to allow fluid to pass through, while inhibiting displacement of the particles from the subsequently formed cavities.

Figure 21E:
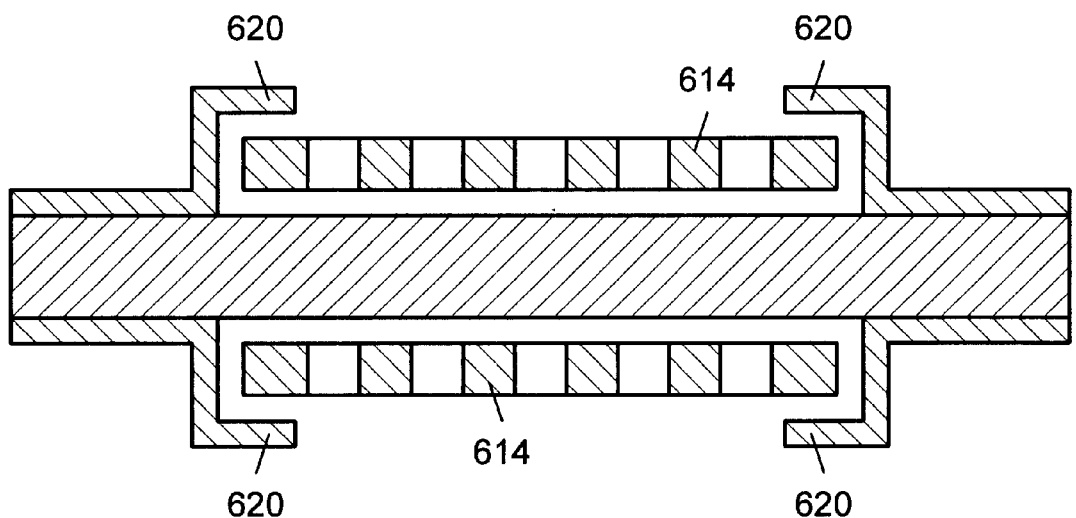

After the openings 622 have been formed, the remainder of the first removable layers 612 and the remainder of the spacer structures 618 may be removed using a wet etch. The removal of the removable layers and the spacer structures creates "floating" covers 614, as depicted in FIG. 21E. The covers 614 may be held in proximity to the silicon substrate 610 by the support structures 620. The covers 614 may now be removed by sliding the covers away from the support structures 620. In this manner removable covers 614 may be formed.

Figure 21F:
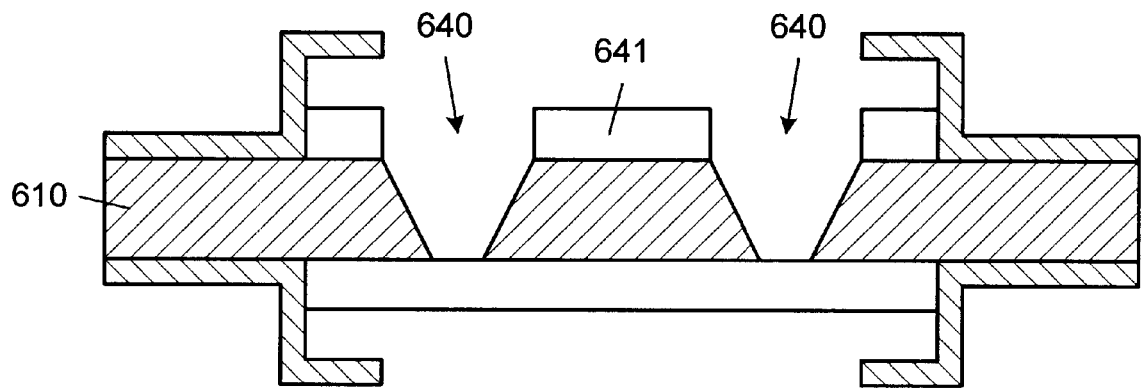

After the covers 614 are removed, cavities 640 may be formed in the silicon substrate 610, as depicted in FIG. 21F. The cavities 640 may be formed by, initially patterning and etching a photoresist material 641 to form a masking layer. After the photoresist material 641 is patterned, the cavities 640 may be etched into the silicon substrate 610 using a hydroxide etch, as described previously.

Figure 21G:
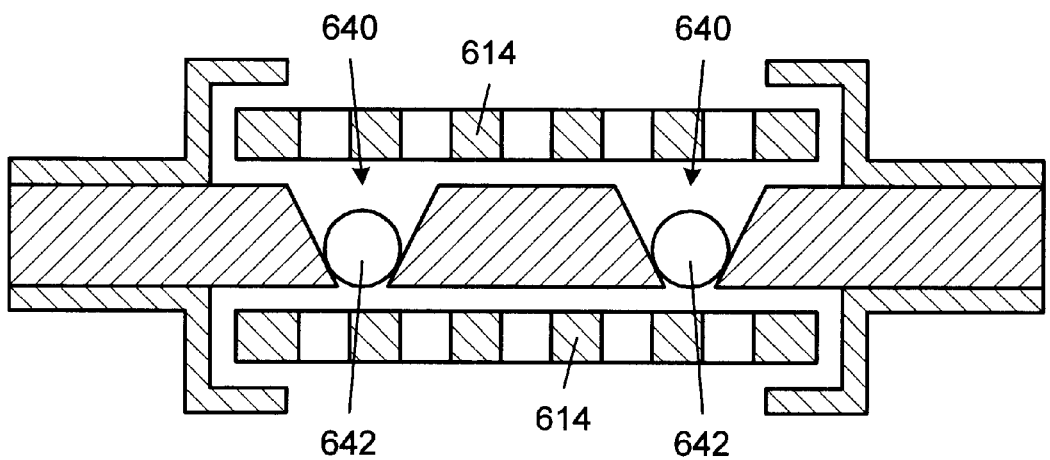

After the cavities 640 are formed, the photoresist material may be removed and particles 642 may be placed within the cavities, as depicted in FIG. 21G. The particles 642, may be inhibited from being displaced from the cavity 640 by placing covers 614 back onto the upper and lower faces of the silicon substrate 610.

Figure 22A:
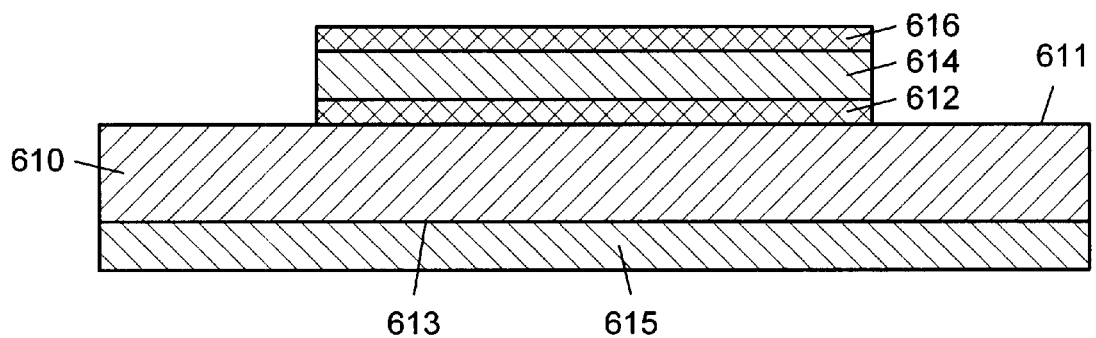
FIGS. 22A–G depict a cross-sectional view of a series of processing steps for the formation of a sensor array which includes a removable top and a stationary bottom cover.

In another embodiment, a sensor array may be formed using a supporting member, a removable cover, and a secured bottom layer. FIGS. 22A–G depict a series of processing steps for the formation of a silicon based supporting member which includes a removable top cover and a secured bottom layer. The removable top cover is preferably configured to allow fluids to pass through the top cover and into the cavity. As depicted in FIG. 22A, a series of layers may be deposited upon both sides of a silicon substrate 610. A first removable layer 612 may be deposited upon the upper face 611 of the silicon substrate 610. The removable layer 612 may be silicon dioxide, silicon nitride, or photoresist material. In one embodiment, a layer of silicon dioxide is deposited upon the silicon substrate 610. A cover 614 may be formed upon the removable layer 612 of the silicon substrate 610. In one embodiment, the cover 614 is formed from a material that differs from the material used to form the removable layer 612 and is substantially transparent to the light source of a detection system. For example, if the removable layer 612 is formed from silicon dioxide, the cover layer 614 may be formed from silicon nitride. In one embodiment, a bottom layer 615 is formed on the bottom surface 613 of the silicon substrate 610. In one embodiment, the bottom layer 615 is formed from a material that is substantially transparent to the light source of a detection system. A second removable layer 616 may be formed upon the cover 614. Second removable layer 616 may be formed from a material that differs from the material used to form the cover layer 614. Second removable layer 616 may be formed from a material similar to the material used to form the first removable layer 612. In one embodiment, first and second removable layers 612 and 616 are formed from silicon dioxide and cover 614 is formed from silicon nitride. The layers formed on the upper surface 611 of the silicon substrate may be patterned and etched using standard photolithographic techniques. In one embodiment, the remaining portions of the layers formed on the upper surface are substantially aligned in the position where the cavities are to be formed in the silicon substrate 610.

Figure 22B:
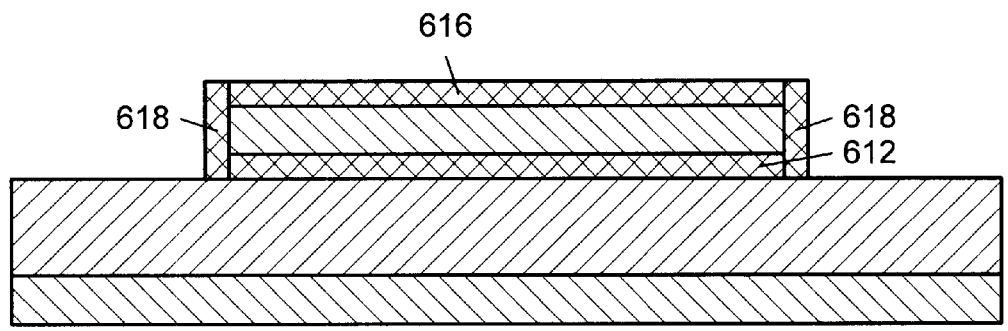

After the layers have been etched, spacer structures may be formed on the side walls of the first removable layer 612, the cover 614, and the second removable layer 616, as depicted in FIG. 22B. The spacer structures may be formed from the same material used to form the second. removable layer 616. In one embodiment, the spacer structures may be formed by depositing a spacer layer of the appropriate material and subjecting the spacer layer to an anisotropic etch. During this etching procedure the spacer layer is preferably removed such that the only regions of the spacer layer which remain may be those regions near substantially vertical surfaces, e.g., spacer structures 618.

Figure 22C:
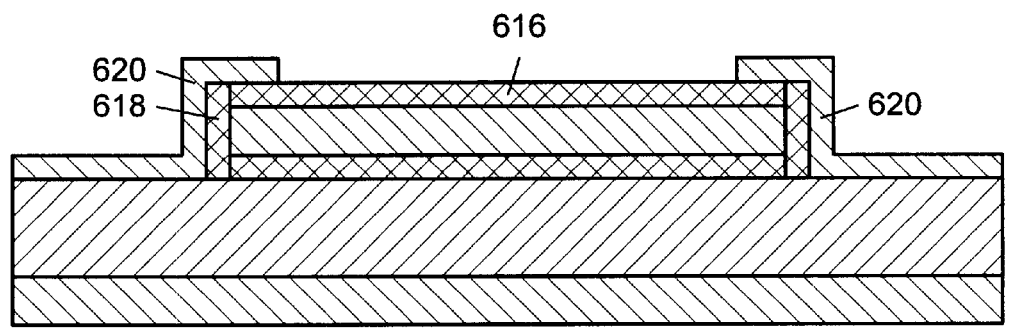

After formation of the spacer structures 618, cover support structures 620, depicted in FIG. 22C, may be formed upon the removable layer 616 and the spacer structures 618. The cover support structures 620 may be formed by depositing a support structure layer upon the second removable layer 616 and spacer structures 618. The support structure layer is then patterned and etched, using standard photolithography, to form the support structures 620. In one embodiment, the support structures are formed from a material that differs from the removable layer materials. In one embodiment, the removable layers may be formed from silicon dioxide while the support structures and cover may be formed from silicon nitride.

Figure 22D:
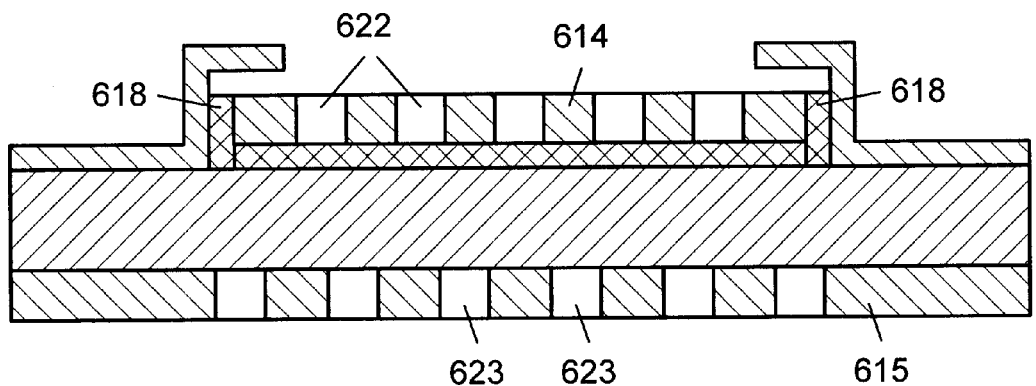

Turning to FIG. 22D, the second removable layer 616 and an upper portion of the spacer structures 618 may be removed using a wet etch process. Removal of the second removable layer leaves the top surface of the cover 614 exposed. This allows the cover 614 to be patterned and etched such that openings 622 are formed extending through the cover 614. These openings 622 may be formed in the cover 614 to allow the passage of fluid through the cover. In one embodiment, the openings 622 are formed to allow fluid to pass through, while inhibiting displacement of the particle from a cavity. The bottom layer 615 may also be similarly patterned and etched such that openings 623 may be formed extending thorough the bottom layer 615.

Figure 22E:
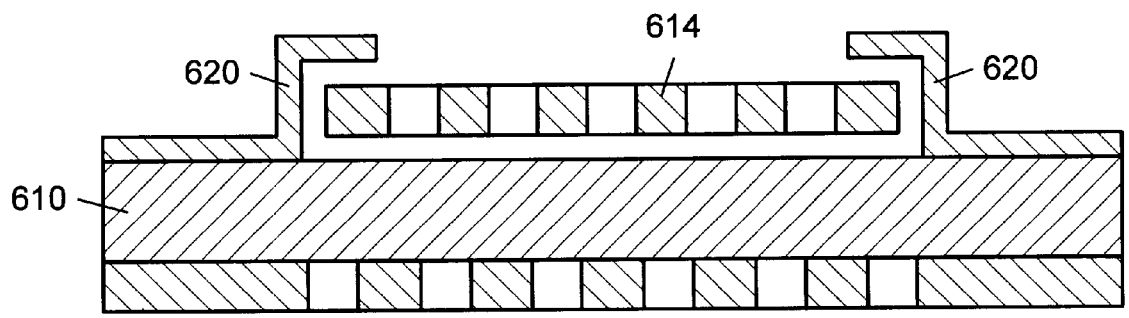
Figure 22F:
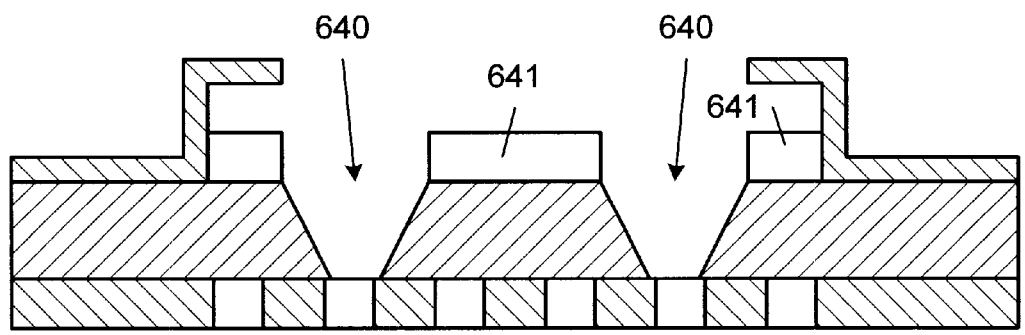

After the openings 622 and 623 are formed, the first removable layer 612 and the remainder of the spacer structures 618 may be removed using a wet etch. The removal of the removable layers and the spacer structures creates a "floating" cover 614, as depicted in FIG. 22E. The cover 614 may be held in proximity to the silicon substrate 610 by the support structures 620. The cover 614 may now be removed by sliding the cover 614 away from the support structures 620. In this manner a removable cover 614 may be formed.

Figure 23A:
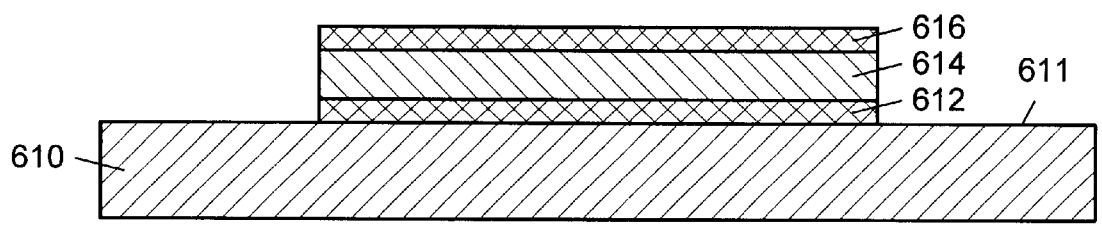
FIGS. 23A–G depict a cross-sectional view of a series of processing steps for the formation of a sensor array which includes a removable top.
Figure 23B:
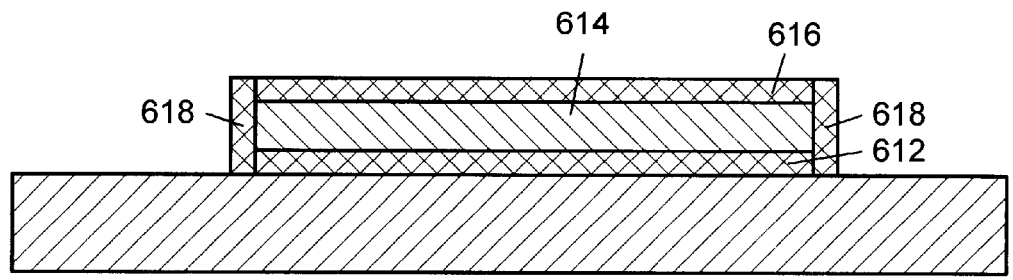
Figure 23C:
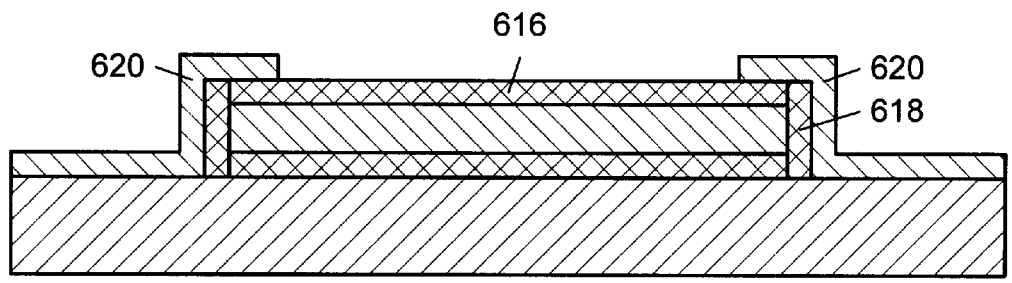
Figure 23D:
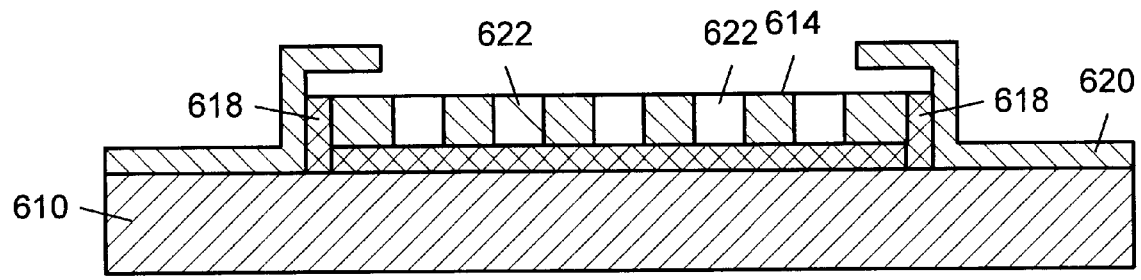
Figure 23E:
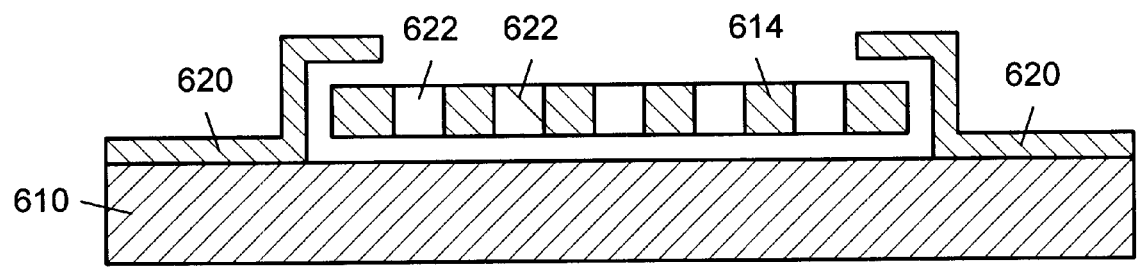
Figure 23F:
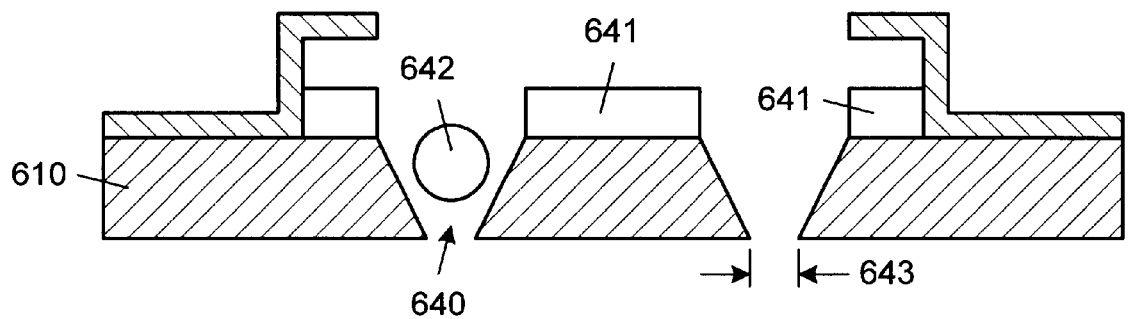

After the cover 614 is removed, cavities 640 may be formed in the silicon substrate 610, as depicted in FIG. 23F. The cavities 640 may be formed by initially depositing and patterning a photoresist material 641 upon the silicon support 610. After the photoresist material 641 is patterned, the cavities 640 may be etched into the silicon substrate 610 using a hydroxide etch, as described previously. The etching of the cavities may be accomplished such that a bottom width of the cavity 643 is less than a width of a particle 642. In one embodiment, the width of the bottom of the cavity may be controlled by varying the etch time. Typically, longer etching times result in a larger opening at the bottom of the cavity. By forming a cavity in this manner, a particle placed in the cavity may be too large to pass through the bottom of the cavity. Thus, a supporting member that does not include a bottom layer may be formed. An advantage of this process is that the processing steps may be reduced making production simpler.

Figure 22G:
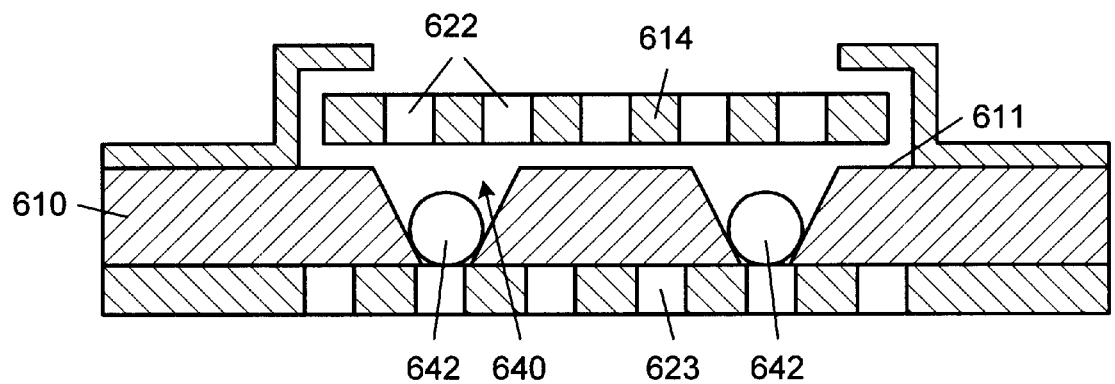

After the cavities 640 are formed, the photoresist material may be removed and particles 642 may be placed within the cavities, as depicted in FIG. 22G. The particles 642, may be inhibited from being displaced from the cavity 640 by placing cover 614 back onto the upper face 611 of the silicon substrate 610. The bottom layer 615 may also aid in inhibiting the particle 642 from being displaced from the cavity 640. Openings 622 in cover 614 and openings 623 in bottom layer 615 may allow fluid to pass through the cavity during use.

In another embodiment, a sensor array may be formed using a supporting member and a removable cover. FIGS. 23A–G depict a series of processing steps for the formation of a silicon based supporting member which includes a removable cover. The removable cover is preferably configured to allow fluids to pass through the cover and into the cavity. As depicted in FIG. 23A, a series of layers may be deposited upon the upper surface 611 of a silicon substrate 610. A first removable layer 612 may be deposited upon the upper face 611 of the silicon substrate 610. The removable layer 612 may be silicon dioxide, silicon nitride, or photoresist material. In one embodiment, a layer of silicon dioxide is deposited upon the silicon substrate 610. A cover 614 may be formed upon the removable layer 612. In one embodiment, the cover is formed from a material which differs from the material used to form the removable layer 612 and which is substantially transparent to the light source of a detection system. For example, if the removable layer 612 is formed from silicon dioxide, the cover 614 may be formed from silicon nitride. A second removable layer 616 may be formed upon the cover 614. Second removable layer 616 may be formed from a material that differs from the material used to form the cover 614. Second removable layer 616 may be formed from a material similar to the material used to form the first removable layer 612. In one embodiment, first and second removable layers 612 and 616 are formed from silicon dioxide and cover 614 is formed from silicon nitride. The layers formed on the upper surface 611 of the silicon substrate may be patterned and etched using standard photolithographic techniques. In one embodiment, the remaining portions of the layers formed on the upper surface are substantially aligned in the position where the cavities are to be formed in the silicon substrate 610.

After the layers have been etched, spacer structures 618 may be formed on the side walls of the first removable layer 612, the cover layer 614, and the second removable layer 616, as depicted in FIG. 23B. The spacer structures 618 may be formed from the same material used to form the second removable layer 616. In one embodiment the spacers may be formed by depositing a spacer layer of the appropriate material upon the second removable layer and subjecting the material to an anisotropic etch. During this etching procedure the spacer layer is preferably removed such that the only regions of the spacer layer which remain may be those regions near substantially vertical surfaces, e.g., spacer structures 618.

After formation of the spacer structures 618, cover support structures 620, depicted in FIG. 23C, may be formed upon the removable layer 616 and the spacer structures 618. The cover support structure may be formed by initially depositing a support structure layer upon the second removable layer 616 and spacer structures 618. The support structure layer is then patterned and etched, using standard photolithography, to form the support structures 620. In one embodiment, the support structures 620 are formed from a material that differs from the removable layer materials. In one embodiment, the removable layers may be formed from silicon dioxide while the support structure and cover layer may be formed from silicon nitride.

Referring to FIG. 23C, the second removable layer 616 and an upper portion of the spacer structures 618 may be removed using a wet etch process. Removal of the second removable layer leaves the top surface of the cover 614 exposed as depicted in FIG. 23D. This allows the cover 614 to be patterned and etched such that openings 622 are formed extending through the cover 614. These openings 622 may be formed in the cover 614 to allow the passage of fluid through the cover 614.

After the openings 622 are formed, the remainder of the first removable layer 612 and the remainder of the spacer structures 618 may be removed using a wet etch. The removal of the removable layers and the spacer structures creates a "floating" cover 614, as depicted in FIG. 23E. The cover 614 is preferably held in proximity to the silicon substrate 610 by the support structures 620. The cover 614 may now be removed by sliding the cover 614 away from the support structures 620. In this manner a removable cover 614 may be formed.

After the cover 614 is removed, cavities 640 may be formed in the silicon substrate 610, as depicted in FIG. 23F. The cavities 640 may be formed by initially depositing and patterning a photoresist material 641 upon the silicon support 610. After the photoresist material 614 is patterned, the cavities 640 may be etched into the silicon substrate 610 using a hydroxide etch, as described previously. The etching of the cavities may be accomplished such that a bottom width of the cavity 643 is less than a width of a particle 642. In one embodiment, the width of the bottom of the cavity may be controlled by varying the etch time. Typically, longer etching times result in a larger opening at the bottom of the cavity. By forming a cavity in this manner, a particle placed in the cavity may be too large to pass through the bottom of the cavity. Thus, a supporting member that does not include a bottom layer may be formed. An advantage of this process is that the processing steps may be reduced making production simpler.

Figure 23G:
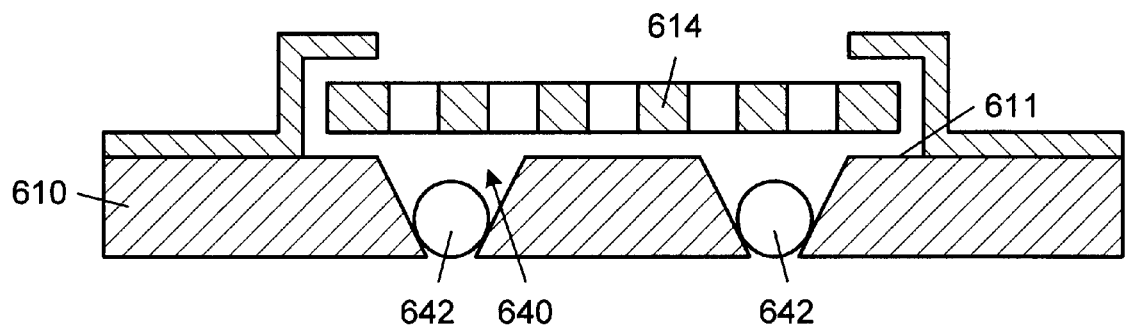

After the cavities 640 are formed, the photoresist material may be removed and particles 642 may be placed within the cavities, as depicted in FIG. 23G. The particles 642, may be inhibited from being displaced from the cavity 640 by placing cover 614 back onto the upper face 611 of the silicon substrate 610. The narrow bottom portion of the cavity may also aid in inhibiting the particle 642 from being displaced from the cavity 640.

Figure 24A:
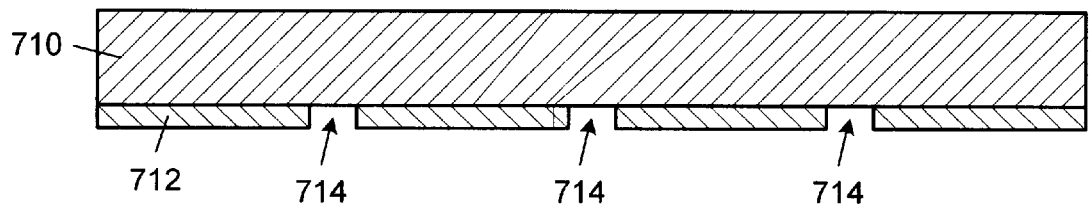
FIGS. 24A–D depict a cross-sectional view of a series of processing steps for the formation of a silicon based sensor array which includes a top and bottom cover with openings aligned with the cavity.

FIGS. 24A–D depict a sequence of processing steps for the formation of a silicon based supporting member which includes a top partial cover and a bottom partial cover. The top partial cover and bottom partial covers are in one embodiment configured to allow fluids to pass into the cavity and out through the bottom of the cavity. As depicted in FIG. 24A, a bottom layer 712 may be deposited onto the bottom surface of a silicon substrate 710. The bottom layer 712 may be silicon dioxide, silicon nitride, or photoresist material. In one embodiment, a layer of silicon nitride 712 is deposited upon the silicon substrate 710. In one embodiment, openings 714 are formed through the bottom layer as depicted in FIG. 24A. Openings 714, in one embodiment, are substantially aligned with the position of the cavities to be subsequently formed. The openings 714 may have a width that is substantially less than a width of a particle. Thus, a particle will be inhibited from passing through the openings 714.

Figure 24B:
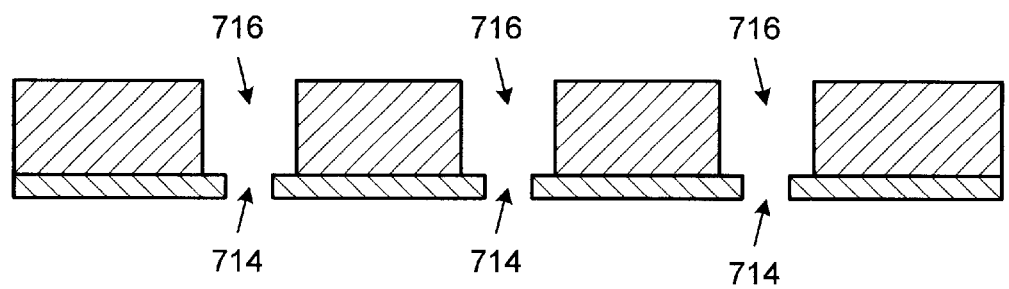

Cavities 716 may be formed in the silicon substrate 710, as depicted in FIG. 24B. The cavities 716 may be formed by initially depositing and patterning a photoresist layer upon the silicon substrate 710. After the photoresist material is patterned, cavities 716 may be etched into the silicon substrate 710 using a number of etching techniques, including wet and plasma etches. The width of the cavities 716 is preferably greater than the width of a particle, thus allowing a particle to be placed within each of the cavities. The cavities 716, in one embodiment, are preferably formed such that the cavities are substantially aligned over the openings 714 formed in the bottom layer.

Figure 24C:
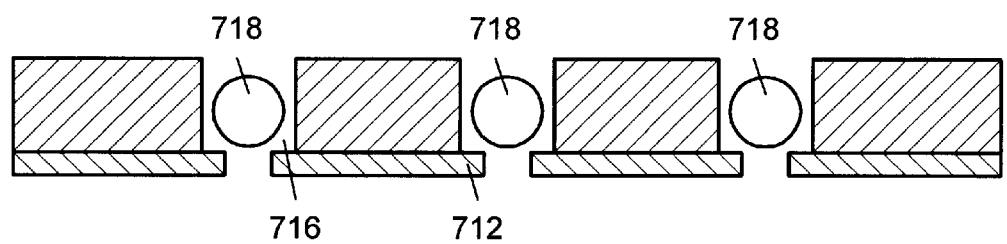

After the cavities have been formed, particles 718 may be inserted into the cavities 716, as depicted in FIG. 24C. The etched bottom layer 712 may serve as a support for the particles 718. Thus the particles 718 may be inhibited from being displaced from the cavities by the bottom layer 712. The openings 714 in the bottom layer 712 may allow fluid to pass through the bottom layer during use.

Figure 24D:
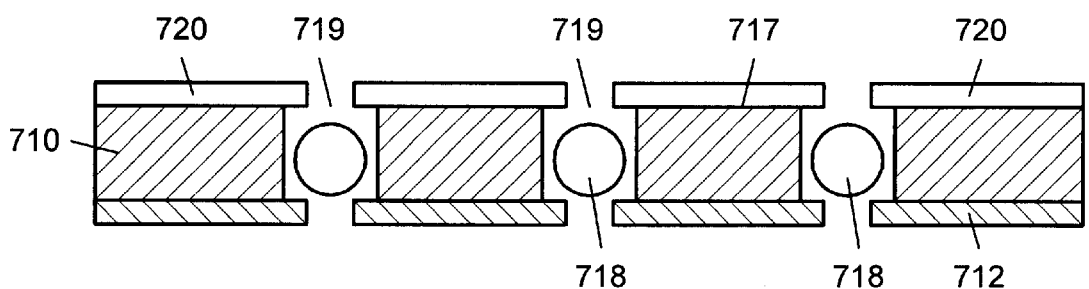

After the particles 718 are placed in the cavities, a top layer 720 may be placed upon the upper surface 717 of the silicon substrate as depicted in FIG. 24D. In one embodiment, the top layer 720 is formed from a material is substantially transparent to the light source of a detection system. The top layer may be formed from silicon nitride, silicon dioxide or photoresist material. In one embodiment, a sheet of photoresist material is used. After the top layer 720 is formed, openings 719 may be formed in the top layer to allow the passage of the fluid into the cavities. If the top layer 720 is composed of photoresist material, after depositing the photoresist material across the upper surface of the silicon substrate, the openings may be initially formed by exposing the photoresist material to the appropriate wavelength and pattern of light. If the top layer is compose of silicon dioxide or silicon nitride the top layer 720 may be developed by forming a photoresist layer upon the top layer, developing the photoresist, and using the photoresist to etch the underlying top layer.

Similar sensor arrays may be produced using materials other than silicon for the supporting member. For example, as depicted in FIG. 25A–D, the supporting member may be composed of photoresist material. In one embodiment, sheets of photoresist film may be used to form the supporting member. Photoresist film sheets are commercially available from E. I. du Pont de Nemours and Company, Wilmington, Del. under the commercial name RISTON. The sheets come in a variety of sizes, the most common having a thickness ranging from about 1 mil. (25 $\mu$m) to about 2 mil. (50 $\mu$m).

Figure 25A:
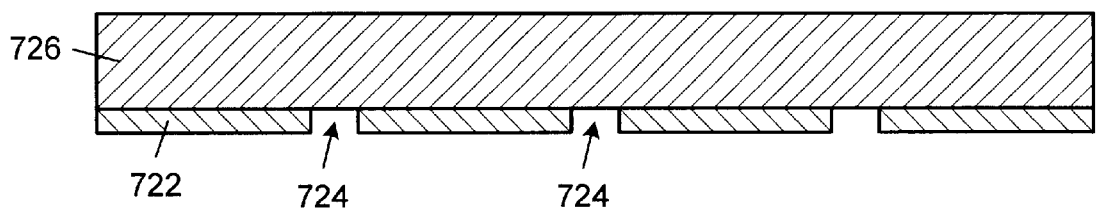
FIGS. 25A–D depict a cross-sectional view of a series of processing steps for the formation of a photoresist based sensor array which includes a top and bottom cover with openings aligned with the cavity.

In an embodiment, a first photoresist layer 722 is developed and etched such that openings 724 are formed as depicted in FIG. 25A. The openings may be formed proximate the location of the subsequently formed cavities. Preferably, the openings have a width that is substantially smaller than a width of the particle. The openings may inhibit displacement of the particle from a cavity. After the first photoresist layer 722 is patterned and etched, a main layer 726 is formed upon the bottom layer. The main layer 726 is preferably formed from a photoresist film that has a thickness substantially greater than a typical width of a particle. Thus, if the particles have a width of about 30 $\mu$m, a main layer may be composed of a 50 $\mu$m photoresist material. Alternatively, the photoresist layer may be composed of a multitude of photoresist layers placed upon each other until the desired thickness is achieved, as will be depicted in later embodiments.

Figure 25B:
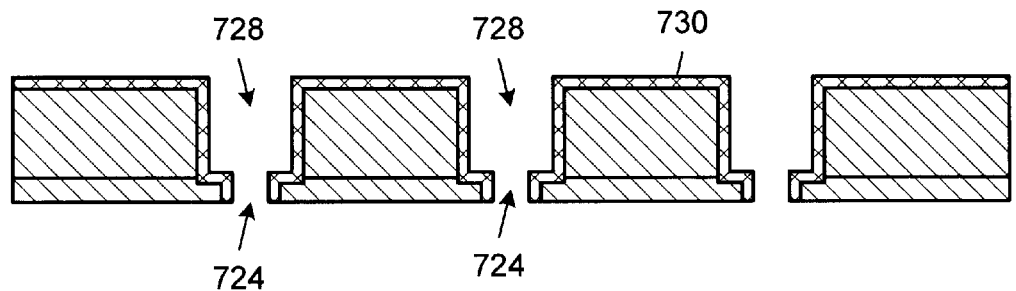

The main photoresist layer may be patterned and etched to form the cavities 728, as depicted in FIG. 25B. The cavities, in one embodiment, are substantially aligned above the previously formed openings 724. Cavities 728, in one embodiment, have a width which is greater than a width of a particle.

For many types of analysis, the photoresist material is substantially transparent to the light source used. Thus, as opposed to a silicon supporting member, the photoresist material used for the main supporting layer may be substantially transparent to the light used by the light source. In some circumstances, the transparent nature of the supporting member may allow light from the cavity to migrate, through the supporting member, into a second cavity. This leakage of light from one cavity to the next may lead to detection problems. For example, if a first particle in a first cavity produces a fluorescent signal in response to an analyte, this signal may be transmitted through the supporting member and detected in a proximate cavity. This may lead to inaccurate readings for the proximately spaced cavities, especially if a particularly strong signal is produced by the interaction of the particle with an analyte.

To reduce the occurrence of this "cross-talk", a substantially reflective layer 730 may be formed along the inner surface of the cavity. In one embodiment, the reflective layer 730 is composed of a metal layer which is formed on the upper surface of the main layer and the inner surface of the cavity. The metal layer may be deposited using chemical vapor deposition or other known techniques for depositing thin metal layers. The presence of a reflective layer may inhibit "cross-talk" between the cavities.

Figure 25C:
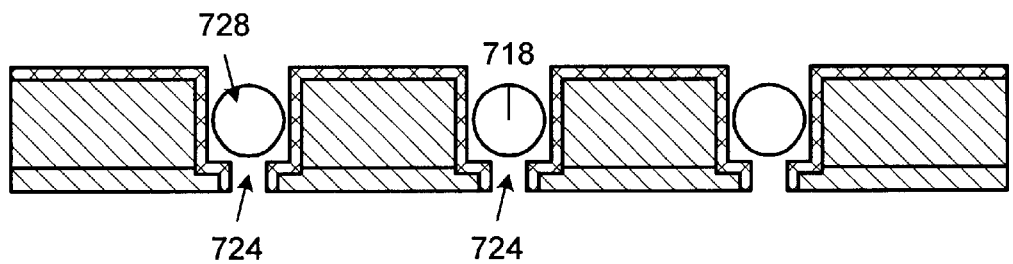

After the cavities 728 have been formed, particles 718 may be inserted into the cavities 728, as depicted in FIG. 25C. The first photoresist layer 722 may serve as a support for the particles 718. The particles may be inhibited from being displaced from the cavities by the first photoresist layer 722. The openings 724 in the first photoresist layer 722 may allow fluid to pass through the bottom layer during use.

Figure 25D:
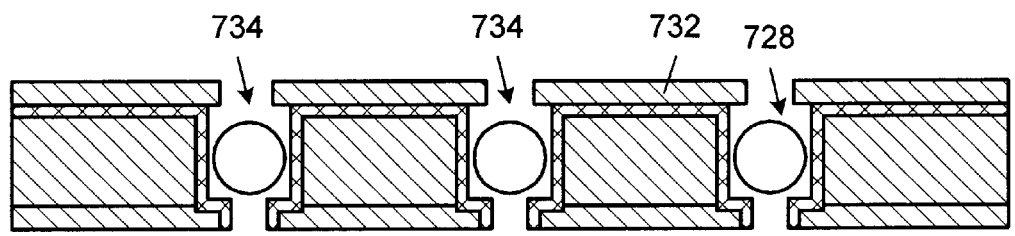

After the particles 718 are placed in the cavities 728, a top photoresist layer 732 may be placed upon the upper surface of the silicon substrate as depicted in FIG. 25D. After the cover layer is formed, openings 734 may be formed in the cover layer to allow the passage of the fluid into the cavities.

Figure 26A:
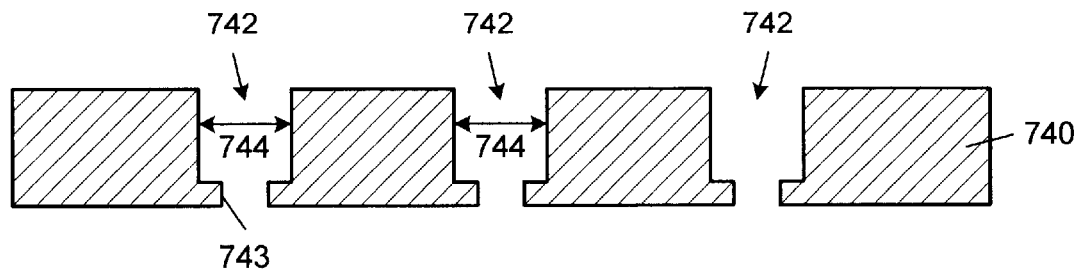
FIGS. 26A–E depict a cross-sectional view of a series of processing steps for the formation of a plastic based sensor array which includes a top and bottom cover with openings aligned with the cavity.
Figure 26B:
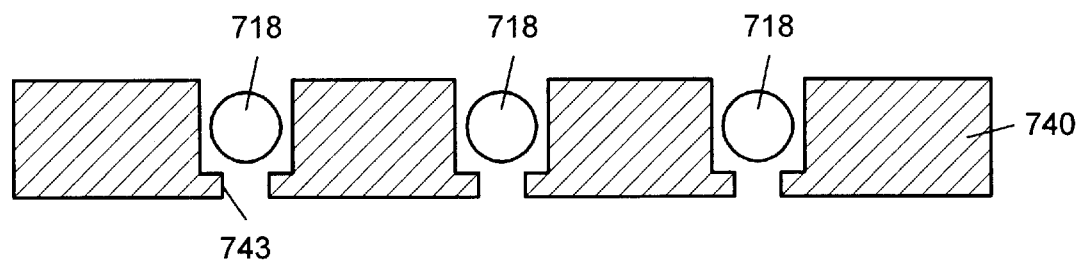
Figure 26C:
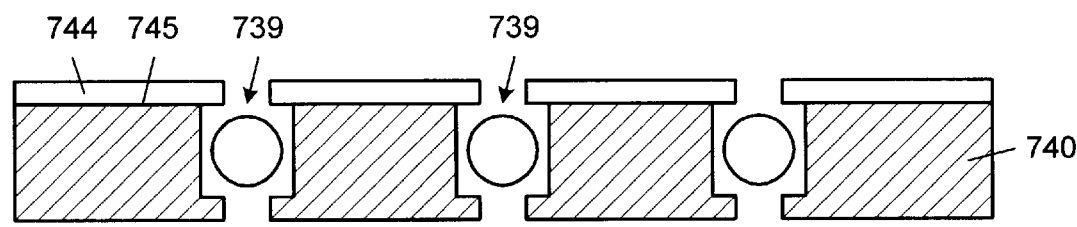
Figure 26D:
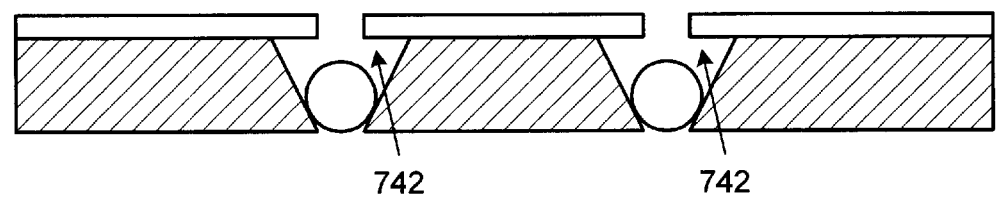

In another embodiment, the supporting member may be formed from a plastic substrate, as depicted in FIG. 26A–E. In one embodiment, the plastic substrate is composed of a material, which is substantially resistant to the fluid, which includes the analyte. Examples of plastic materials which may be used to form the plastic substrate include, but are not limited to, acrylic resins, polycarbonates, polyester resins, polyethylenes, polyimides, polyvinyl polymers (e.g., polyvinyl chloride, polyvinyl acetate, polyvinyl dichloride, polyvinyl fluoride, etc.), polystyrenes, polypropylenes, polytetrafluoroethylenes, and polyurethanes. The plastic substrate may be substantially transparent or substantially opaque to the light produced by the light source. After obtaining a suitable plastic material 740, a series of cavities 742 may be formed in the plastic material. The cavities 742 may be formed by drilling (either mechanically or with a laser), transfer molding (e.g., forming the cavities when the plastic material is formed using appropriately shaped molds), or using a punching apparatus to punch cavities into the plastic material. In one embodiment, the cavities 742 are formed such that a lower portion 743 of the cavities is substantially narrower than an upper portion 744 of the cavities. The lower portion 743 of the cavities may have a width substantially less than a width of a particle. The lower portion 743 of the cavities 742 may inhibit the displacement of a particle from the cavity 742. While depicted as rectangular, with a narrower rectangular opening at the bottom, it should be understood that the cavity may be formed in a number of shapes including but not limited to pyramidal, triangular, trapezoidal, and oval shapes. An example of a pyramidal cavity, which is tapered such that the particle is inhibited from being displaced from the cavity, is depicted in FIG. 26D.

After the cavities 742 are formed, particles 718 may be inserted into the cavities 742, as depicted in FIG. 26B. The lower portion 743 of the cavities may serve as a support for the particles 718. The particles 718 may be inhibited from being displaced from the cavities 742 by the lower portion 743 of the cavity. After the particles are placed in the cavities 742, a cover 744 may be placed upon the upper surface 745 of the plastic substrate 740, as depicted in FIG. 26C. In one embodiment, the cover is formed from a film of photoresist material. After the cover 744 is placed on the plastic substrate 740, openings 739 may be formed in the cover layer to allow the passage of the fluid into the cavities.

After the cavities 742 are formed, particles 718 may be inserted into the cavities 742, as depicted in FIG. 26B. The lower portion 743 of the cavities may serve as a support for the particles 718. The particles 718 may be inhibited from being displaced from the cavities 742 by the lower portion 743 of the cavity. After the particles are placed in the cavities 740, a cover 744 may be placed upon the upper surface 745 of the plastic substrate 740, as depicted in FIG. 26C. In one embodiment, the cover is formed from a film of photoresist material. After the cover 744 is placed on the plastic substrate 740, openings 739 may be formed in the cover layer to allow the passage of the fluid into the cavities.

Figure 26E:
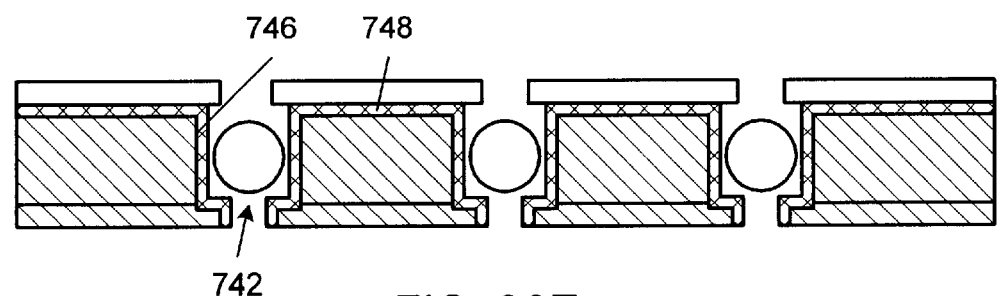

In some circumstances a substantially transparent plastic material may be used. As described above, the use of a transparent supporting member may lead to "cross-talk" between the cavities. To reduce the occurrence of this "cross-talk", a substantially reflective layer 748 may be formed on the inner surface 746 of the cavity, as depicted in FIG. 26E. In one embodiment, the reflective layer 748 is composed of a metal layer which is formed on the inner surface of the cavities 742. The metal layer may be deposited using chemical vapor deposition or other techniques for depositing thin metal layers. The presence of a reflective layer may inhibit cross-talk between the cavities.

Figure 27A:
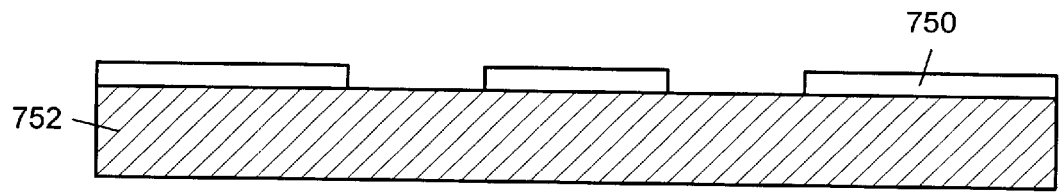
FIGS. 27A–D depict a cross-sectional view of a series of processing steps for the formation of a silicon based sensor array which includes a top cover with openings aligned with the cavity and a tapered cavity.

In another embodiment, a silicon based supporting member for a sensing particle may be formed without a bottom layer. In this embodiment, the cavity may be tapered to inhibit the passage of the particle from the cavity, through the bottom of the supporting member. FIG. 27A–D depicts the formation of a supporting member from a silicon substrate. In this embodiment, a photoresist layer 750 is formed upon an upper surface of silicon based supporting member 752, as depicted in FIG. 27A. The photoresist layer 750 may be patterned and developed such that the regions of the silicon substrate in which the cavities will be formed are exposed.

Figure 27B:
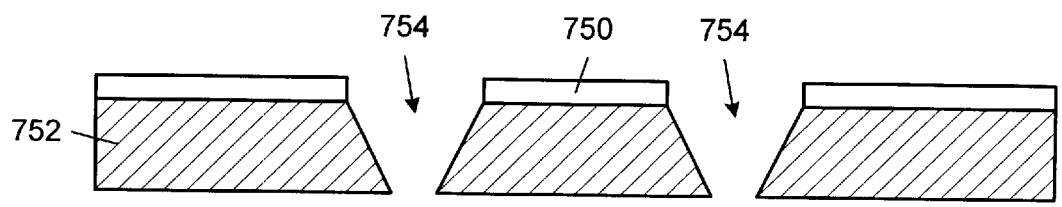
Figure 27C:
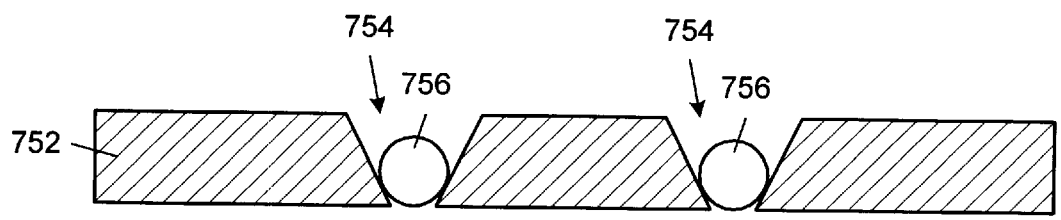
Figure 27D:
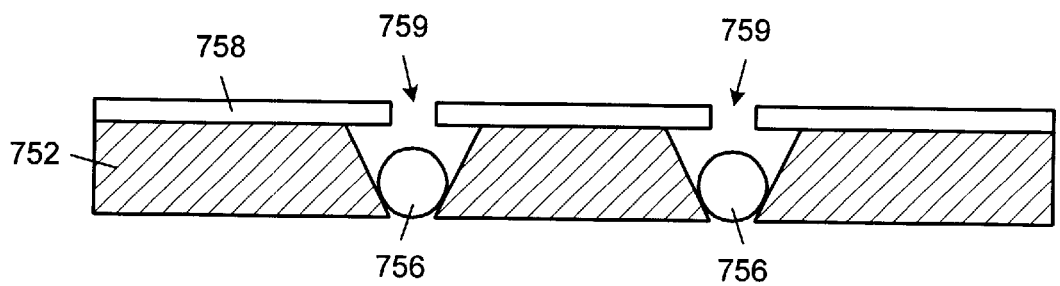

Cavities 754 may now be formed, as depicted in FIG. 27B, by subjecting the silicon substrate to an anisotropic etch. In one embodiment, a potassium hydroxide etch is used to produced tapered cavities. The etching may be controlled such that the width of the bottom of the cavities 754 is less than a width of the particle. After the cavities have been etched, a particle 756 may be inserted into the cavities 754 as depicted in FIG. 27C. The particle 756 may be inhibited from passing out of the cavities 754 by the narrower bottom portion of the cavities. After the particle is positioned within the cavities 754, a cover 758 may be formed upon the silicon based supporting member 752, as depicted in FIG. 27D. The cover may be formed of any material substantially transparent to the light produced by the light source used for analysis. Openings 759 may be formed in the cover 758 to allow the fluid to pass into the cavity from the top face of the silicon based supporting member 752. The openings 759 in the cover and the opening at the bottom of the cavities 754 together may allow fluid to pass through the cavity during use.

Figure 28A:
FIGS. 28A–E depict a cross-sectional view of a series of processing steps for the formation of a photoresist based sensor array which includes a top cover with openings aligned with the cavity and a tapered cavity.
Figure 28B:
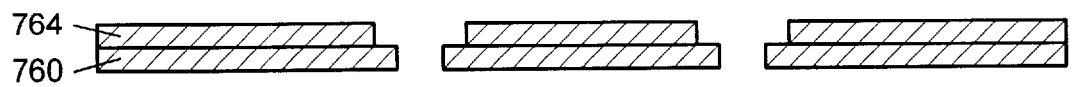

In another embodiment, a supporting member for a sensing particle may be formed from a plurality of layers of a photoresist material. In this embodiment, the cavity may be tapered to inhibit the passage of the particle from the cavity, through the bottom of the supporting member. FIGS. 28A–E depict the formation of a supporting member from a plurality of photoresist layers. In an embodiment, a first photoresist layer 760 is developed and etched to form a series of openings 762 which are positioned at the bottom of subsequently formed cavities, as depicted in FIG. 28A. As depicted in FIG. 28B, a second layer of photoresist material 764 may be formed upon the first photoresist layer 760. The second photoresist layer may be developed and etched to form openings substantially aligned with the openings of the first photoresist layer 760. The openings formed in the second photoresist layer 764, in one embodiment, are substantially larger than the layers formed in the first photoresist layer 760. In this manner, a tapered cavity may be formed while using multiple photoresist layers.

Figure 28C:
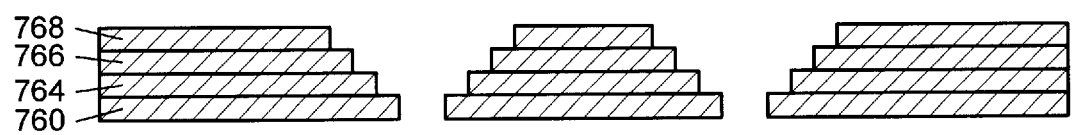

As depicted in FIG. 28C, additional layers of photoresist material 766 and 768 may be formed upon the second photoresist layer 764. The openings of the additional photoresist layers 766 and 768 may be progressively larger as each layer is added to the stack. In this manner, a tapered cavity may be formed. Additional layers of photoresist material may be added until the desired thickness of the supporting member is obtained. The thickness of the supporting member, in one embodiment, is greater than a width of a particle. For example, if a layer of photoresist material has a thickness of about 25 $\mu$m and a particle has a width of about 100 $\mu$m, a supporting member may be formed from four or more layers of photoresist material. While depicted as pyramidal, the cavity may be formed in a number of different shapes, including but not limited to, rectangular, circular, oval, triangular, and trapezoidal. Any of these shapes may be obtained by appropriate patterning and etching of the photoresist layers as they are formed.

Figure 28D:
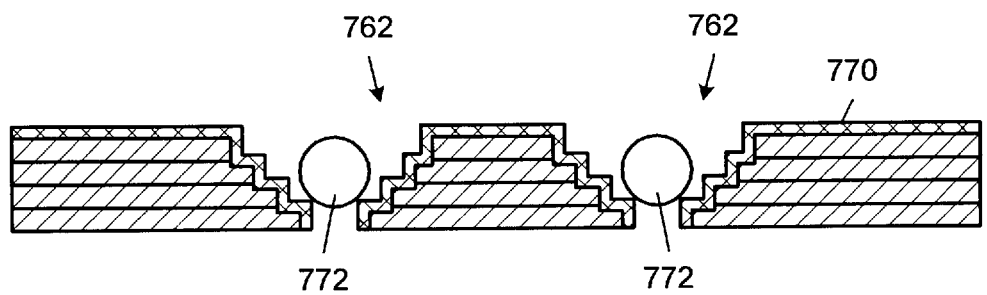

In some instances, the photoresist material may be substantially transparent to the light produced by the light source. As described above, the use of a transparent supporting member may lead to "cross-talk" between the cavities. To reduce the occurrence of this "cross-talk", a substantially reflective layer 770 may be formed along the inner surface of the cavities 762, as depicted in FIG. 28D. In one embodiment, the reflective layer is composed of a metal layer which is formed on the inner surface of the cavities 762. The metal layer may be deposited using chemical vapor deposition or other techniques for depositing thin metal layers. The presence of a reflective layer may inhibit "cross-talk" between the cavities.

Figure 28E:
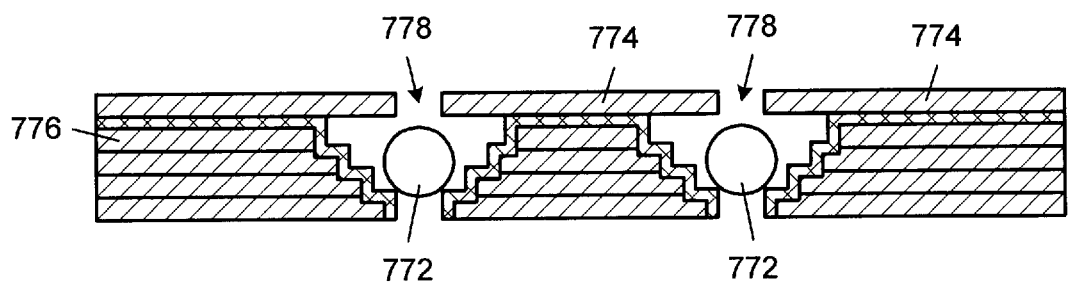

After the cavities 762 are formed, particles 772 may be inserted into the cavities 762, as depicted in FIG. 28D. The narrow portions of the cavities 762 may serve as a support for the particles 772. The particles 772 may be inhibited from being displaced from the cavities 762 by the lower portion of the cavities. After the particles 772 are placed in the cavities 762, a cover 774 may be placed upon the upper surface of the top layer 776 of the supporting member, as depicted in FIG. 28E. In one embodiment, the cover 774 is also formed from a film of photoresist material. After the cover layer is formed, openings 778 may be formed in the cover 774 to allow the passage of the fluid into the cavities.

Figure 29A:
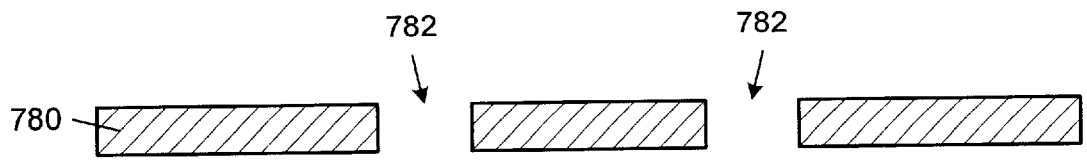
FIGS. 29A–E depict a cross-sectional view of a series of processing steps for the formation of a photoresist based sensor array which includes a top cover with openings aligned with the cavity and a bottom cover.
Figure 29B:
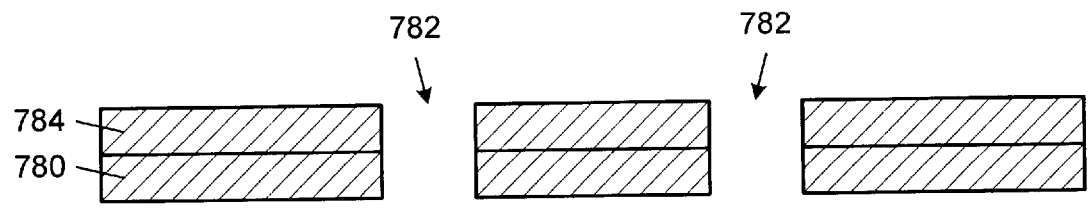

In another embodiment, a supporting member for a sensing particle may be formed from photoresist material which includes a particle support layer. FIGS. 29A–E depict the formation of a supporting member from a series of photoresist layers. In an embodiment, a first photoresist layer 780 is developed and etched to form a series of openings 782 which may become part of subsequently formed cavities. In another embodiment, a cavity having the appropriate depth may be formed by forming multiple layers of a photoresist material, as described previously. As depicted in FIG. 29B, a second photoresist layer 784 may be formed upon the first photoresist layer 780. The second photoresist layer 784 may be patterned to form openings substantially aligned with the openings of the first photoresist layer 782. The openings formed in the second photoresist layer 784 may be substantially equal in size to the previously formed openings. Alternatively, the openings may be variable in size to form different shaped cavities.

Figure 29C:
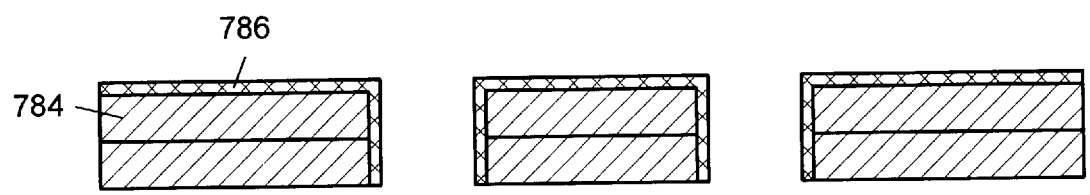

For reasons described above, a substantially reflective layer 786 may be formed along the inner surface of the cavities 782 and the upper surface of the second photoresist layer 784, as depicted in FIG. 29C. In one embodiment, the reflective layer is composed of a metal layer. The metal layer may be deposited using chemical vapor deposition or other techniques for depositing thin metal layers. The presence of a reflective layer may inhibit "cross-talk" between the cavities.

Figure 29D:
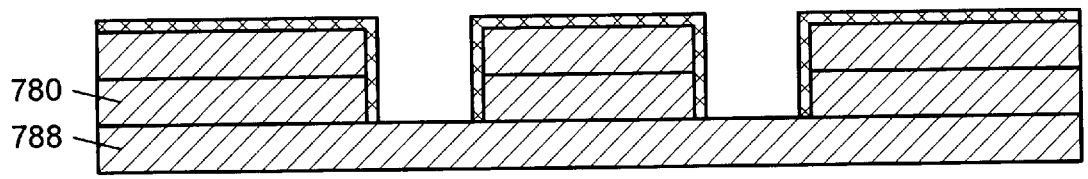

After the metal layer is deposited, a particle support layer 788 may be formed on the bottom surface of the first photoresist layer 780, as depicted in FIG. 29D. The particle support layer 788 may be formed from photoresist material, silicon dioxide, silicon nitride, glass or a substantially transparent plastic material. The particle support layer 788 may serve as a support for the particles placed in the cavities 782. The particle support layer, in one embodiment, is formed from a material that is substantially transparent to the light produced by the light source.

Figure 29E:
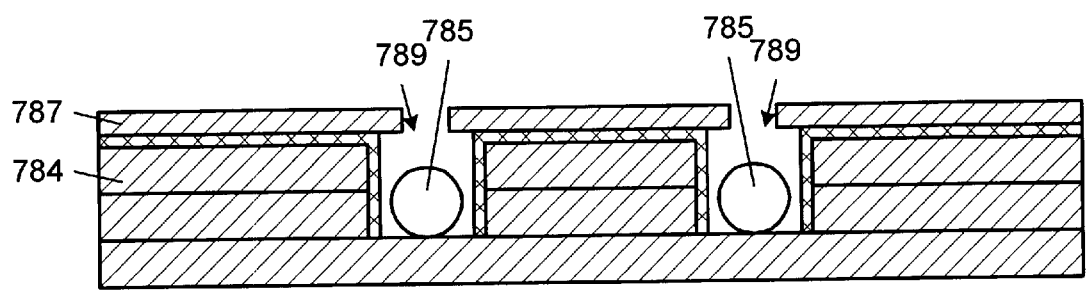

After the particle supporting layer 788 is formed, particles 785 may be inserted into the cavities 782, as depicted in FIG. 29E. The particle support layer 788 may serve as a support for the particles. Thus the particles 785 may be inhibited from being displaced from the cavities by the particle support layer 788. After the particles 785 are placed in the cavities 782, a cover 787 may be placed upon the upper surface of the second photoresist layer 784, as depicted in FIG. 29E. In one embodiment, the cover is also formed from a film of photoresist material. After the cover is formed, openings 789 may be formed in the cover 787 to allow the passage of the fluid into the cavities. In this embodiment, the fluid is inhibited from flowing through the supporting member. Instead, the fluid may flow into and out of the cavities via the openings 789 formed in the cover 787.

Figure 30A:
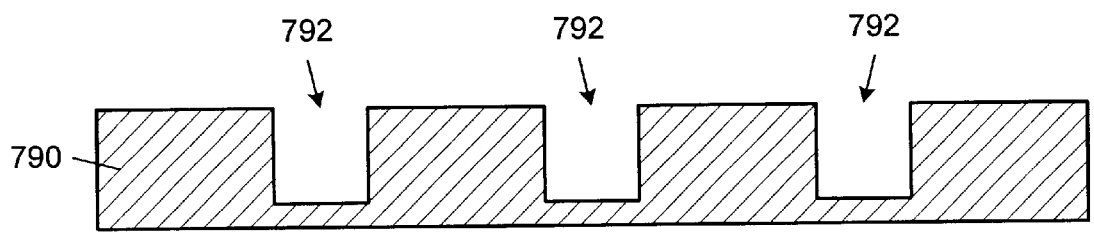
FIGS. 30A–D depict a cross-sectional view of a series of processing steps for the formation of a plastic based sensor array which includes a top cover with openings aligned with the cavity and a bottom cover.
Figure 30B:
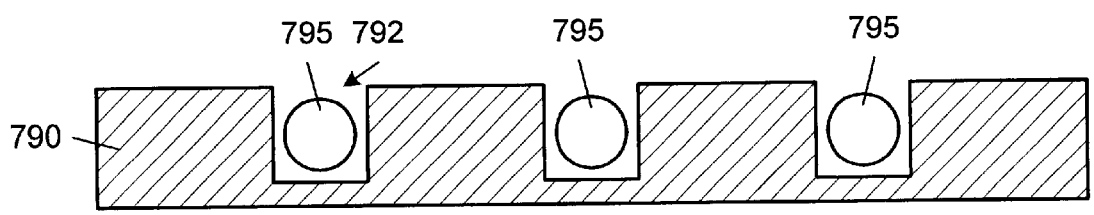
Figure 30C:
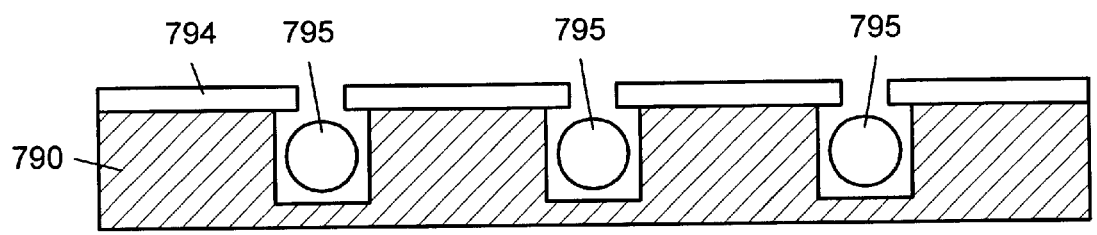
Figure 30D:
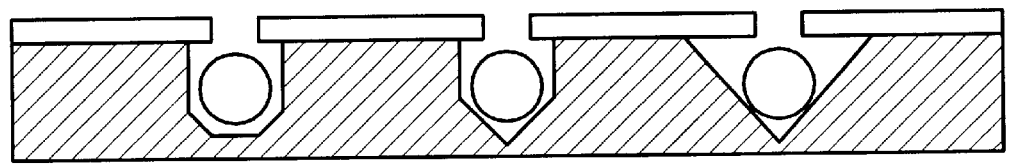

A similar supporting member may be formed from a plastic material, as depicted in FIGS. 30A–D. The plastic material may be substantially resistant to the fluid which includes the analyte. The plastic material may be substantially transparent or substantially opaque to the light produced by the light source. After obtaining a suitable plastic substrate 790, a series of cavities 792 may be formed in the plastic substrate 790. The cavities may be formed by drilling (either mechanically or with a laser), transfer molding (e.g., forming the cavities when the plastic substrate is formed using appropriately shaped molds), or using a punching machine to form the cavities. In one embodiment, the cavities extend through a portion of the plastic substrate, terminating proximate the bottom of the plastic substrate, without passing through the plastic substrate. After the cavities 792 are formed, particles 795 may be inserted into the cavities 792, as depicted in FIG. 30B. The bottom of the cavity may serve as a support for the particles 795. After the particles are placed in the cavities, a cover 794 may be placed upon the upper surface of the plastic substrate 790, as depicted in FIG. 30C. In one embodiment, the cover may be formed from a film of photoresist material. After the cover 794 is formed, openings 796 may be formed in the cover to allow the passage of the fluid into the cavities. While depicted as rectangular, is should be understood that the cavities may be formed in a variety of different shapes, including triangular, pyramidal, pentagonal, polygonal, oval, or circular. It should also be understood that cavities having a variety of different shapes may be formed into the same plastic substrate, as depicted in FIG. 30D.

Figure 31:
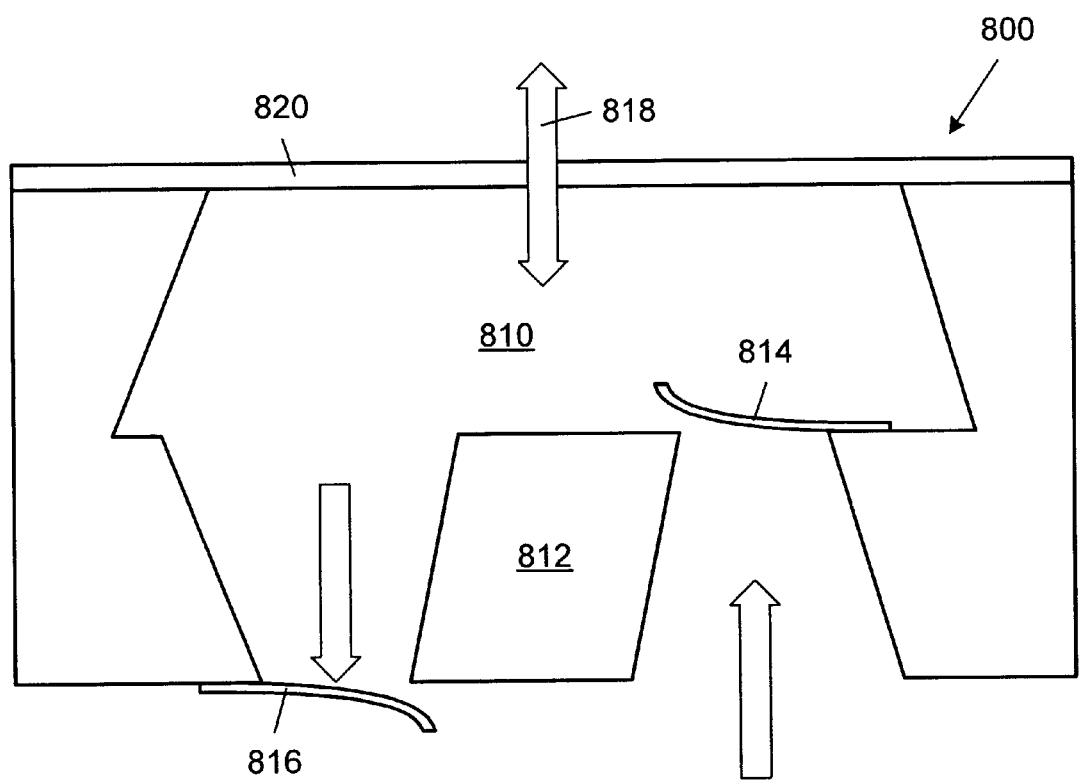
FIG. 31 depicts a cross-sectional view of a schematic of a micropump.

In one embodiment, a series of channels may be formed in the supporting member interconnecting some of the cavities, as depicted in FIG. 3. Pumps and valves may also be incorporated into the supporting member to aid passage of the fluid through the cavities. A schematic figure of a diaphragm pump 800 is depicted in FIG. 31. Diaphragm pumps, in general, include a cavity 810, a flexible diaphragm 812, an inlet valve 814, and an outlet valve 816. The flexible diaphragm 812, during use, is deflected as shown by arrows 818 to create a pumping force. As the diaphragm is deflected toward the cavity 810 it may cause the inlet valve 814 to close, the outlet valve 816 to open and any liquid which is in the cavity 810 will be forced toward the outlet 816. As the diaphragm moves away from the cavity 810, the outlet valve 816 may be pulled to a closed position, and the inlet valve 814 may be opened, allowing additional fluid to enter the cavity 810. In this manner a pump may be used to pump fluid through the cavities. It should be understood that the pump depicted in FIG. 31 is a generalized version of a diaphragm based pump. Actual diaphragm pumps may have different shapes or may have inlet and outlet valves which are separate from the pumping device.

In one embodiment, the diaphragm 810 may be made from a piezoelectric material. This material will contract or expand when an appropriate voltage is applied to the diaphragm. Pumps using a piezoelectric diaphragms are described in U.S. Pat. Nos. 4,344,743, 4,938,742, 5,611,676, 5,705,018, and 5,759,015, all of which are incorporated herein by reference. In other embodiments, the diaphragm may be activated using a pneumatic system. In these systems, an air system may be coupled to the diaphragm such that changes in air density about the diaphragm, induced by the pneumatic system, may cause the diaphragm to move toward and away from the cavity. A pneumatically controlled pump is described in U.S. Pat. No. 5,499,909 which is incorporated herein by reference. The diaphragm may also be controlled using a heat activated material. The diaphragm may be formed from a temperature sensitive material. In one embodiment, the diaphragm may be formed from a material which is configured to expand and contract in response to temperature changes. A pump system which relies on temperature activated diaphragm is described in U.S. Pat. No. 5,288,214 which is incorporated herein by reference.

Figure 32:
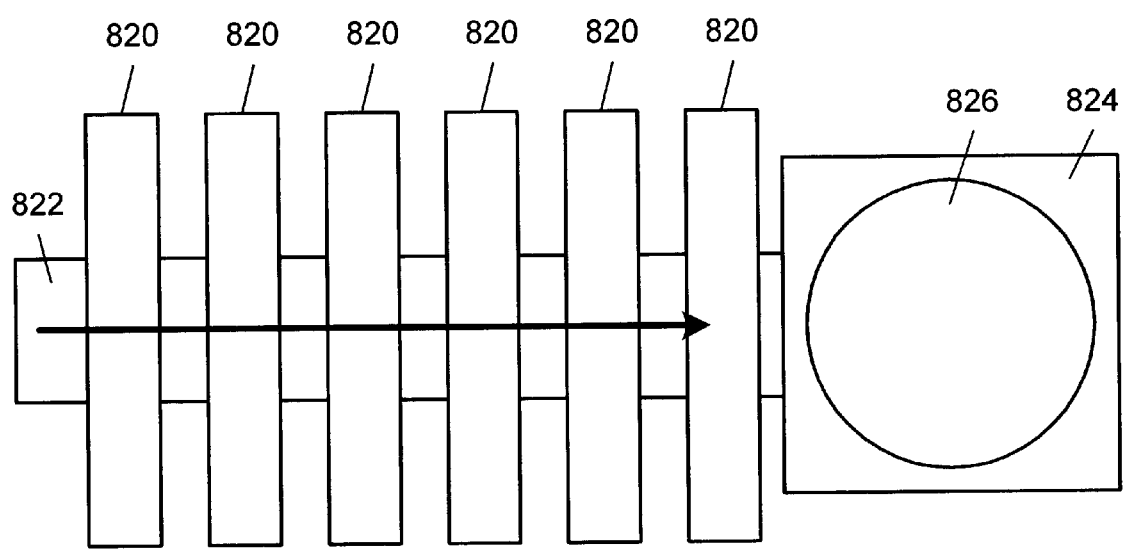
FIG. 32 depicts a top view of an electrohydrodynamic pump.

In another embodiment, an electrode pump system may be used. FIG. 32 depicts a typical electrode based system. A series of electrodes 820 may be arranged along a channel 822 which may lead to a cavity 824 which includes a particle 826. By varying the voltage in the electrodes 820 a current flow may be induced in the fluid within the channel 822. Examples of electrode based systems include, but are not limited to, electroosmosis systems, electrohydrodynamic systems, and combinations of electroosmosis and electrohydrodynamic systems.

Electrohydrodynamic pumping of fluids is known and may be applied to small capillary channels. In an electrohydrodynamic system electrodes are typically placed in contact with the fluid when a voltage is applied. The applied voltage may cause a transfer in charge either by transfer or removal of an electron to or from the fluid. This electron transfer typically, induces liquid flow in the direction from the charging electrode to the oppositely charged electrode. Electrohydrodynamic pumps may be used for pumping fluids such as organic solvents.

Electroosmosis, is a process which involves applying a voltage to a fluid in a small space, such as a capillary channel, to cause the fluid to flow. The surfaces of many solids, including quartz, glass and the like, become variously charged, negatively or positively, in the presence of ionic materials, such as for example salts, acids or bases. The charged surfaces will attract. oppositely charged (positive or negative) counterions in aqueous solutions. The application of a voltage to such a solution results in a migration of the counterions to the oppositely charged electrode, and moves the bulk of the fluid as well. The volume flow rate is proportional to the current, and the volume flow generated in the fluid is also proportional to the applied voltage. An electroosmosis pump system is described in U.S. Pat. No. 4,908,112 which is incorporated herein by reference.

In another embodiment, a combination of electroosmosis pumps and electrohydrodynamic pumps may be used. Wire electrodes may be inserted into the walls of a channel at preselected intervals to form alternating electroosmosis and electrohydrodynarnic devices. Because electroosmosis and electrohydrodynamic pumps are both present, a plurality of different solutions, both polar and non-polar, may be pump along a single channel. Alternatively, a plurality of different solutions may be passed along a plurality of different channels connected to a cavity. A system which includes a combination of electroosmosis pumps and electrohydrodynamic pumps is described in U.S. Pat. No. 5,632,876 which is incorporated herein by reference.

Figure 33:
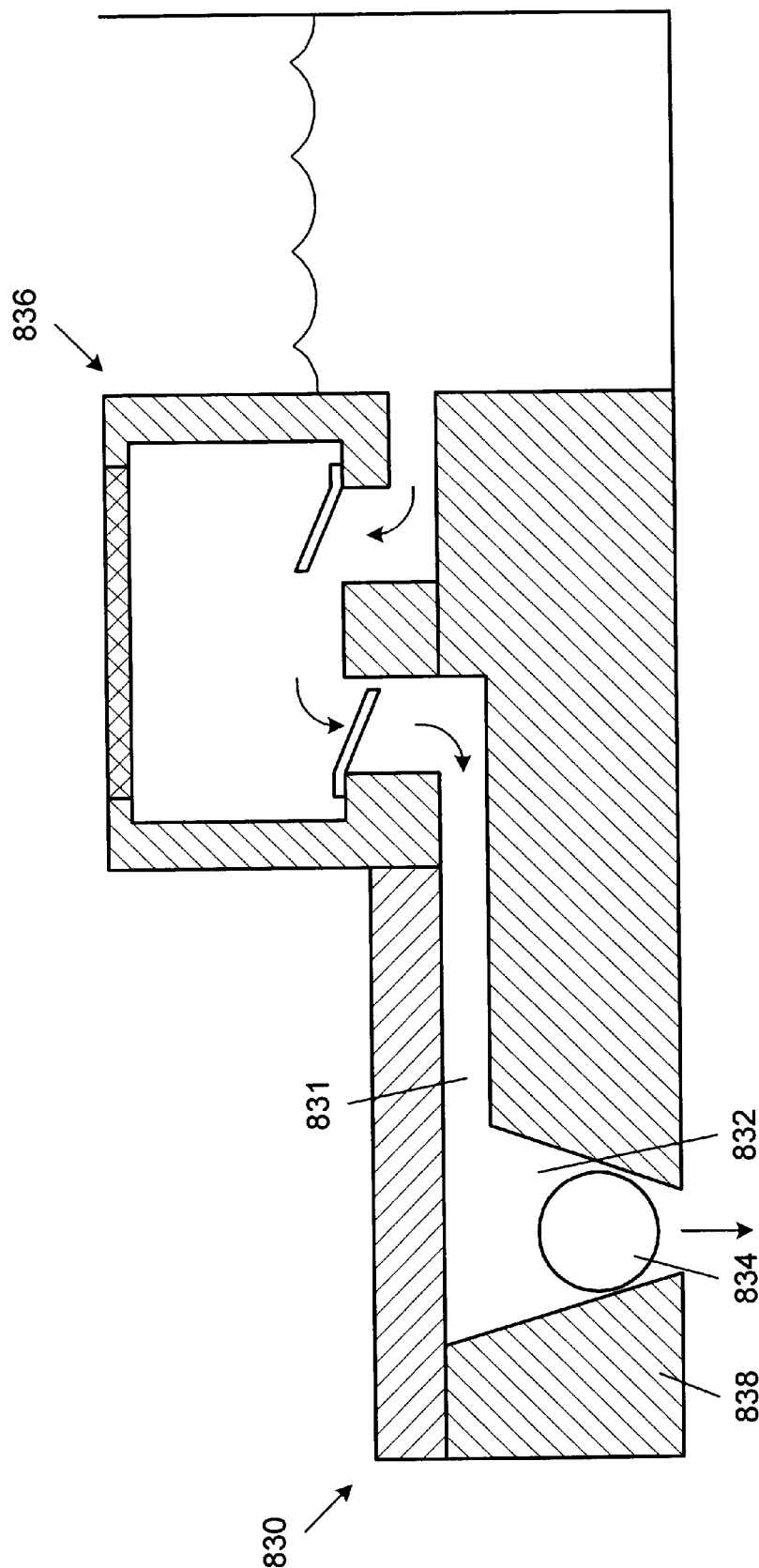
FIG. 33 depicts a cross-sectional view of a sensor array which includes a micropump.

In an embodiment, a pump may be incorporated into a sensor array system, as depicted in FIG. 33. A sensor array 830 includes at least one cavity 832 in which a particle 834 may be placed. The cavity 832 may be configured to allow fluid to pass through the cavity during use. A pump 836 may be incorporated onto a portion of the supporting member 838. A channel 831 may be formed in the supporting member 838 coupling the pump 836 to the cavity 832. The channel 831 may be configured to allow the fluid to pass from the pump 836 to the cavity 832. The pump 836 may be positioned away from the cavity 832 to allow light to be directed through the cavity during use. The supporting member 838 and the pump 836 may be formed from a silicon substrate, a plastic material, or photoresist material. The pump 836 may be configured to pump fluid to the cavity via the channel, as depicted by the arrows in FIG. 33. When the fluid reaches the cavity 832, the fluid may flow past the particle 834 and out through the bottom of the cavity. An advantage of using pumps is that better flow through the channels may be achieved. Typically, the channels and cavities may have a small volume. The small volume of the cavity and channel tends to inhibit flow of the fluid through the cavity. By incorporating a pump, the flow of fluid to the cavity and through the cavity may be increased, allowing more rapid testing of the fluid sample. While a diaphragm based pump system is depicted in FIG. 33, it should be understood that electrode based pumping systems might also be incorporated into the sensor array to produce fluid flows.

Figure 34:
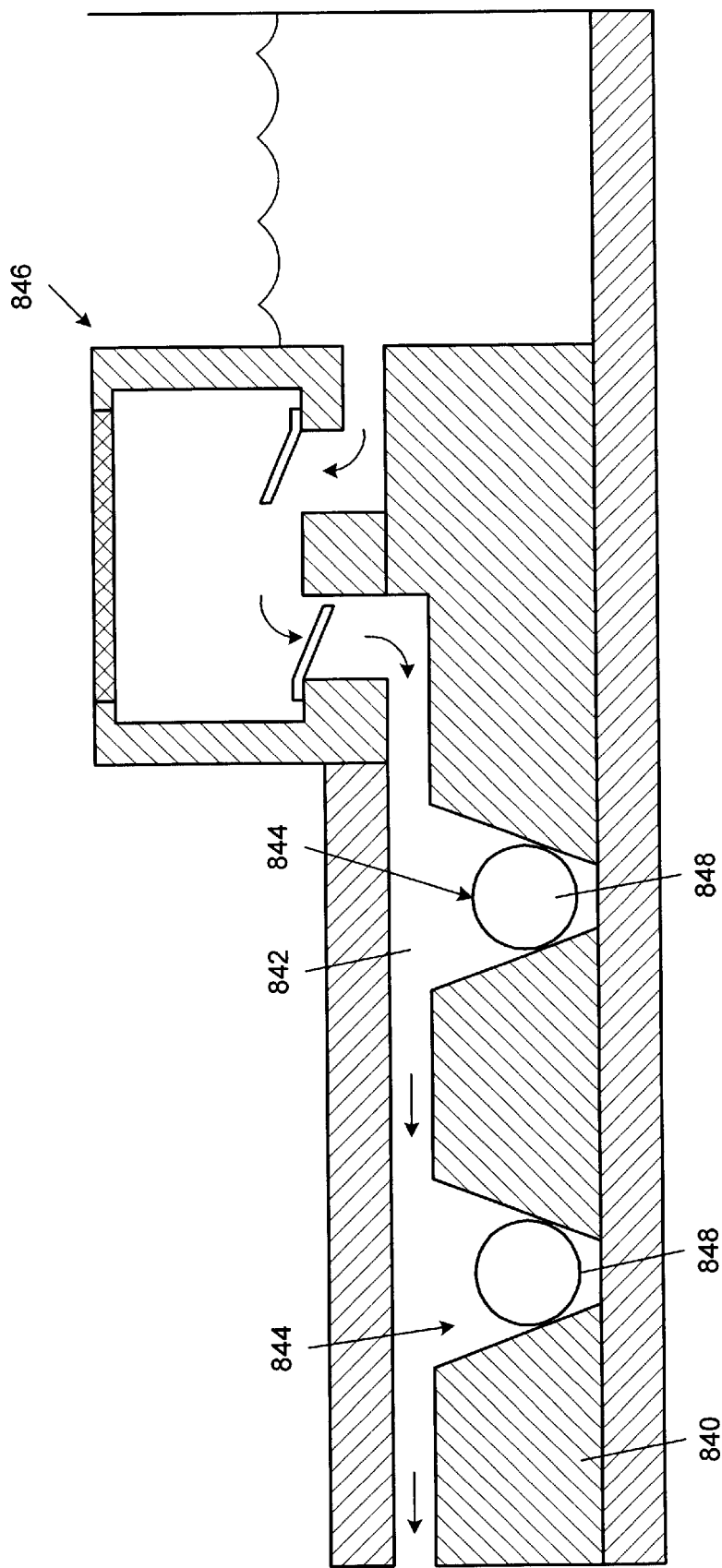
FIG. 34 depicts a cross-sectional view of a sensor array which includes a micropump and channels which are coupled to the cavities.

In another embodiment, a pump may be coupled to a supporting member for analyzing analytes in a fluid stream, as depicted in FIG. 34. A channel 842 may couple a pump 846 to multiple cavities 844 formed in a supporting member 840. The cavities 842 may include sensing particles 848. The pump may be configured to create a flow of the fluid through the channel 842 to the cavities 848. In one embodiment, the cavities may inhibit the flow of the fluid through the cavities 844. The fluid may flow into the cavities 844 and past the particle 848 to create a flow of fluid through the sensor array system. In this manner, a single pump may be used to pass the fluid to multiple cavities. While a diaphragm pump system is depicted in FIG. 34, it should be understood that electrode pumping systems might also be incorporated into the supporting member to create similar fluid flows.

Figure 35:
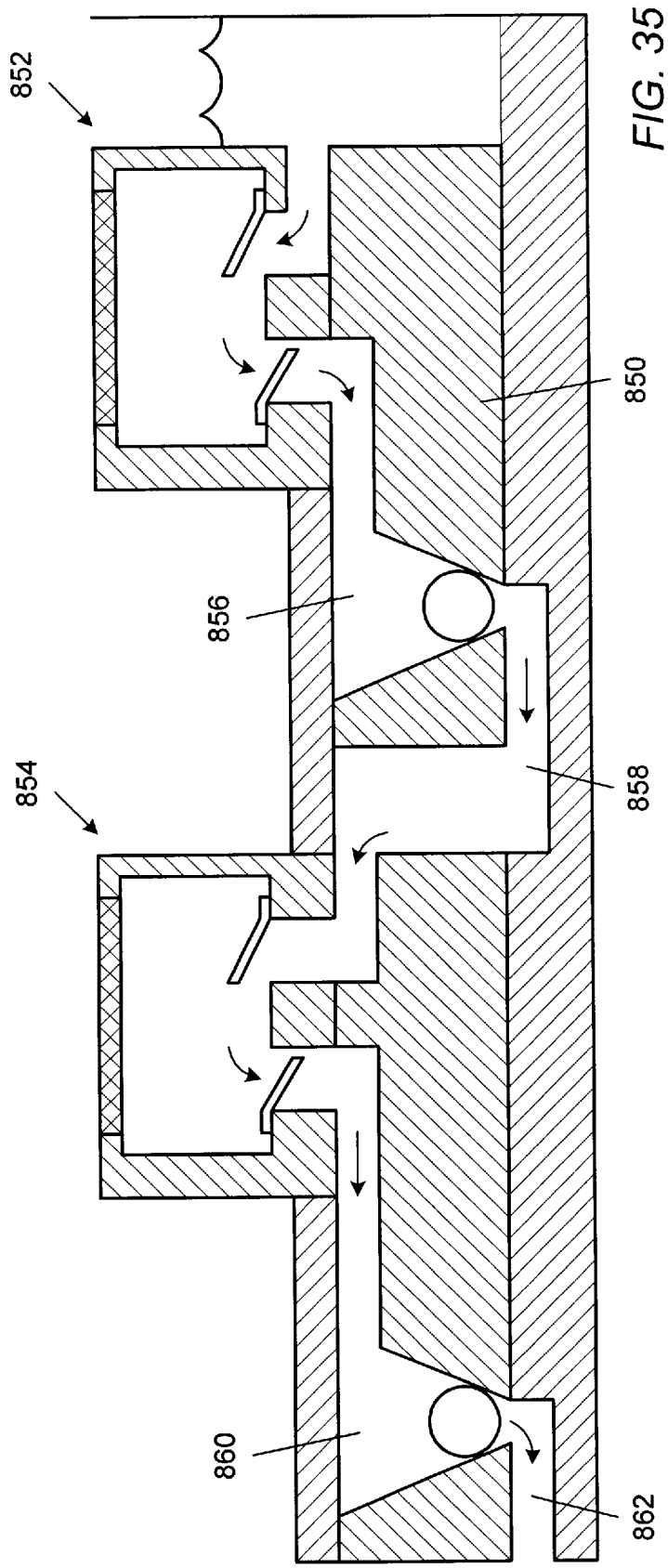
FIG. 35 depicts a cross-sectional view of a sensor array which includes multiple micropumps each micropump being coupled to a cavity.

In another embodiment, multiple pumps may be coupled to a supporting member of a sensor array system. In one embodiment, the pumps may be coupled in series with each other to pump fluid to each of the cavities. As depicted in FIG. 35, a first pump 852 and a second pump 854 may be coupled to a supporting member 850. The first pump 852 may be coupled to a first cavity 856. The first pump may be configured to transfer fluid to the first cavity 856 during use. The cavity 856 may be configured to allow the fluid to pass through the cavity to a first cavity outlet channel 858. A second pump 854 may also be coupled to the supporting member 850. The second pump 854 may be coupled to a second cavity 860 and the first cavity outlet channel 858. The second pump 854 may be configured to transfer fluid from the first cavity outlet channel 858 to the second cavity 860. The pumps may be synchronized such that a steady flow of fluid through the cavities is obtained. Additional pumps may be coupled to the second cavity outlet channel 862 such that the fluid may be pumped to additional cavities. In one embodiment, each of the cavities in the supporting member is coupled to a pump configured to pump the fluid stream to the cavity.

Figure 36:
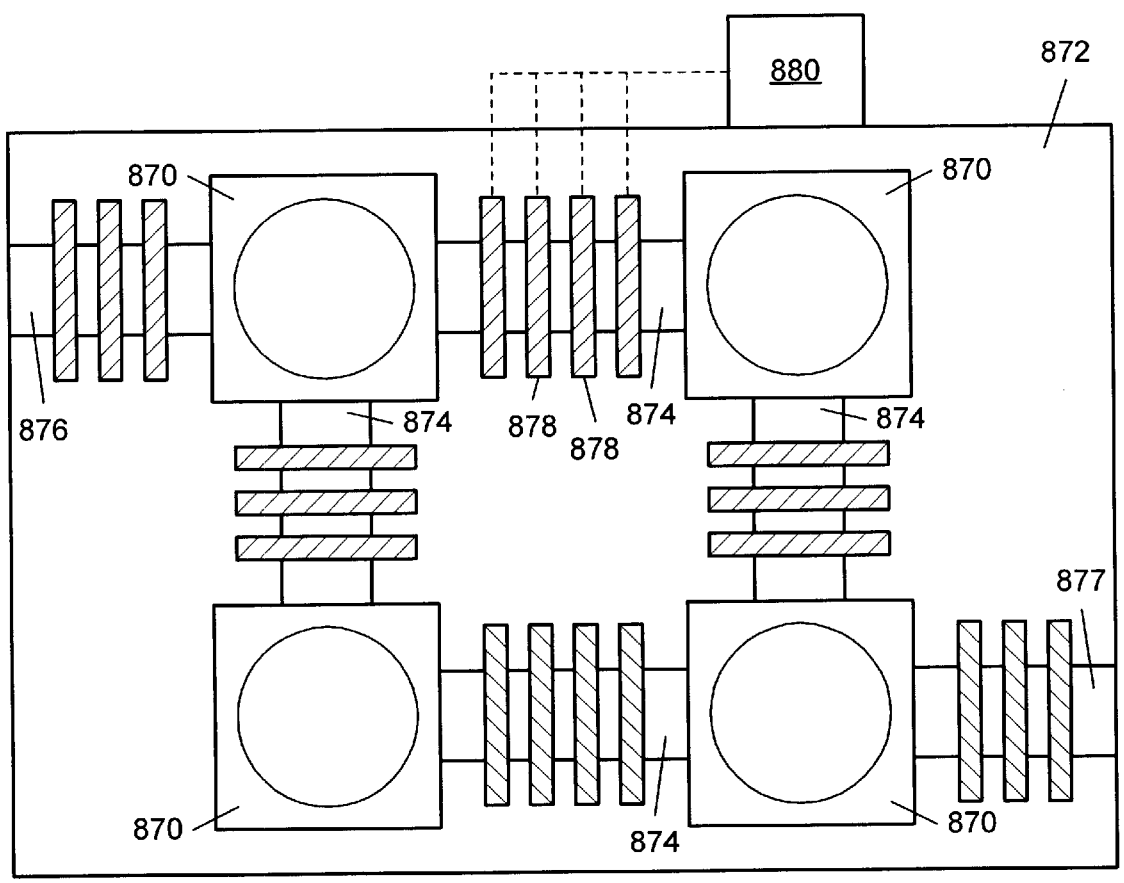
FIG. 36 depicts a top view of a sensor array which includes multiple electrohydrodynamic pumps.

In another embodiment, multiple electrode based pumps may be incorporated herein into the sensor array system. The pumps may be formed along the channels which couple the cavities. As depicted in FIG. 36, a plurality of cavities 870 may be formed in a supporting member 872 of a sensor array. Channels 874 may also be formed in the supporting member 872 interconnecting the cavities 870 with each other. An inlet channel 876 and an outlet channel 877, which allow the fluid to pass into and out of the sensor array, respectively, may also be formed. A series of electrodes 878 may be positioned over the channels 874, 876, and 877. The electrodes may be used to form an electroosmosis pumping system or an electrohydrodynamic pumping system. The electrodes may be coupled to a controller 880 which may apply the appropriate voltage to the appropriate electrodes to produce a flow of the fluid through the channels. The pumps may be synchronized such that a steady flow of fluid through the cavities is obtained. The electrodes may be positioned between the cavities such that the electrodes do not significantly interfere with the application of light to the cavities.

Figure 37:
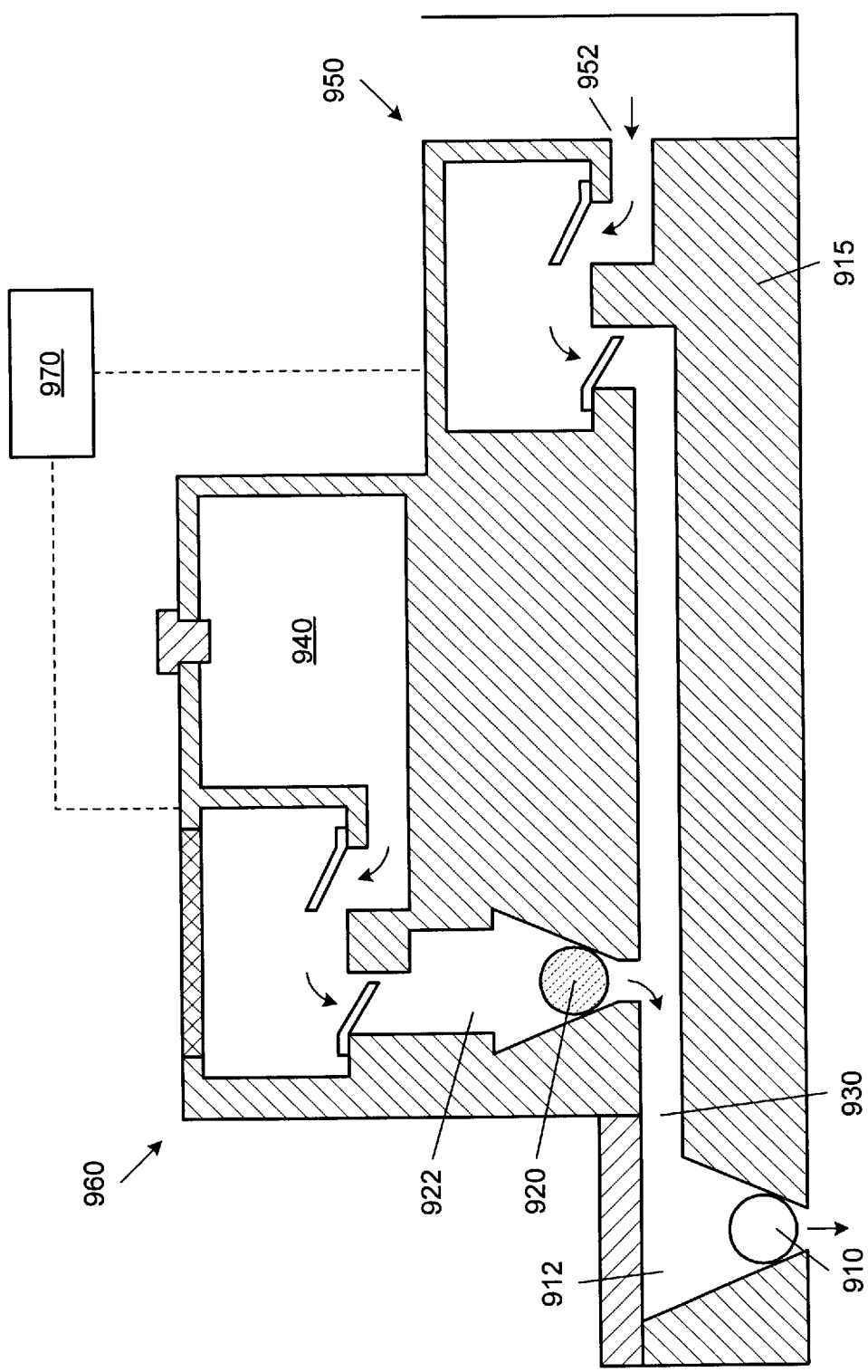
FIG. 37 depicts a cross-sectional view of a sensor array which includes a system for delivering a reagent from a reagent particle to a sensing cavity.

In some instances, it may be necessary to add a reagent to a particle before, during or after an analysis process. Reagents may include receptor molecules or indicator molecules. Typically, such reagents may be added by passing a fluid stream, which includes the reagent over the sensor array. In an embodiment, the reagent may be incorporated herein into the sensor array system, which includes two particles. In this embodiment, a sensor array system may include two particles 910 and 920 for each sensing position of the sensor array, as depicted in FIG. 37. The first particle 910 may be positioned in a first cavity 912. The second particle 920 may be positioned in a second cavity 922. In one embodiment, the second cavity is coupled to the first cavity via a channel 930. The second particle includes a reagent, which is at least partially removable from the second particle 920. The reagent may also be configured to modify the first particle 910, when the reagent is contacted with the first particle, such that the first particle will produce a signal when the first particle interacts with an analyte during use. The reagent may be added to the first cavity before, during or after a fluid analysis. The reagent is preferably coupled to the second particle 920. A portion of the reagent coupled to the second particle may be decoupled from the particle by passing a decoupling solution past the second particle. The decoupling solution may include a decoupling agent, which will cause at least a portion of the reagent to be at released by the particle. A reservoir 940 may be formed on the sensor array to hold the decoupling solution.

A first pump 950 and a second pump 960 may also be coupled to the supporting member 915. The first pump 950 may be configured to pump fluid from a fluid inlet 952 to the first cavity 912 via channel 930. The fluid inlet 952 is the location where the fluid, which includes the analyte, is introduced into the sensor array system. A second pump 950 may be coupled to the reservoir 940 and the second cavity 922. The second pump 960 may be used to transfer the decoupling solution from the reservoir to the second cavity 922. The decoupling solution may pass through the second cavity 922 and into first cavity 912. Thus, as the reagent is removed the second particle it may be transferred to the first cavity 912, where the reagent may interact with the first particle 910. The reservoir may be refilled by removing the reservoir outlet 942, and adding additional fluid to the reservoir 940. While diaphragm based pump systems are depicted in FIG. 37, it should be understood that electrode based pumping systems may also be incorporated herein into the sensor array to produce fluid flows.

The use of such a system is described by way of example. In some instances it may be desirable to add a reagent to the first particle prior to passing the fluid which includes the analyte to the first particle. The reagent may be coupled to the second particle and placed in the sensor array prior to use, typically during construction of the array. A decoupling solution may be added to the reservoir before use. A controller 970 may also be coupled to the system to allow automatic operation of the pumps. The controller 970 may be configured to initiate the analysis sequence by activating the second pump 960, causing the decoupling solution to flow from the reservoir 940 to the second cavity 922. As the fluid passes through the second cavity 922, the decoupling solution may cause at least some of the reagent molecules to be released from the second particle 920. The decoupling solution may be passed out of the second cavity 922 and into the first cavity 912. As the solution passes through the first cavity, some of the reagent molecules may be captured by the first particle 910. After a sufficient number of molecules have been captured by the first particle 910, flow of fluid thorough the second cavity 922 may be stopped. During this initialization of the system, the flow of fluid through the first pump may be inhibited.

After the system is initialized, the second pump may be stopped and the fluid may be introduced to the first cavity. The first pump may be used to transfer the fluid to the first cavity. The second pump may remain off, thus inhibiting flow of fluid from the reservoir to the first cavity. It should be understood that the reagent solution may be added to the first cavity while the fluid is added to the first cavity. In this embodiment, both the first and second pumps may be operated substantially simultaneously.

Alternatively, the reagent may be added after an analysis. In some instances, a particle may interact with an analyte such that a change in the receptors attached to the first particle occurs. This change may not, however produce a detectable signal. The reagent attached to the second bead may be used to produce a detectable signal when it interacts with the first particle, if a specific analyte is present. In this embodiment, the fluid is introduced into the cavity first. After the analyte has been given time to react with the particle, the reagent may be added to the first cavity. The interaction of the reagent with the particle may produce a detectable signal. For example, an indicator reagent may react with a particle which has been exposed to an analyte to produce a color change on the particle. Particle which have not been exposed to the analyte may remain unchanged or show a different color change.

As shown in FIG. 1, a system for detecting analytes in a fluid may include a light source 110, a sensor array 120 and a detector 130. The sensor array 120 is preferably formed of a supporting member which is configured to hold a variety of particles 124 in an ordered array. A high sensitivity CCD array may be used to measure changes in optical characteristics which occur upon binding of the biological/chemical agents. Data acquisition and handling is preferably performed with existing CCD technology. As described above, colorimetric analysis may be performed using a white light source and a color CCD detector. However, color CCD detectors are typically more expensive than gray scale CCD detectors.

In one embodiment, a gray scale CCD detector may be used to detect colorimetric changes. In one embodiment, a gray scale detector may be disposed below a sensor array to measure the intensity of light being transmitted through the sensor array. A series of lights (e.g., light emitting diodes) may be arranged above the sensor array. In one embodiment, groups of three LED lights may be arranged above each of the cavities of the array. Each of these groups of LED lights may include a red, blue and a green light. Each of the lights may be operated individually such that one of the lights may be on while the other two lights are off. In order to provide color information while using a gray scale detector, each of the lights is sequentially turned on and the gray scale detector is used to measure the intensity of the light passing through the sensor array. After information from each of the lights is collected, the information may be processed to derive the absorption changes of the particle.

In one embodiment, the data collected by the gray scale detector may be recorded using 8 bits of data. Thus, the data will appear as a value between 0 and 255. The color of each chemical sensitive element may be represented as a red, blue and green value. For example, a blank particle (i.e., a particle which does not include a receptor) will typically appear white. When each of the LED lights (red, blue and green) are operated the CCD detector will record a value corresponding to the amount of light transmitted through the cavity. The intensity of the light may be compared to a blank particle, to determine the absorbance of a particle with respect to the LED light which is used. Thus, the red, green and blue components may be recorded individually without the use of a color CCD detector. In one embodiment, it is found that a blank particle exhibits an absorbance of about 253 when illuminated with a red LED, a value of about 250 when illuminated by a green LED, and a value of about 222 when illuminated with a blue LED. This signifies that a blank particle does not significantly absorb red, green or blue light. When a particle with a receptor is scanned, the particle may exhibit a color change, due to absorbance by the receptor. For example, it was found that when a particle which includes a 5-carboxyfluorescein receptor is subjected to white light, the particle shows a strong absorbance of blue light. When a red LED is used to illuminate the particle, the gray scale CCD detector may detect a value of about 254. When the green LED is used, the gray scale detector may detect a value of about 218. When a blue LED light is used, a gray scale detector may detect a value of about 57. The decrease in transmittance of blue light is believed to be due to the absorbance of blue light by the 5-carboxyfluorescein. In this manner the color changes of a particle may be quantitatively characterized using a gray scale detector.

As described above, after the cavities are formed in the supporting member, a particle may be positioned at the bottom of a cavity using a micromanipulator. This allows the location of a particular particle to be precisely controlled during the production of the array. The use of a micromanipulator may, however, be impractical for production of sensor array systems. An alternate method of placing the particles into the cavities may involve the use of a silk screen like process. A series of masking materials may be placed on the upper surface of the sensor array prior to filling the cavities. The masking materials may be composed of glass, metal or plastic materials. A collection of particles may be placed upon the upper surface of the masking materials and the particles may be moved across the surface. When a cavity is encountered, a particle may drop into the cavity if the cavity is unmasked. Thus particles of known composition are placed in only the unmasked regions. After the unmasked cavities are filled, the masking pattern may be altered and a second type of particles may be spread across the surface. Preferably, the masking material will mask the cavities that have already been filled with particle. The masking material may also mask other non-filled cavities. This technique may be repeated until all of the cavities are filled. After filling the cavities, a cover may be placed on the support member, as described above, to inhibit the displacement and mixing of the particles. An advantage of such a process is that it may be more amenable to industrial production of supporting members.

2. Further System Improvements

One challenge in a chemical sensor system is keeping dead volume to a minimum. This is especially problematic when an interface to the outside world is required (e.g., a tubing connection). In many cases the "dead volume" associated with the delivery of the sample to the reaction site in a "lab-on-a-chip" may far exceed the actual amount of reagent required for the reaction. Filtration is also frequently necessary to prevent small flow channels in the sensor arrays from plugging. Here the filter can be made an integral part of the sensor package.

Figure 38:
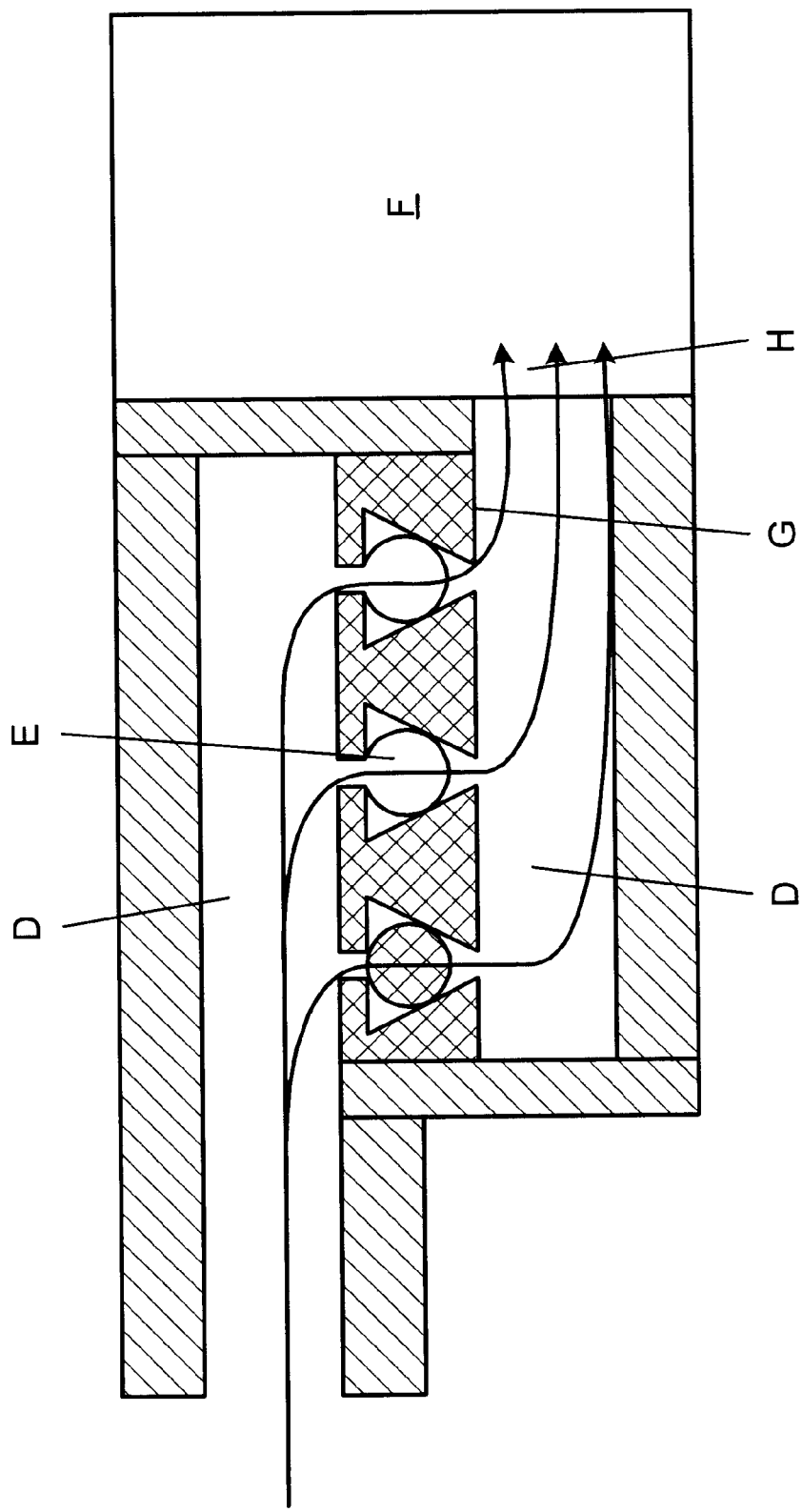
FIG. 38 depicts a cross-sectional view of a sensor array which includes a vacuum chamber.

In an embodiment, a system for detecting an analyte in a fluid includes a conduit coupled to a sensor array and a vacuum chamber coupled to the conduit. FIG. 38 depicts a system in which a fluid stream (E) passes through a conduit (D), onto a sensor array (G), and into a vacuum apparatus (F). The vacuum apparatus (F) may be coupled to the conduit (D) downstream from the sensor array (G). A vacuum apparatus is herein defined to be any system capable of creating or maintaining a volume at a pressure below atmospheric. Examples of vacuum apparatus include vacuum chambers. Vacuum chamber, in one embodiment, may be sealed tubes from which a portion of the air has been evacuated, creating a vacuum within the tube. A commonly used example of such a sealed tube is a "vacutainer" system commercially available from Becton Dickinson. Alternatively, a vacuum chamber which is sealed by a movable piston may also be used to generate a vacuum. For example, a syringe may be coupled to the conduit. Movement of the piston (i.e., the plunger) away from the chamber will create a partial vacuum within the chamber. Alternatively, the vacuum apparatus may be a vacuum pump or vacuum line. Vacuum pumps may include direct drive pumps, oil pumps, aspirator pumps or micropumps. Micropumps that may be incorporated into a sensor array system have been previously described.

Figure 39:
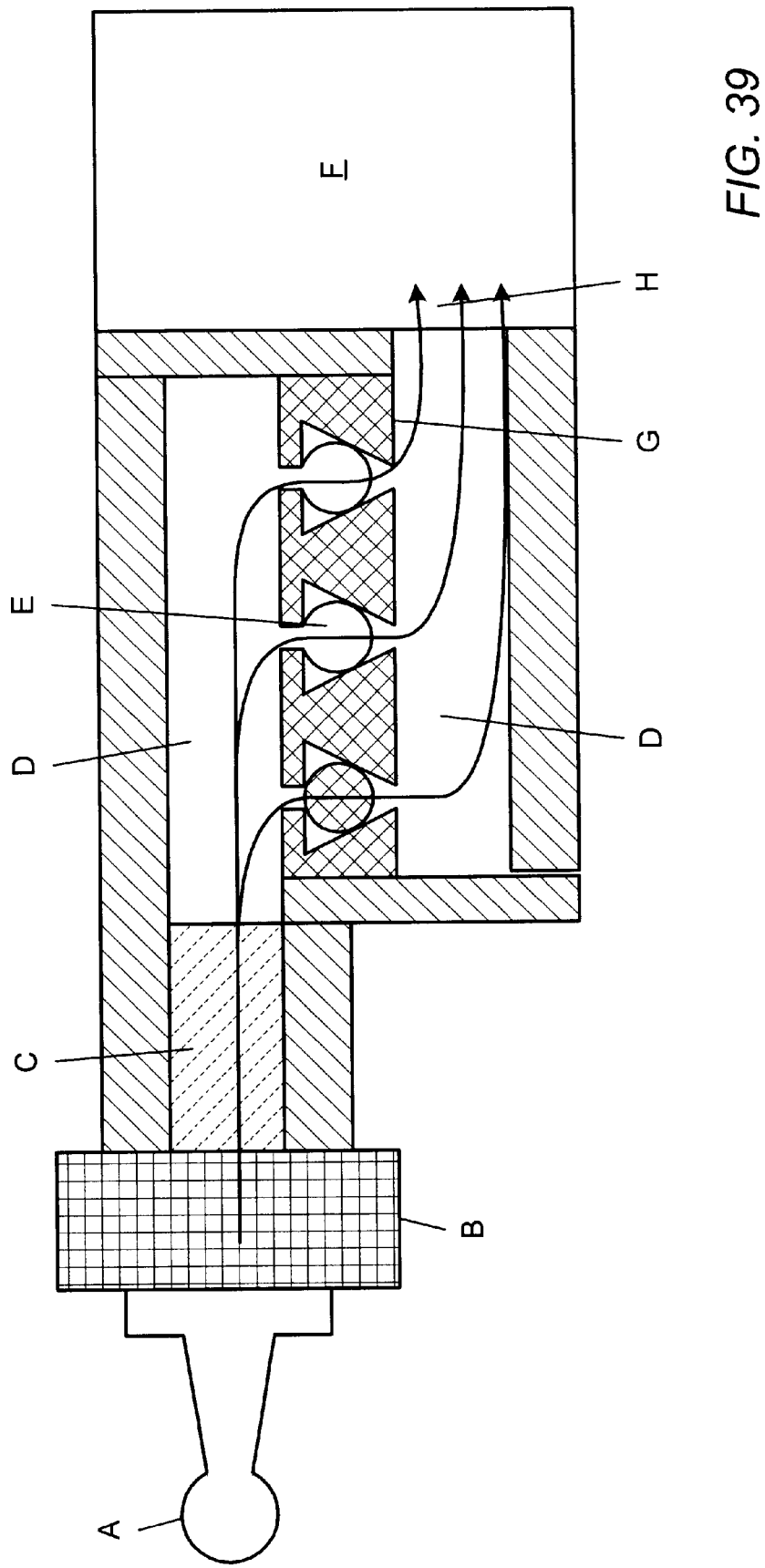
FIG. 39 depicts a cross-sectional view of a sensor array which includes a vacuum chamber, a filter, and a reagent reservoir.

As opposed to previously described methods, in which a pump as used to force a fluid stream through a sensor array, the use of a vacuum apparatus allows the fluid to be pulled through the sensor array. Referring to FIG. 39, the vacuum apparatus (F) is coupled to downstream from a sensor array (G). When coupled to the conduit (D), the vacuum apparatus may exert a suction force on the fluid stream (E), forcing a portion of the stream to pass over, and in some instances, through the sensor array. In some embodiments, the fluid may continue to pass through the conduit, after passing the sensor array, and into the vacuum apparatus. In an embodiment where the vacuum apparatus is a pre-evacuated tube, the fluid flow will continue until the air within the tube is at a pressure substantially equivalent to the atmospheric pressure. The vacuum apparatus may include a penetrable wall (H). The penetrable wall forms a seal inhibiting air from entering the vacuum apparatus. When the wall is broken or punctured, air from outside of the system will begin to enter the vacuum apparatus. In one embodiment, the conduit includes a penetrating member, (e.g., a syringe needle), which allows the penetrable wall to be pierced. Piercing the penetrable wall causes air and fluid inside the conduit to be pulled through the conduit into the vacuum apparatus until the pressure between the vacuum apparatus and the conduit is equalized.

The sensor array system may also include a filter (B) coupled to the conduit (D) as depicted in FIG. 39. The filter (B) may be positioned along the conduit, upstream from the sensor array. Filter (B) may be a porous filter which includes a membrane for removing components from the fluid stream. In one embodiment, the filter may include a membrane for removal of particulates above a minimum size. The size of the particulates removed will depend on the porosity of the membrane as is known in the art. Alternatively, the filter may be configured to remove unwanted components of a fluid stream. For example, if the fluid stream is a blood sample, the filter may be configured to remove red and white blood cells from the stream, while leaving in the blood stream blood plasma and other components therein.

The sensor array may also include a reagent delivery reservoir (C). The reagent delivery system is preferably coupled to the conduit upstream from the sensor array. The reagent delivery reservoir may be formed from a porous material which includes a reagent of interest. As the fluid passes through this reservoir, a portion of the reagent within the regent delivery reservoir passes into the fluid stream. The fluid reservoir may include a porous polymer or filter paper on which the reagent is stored. Examples of reagents which may be stored within the reagent delivery reservoir include, but are not limited to, visualization agents (e.g., dye or fluorophores), co-factors, buffers, acids, bases, oxidants, and reductants.

The sensor array may also include a fluid sampling device (A) coupled to the conduit (D). The fluid sampling device is configured to transfer a fluid sample from outside the sensor array to the conduit. A number of fluid sampling devices may be used including, but not limited to a syringe needle, a tubing connector, a capillary tube, or a syringe adapter.

The sensor array may also include a micropump or a microvalve system, coupled to the conduit to further aid in the transfer of fluid through the conduit. Micropumps and valves have been previously described. In one embodiment, a micro-valve or micropump may be used to keep a fluid sample or a reagent solution separated from the sensor array. Typically, these microvalves and micropumps include a thin flexible diaphragm. The diaphragm may be moved to an open position, in one embodiment, by applying a vacuum to the outside of the diaphragm. In this way, a vacuum apparatus coupled to the sensor array may be used to open a remote microvalve or pump.

In another embodiment, a microvalve may be used to control the application of a vacuum to the system. For example, a microvalve may be positioned adjacent to the vacuum apparatus. The activation of the microvalve may allow the vacuum apparatus to communicate with the conduit or sensor array. The microvalve may be remotely activated at controlled times and for controlled intervals.

In one embodiment, a sensor array system, such as depicted in FIG. 39, may be used for analysis of blood samples. A micropuncture device (A) is used to extract a small amount of blood from the patient, e.g., through a finger prick. The blood may be drawn through a porous filter that serves to remove the undesirable particulate matter. For the analysis of antibodies or antigens in whole blood, the filtering agent may be chosen to remove both the white and red blood cells, while leaving in the fluid stream blood plasma and all of the components therein. Methods of filtering blood cells from whole blood are taught, for example, in U.S. Pat. Nos. 5,914,042; 5,876,605, and 5,211,850 which are incorporated by reference. The filtered blood may also be passed through a reagent delivery reservoir that may consist of a porous layer that is impregnated with the reagent(s) of interest. In many cases, a visualization agent will be included in this layer so that the presence of the analytes of interest in the chip can be resolved. The treated fluid may be passed above the electronic tongue chip through a capillary layer, down through the various sensing particles and through the chip onto the bottom capillary layer. After exiting the central region, the excess fluid flows into the vacuum apparatus. This excess fluid may serve as a source of sample for future measurements should more detailed analyses be warranted. A "hard copy" of the sample is thus created to back up the electronic data recorded for the specimen.

Other examples of testing procedures for bodily fluids are described in the following U.S. Pat. Nos. 4,596,657, 4,189,382, 4,115,277, 3,954,623, 4,753,776, 4,623,461, 4,069,017, 5,053,197, 5,503,985, 3,696,932, 3,701,433, 4,036,946, 5,858,804, 4,050,898, 4,477,575, 4,810,378, 5,147,606, 4,246,107, and 4,997,577 all of which are incorporated by reference.

Figure 40A:
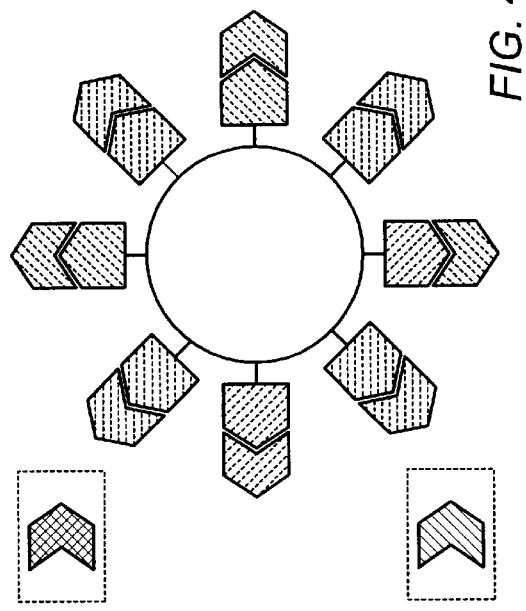
FIG. 40 depicts a general scheme for the testing of an antibody analyte.
Figure 40B:
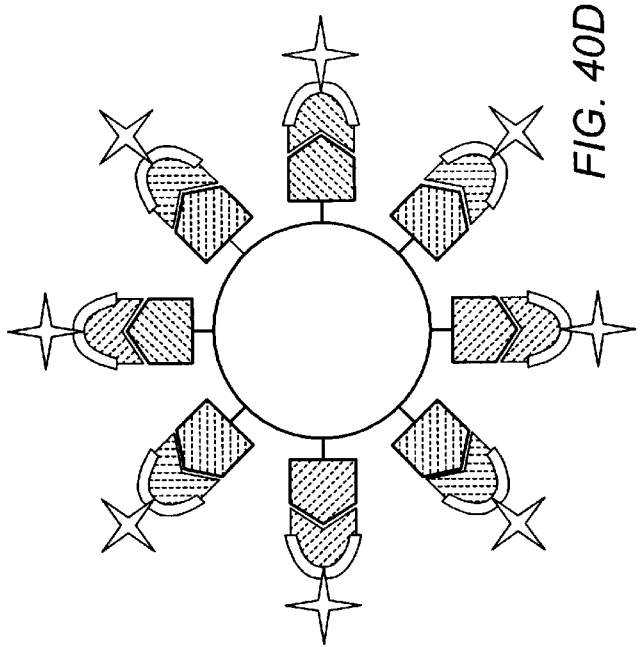
Figure 40C:
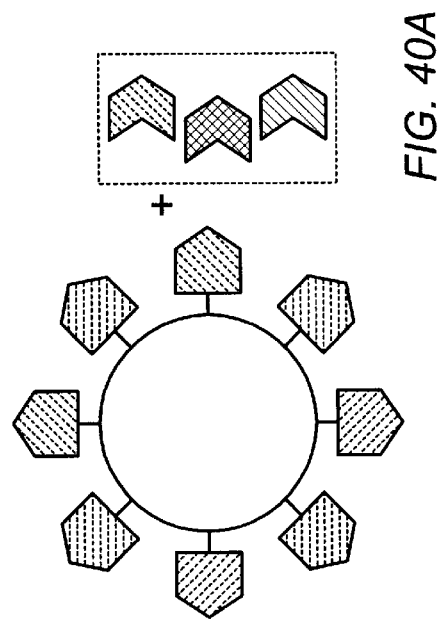
Figure 40D:
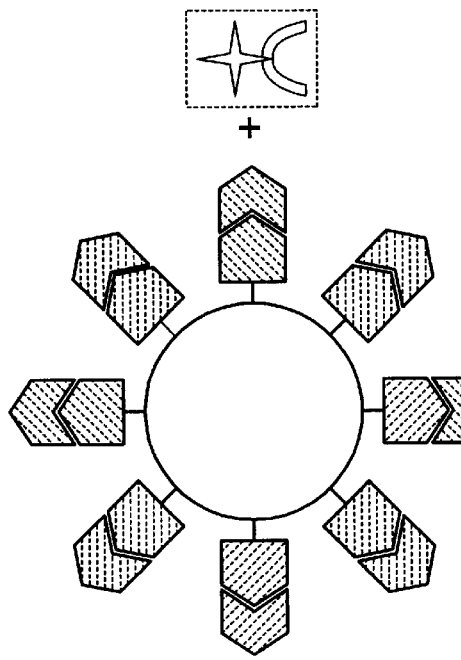
Figure 41A:
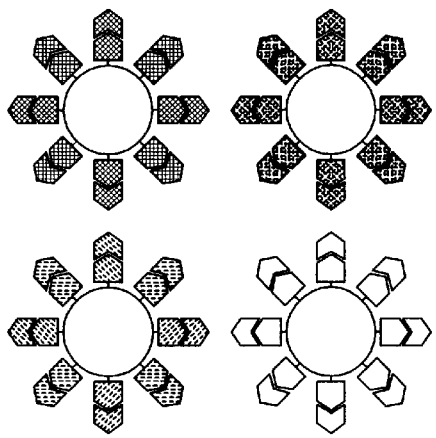
FIGS. 41A–D depicts general scheme for the detection of antibodies which uses a sensor array composed of four individual beads.
Figure 41B:
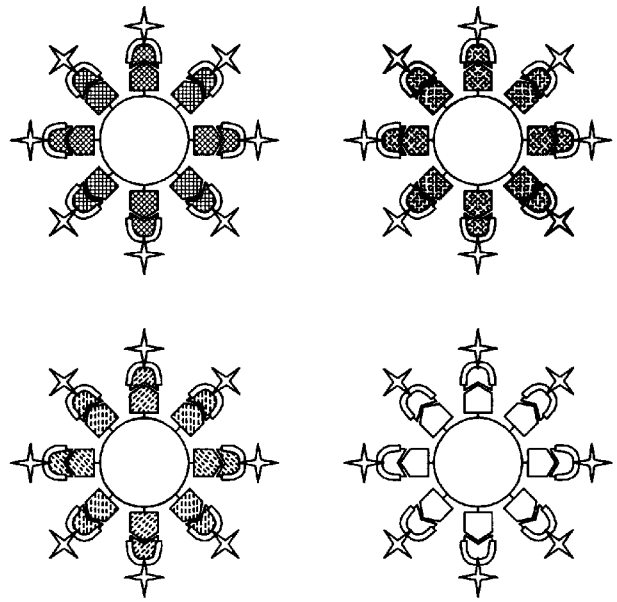
Figure 41C:
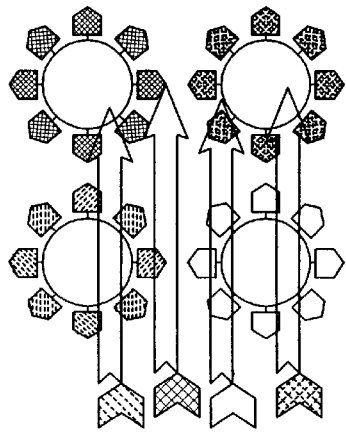
Figure 41D:
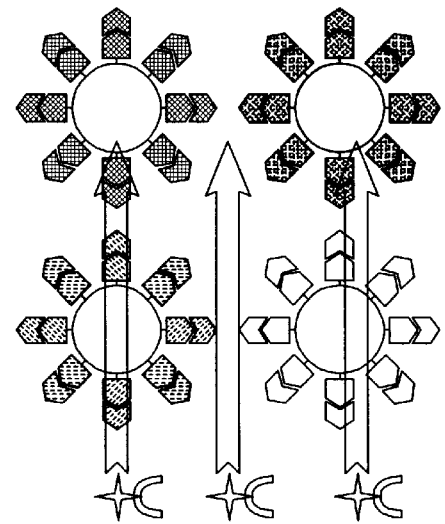

This generally described sampling method may also be used for either antibody or antigen testing of bodily fluids. A general scheme for the testing of antibodies is depicted in FIG. 40. FIG. 40A depicts a polymer bead having a protein coating that can be recognized in a specific manner by a complimentary antibody. Three antibodies (within the dashed rectangle) are shown to be present in a fluid phase that bathes the polymer bead. Turning to FIG. 40B, the complimentary antibody binds to the bead while the other two antibodies remain in the fluid phase. A large increase in the complimentary antibody concentration is noted at this bead. In FIG. 40C a visualization agent such as protein A (within the dashed rectangle) is added to the fluid phase. The visualization agent is chosen because it possesses either a strong absorbance property or it exhibits fluorescence characteristics that can be used to identify the species of interest via optical measurements. Protein A is an example of a reagent that associates with the common region of most antibodies. Chemical derivatization of the visualization agent with dyes, quantum particles or fluorophores is used to evoke the desired optical characteristics. After binding to the bead-localized antibodies, as depicted in FIG. 40D, the visualization agent reveals the presence of the complimentary antibodies at the specific polymer bead sites.

FIG. 41 depicts another general scheme for the detection of antibodies which uses a sensor array composed of four individual beads. Each of the four beads is coated with a different antigen (i.e. a protein coating). As depicted in FIG. 41A, the beads are washed with a fluid sample which includes four antibodies. Each of the four antibodies binds to its complimentary antigen coating, as depicted in FIG. 41B. A visualization agent may be introduced into the chamber, as depicted in FIG. 41C. The visualization agent, in one embodiment, may bind to the antibodies, as depicted in FIG. 41D. The presence of the labeled antibodies is assayed by optical means (absorbance, reflectance, fluorescence). Because the location of the antigen coatings is known ahead of time, the chemical/biochemical composition of the fluid phase can be determined from the pattern of optical signals recorded at each site.

In an alternative methodology, not depicted, the antibodies in the sample may be exposed to the visualization agent prior to their introduction into the chip array. This may render the visualization step depicted in 41C unnecessary.

Figure 42:
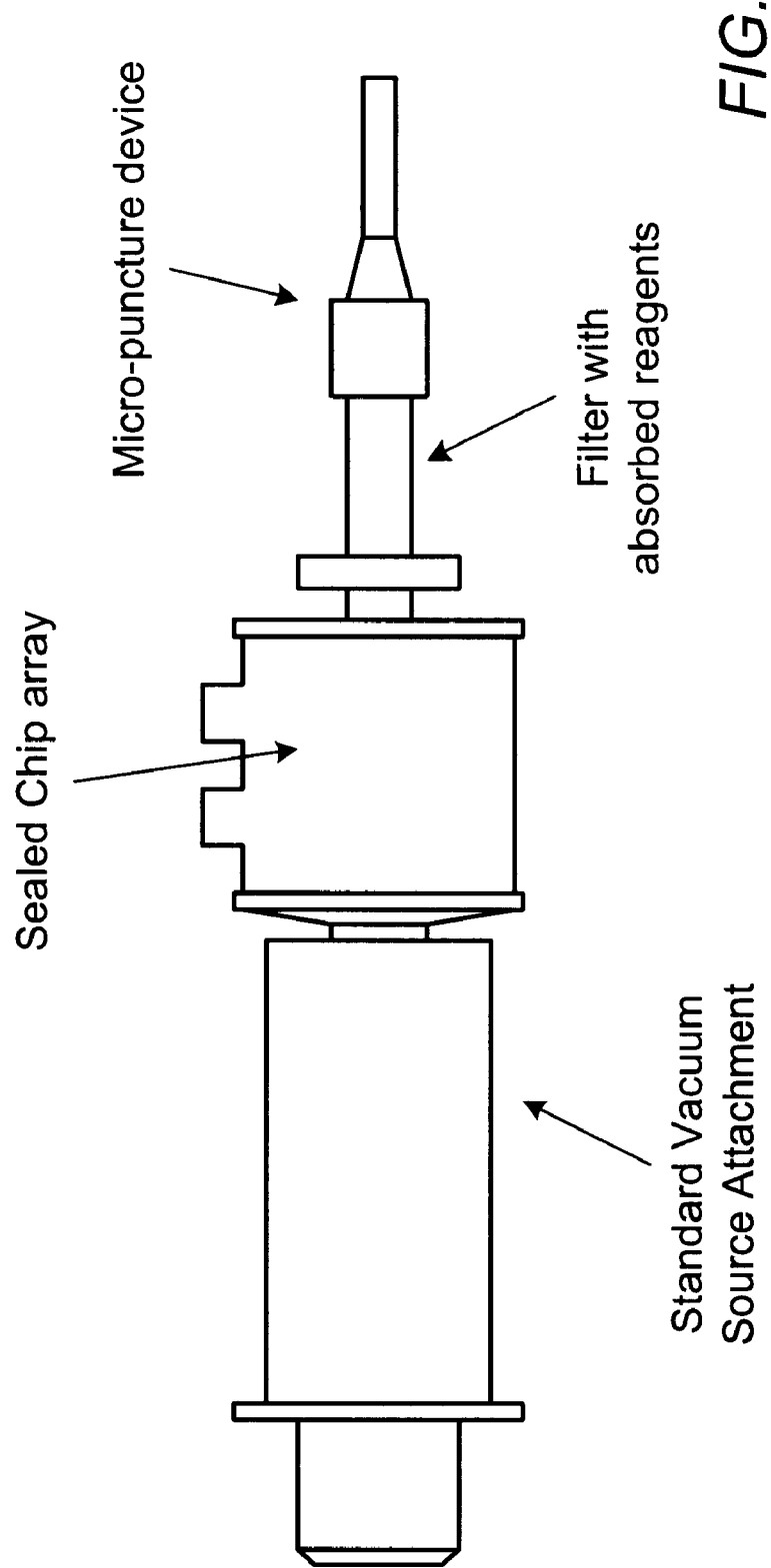
FIG. 42 depicts a sensor array which includes a vacuum chamber, a sensor array chamber, and a sampling device.

FIG. 42 depicts a system for detecting an analyte in a fluid stream. The system includes a vacuum apparatus, a chamber in which a sensor array may be disposed, and an inlet system for introducing the sample into the chamber. In this embodiment, the inlet system is depicted as a micropuncture device. The chamber holding the sensor array may be a Sikes-Moore chamber, as previously described. The vacuum apparatus is a standard "vacutainer" type vacuum tube. The micro puncture device includes a Luer-lock attachment which can receive a syringe needle. Between the micro-puncture device and the chamber a syringe filter may be placed to filter the sample as the sample enters the chamber. Alternatively, a reagent may be placed within the filter. The reagent may be carried into the chamber via the fluid as the fluid passes through the filter.

Figure 43:
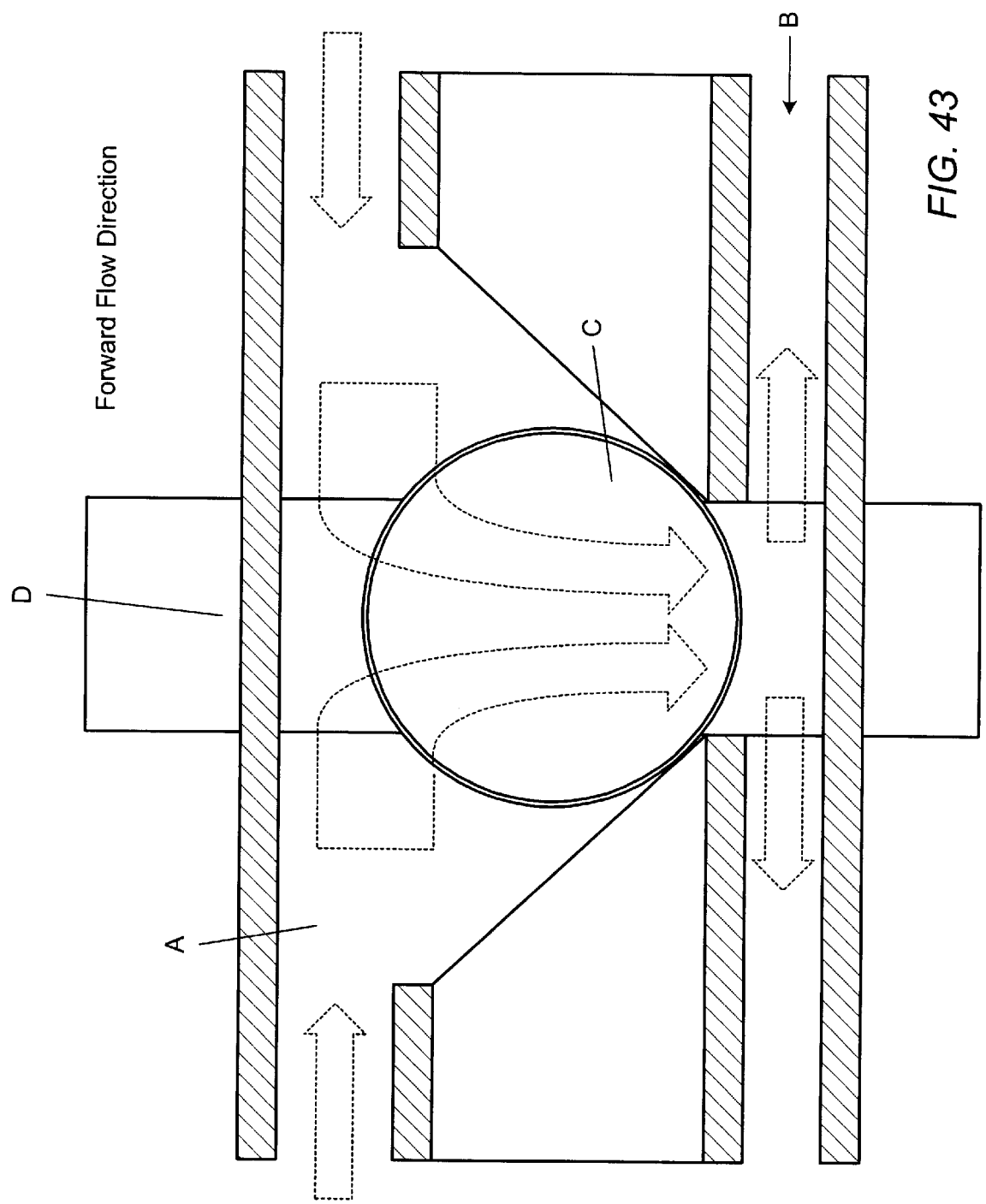
FIG. 43 depicts a flow path of a fluid stream through a sensor array from the top toward the bottom of the sensor array.

As has been previously described, a sensor array may be configured to allow the fluid sample to pass through the sensor array during use. The fluid delivery to the sensor array may be accomplished by having the fluid enter the top of the chip through the shown capillary (A), as depicted in FIG. 43. The fluid flow traverses the chip and exits from the bottom capillary (B). Between the top and bottom capillaries, the fluid is passed by the bead (C). Here the fluid containing analytes have an opportunity to encounter the receptor sites. The presence of such analytes may be identified using optical means. The light pathway is shown here (D). In the forward flow direction, the beads are typically forced towards the bottom of the pit. Under these circumstances, the bead placement is ideal for optical measurements.

Figure 44:
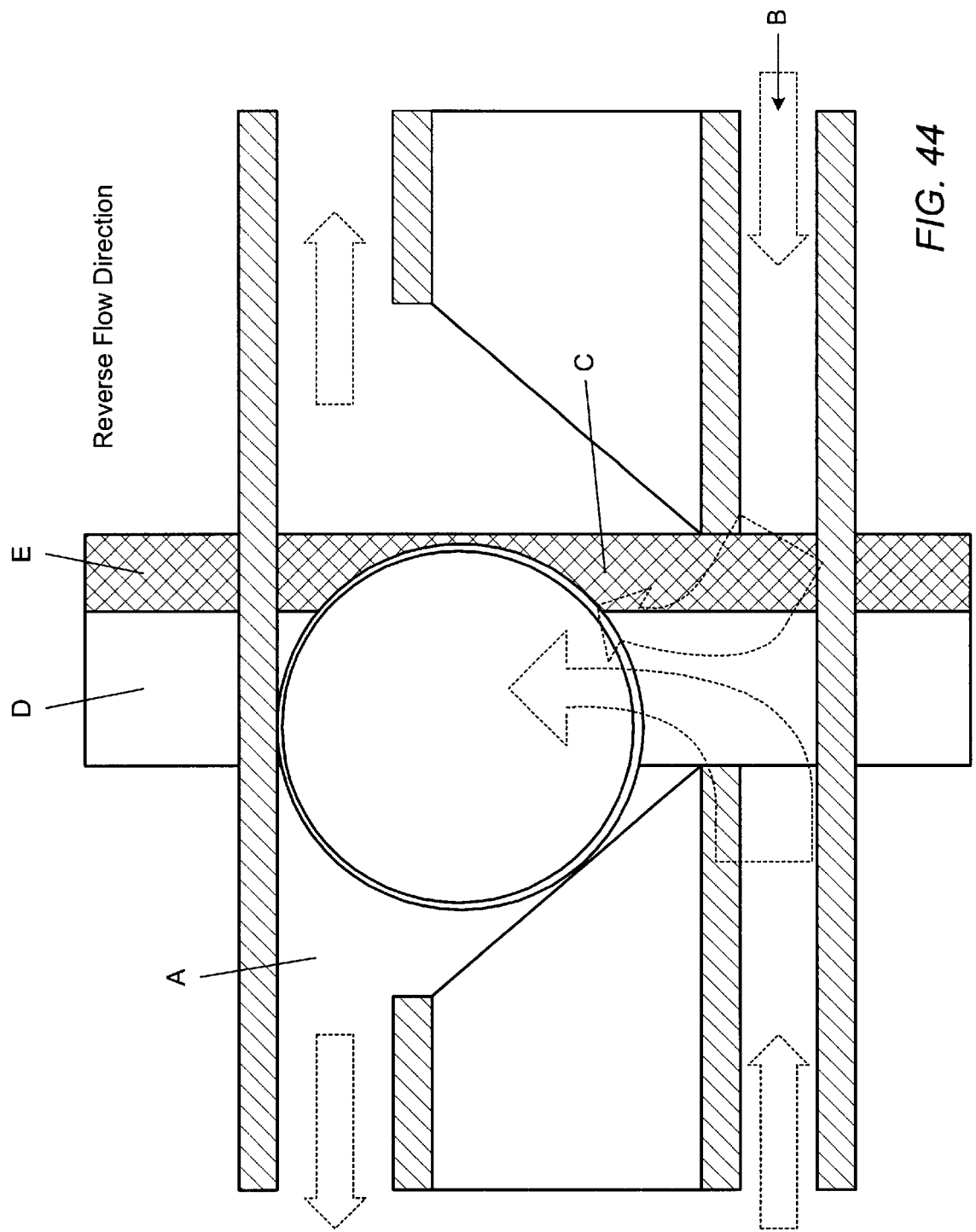
FIG. 44 depicts a flow path of a fluid stream through a sensor array from the bottom toward the top of the sensor array.

In another embodiment, the fluid flow may go from the bottom of the sensor array toward the top of the sensor array, as depicted in FIG. 44. The fluid exits from the top of the chip through the shown capillary (A). The fluid flow traverses the chip and enters from the bottom capillary (B). Between the top and bottom capillaries, the fluid can avoid the bead somewhat by taking an indirect pathway (C). The presence of analytes is identified using optical means as before. The light pathway is shown as (D). Unfortunately, only a portion of the light passes through the bead. In the reverse flow direction, the beads can be dislodged away from the analysis beam by the upward pressure of the fluid, as shown in FIG. 44. Under these circumstances, some of the light may traverse the chip and enter the detector (not shown) without passing through the sensor bead (Path E).

In any microfluidic chemical sensing system there may be a need to "store" the chemically sensitive elements in an "inert" environment. Typically, the particles may be at least partially surrounded by an inert fluid such as an inert, non reactive gas, a non-reactive solvent, or a liquid buffer solution. Alternatively, the particles may be maintained under a vacuum. Before exposure of the particles to the analyte, the inert environment may need to be removed to allow proper testing of the sample. In one embodiment, a system may include a fluid transfer system for the removal of an inert fluid prior to the introduction of the sample with minimum dead volume.

In one embodiment, a pumping system may be used to pull the inert fluid through from one side (by any pumping action, such as that provided by a vacuum downstream from the array). The inert fluid may be efficiently removed while the beads remain within the sensor array. Additionally, the analyte sample may be drawn toward the sensor array as the inert fluid is removed from the sensor array. A pocket of air may separate the analyte sample from the inert fluid as the sample move through the conduit. Alternatively, the sample may be pumped from "upstream" using a micropump. Note that a vacuum downstream can produce a maximum of one atmosphere of head pressure, while an upstream pump could in principle produce an arbitrarily high head pressure. This can effect the fluid transport rates through the system, but for small volume microfluidic systems, even with low flow coefficients, one atmosphere of head pressure should provide acceptable transfer rates for many applications.

In another embodiment, the vacuum apparatus may be formed directly into a micromachined array. The vacuum apparatus may be configured to transmit fluid to and from a single cavity or a plurality of cavities. In one embodiment, a separate vacuum apparatus may be coupled to each of the cavities.

3. Chemical Improvements

The development of smart sensors capable of discrimination of different analytes, toxins, and bacteria has become increasingly important for environmental, health and safety, remote sensing, military, and chemical processing applications. Although many sensors capable of high sensitivity and high selectivity detection have been fashioned for single analyte detection, only in a few selected cases have array sensors been prepared which display multi-analyte detection capabilities. The obvious advantages of such array systems are their utility for the analysis of multiple analytes and their ability to be "trained" to respond to new stimuli. Such on site adaptive analysis capabilities afforded by the array structures makes their utilization promising for a variety of future applications.

Single and multiple analyte sensors both typically rely on changes in optical signals. These sensors typically make use of an indicator that undergoes a perturbation upon analyte binding. The indicator may be a chromophore or a fluorophore. A fluorophore is a molecule that. absorbs light at a characteristic wavelength and then re-emits the light most typically at a characteristically different wavelength. Fluorophores include, but are not limited to rhodamine and rhodamine derivatives, fluorescein and fluorescein derivatives, coumarins and chelators with the lanthanide ion series. The emission spectra, absorption spectra and chemical composition of many fluorophores may be found, e.g., in the "Handbook of Fluorescent Probes and Research Chemicals", R. P. Haugland, ed. which is incorporated herein by reference. A chromophore is a molecule which absorbs light at a characteristic wavelength, but does not re-emit light.

As previously described, the receptor itself may incorporate the indicator. The binding of the analyte to the receptor may directly lead to a modulation of the properties of the indicator. Such an approach typically requires a covalent attachment or strong non-covalent binding of the indicator onto or as part of the receptor, leading to additional covalent architecture. Each and every receptor may need a designed signaling protocol that is typically unique to that receptor. General protocols for designing in a signal modulation that is versatile and general for most any receptor would be desirable.

In one embodiment, a general method for the creation of optical signal modulations for most any receptor that is coupled to an immobilized matrix has been developed. Immobilized matrices include, but are not limited to, resins, beads, and polymer surfaces. By immobilization of the receptor to the matrix, the receptor is held within a structure that can be chemically modified, allowing one to tune and to create an environment around the receptor that is sensitive to analyte binding. Coupling of the indicator to an immobilization matrix may make it sensitive to microenvironment changes which foster signal modulation of the indicator upon analyte binding. Further, by coupling the indicator to an immobilization matrix, the matrix itself becomes the signaling unit, not requiring a specific new signaling protocol for each and every receptor immobilized on the matrix.

In an embodiment, a receptor for a particular analyte or class of analytes may be designed and created with the chemical handles appropriate for immobilization on and/or in the matrix. A number of such receptors have been described above. The receptors can be, but are not limited to, antibodies, aptamers, organic receptors, combinatorial libraries, enzymes, and imprinted polymers.

Signaling indicator molecules may be created or purchased which have appropriate chemical handles for immobilization on and/or in the immobilization matrix. The indicators may possess chromophores or fluorophores that are sensitive to their microenvironment. This chromophore or fluorophore may be sensitive to microenvironment changes that include, but are not limited to, a sensitivity to local pH, solvatophobic or solvatophilic properties, ionic strength, dielectric, ion pairing, and/or hydrogen bonding. Common indicators, dyes, quantum particles, and semiconductor particles, are all examples of possible probe molecules. The probe molecules may have epitopes similar to the analyte, so that a strong or weak association of the probe molecules with the receptor may occur. Alternatively, the probe molecules may be sensitive to a change in their microenvironment that results from one of the affects listed in item above.

Binding of the analyte may do one of the following things, resulting in a signal modulation: 1) displace a probe molecule from the binding site of the receptor, 2) alter the local pH, 3) change the local dielectric properties, 4) alter the features of the solvent, 5) change the fluorescence quantum yield of individual dyes, 6) alter the rate/efficiency of fluorescence resonance energy transfer (FRET) between donor-acceptor fluorophore pairs, or 7) change the hydrogen bonding or ion pairing near the probe.

In an alternative embodiment, two or more indicators may be attached to the matrix. Binding between the receptor and analyte causes a change in the communication between the indicators, again via either displacement of one or more indicators, or changes in the microenvironment around one or more indicators. The communication between the indicators may be, but is not limited to, fluorescence resonance energy transfer, quenching phenomenon, and/or direct binding.

In an embodiment, a particle for detecting an analyte may be composed of a polymeric resin. A receptor and an indicator may be coupled to the polymeric resin. The indicator and the receptor may be positioned on the polymeric resin such that the indicator produces a signal in when the analyte interacts with the receptor. The signal may be a change in absorbance (for chromophoric indicators) or a change in fluorescence (for fluorophoric indicators).

A variety of receptors may be used, in one embodiment, the receptor may be a polynucleotide, a peptide, an oligosaccharide, an enzyme, a peptide mimetic, or a synthetic receptor.

In one embodiment, the receptor may be a polynucleotide coupled to a polymeric resin. For the detection of analytes, the polynucleotide may be a double stranded deoxyribonucleic acid, single stranded deoxyribonucleic acid, or a ribonucleic acid. Methods for synthesizing and/or attaching a polynucleotide to a polymeric resin are described, for example, in U.S. Pat. No. 5,843,655 which is incorporated herein by reference. "Polynucleotides" are herein defined as chains of nucleotides. The nucleotides are linked to each other by phosphodiester bonds. "Deoxyribonucleic acid" is composed of deoxyribonucleotide residues, while "Ribonucleic acid" is composed of ribonucleotide residues.

In another embodiment, the receptor may be a peptide coupled to a polymeric resin. "Peptides" are herein defined as chains of amino acids whose α-carbons are linked through peptide bonds formed by a condensation reaction between the a carboxyl group of one amino acid and the amino group of another amino acid. Peptides is intended to include proteins. Methods for synthesizing and/or attaching a protein or peptides to a polymeric resin are described, for example, in U.S. Pat. Nos. 5,235,028 and 5,182,366 which is incorporated herein by reference.

Alternatively, peptide mimetics may be used as the receptor. Peptides and proteins are sequences of amide linked amino acid building blocks. A variety of peptide mimetics may be formed by replacing or modifying the amide bond. In one embodiment, the amide bond may be replaced by alkene bonds. In another embodiment, the amide may be replaced by a sulphonamide bond. In another embodiment the amino acid side chain may be placed on the nitrogen atom, such compounds are commonly known as peptoids. Peptides may also be formed from non-natural D-stereo-isomers of amino acids. Methods for synthesizing and/or attaching a peptide mimetic to a polymeric resin is described, for example, in U.S. Pat. No. 5,965,695 which is incorporated herein by reference.

In another embodiment, the receptor may include an oligosaccharide coupled to a polymeric resin. An "oligosaccharide" is an oligomer composed of two or more monosaccharides, typically joined together via ether linkages. Methods for synthesizing and/or attaching oligosaccharides to a polymeric resin are described, for example, in U.S. Pat. Nos. 5,278,303 and 5,616,698 which are incorporated herein by reference.

In another embodiment, polynucleotides, peptides and/or oligosaccharides may be coupled to base unit to form a receptor. In one embodiment, the base unit may have the general structure:

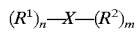

$(R^1)_n$—X—$(R^2)_m$ wherein X comprises carbocyclic systems or $C_1$–$C_{10}$ alkanes, n is an integer of at least 1, m is an integer of at least 1; and wherein each of $R^1$ independently represents —$(CH_2)_y$—$NR^3$—$C(NR^4)$—$NR^5$, —$(CH_2)_y$—$NR^6R^7$, —$(CH_2)_y$—NH—Y, —$(CH_2)_y$—O—Z;

where y is an integer of at least 1;

where $R^3$, $R^4$, and $R^5$ independently represent hydrogen, alkyl, aryl, alkyl carbonyl of 1 to 10 carbon atoms, or alkoxy carbonyl of 1 to 10 carbon atoms, or $R^4$ and $R^5$ together represent a cycloalkyl group;

where $R^6$ represents hydrogen, alkyl, aryl, alkyl carbonyl of 1 to 10 carbon atoms, or alkoxy carbonyl of 1 to 10 carbon atoms;

where $R^7$ represents alkyl, aryl, alkyl carbonyl of 1 to 10 carbon atoms, or alkoxy carbonyl of 1 to 10 carbon atoms;

where $R^6$ and $R^7$ together represent a cycloalkyl group;

where Y is a peptide, or hydrogen and where Z is a polynucleotide, an oligosaccharide or hydrogen; and wherein each of $R^2$ independently represents hydrogen, alkyl, alkenyl, alkynyl, phenyl, phenylalkyl, arylalkyl, aryl, or together with another $R^2$ group represent a carbocyclic ring. The use of a base unit such as described above may aid in the placement and orientation of the side groups to create a more effective receptor.

The receptor and indicators may be coupled to the polymeric resin by a linker group. A variety of linker groups may be used. The term "linker", as used herein, refers to a molecule that may be used to link a receptor to an indicator; a receptor to a polymeric resin or another linker, or an indicator to a polymeric resin or another linker. A linker is a hetero or homobifunctional molecule that includes two reactive sites capable of forming a covalent linkage with a receptor, indicator, other linker or polymeric resin. Suitable linkers are well known to those of skill in the art and include, but are not limited to, straight or branched-chain carbon linkers, heterocyclic carbon linkers, or peptide linkers. Particularly preferred linkers are capable of forming covalent bonds to amino groups, carboxyl groups, or sulfhydryl groups or hydroxyl groups. Amino binding linkers include reactive groups such as carboxyl groups, isocyanates, isothiocyanates, esters, haloalkyls, and the like. Carboxyl-binding linkers are capable of forming include reactive groups such as various amines, hydroxyls and the like. Sulfhydryl-binding linkers include reactive groups such as sulfhydryl groups, acrylates, isothiocyanates, isocyanates and the like. Hydroxyl binding groups include reactive groups such as carboxyl groups, isocyanates, isothiocyanates, esters, haloalkyls, and the like. The use of some such linkers is described in U.S. Pat. No. 6,037,137 which is incorporated herein by reference.

Figure 55A:
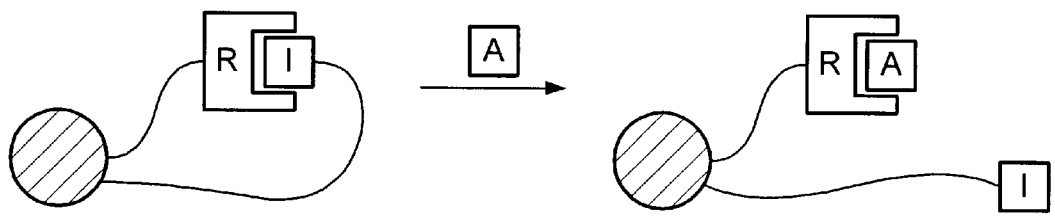
FIGS. 55A–I depict various sensing protocols for receptor-indicator-polymeric resin particles.
Figure 55B:
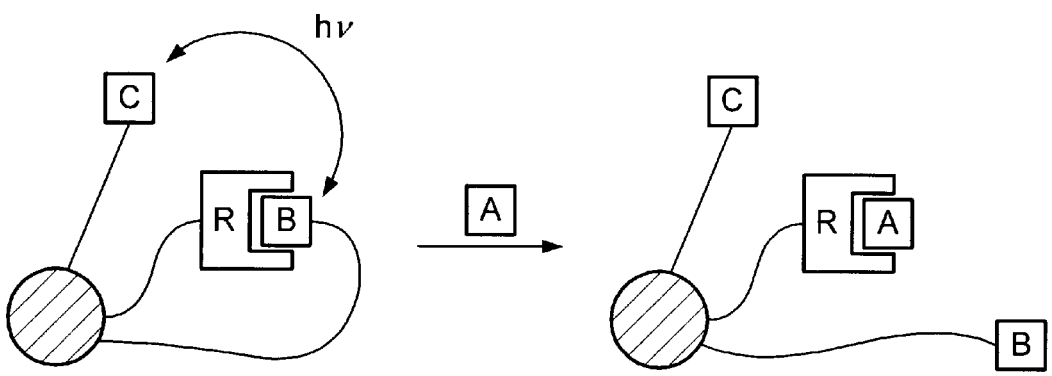

In another embodiment, depicted in FIG. 55B, a receptor (R) may be coupled to a polymeric resin. The receptor may be directly formed on the polymeric resin, or be coupled to the polymeric resin via a linker. An indicator (B) may also be coupled to the polymeric resin. The indicator may be directly coupled to the polymeric resin or coupled to the polymeric resin by a linker. In some embodiments, the linker coupling the indicator to the polymeric resin is of sufficient length to allow the indicator to interact with the receptor in the absence of an analyte (A). An additional indicator (C) may also be coupled to the polymeric resin. The additional indicator may be directly coupled to the polymeric resin or coupled to the polymeric resin by a linker. In some embodiments, the additional indicator is coupled to the polymeric resin, such that the additional indicator is proximate the receptor during use.

In another embodiment, depicted in FIG. 55B, a receptor (R) may be coupled to a polymeric resin. The receptor may be directly formed on the polymeric resin, or be coupled to the polymeric resin via a linker. An indicator (B) may also be coupled to the polymeric resin. The indicator may be directly coupled to the polymeric resin or coupled to the polymeric resin by a linker. In some embodiments, the linker coupling the indicator to the polymeric resin is of sufficient length to allow the indicator to interact with the receptor in the absence of an analyte. An additional indicator (C) may also be coupled to the polymeric resin. The additional indicator may be directly coupled to the polymeric resin or coupled to the polymeric resin by a linker. In some embodiments, the additional indicator is coupled to the polymeric resin, such that the additional indicator is proximate the receptor during use.

Figure 55C:
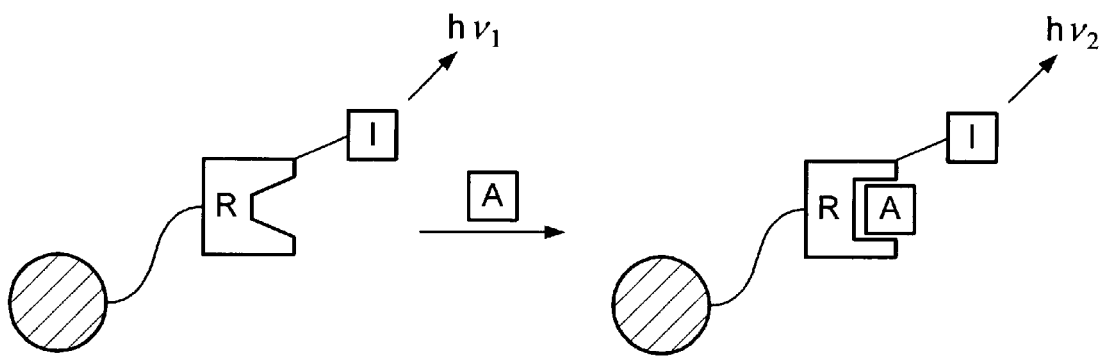

In another embodiment, depicted in FIG. 55C, a receptor (R) may be coupled to a polymeric resin. The receptor may be directly formed on the polymeric resin, or be coupled to the polymeric resin via a linker. An indicator (I) may be coupled to the receptor. The indicator may be directly coupled to the receptor or coupled to the receptor by a linker. In some embodiments, the linker coupling the indicator to the polymeric resin is of sufficient length to allow the indicator to interact with the receptor in the absence of an analyte (A), as depicted in FIG. 55E.

Figure 55D:
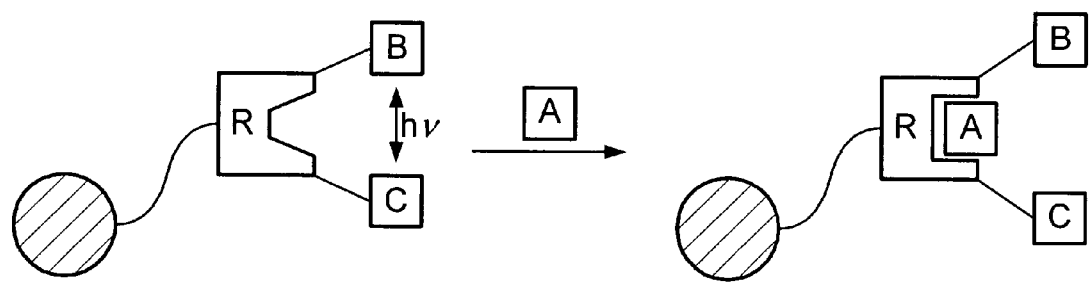
Figure 55E:
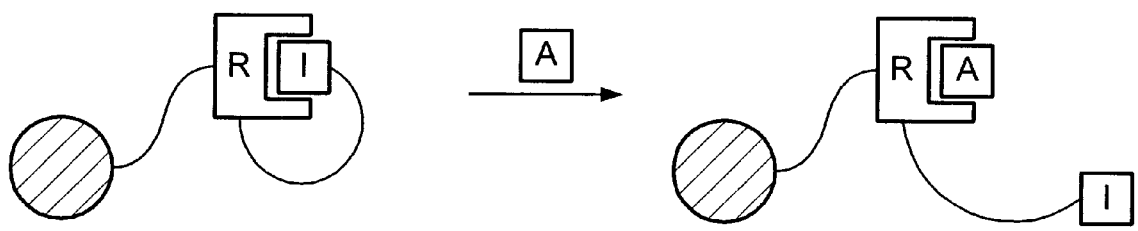
Figure 55F:
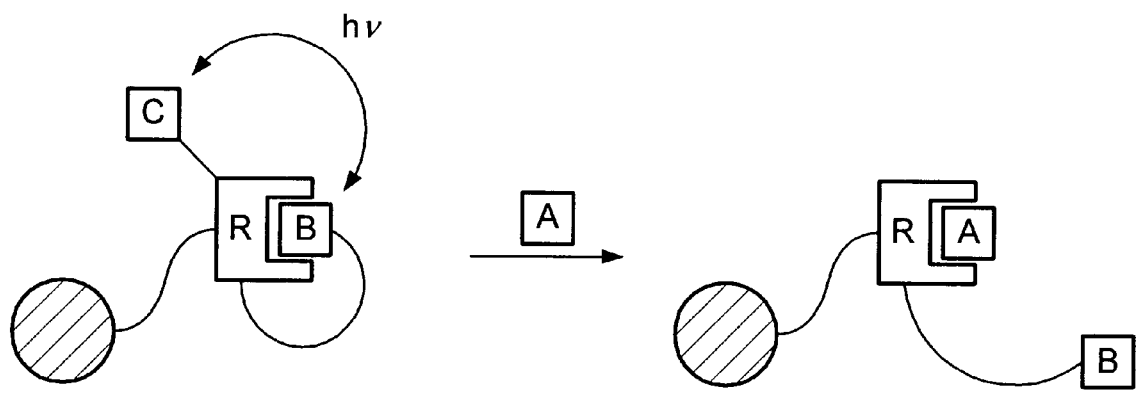

In another embodiment, depicted in FIG. 55D, a receptor (R) may be coupled to a polymeric resin. The receptor may be directly formed on the polymeric resin, or be coupled to the polymeric resin via a linker. An indicator (B) may be coupled to the receptor. The indicator may be directly coupled to the receptor or coupled to the receptor by a linker. An additional indicator (C) may also be coupled to the receptor. The additional indicator may be directly coupled to the receptor or coupled to the receptor by a linker. In some embodiments, the linker coupling the indicator (B) to the polymeric resin is of sufficient length to allow the indicator to interact with the receptor in the absence of an analyte (A), as depicted in FIG. 55F.

Figure 55G:
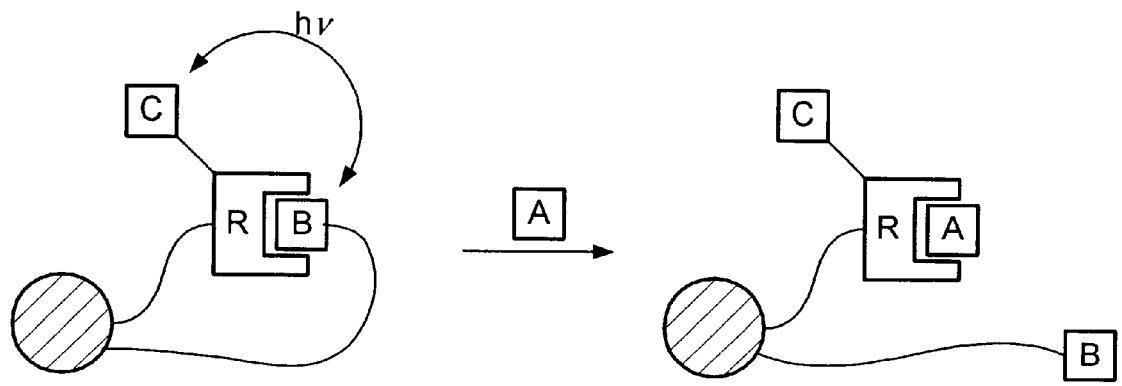

In another embodiment, depicted in FIG. 55G, a receptor (R) may be coupled to a polymeric resin. The receptor may be directly formed on the polymeric resin, or be coupled to the polymeric resin via a linker. An indicator (B) may be coupled to the polymeric resin. The indicator may be directly coupled to the polymeric resin or coupled to the polymeric resin by a linker. In some embodiments, the linker coupling the indicator to the polymeric resin is of sufficient length to allow the indicator to interact with the receptor in the absence of an analyte (A). An additional indicator (C) may also be coupled to the receptor. The additional indicator may be directly coupled to the receptor or coupled to the receptor by a linker.

Figure 55H:
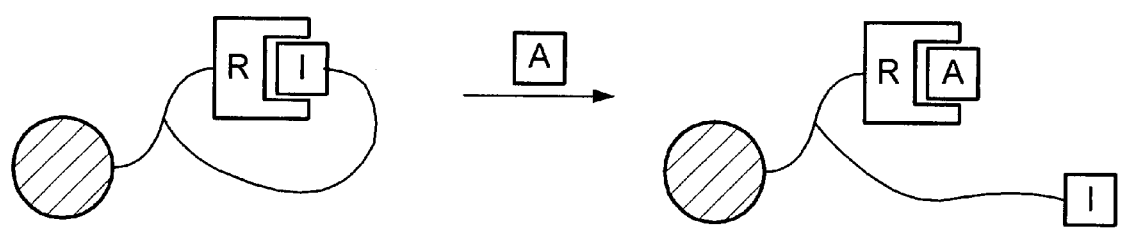

In another embodiment, depicted in FIG. 55H, a receptor (R) may be coupled to a polymeric resin by a first linker. An indicator (I) may be coupled to the first linker. The indicator may be directly coupled to the first linker or coupled to the first linker by a second linker. In some embodiments, the second linker coupling the indicator to the polymeric resin is of sufficient length to allow the indicator to interact with the receptor in the absence of an analyte (A).

Figure 55I:
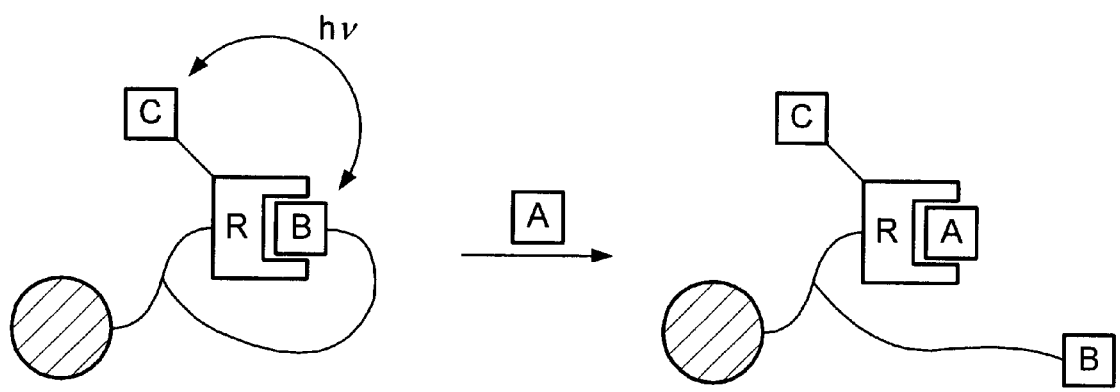

In another embodiment, depicted in FIG. 55I, a receptor (R) may be coupled to a polymeric resin by a first linker. An indicator (B) may be coupled to the first linker. The indicator may be directly coupled to the first linker or coupled to the first linker by a second linker. In some embodiments, the second linker coupling the indicator to the first linker is of sufficient length to allow the indicator to interact with the receptor in the absence of an analyte (A). An additional indicator (C) may be coupled to the receptor. The additional indicator may be directly coupled to the receptor or coupled to the receptor by a linker.

These various combinations of receptors, indicators, linkers and polymeric resins may be used in a variety of different signalling protocols. Analyte-receptor interactions may be transduced into signals through one of several mechanisms. In one approach, the receptor site may be preloaded with an indicator, which can be displaced in a competition with analyte ligand. In this case, the resultant signal is observed as a decrease in a signal produced by the indicator. This indicator may be a fluorophore or a chromophore. In the case of a fluorophore indicator, the presence of an analyte may be determined by a decrease in the fluorescence of the particle. In the case of a chromophore indicator, the presence of an analyte may be determined by a decrease in the absorbance of the particle.

A second approach that has the potential to provide better sensitivity and response kinetics is the use of an indicator as a monomer in the combinatorial sequences (such as either structure shown in FIG. 14), and to select for receptors in which the indicator functions in the binding of ligand. Hydrogen bonding or ionic substituents on the indicator involved in analyte binding may have the capacity to change the electron density and/or rigidity of the indicator, thereby changing observable spectroscopic properties such as fluorescence quantum yield, maximum excitation wavelength, maximum emission wavelength, and/or absorbance. This approach may not require the dissociation of a preloaded fluorescent ligand (limited in response time by $k_{off}$), and may modulate the signal from essentially zero without analyte to large levels in the presence of analyte.

In one embodiment, the microenvironment at the surface and interior of the resin beads may be conveniently monitored using spectroscopy when simple pH sensitive dyes or solvachromic dyes are imbedded in the beads. As a guest binds, the local pH and dielectric constants of the beads change, and the dyes respond in a predictable fashion. The binding of large analytes with high charge and hydrophobic surfaces, such as DNA, proteins, and steroids, should induce large changes in local microenvironment, thus leading to large and reproducible spectral changes. This means that most any receptor can be attached to a resin bead that already has a dye attached, and that the bead becomes a sensor for the particular analyte.

In one embodiment, a receptor that may be covalently coupled to an indicator. The binding of the analyte may perturb the local microenvironment around the receptor leading to a modulation of the absorbance or fluorescence properties of the sensor.

In one embodiment, receptors may be used immediately in a sensing mode simply by attaching the receptors to a bead that is already derivatized with a dye sensitive to its microenvironment. This is offers an advantage over other signalling methods because the signaling protocol becomes routine and does not have to be engineered; only the receptors need to be engineered. The ability to use several different dyes with the same receptor, and the ability to have more than one dye on each bead allows flexibility in the design of a sensing particle.

Changes in the local pH, local dielectric, or ionic strength, near a fluorophore may result in a signal. A high positive charge in a microenvironment leads to an increased pH since hydronium migrates away from the positive region. Conversely, local negative charge decreases the microenvironment pH. Both changes result in a difference in the protonation state of pH sensitive indicators present in that microenvironment. Many common chromophores and fluorophores are pH sensitive. The interior of the bead may be acting much like the interior of a cell, where the indicators should be sensitive to local pH.

The third optical transduction scheme involves fluorescence energy transfer. In this approach, two fluorescent monomers for signaling may be mixed into a combinatorial split synthesis. Examples of these monomers are depicted in FIG. 14. Compound 470 (a derivative of fluorescein) contains a common colorimetric/fluorescent probe that may be mixed into the oligomers as the reagent that will send out a modulated signal upon analyte binding. The modulation may be due to resonance energy transfer to monomer 475 (a derivative of rhodamine). When an analyte binds to the receptor, structural changes in the receptor will alter the distance between the monomers (schematically depicted in FIG. 8, 320 corresponds to monomer 470 and 330 corresponds to monomer 475). It is well known that excitation of fluorescein may result in emission from rhodamine when these molecules are oriented correctly. The efficiency of resonance energy transfer from fluorescein to rhodamine will depend strongly upon the presence of analyte binding; thus measurement of rhodamine fluorescence intensity (at a substantially longer wavelength than fluorescein fluorescence) will serve as a indicator of analyte binding. To greatly improve the likelihood of a modulatory fluorescein-rhodamine interaction, multiple rhodamine tags can be attached at different sites along a combinatorial chain without substantially increasing background rhodamine fluorescence (only rhodamine very close to fluorescein will yield appreciable signal). In one embodiment, depicted in FIG. 8, when no ligand is present, short wavelength excitation light (blue light) excites the fluorophore 320, which fluoresces (green light). After binding of analyte ligand to the receptor, a structural change in the receptor molecule brings fluorophore 320 and fluorophore 330 in proximity, allowing excited-state fluorophore 320 to transfer its energy to fluorophore 330. This process, fluorescence resonance energy transfer, is extremely sensitive to small changes in the distance between dye molecules (e.g., efficiency~ $[distance]^{-6}$).

In another embodiment, photoinduced electron transfer (PET) may be used to analyze the local microenvironment around the receptor. The methods generally includes a fluorescent dye and a fluorescence quencher. A fluorescence quencher is a molecule that absorbs the emitted radiation from a fluorescent molecule. The fluorescent dye, in its excited state, will typically absorbs light at a characteristic wavelength and then re-emit the light at a characteristically different wavelength. The emitted light, however, may be reduced by electron transfer with the fluorescent quncher, which results in quenching of the fluorescence. Therefore, if the presence of an analyte perturbs the quenching properties of the fluorescence quencher, a modulation of the fluorescent dye may be observed.

The above described signalling methods may be incorporated into a variety of receptor-indicator-polymeric resin systems. Turning to FIG. 55A, an indicator (I) and receptor (R) may be coupled to a polymeric resin. In the absence of an analyte, the indicator may produce a signal in accordance with the local microenvironment. The signal may be an absorbance at a specific wavelength or a fluorescence. When the receptor interacts with an analyte, the local microenvironment may be altered such that the produced signal is altered. In one embodiment, depicted in FIG. 55A, the indicator may partially bind to the receptor in the absence of an analyte. When the analyte is present the indicator may be displaced from the receptor by the analyte. The local microenvironment for the indicator therefore changes from an environment where the indicator is binding with the receptor, to an environment where the indicator is no longer bound to the receptor. Such a change in environment may induce a change in the absorbance or fluorescence of the indicator.

In another embodiment, depicted in Turning to FIG. 55C, an indicator (I) may be coupled to a receptor (R). The receptor may be coupled to a polymeric resin. In the absence of an analyte, the indicator may produce a signal in accordance with the local microenvironment. The signal may be an absorbance at a specific wavelength or a fluorescence. When the receptor interacts with an analyte, the local microenvironment may be altered such that the produced signal is altered. In contrast to the case depicted in FIG. 55A, the change in local microenvironment may be due to a conformation change of the receptor due to the biding of the analyte. Such a change in environment may induce a change in the absorbance or fluorescence of the indicator.

In another embodiment, depicted in FIG. 55E, an indicator (I) may be coupled to a receptor by a linker. The linker may have a sufficient length to allow the indicator to bind to the receptor in the absence of an analyte. The receptor (R) may be coupled to a polymeric resin. In the absence of an analyte, the indicator may produce a signal in accordance with the local microenvironment. As depicted in FIG. 55E, the indicator may partially bind to the receptor in the absence of an analyte. When the analyte is present the indicator may be displaced from the receptor by the analyte. The local microenvironment for the indicator therefore changes from an environment where the indicator is binding with the receptor, to an environment where the indicator is no longer bound to the receptor. Such a change in environment may induce a change in the absorbance or fluorescence of the indicator.

In another embodiment, depicted in FIG. 55H, a receptor (R) may be coupled to a polymeric resin by a first linker. An indicator may be coupled to the first linker. In the absence of an analyte, the indicator may produce a signal in accordance with the local microenvironment. The signal may be an absorbance at a specific wavelength or a fluorescence. When the receptor interacts with an analyte, the local microenvironment may be altered such that the produced signal is altered. In one embodiment, as depicted in FIG. 55H, the indicator may partially bind to the receptor in the absence of an analyte. When the analyte is present the indicator may be displaced from the receptor by the analyte. The local microenvironment for the indicator therefore changes from an environment where the indicator is binding with the receptor, to an environment where the indicator is no longer bound to the receptor. Such a change in environment may induce a change in the absorbance or fluorescence of the indicator.

In another embodiment, the use of fluorescence resonance energy transfer or photoinduced electron transfer may be used to detect the presence of an analyte. Both of these methodologies involve the use of two fluorescent molecules. Turning to FIG. 55B, a first fluorescent indicator (B) may be coupled to receptor (R). Receptor (R) may be coupled to a polymeric resin. A second fluorescent indicator (C) may also be coupled to the polymeric resin. In the absence of an analyte, the first and second fluorescent indicators may be positioned such that fluorescence energy transfer may occur. In one embodiment, excitation of the first fluorescent indicator may result in emission from the second fluorescent indicator when these molecules are oriented correctly. Alternatively, either the first or second fluorescent indicator may be a fluorescence quencher. When the two indicators are properly aligned, the excitation of the fluorescent indicators may result in very little emission due to quenching of the emitted light by the fluorescence quencher. In both cases, the receptor and indicators may be positioned such that fluorescent energy transfer may occur in the absence of an analyte. When the analyte is presence the orientation of the two indicators may be altered such that the fluorescence energy transfer between the two indicators is altered. In one embodiment, the presence of an analyte may cause the indicators to move further apart. This has an effect of reducing the fluorescent energy transfer. If the two indicators interact to produce an emission signal in the absence of an analyte, the presence of the analyte may cause a decrease in the emission signal. Alternatively, if one the indicators is a fluorescence quencher, the presence of an analyte may disrupt the quenching and the fluorescent emission from the other indicator may increase. It should be understood that these effects will reverse if the presence of an analyte causes the indicators to move closer to each other.

In another embodiment, depicted in FIG. 55D, a first fluorescent indicator (B) may be coupled to receptor (R). A second fluorescent indicator (C) may also be coupled to the receptor. Receptor (R) may be coupled to a polymeric resin. In the absence of an analyte, the first and second fluorescent indicators may be positioned such that fluorescence energy transfer may occur. In one embodiment, excitation of the first fluorescent indicator may result in emission from the second fluorescent indicator when these molecules are oriented correctly. Alternatively, either the first or second fluorescent indicator may be a fluorescence quencher. When the two indicators are properly aligned, the excitation of the fluorescent indicators may result in very little emission due to quenching of the emitted light by the fluorescence quencher. In both cases, the receptor and indicators may be positioned such that fluorescent energy transfer may occur in the absence of an analyte. When the analyte is presence the orientation of the two indicators may be altered such that the fluorescence energy transfer between the two indicators is altered. In one embodiment, depicted in FIG. 55D, the presence of an analyte may cause the indicators to move further apart. This has an effect of reducing the fluorescent energy transfer. If the two indicators interact to produce an emission signal in the absence of an analyte, the presence of the analyte may cause a decrease in the emission signal. Alternatively, if one the indicators is a fluorescence quencher, the presence of an analyte may disrupt the quenching and the fluorescent emission from the other indicator may increase. It should be understood that these effects will reverse if the presence of an analyte causes the indicators to move closer to each other.

In a similar embodiment to FIG. 55D, the first fluorescent indicator (B) and second fluorescent indicator (C) may be both coupled to receptor (R), as depicted in FIG. 55F. Receptor (R) may be coupled to a polymeric resin. First fluorescent indicator (B) may be coupled to receptor (R) by a linker group. The linker group may allow the first indicator to bind the receptor, as depicted in FIG. 55F. In the absence of an analyte, the first and second fluorescent indicators may be positioned such that fluorescence energy transfer may occur. When the analyte is presence, the first indicator may be displaced from the receptor, causing the fluorescence energy transfer between the two indicators to be altered.

In another embodiment, depicted in FIG. 55G, a first fluorescent indicator (B) may be coupled to a polymeric resin. Receptor (R) may also be coupled to a polymeric resin. A second fluorescent indicator (C) may be coupled to the receptor (R). In the absence of an analyte, the first and second fluorescent indicators may be positioned such that fluorescence energy transfer may occur. In one embodiment, excitation of the first fluorescent indicator may result in emission from the second fluorescent indicator when these molecules are oriented correctly. Alternatively, either the first or second fluorescent indicator may be a fluorescence quencher. When the two indicators are properly aligned, the excitation of the fluorescent indicators may result in very little emission due to quenching of the emitted light by the fluorescence quencher. In both cases, the receptor and indicators may be positioned such that fluorescent energy transfer may occur in the absence of an analyte. When the analyte is presence the orientation of the two indicators may be altered such that the fluorescence energy transfer between the two indicators is altered. In one embodiment, the presence of an analyte may cause the indicators to move further apart. This has an effect of reducing the fluorescent energy transfer. If the two indicators interact to produce an emission signal in the absence of an analyte, the presence of the analyte may cause a decrease in the emission signal. Alternatively, if one the indicators is a fluorescence quencher, the presence of an analyte may disrupt the quenching and the fluorescent emission from the other indicator may increase. It should be understood that these effects will reverse if the presence of an analyte causes the indicators to move closer to each other.

In another embodiment, depicted in FIG. 55I, a receptor (R) may be coupled to a polymeric resin by a first linker. A first fluorescent indicator (B) may be coupled to the first linker. A second fluorescent indicator (C) may be coupled to the receptor (R). In the absence of an analyte, the first and second fluorescent indicators may be positioned such that fluorescence energy transfer may occur. In one embodiment, excitation of the first fluorescent indicator may result in emission from the second fluorescent indicator when these molecules are oriented correctly. Alternatively, either the first or second fluorescent indicator may be a fluorescence quencher. When the two indicators are properly aligned, the excitation of the fluorescent indicators may result in very little emission due to quenching of the emitted light by the fluorescence quencher. In both cases, the receptor and indicators may be positioned such that fluorescent energy transfer may occur in the absence of an analyte. When the analyte is presence the orientation of the two indicators may be altered such that the fluorescence energy transfer between the two indicators is altered. In one embodiment, the presence of an analyte may cause the indicators to move further apart. This has an effect of reducing the fluorescent energy transfer. If the two indicators interact to produce an emission signal in the absence of an analyte, the presence of the analyte may cause a decrease in the emission signal. Alternatively, if one the indicators is a fluorescence quencher, the presence of an analyte may disrupt the quenching and the fluorescent emission from the other indicatormay increase. It should be understood that these effects will reverse if the presence of an analyte causes the indicators to move closer to each other.

In one embodiment, polystyrene/polyethylene glycol resin beads may be used as a polymeric resin since they are highly water permeable, and give fast response times to penetration by analytes. The beads may be obtained in sizes ranging from 5 microns to 250 microns. Analysis with a confocal microscope reveals that these beads are segregated into polystyrene and polyethylene glycol microdomains, at about a 1 to 1 ratio. Using the volume of the beads and the reported loading of 300 pmol/bead, we can calculate an average distance of 35 Å between terminal sites. This distance is well within the Forester radii for the fluorescent dyes that we are proposing to use in our fluorescence resonance energy transfer ("FRET") based signaling approaches. This distance is also reasonable for communication between binding events and microenvironment changes around the fluorophores.

The derivatization of the beads with our receptors and with the indicators may be accomplished by coupling carboxylic acids and amines using EDC and HOBT. Typically, the efficiency of couplings are greater that 90% using quantitative ninhydrin tests. (See Nuikura, K.; Metzger, A.; and Anslyn, E. V. "A Sensing Ensemble with Selectivity for Iositol Trisphosphate", *J. Am. Chem. Soc.* 1998, 120, 0000, which is incorporated herein by reference). The level of derivatization of the beads is sufficient to allow the loading of a high enough level of indicators and receptors to yield successful assays. However, an even higher level of loading may be advantageous since it would increase the multivalency effect for binding analytes within the interior of the beads. We may increase the loading level two fold and ensure that two amines are close in proximity by attaching an equivalent of lysine to the beads (see FIG. 45D). The amines may be kept in proximity so that binding of an analyte to the receptor will influence the environment of a proximal indicator.

Even though a completely random attachment of indicator and a receptor lead to an effective sensing particle, it may be better to rationally place the indicator and receptor in proximity. In one embodiment, lysine that has different protecting groups on the two different amines may be used, allowing the sequential attachment of an indicator and a receptor. If needed, additional rounds of derivatization of the beads with lysine may increase the loading by powers of two, similar to the synthesis of the first few generations of dendrimers.

In contrast, too high a loading of fluorophores will lead to self-quenching, and the emission signals may actually decrease with higher loadings. If self quenching occurs for fluorophores on the commercially available beads, we may incrementally cap the terminal amines thereby giving incrementally lower loading of the indicators.

Moreover, there should be an optimum ratio of receptors to indicators. The optimum ratio is defined as the ratio of indicator to receptor to give the highest response level. Too few indicators compared to receptors may lead to little change in spectroscopy since there will be many receptors that are not in proximity to indicators. Too many indicators relative to receptors may also lead to little change in spectroscopy since many of the indicators will not be near receptors, and hence a large number of the indicators will not experience a change in microenvironment. Through iterative testing, the optimum ratio may be determined for any receptor indicator system.

This iterative sequence will be discussed in detail for a particle designed to signal the presence of an analyte in a fluid. The sequence begins with the synthesis of several beads with different loadings of the receptor. The loading of any receptor may be quantitated using the ninhydrin test. (The ninhydrin test is described in detail in Kaiser, E.; Colescott, R. L.; Bossinger, C. D.; Cook, P. I. "Color Test for Detection of Free Terminal Amino Groups in the Solid-Phase Synthesis of Peptides", *Anal. Biochem.* 1970, 34, 595–598 which is incorporated herein by reference). The number of free amines on the bead is measured prior to and after derivatization with the receptor, the difference of which gives the loading. Next, the beads undergo a similar analysis with varying levels of molecular probes. The indicator loading may be quantitated by taking the absorption spectra of the beads. In this manner, the absolute loading level and the ratio between the receptor and indicators may be adjusted. Creating calibration curves for the analyte using the different beads will allow the optimum ratios to be determined.

The indicator loading may be quantitated by taking the absorption spectra of a monolayer of the beads using our sandwich technique (See FIG. 46D). The sandwich technique involves measuring the spectroscopy of single monolayers of the beads. The beads may be sandwiched between two cover slips and gently rubbed together until a monolayer of the beads is formed. One cover slip is removed, and mesh with dimensions on the order of the beads is then place over the beads, and the cover slip replaced. This sandwich is then placed within a cuvette, and the absorbance or emission spectra are recorded. Alternatively, an sensor array system, as described above, may be used to analyze the interaction of the beads with the analyte.

Figure 47:
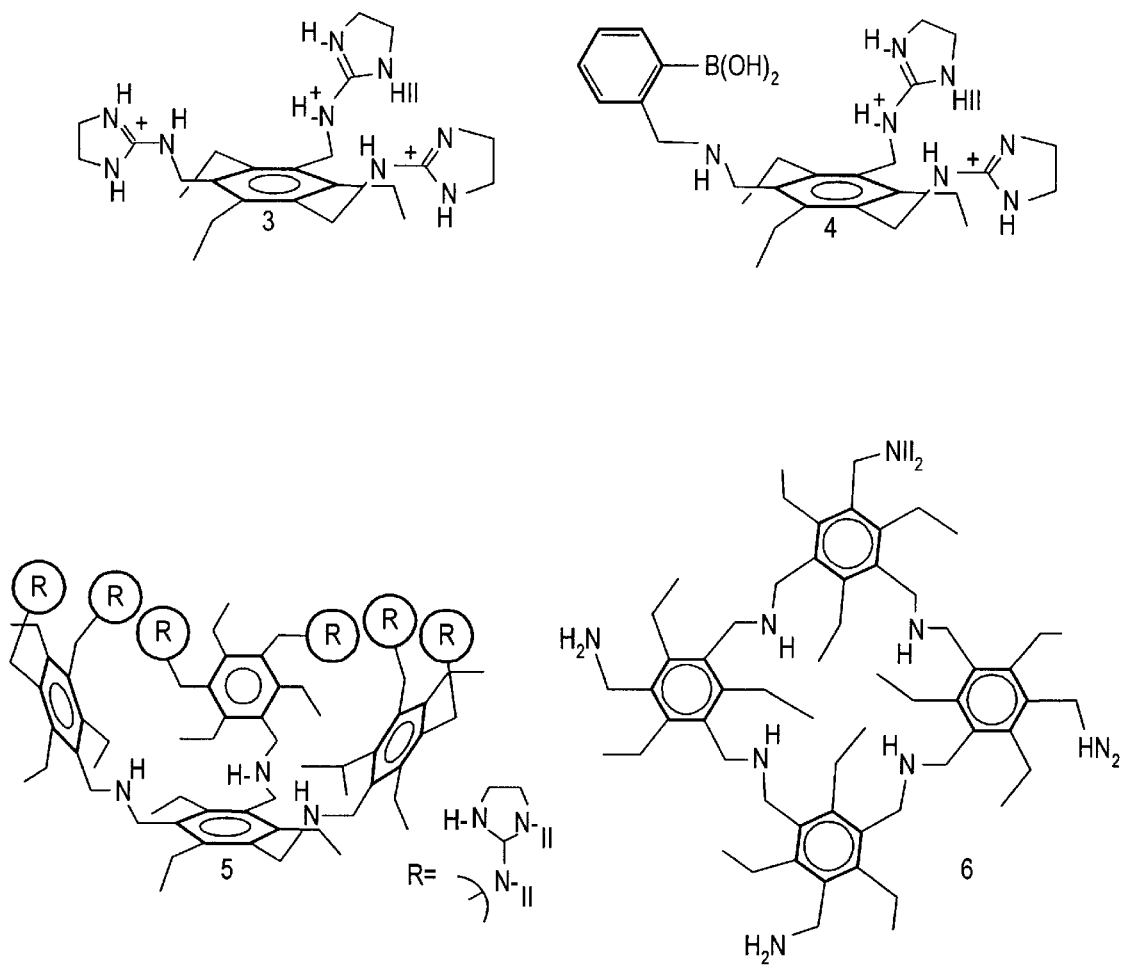
FIG. 47 depicts receptors 3–6.

A variety of receptors may be coupled to the polymeric beads. Many of these receptors have been previously described. Other receptors are shown in FIG. 47.

Figure 48:
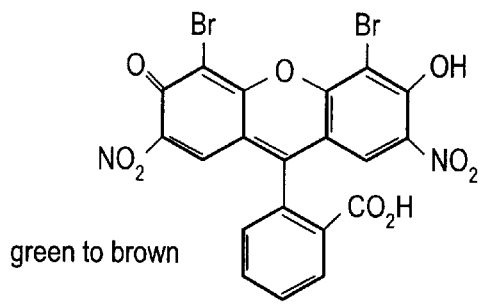
FIG. 48 depicts pH indicators which may be coupled to a particle.
Figure 48:
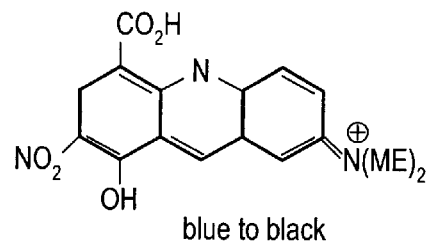
Figure 48:
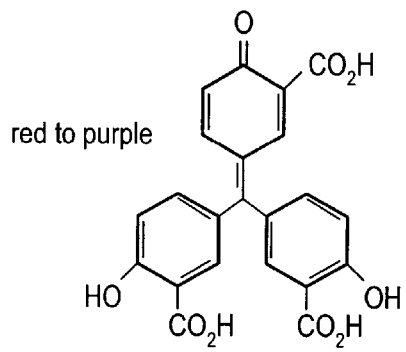
Figure 48:
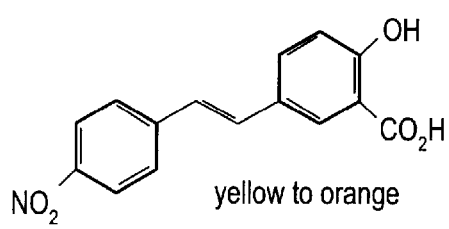
Figure 48:
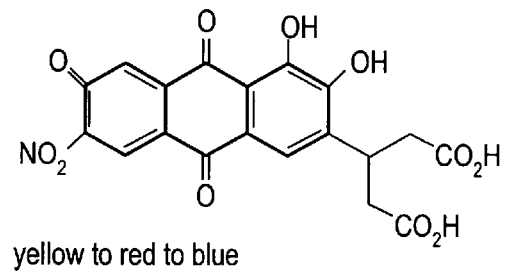

As described generally above, an ensemble may be formed by a synthetic receptor and a probe molecule, either mixed together in solution or bound together on a resin bead. The modulation of the spectroscopic properties of the probe molecule results from perturbation of the microenvironment of the probe due to interaction of the receptor with the analyte; often a simple pH effect. The use of a probe molecule coupled to a common polymeric support may produce systems that give color changes upon analyte binding. A large number of dyes are commercially available, many of which may be attached to the bead via a simple EDC/HOBT coupling (FIG. 48 shows some examples of indicators). These indicators are sensitive to pH, and also respond to ionic strength and solvent properties. When contacted with an analyte, the receptor interacts with the analyte such that microenvironment of the polymeric resin may become significantly changed. This change in the microenvironment may induce a color change in the probe molecule. This may lead to an overall change in the appearance of the particle indicating the presence of the analyte.

Since many indicators are sensitive to pH and local ionic strength, index of refraction, and/or metal binding, lowering the local dielectric constant near the indicators may modulate the activity of the indicators such that they are more responsive. A high positive charge in a microenvironment leads to an increased pH since hydronium ions migrate away from the positive region. Conversely, local negative charge decreases the microenvironment pH. Both changes result in a difference on the protonation state of a pH sensitive indicator present in that microenvironment. The altering of the local dielectric environment may be produced by attaching molecules of differing dielectric constants to the bead proximate to the probe molecules. Examples of molecules which may be used to alter the local dielectric environment include, but are not limited to, planar aromatics, long chain fatty acids, and oligomeric tracts of phenylalanine, tyrosine, and tryptophan. Differing percentages of these compounds may be attached to the polymeric bead to alter the local dielectric constant.

Competition assays may also be used to produce a signal to indicate the presence of an analyte. The high specificity of antibodies makes them the current tools of choice for the sensing and quantitation of structurally complex molecules in a mixture of analytes. These assays rely on a competition approach in which the analyte is tagged and bound to the antibody. Addition of the untagged analyte results in a release of the tagged analytes and spectroscopic modulation is monitored. Surprisingly, although competition assays have been routinely used to determine binding constants with synthetic receptors, very little work has been done exploiting competition methods for the development of sensors based upon synthetic receptors. Yet, all the ways in which the microenvironment of the chromophore can be altered, as described above, may be amenable to the competition approach. Those that have been developed using synthetic receptors are mostly centered upon the use of cyclodextrins. (See e.g., Hamasaki, K.; Ikeda, H.; Nakamura, A.; Ueno, A.; Toda, F.; Suzuki, I.; Osa, T. "Fluorescent Sensors of Molecular Recognition. Modified Cyclodextrins Capable of Exhibiting Guest-Responsive Twisted Intramolecular Charge Transfer Fluorescence" *J. Am. Chem. Soc.* 1993, 115, 5035, and reference (5) therein, which are incorporated herein by reference) A series of parent and derivatized cyclodextrins have been combined with chromophores that are responsive to the hydrophobicity of their microenvironment to produce a sensor system. Displacement of the chromophores from the cyclodextrin cavity by binding of a guest leads to a diagnostic spectroscopy change.

This competitive approach has been used successfully, in one embodiment, for the detection of carbohydrates such as inositol-1,4,5-triphosphate ($IP_3$). In one embodiment, a synthetic receptor 5 may be paired with an optical signaling molecule 5-carboxyfluorescein, to quantitate $EP_3$ at nM concentrations. A competition assay employing an ensemble of 5-carboxyfluorescein and receptor 5 was used to measure binding constants. The addition of receptor 5 to 5-carboxyfluorescein resulted in a red shift of the absorption of 5-carboxyfluorescein. Monitoring the absorption at 502 nm, followed by analysis of the data using the Benesi-Hildebrand method, gave affinity constants of $2.2 \times 10^4$ M for 5-carboxyfluorescein binding to receptor 5. Addition of $IP_3$ to a solution of the complexes formed between 5 and 5-carboxyfluorescein resulted in displacement of 5-carboxyfluorescein and a subsequent blue shift.

In order to enhance the affinity of receptor 5 for $IP_3$, similar assays were repeated in methanol, and with 2% of the surfactant Triton-X. In methanol and the detergent solutions, 5-carboxyfluorescein prefers a cyclized form in which the 2-carboxylate has undergone an intramolecular conjugate addition to the quinoid structure. This form of 5-carboxyfluorescein is colorless and nonfluorescent. Upon addition of receptor 5 the yellow color reappears as does the fluorescence. The positive character of the receptor induces a ring opening to give the colored/fluorescent form of 5-carboxyfluorescein. Using the Benesi-Hildebrand method applied to absorption data a binding constant of $1.2 \times 10^5$ M$^{-1}$ was found for receptor 5 and 5-carboxyfluorescein. As anticipated based upon the differences in the spectroscopy of 5-carboxyfluorescein when it is bound to receptor 5 or free in solution, addition of $IP_3$ to a solution of receptor 5 and 5-carboxyfluorescein resulted in a decrease of absorbance and fluorescence due to release of 5-carboxyfluorescein into the methanol solution. Binding constants of $1.0 \times 10^8$ $M^{-1}$ and $1.2 \times 10^7$ $M^{-1}$ for $IP_3$ and receptor 5 were found for methanol and the surfactant solution respectively.

Since fluorescence spectroscopy is a much more sensitive technique than UV/visible spectroscopy, and the use of methanol gave significantly stronger binding between receptor 5 and 5-carboxyfluorescein, as well as between receptor 5 and $IP_3$, the monitoring of fluorescence was found to be the method of choice for sensing nM concentrations of $IP_3$. We find that the addition of $IP_3$ to an ensemble of receptor 5 and 5-carboxyfluorescein in water may detect and quantitate $IP_3$ at a concentration as low as 1 mM. Importantly, in methanol a 10 nM $IP_3$ concentration was easily detected. A detection level in the nM range is appropriate for the development of an assay using methanol or surfactant as an eluent and capillary electrophoresis to sample and fractionate cellular components.

Figure 49:
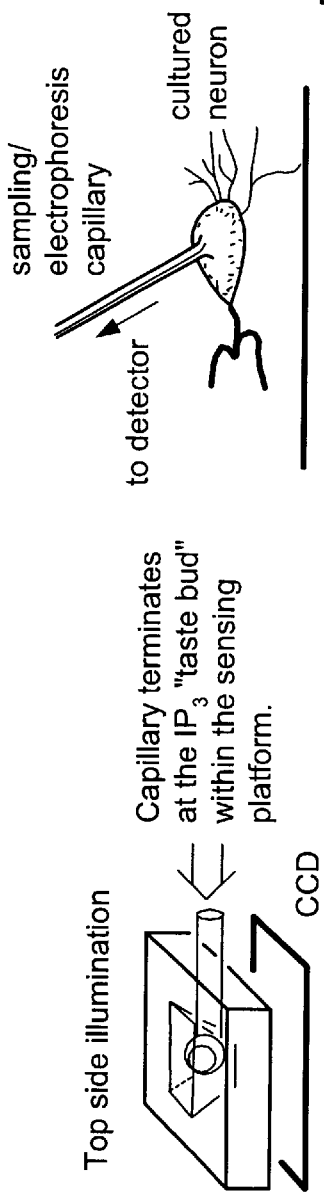
FIG. 49 depicts a device for the analysis of IP$_3$ in cells.

We have shown that receptor 5 binds $IP_3$ quite selectively over other similarly charged species present in cells. Polyanions with charges higher than $IP_3$, such as $IP_4$, $EP_5$, and oligonucleotides, however, are expected to bind with higher affinities. In order to fractionate the cellular components during signal transduction, and specifically monitor $IP_3$, a combination of a chemically sensitive particle and capillary electrophoresis (CE) may be used. As has been described above, a sensor array may include a well in which the particle is placed, along with a groove in which the capillary will reside. The capillary will terminate directly into the interior of the bead (See FIG. 49). Illumination from above and CCD analysis from below may be used to analyze the particle. Samples as small as 100 femtoliters may be introduced into an electrophoresis capillary for analysis. Using high sensitivity multiphoton-excited fluorescence as few as ~50,000 molecules of various precursors/metabolites of the neurotransmitter, serotonin may be detected. Cytosolic samples may be collected and fractionated in micron-diameter capillary electrophoresis channels. At the capillary outlet, components may migrate from the channel individually, and will be directed onto a bead that houses immobilized receptor 5 and the dyes appropriate for our various signaling strategies. Receptor binding of $IP_3$ or $IP_4$ will elicit modulations in the emission and/or absorption properties.

Dramatic spectroscopy changes accompany the chelation of metals to ligands that have chromophores. In fact, most colorimetric/fluorescent sensors for metals rely upon such a strategy. Binding of the metal to the inner sphere of the ligand leads to ligand/metal charge transfer bands in the absorbance spectra, and changes in the HOMO-LUMO gap that leads to fluorescence modulations.

Figure 50:
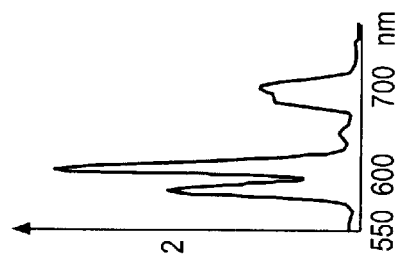
FIG. 50 depicts the structure of Indo-1 and compound 2 and the emission spectra of Indo-1 and compound 2 in the presence of Ca(II) and Ce(III), respectively.
Figure 50:
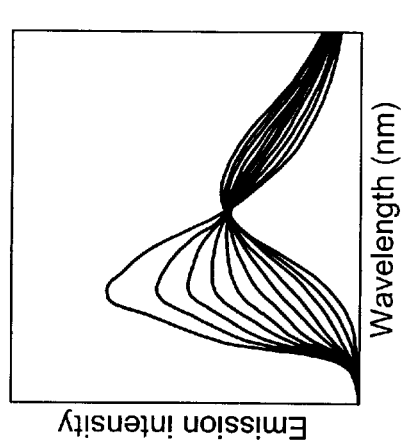
Figure 50:
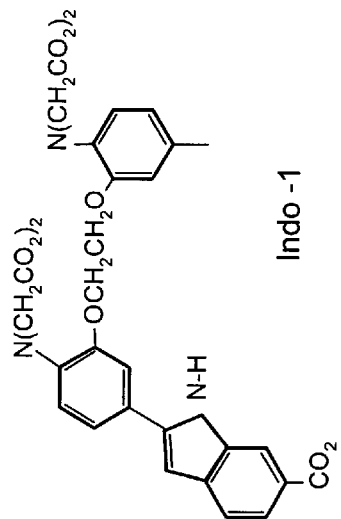

In one embodiment, the binding of an analyte may be coupled with the binding of a metal to a chromophoric ligand, such that the metal may be used to trigger the response of the sensor for the analyte. The compound known as Indo-1 (see FIG. 50 for the structure and emission properties) is a highly fluorescent indicator that undergoes a large wavelength shift upon exposure to Ca(II). Further, compound 2 binds Ce(III) and the resulting complex is fluorescent. In one embodiment, the binding of Ca(II) or Ce(III) to these sensors may be altered by the addition of an analyte of interest. By altering the binding of these metals to a receptor a signal may be generated indicating the presence of the receptor.

Figure 51:
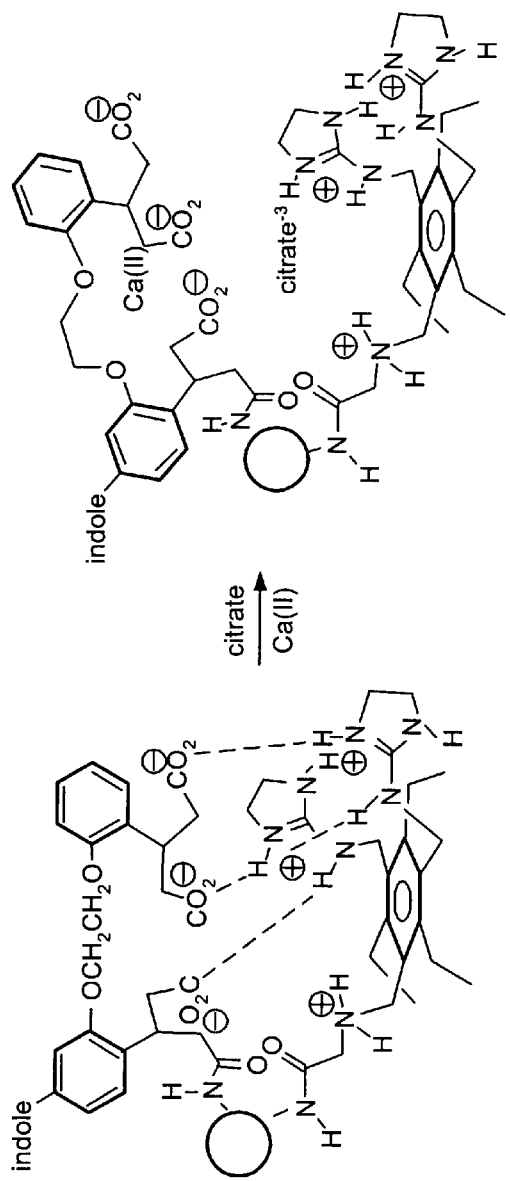
FIG. 51 depicts a scheme wherein binding of citrate to a receptor frees up the Indo-1 for Ca(II) binding.

In one embodiment, fluorescent indicators that have been used to monitor Ca(II) and Ce(III) levels in other applications may be applied to a polymeric supported system. Using the Ca(II) sensor Indo-1 as an example, the strategy is shown in FIG. 51. Indo-1 binds Ca(II) at nM concentrations (see FIG. 50). Attachment of Indo-1 and one of our guanidinium/amine based receptors 3–6 to a resin bead (derivatized with lysine as depicted in FIG. 45D) may lead to intramolecular interactions between the carboxylates of Indo-1 and the guanidiniums/ammoniums of a receptor. The coordination of the carboxylates of Indo-1 may result in a decreased affinity for Ca(II). However, there should be cooperative binding of Ca(II) and our analytes. Once one of the anionic analytes is bound to its respective receptor, it will competitively displace the carboxylates of Indo-1 leading to increased Ca(II) binding, which in turn will result in a fluorescence modulation. Similarly, binding of Ca(II) to Indo-1 leaves the guanidiniums of the receptors free to bind citrate. The assays will likely be most sensitive at concentrations of the analytes and Ca(II) near their dissociation constants, where neither receptor is saturated and small changes in the extent of binding lead to large changes in fluorescence.

We also may swit such the role of the metal and the ligand. Indo-1 is fluorescent with and without the Ca(II). However, compound 2 is not fluorescent until Ce(III) binds to it. Thus, a similar assay that relies upon a change of microenvironment in the interior of the bead depending upon the presence or absence of the analyte should perturb the binding of Ce(III) to compound 2. In this case, a repulsive interaction is predicted for the binding of Ce(III) when the positive charges of the guanidinium based receptors are not neutralized by binding to the anionic analytes.

In one embodiment, an indicator may be coupled to a bead and further may be bound to a receptor that is also coupled to the bead. Displacement of the indicator by an analyte will lead to signal modulation. Such a system may also take advantage of fluorescent resonance energy transfer to produce a signal in the presence of an analyte. Fluorescence resonance energy transfer is a technique that can be used to shift the wavelength of emission from one position to another in a fluorescence spectra. In this manner it creates a much more sensitive assay since one can monitor intensity at two wavelengths. The method involves the radiationless transfer of excitation energy from one fluorophore to another. The transfer occurs via coupling of the oscillating dipoles of the donor with the transition dipole of the acceptor. The efficiency of the transfer is described by equations first derived by Forester. They involve a distance factor (R), orientation factor (k), solvent index of refraction (N), and spectral overlap (J).

In order to incorporate fluorescence resonance energy transfer into a particle a receptor and two different indicators may be incorporated onto a polymeric bead. In the absence of an analyte the fluorescence resonance energy transfer may occur giving rise to a detectable signal. When an analyte interacts with a receptor, the spacing between the indicators may be altered. Altering this spacing may cause a change in the fluorescence resonance energy transfer, and thus, a change in the intensity or wavelength of the signal produced. The fluorescence resonance energy transfer efficiency is proportional to the distance (R) between the two indicators by $1/R^6$. Thus slight changes in the distance between the two indicators may induce significant changes in the fluorescence resonance energy transfer.

Figure 52:
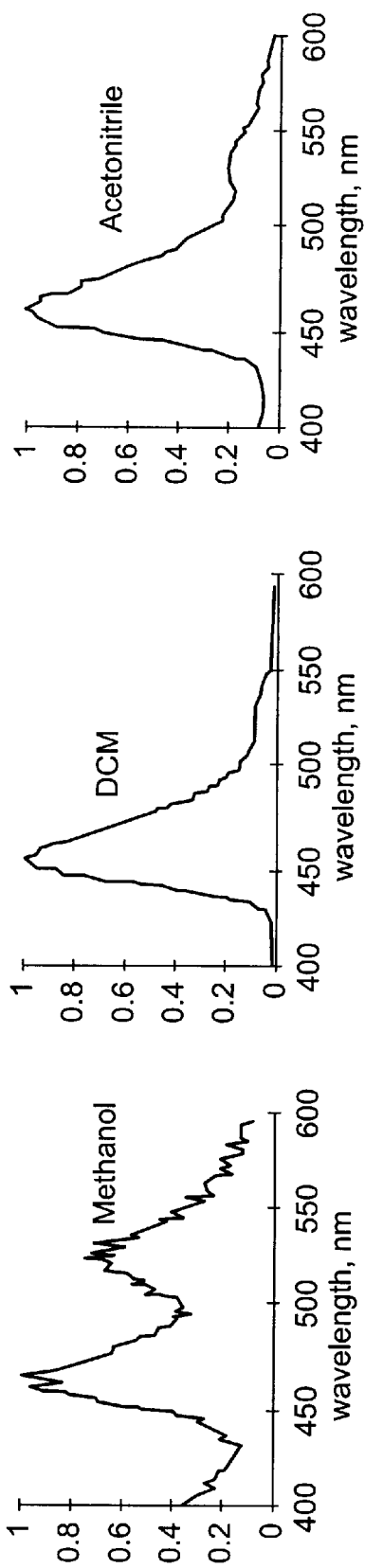
FIG. 52 depicts the change in FRET between coumarin and 5-carboxyfluorescein on resin beads as a function of the solvent.

In one embodiment, various levels of coumarin and fluorescein may be loaded onto resin beads so as to achieve gradiations in FRET levels from zero to 100%. FIG. 52 shows a 70/30 ratio of emission from 5-carboxyfluorescein and coumarin upon excitation of coumarin only in water. However, other solvents give dramatically different extents of FRET. This shows that the changes in the interior of the beads does lead to a spectroscopic response. This data also shows that differential association of the various solvents and 5-carboxyfluorescein on resin beads as a function of solvents. This behavior is evoked from the solvent association with the polymer itself, in the absence of purposefully added receptors. We may also add receptors which exhibit strong/selective association with strategic analytes. Such receptors may induce a modulation in the ratio of FRET upon analyte binding, within the microenvironment of the polystyrene/polyethylene glycol matrices.

In order to incorporate a wavelength shift into a fluorescence assays, receptors 3–6 may be coupled to the courmarin/5-carboxyfluorescein beads discussed above. When 5-carboxyfluorescein is bound to the various receptors and coumarin is excited, the emission will be primarily form coumarin since the fluorescein will be bound to the receptors. Upon displacement of the 5-carboxyfluorescein by the analytes, emission should shift more toward 5-carboxyfluorescein since it will be released to the bead environment which possesses coumarin. This will give us a wavelength shift in the fluorescence which is inherently more sensitive than the modulation of intensity at a signal wavelength.

There should be large changes in the distance between indicators (R) on the resin beads. When the 5-carboxyfluorescein is bound, the donor/acceptor pair should be farther than when displacement takes place; the FRET efficiency scales as $1/R^6$. The coumarin may be coupled to the beads via a floppy linker, allowing it to adopt many conformations with respect to a bound 5-carboxyfluorescein. Hence, it is highly unlikely that the transition dipoles of the donor and acceptor will be rigorously orthogonal.

In one embodiment, a receptor for polycarboxylic acids and an appropriate probe molecule may be coupled to a polymeric resin to form a particle for the detection of polycarboxylic acid molecules. Receptors for polycarboxylic acids, as well as methods for their use in the detection of polycarboxylic acids, have been described in U.S. Pat. No. 6,045,579 which is incorporated herein by reference. This system involves, in one embodiment, the use of a receptor 3 which was found to be selective for the recognition of a tricarboxylic acid (e.g., citrate) in water over dicarboxylates, monocarboxylates, phosphates, sugars, and simple:salts. The receptor includes guanidinium groups for hydrogen bonding and charge pairing with the tricarboxylic acid.

An assay for citrate has employed an ensemble of 5-carboxyfluorescein and 3. The binding between 3 and 5-carboxyfluorescein resulted in a lowering of the phenol $pK_a$ of 5-carboxyfluorescein, due to the positive microenvironment presented by 3. This shift in $pK_a$ (local pH) caused the phenol moiety to be in a higher state of protonation when 5-carboxyfluorescein was free in solution. The absorbance or fluorescence of 5-carboxyfluorescein decreases with higher protonation of the phenol. The intensity of absorbance increases with addition of host 3 to 5-carboxyfluorescein, and as predicted the intensity decreases upon addition of citrate to the ensemble of 3 and 5-carboxyfluorescein. The same effect was seen in the fluorescence spectrum ($\lambda$max=525 nm).

In an embodiment, a metal may be used to trigger the response of a chromophore to the presence of an analyte. For example, compound 7 binds Cu(II) with a binding constant of $4.9 \times 10^5$ M$^{-1}$ (See FIG. 53). Addition of 1 eq. of Cu(II) increases the binding constant of citrate to compound 7 by a factor of at least 5. Importantly, the addition of citrate increases the binding of Cu(II) to the receptor by a factor of at least 10. Therefore the citrate and Cu(II) enhance each other's binding in a cooperative manner. Further, the emission spectra of compound 7 is quite sensitive to the addition of citrate when Cu(II) is present, but has no response to the addition of citrate in the absence of Cu(II). Thus the binding of a "trigger" may be perturbed with an analyte of interest, and the perturbation of the binding of the trigger may be used to spectroscopically monitor the binding of the analyte. The triggering of the sensing event by an added entity is similar to the requirement for enzymes in saliva to degrade food particulants into tastants recognizable by the receptors on mammalian taste buds.

In one embodiment, citrate receptor 3 may be immobilized on a polystyrene/polyethylene glycol bead, where on the same bead may also be attached a fluorescent probe molecule (FIG. 54). Solutions of citrate at different concentrations may be added to the beads, and the fluorescence spectra of the monolayer recorded. We find exactly the same fluorescence response toward citrate for the ensemble of receptor 3 and 5-carboxyfluorescein on the beads as in solution. Apparently, a similar microenvironment change to modulate the spectroscopy of 5-carboxyfluorescein occurs in the beads, although both 5-carboxyfluorescein and receptor 3 are just randomly placed throughout the bead.

Additional sensor system include sensors for tartrate and tetracyclin. Compound 4 binds tartrate in buffered water (pH 7.4) with a binding constant of approximately $10^5$ M$^{-1}$. The binding is slow on the NMR time scale, since we can observe both the bound and free receptor and tartrate. This binding is surprisingly strong for pure water. It must reflect good cooperativity between the host's boronic acid moiety and the two guanidinium groups for the recognition of the guest's vicinal diol and two carboxylates respectively. Compound 6 may act as a molecular receptor for tetracyclin. The compound has been synthesized, and by variable temperature NMR it has been found to be in a bowl conformation. Its binding properties with several indicators have been explored (most bind with affinities near $10^4$ M$^{-1}$). More importantly, the binding of tetracyclin has also been explored, and our preliminary results suggests that the binding constant in water is above $10^3$ M$^{-1}$.

Figure 56:
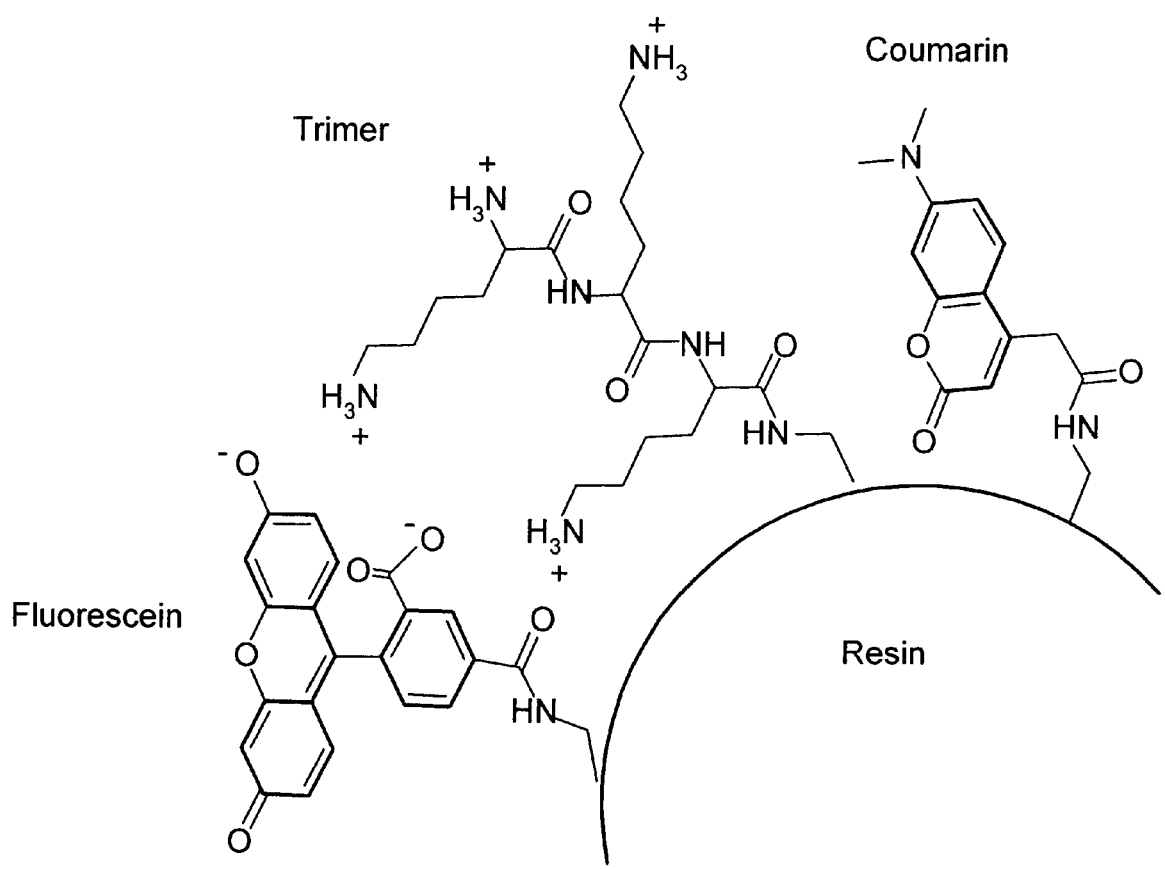
FIG. 56 depicts a peptide trimer receptor and a pair of fluorescent indicators coupled to a polymeric resin.

In another embodiment, a sensing particle may include an oligomer of amino acids with positively charged side chains such as the lysine trimer, depicted in FIG. 56, designed to act as the anion receptor, and an attached FRET pair for signaling. Sensing of different anions may be accomplished by optically monitoring intensity changes in the signal of the FRET pair as the analyte interacts with the oligomer.

Upon introduction of an anionic species to 1, the analyte may bind to the trimer, disturbing the trimer-fluorescein interaction, thereby, altering the fluorescein's ability to participate in the energy transfer mechanism. Using a monolayer of resin in a conventional fluorometer, the ratio of D:A emission for the FRET pair attached to TG-NH$_2$ resin is sensitive to different solvents as well as to the ionic strength of the solution. Epifluorescence studies may be performed to test the solvent dependence, ionic strength, and binding effects of different anions on the FRET TG-NH$_2$ resins. The images of the FRET TG-NH$_2$ resins within a sensor array, taken by a charged coupled device (CCD) may result in three output channels of red, green, and blue light intensities. The RGB light intensities will allow for comparison of the results obtained using a conventional fluorometer.

The signal transduction of 1 may be studied using a standard fluorometer and within the array platform using epifluorescence microscopy. The RGB analysis may be used to characterize the relative changes in emission of the FRET pair. Other resin-bound sensors may be synthesized by varying the amino acid subunits within the oligomers and the length of the peptide chains.

Figure 57:
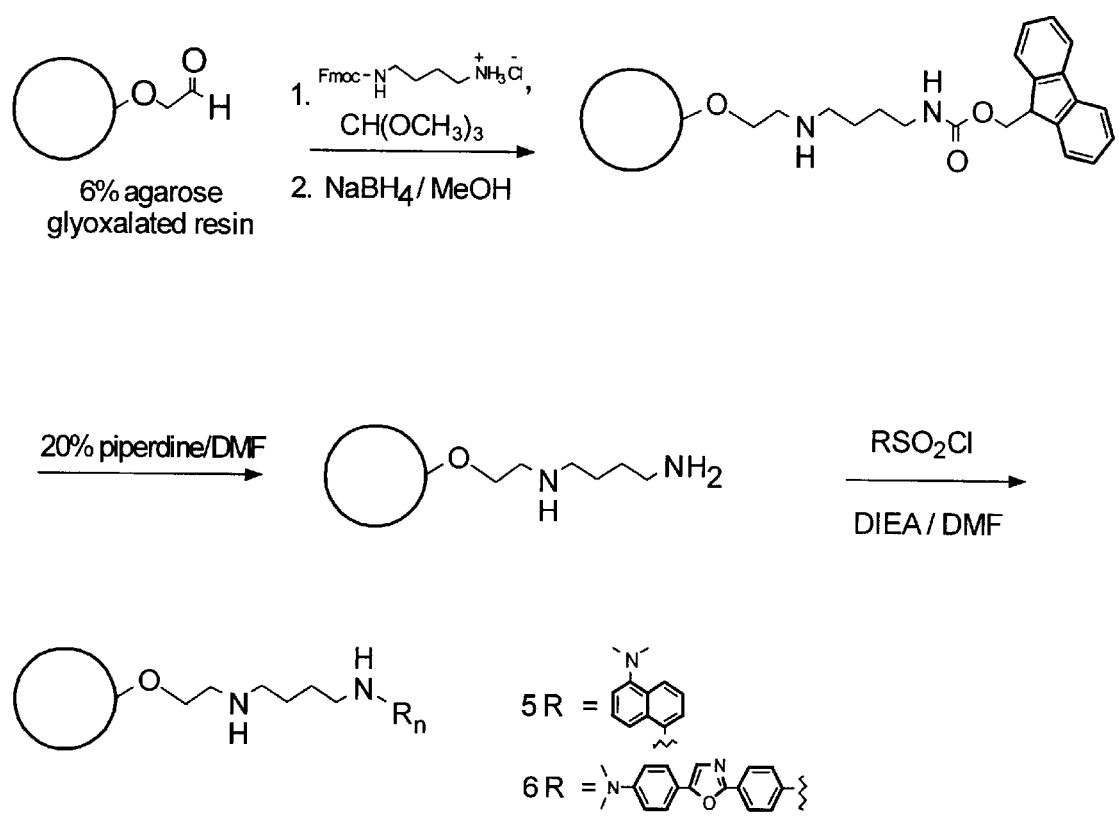
FIG. 57 depicts a synthetic scheme for anchoring dansyl and dapoxyl indicators to 6% agarose glyoxalated resin beads.

In another embodiment, solvatochromic dyes may be covalently linked to a receptor unit tethered to a resin bead that is capable of binding to small organic guests. In one example, dansyl and dapoxyl may act as sensitive probes of their microenvironment. When selecting a dye for use, characteristics such as high extinction coefficients, high fluorescence quantum yields, and large Stoke's shifts should be considered. Dapoxyl and dansyl were anchored to 6% agarose resin beads, in an effort to enhance the signaling response of these resin bound fluorophores in various solvent systems. Agarose beads are crosslinked galactose polymers that are more hydrophilic than the polystyrene-polyethylene glycol resins. The attachment of these solvatochromic dyes to the agarose resin beads is outlined in FIG. 57.

The dapoxyl labeled resin (6) was formed by reductively aminating glyoxalated agarose resin with mono (Fmoc)-butyldiamine hydrochloride salt using sodium borohydride as the reducing agent. The base labile protecting group, Fmoc, was removed from 3 with dilute base, and the solvatochromic dye was anchored to 4 through a reaction to form a sulfonamide bond resulting in 6. The tethering of dansyl to agarose resin was performed similarly.

Analysis of the agarose resins derivatized with dansyl and dapoxyl was attempted several times using a monolayer sample cell in a conventional fluorometer. However, satisfactory emission spectra of 5 and 6 in different solvent systems were not obtained due to the fragile nature of the agarose resin which placed restrictions on the manufacturing of the monolayer sample cell.

Significant signal enhancement of 5 and 6 was seen when the solvent system was changed from a 50 mM phosphate buffer (pH=7.0) to ethanol (EtOH), methanol (MeOH), and acetonitrile ($CH_3CN$). The emission of 6 increased three fold in EtOH and five fold in $CH_3CN$ when compared to the emission of 6 in a buffer. The agarose-dansyl resin, 5, demonstrated similar trends in response to different solvents; however, the intensities were smaller than for 6. For instance, the emission of 5 in EtOH for the red channel was 61% smaller in intensity units compared to 6 (2200 vs. 5800 arbitrary intensity units). This observation has been attributed to the lower quantum yield of fluorescence and the smaller extinction coefficient of dansyl to that of dapoxyl. From these initial studies, the average fluorescence intensity of the three beads of type 6 in EtOH across the red channel was 5800±300 arbitrary intensity counts with a percent standard deviation of 5.0%. Also, before changing to a new solvent, the agarose beads were flushed with the buffer for 5 minutes in order to return the agarose-dye resin to a "zero" point of reference. The background variance of the fluorescence intensity of 6 when exposed to each of the buffer washes between each solvent system was 5.0% and 4.0% in the red and green channels, respectively.

Figure 58:
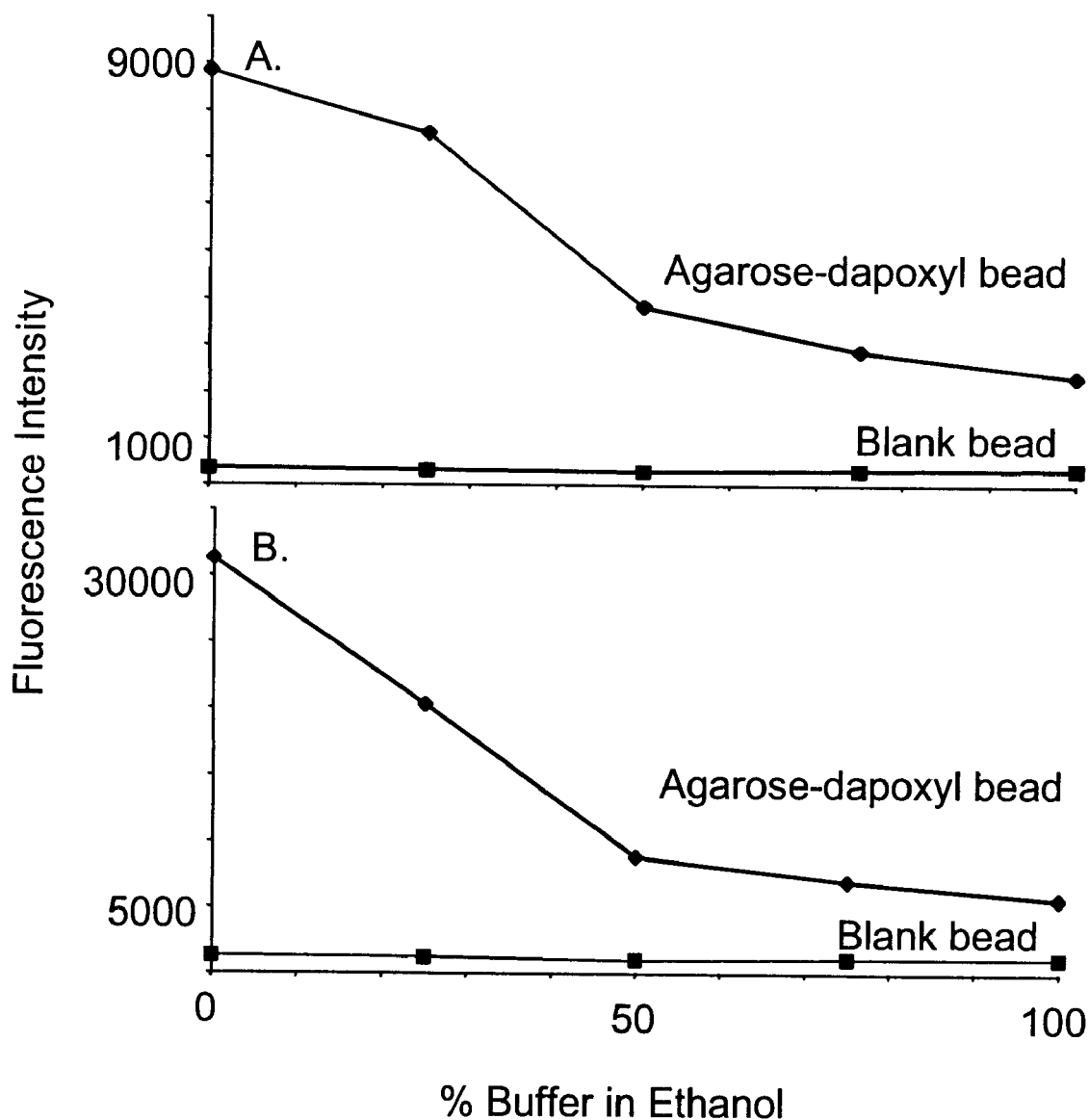
FIG. 58 depicts the RGB epifluorescence of 6 in EtOH with varying ratio buffer concentrations.

The response of 5 and 6 to varying ratios of two different solvents was also studied. As seen in FIG. 58, a detectable decrease in the emission of 6 is observed as the percent of the 50 mM phosphate buffer (pH=7) is increased in ethanol. The fluorescence intensity of 6 decreased by three fold from its original value in 100% EtOH to 100% buffer. There was an incremental decrease in the fluorescence emission intensities of 6 in both the red and green channels. Once again, 5 demonstrated similar trends in response to the varying ratios of mixed solvent systems; however, the intensities were smaller than 6.

Figure 59:
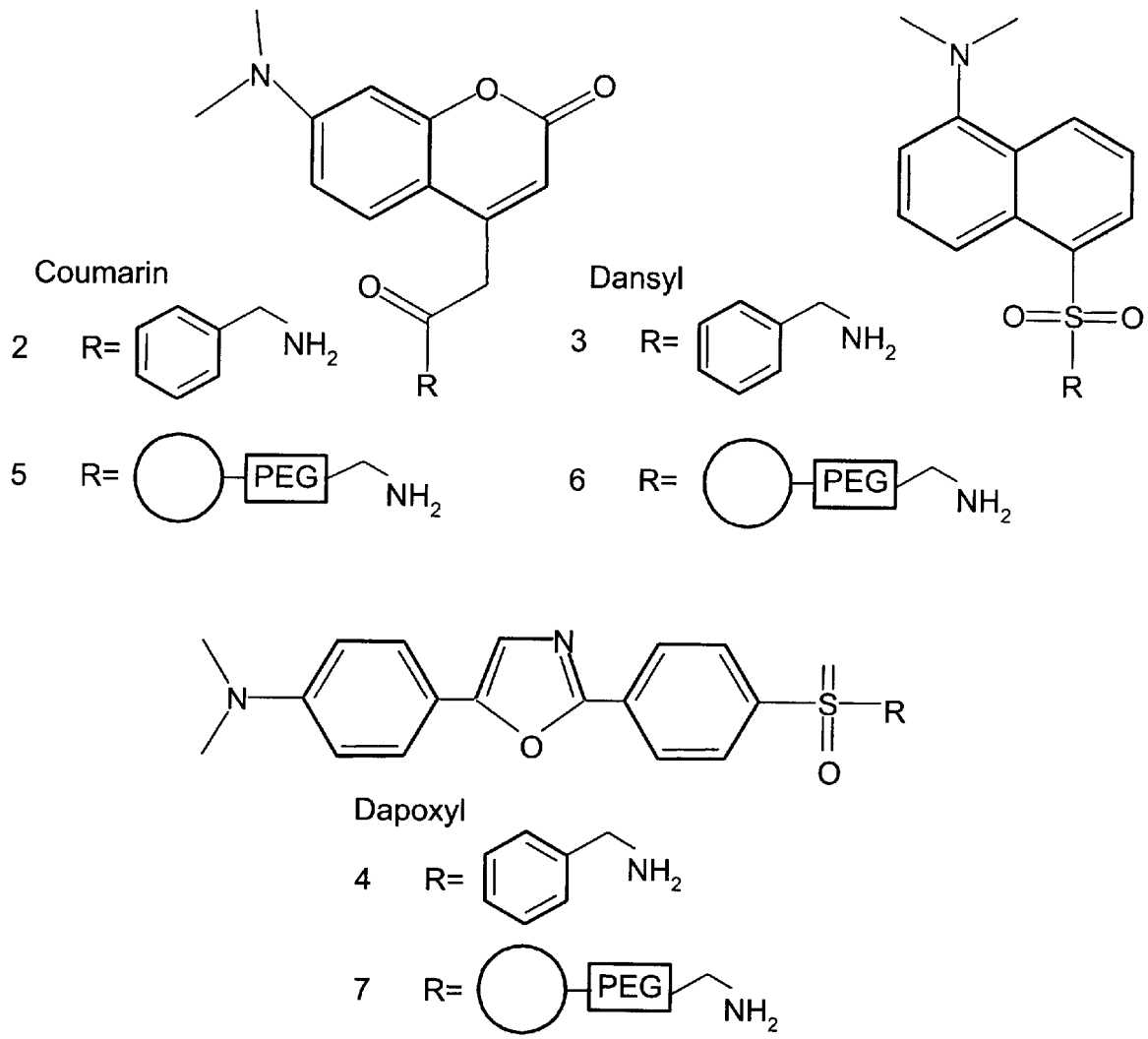
FIG. 59 depicts indicators and polymeric beads used for fluorescence studies.

In another example, each dye was derivatized with benzyl amine (2–4) for studies in solution phase and anchored to resin (5–7) for studies using the sandwich method and epi-fluorescence. The dyes and corresponding resins are depicted in FIG. 59.

Figure 60A:
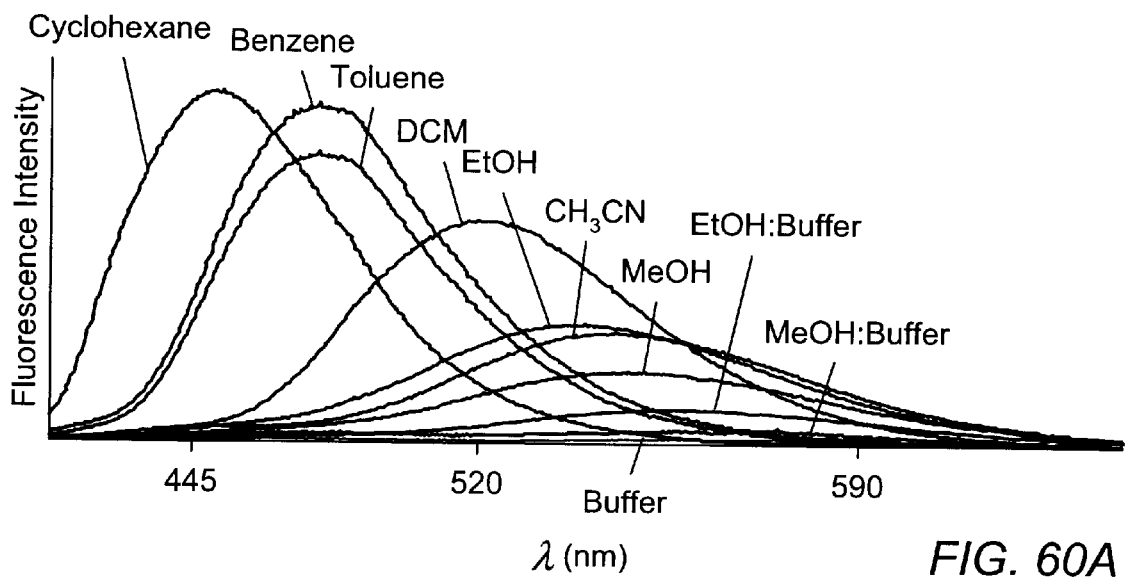
FIGS. 60A–B depicts Emission spectra of derivatized dapoxyl dyes in various solvents.
Figure 60B:
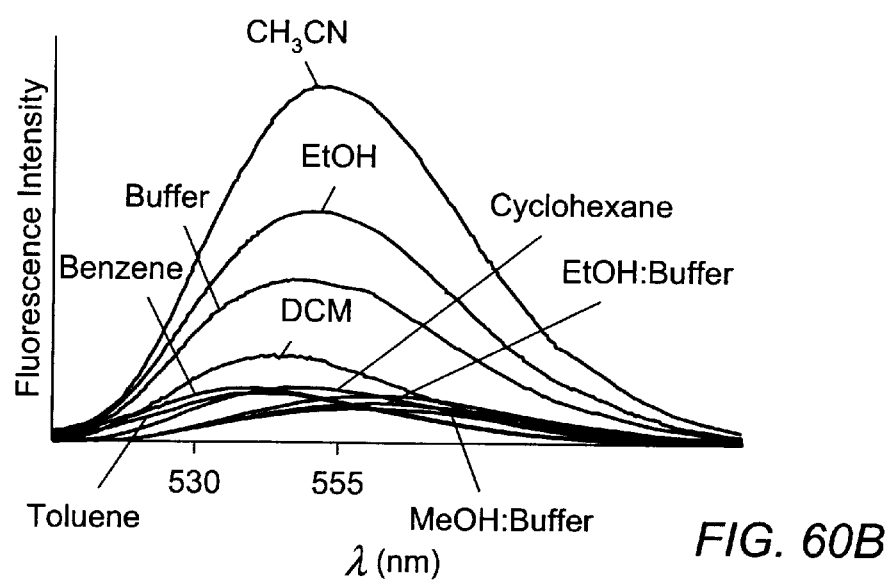

Fluorescence studies have been performed for each dye in solution phase and attached to resin. FIG. 60 illustrates an example of the emission changes in 4 (part A.) and 7 (part B.) that result from exposure to different solvent systems. The quantum yield of 4 diminished in more polar protic media (i.e. ethanol); whereas, the quantum yield of 4 increased in more hydrophobic environments (i.e. cyclohexane). Also, the Stoke's shift of each probe changed significantly between nonpolar and polar media. For example, the Stoke's shift of 4 ($\lambda_{em-\lambda abs}$) in 1:1 mixture of methanol and 1.0 M aqueous phosphate buffer was 221 nm, but the Stoke's shift of 4 was 80 nm in cyclohexane. 7 displayed similar trends, but the Stoke's shift from solvent to solvent was not as dramatic. The optical properties of 5–7 only varied slightly when compared to their homogeneous analogs.

Of the three fluorophores, the solvatochromic properties of coumarin were not as dramatic when compared to dansyl and dapoxyl. 6 and 7 displayed the largest Stoke's shifts. The emission wavelength for 5–7 red shifted when placed in more polar solvents. However, when 6 was placed in water, the Stoke's shift was the same as in when placed in cyclohexane as seen in FIG. 60. This trend was observed with each fluoresently labeled resin, and may be explained by the fact that these probes are hydrophobic and that they may actually reside within the hydrophobic core of the PEG-PS resin when submerged in water.

Figure 61:
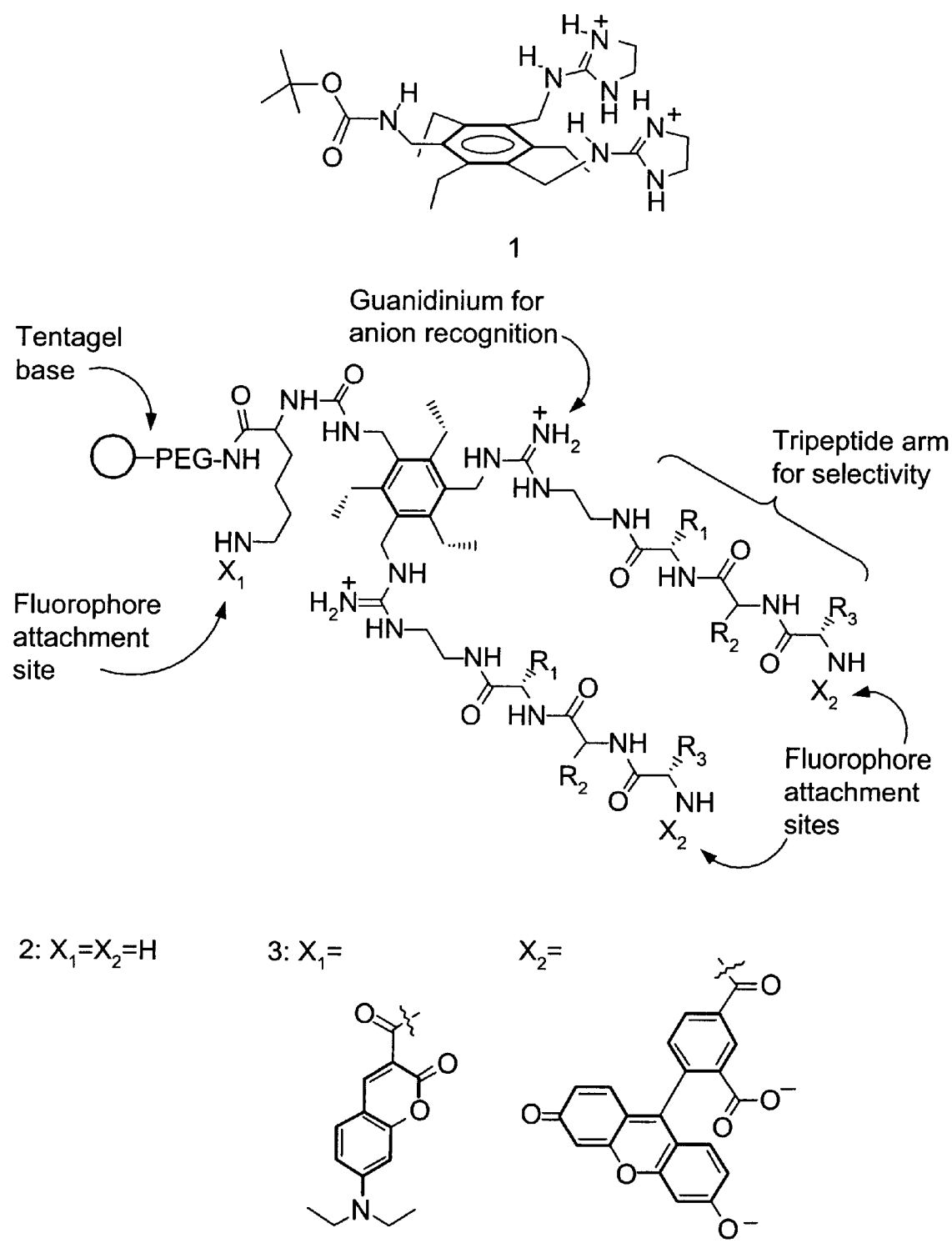
FIG. 61 depicts a general structure of a chemically sensitive particle that includes a receptor and multiple indicators coupled to a polymeric resin.

In another example a selective chemosensor for ATP was found. A bead with a polyethylene-glycol base was attached via guanidinium to two long polypeptide arms that were known to interact with the adenine group of ATP, as depicted in FIG. 61. The tripeptide arms contained two fluorophore attachment sites for 5-carboxyfluorescein (fluorescein), and an attachment site for 7-diethylaminocoumarin-3-carboxylic acid (coumarin) located on the terminal end of the lysine that was attached to the core structure. The fluorophores act as receptors for the desired analyte. The fluorophores also act as indicators to signal changes in the environment before and after the addition of analytes.

Fluorescently labeled N-methylanthraniloyl-ATP were chosen to screen for ATP receptors. Sequences of amino acids were linked as tripeptides and equilibrated with a buffer. The resin was transferred to a microscope slide and illuminated with UV light. The results yielded 6 sequences with active beads that displayed fluorescent activity, and 3 sequences with inactive beads where there was no detectable fluorescent activity.

Three of the 6 active beads, and 1 of the 3 inactive beads were arbitrarily chosen to react with ATP (Sequences below in bold). When the fluorescein and coumarin were excited, there was no detectable difference in the FRET upon addition of ATP. This may be due to there being an average distance between the fluorophores within the beads, which does not significantly change upon binding ATP. However, all but one active bead (Thr-Val-Asp) exhibited a fluorescence modulation upon excitation of fluorescein. The lack of response from an active bead shows that screening against a derivatized analyte (MANT-ATP in this case) will not guarantee that the active beads are successful sensors when synthesized with attached fluorophores. Either this active bead binds the MANT protein of MANT-ATP or there is no significant microenvironment change around the fluorophores of the Thr-Val-Asp receptor upon binding ATP.

| Active Beads | Inactive Beads |
|---|---|
| His-Ala-Asp | His-Phe-Gly |
| Glu-Pro-Thr | Ser-Ala-Asp |
| Thr-Val-Asp | Trp-Asn-Glu |
| Met-Thr-His | |
| Asp-Ala-Asp | |
| Ser-Tyr-Ser | |

A large spectral response upon addition of ATP was observed with the Ser-Tyr-Ser sequence in the active bead. The increase in fluorescein emission is possibly due to a higher local pH around the fluorescein upon binding of ATP. Further studies were performed with the Ser-Tyr-Ser sequence and analytes, AMP, and GTP, which are structurally similar to ATP. This peptidic library member exhibited very high detection selectivity for ATP over these structurally similar potentially competing analytes. The lack of response to AMP suggests the necessity for triphosphates to bind strongly to the guanidinium entities of the receptor, while the lack of response to GTP indicates the specificity for nucleotide bases imparted by the tripeptide arms. The combination of serine and tyrosine suggests π-stacking between the phenol of tyr and adenine and hydrogen bonding interactions between the serine OH and/or the ribose or adenine. These studies have demonstrated that the union of a proven core with combinatorial methods, followed by the attachment of fluorophores, can create resin bound chemosensors with excellent selectivity.

As described above, a particle, in some embodiments, possesses both the ability to interact with the analyte of interest and to create a modulated signal. In one embodiment, the particle may include receptor molecules which undergo a chemical change in the presence of the analyte of interest. This chemical change may cause a modulation in the signal produced by the particle. Chemical changes may include chemical reactions between the analyte and the receptor. Receptors may include biopolymers or organic molecules. Such chemical reactions may include, but are not limited to, cleavage reactions, oxidations, reductions, addition reactions, substitution reactions, elimination reactions, and radical reactions.

In one embodiment, the mode of action of the analyte on specific biopolymers may be taken advantage of to produce an analyte detection system. As used herein biopolymers refers to natural and unnatural: peptides, proteins, polynucleotides, and oligosaccharides. In some instances, analytes, such as toxins and enzymes, will react with biopolymer such that cleavage of the biopolymer occurs. In one embodiment, this cleavage of the biopolymer may be used to produce a detectable signal. A particle may include a biopolymer and an indicator coupled to the biopolymer. In the presence of the analyte the biopolymer may be cleaved such that the portion of the biopolymer which includes the indicator may be cleaved from the particle. The signal produced from the indicator is then displaced from the particle. The signal of the bead will therefore change thus indicating the presence of a specific analyte.

Proteases represent a number of families of proteolytic enzymes that catalytically hydrolyze peptide bonds. Principal groups of proteases include metalloproteases, serine porteases, cysteine proteases and aspartic proteases. Proteases, in particular serine proteases, are involved in a number of physiological processes such as blood coagulation, fertilization, inflammation, hormone production, the immune response and fibrinolysis.

Numerous disease states are caused by and may be characterized by alterations in the activity of specific proteases and their inhibitors. For example emphysema, arthritis, thrombosis, cancer metastasis and some forms of hemophilia result from the lack of regulation of serine protease activities. In case of viral infection, the presence of viral proteases have been identified in infected cells. Such viral proteases include, for example, HIV protease associated with AIDS and NS3 protease associated with Hepatitis C. Proteases have also been implicated in cancer metastasis. For example, the increased presence of the protease urokinase has been correlated with an increased ability to metastasize in many cancers.

In one embodiment, the presence of a protease may be detected by the use of a biopolymer coupled to a polymeric resin. For the detection of proteases, the biopolymer may be a protein or peptide. Methods for synthesizing and/or attaching a protein or peptides to a polymeric resin are described, for example, in U.S. Pat. No. 5,235,028 which is incorporated herein by reference. "Proteins" and "peptides" are herein defined as chains of amino acids whose α-carbons are linked through peptide bonds formed by a condensation reaction between the a carboxyl group of one amino acid and the amino group of another amino acid. Peptides also include peptide mimetics such as amino acids joined by an ether as opposed to an amide bond.

The term "protease binding site" as used herein refers to an amino acid sequence that may be recognized and cleaved by a protease. The protease binding site contains a peptide bond that is hydrolyzed by the protease and the amino acid residues joined by this peptide bond are said to form the cleavage site. The protease binding site and conformation determining regions form a contiguous amino acid sequence. The protease binding site may be an amino acid sequence that is recognized and cleaved by a particular protease. It is well known that various proteases may cleave peptide bonds adjacent to particular amino acids. Thus, for example, trypsin cleaves peptide bonds following basic amino acids such as arginine and lysine and chymotrypsin cleaves peptide bonds following large hydrophobic amino acid residues such as tryptophan, phenylalanine, tyrosine and leucine. The serine protease elastase cleaves peptide bonds following small hydrophobic residues such as alanine. A particular protease, however, may not cleave every bond in a protein that has the correct adjacent amino acid. Rather, the proteases may be specific to particular amino acid sequences which serve as protease binding sites for each particular protease. Any amino acid sequence that comprises a protease binding site and may be recognized and cleaved by a protease is a suitable protease receptor. Known protease binding sites and peptide inhibitors of proteases posses amino acid sequences that are recognized by the specific protease they are cleaved by or that they inhibit. Thus known substrate and inhibitor sequences provide the basic sequences suitable for use as a protease receptor. A number of protease substrates and inhibitor sequences suitable for use as protease binding sites are described in U.S. Pat. No. 6,037,137 which is incorporated herein by reference. One of skill will appreciate that the protease substrates listed in U.S. Pat. No. 6,037,137 is not a complete list and that other protease substrates or inhibitor sequences may be used.

Figure 45A:
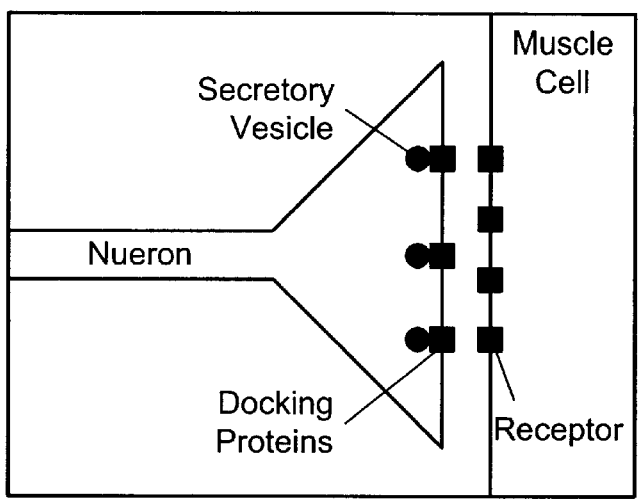
FIGS. 45A–C depict the disruption of neuromuscular communication by a toxin.
Figure 45B:
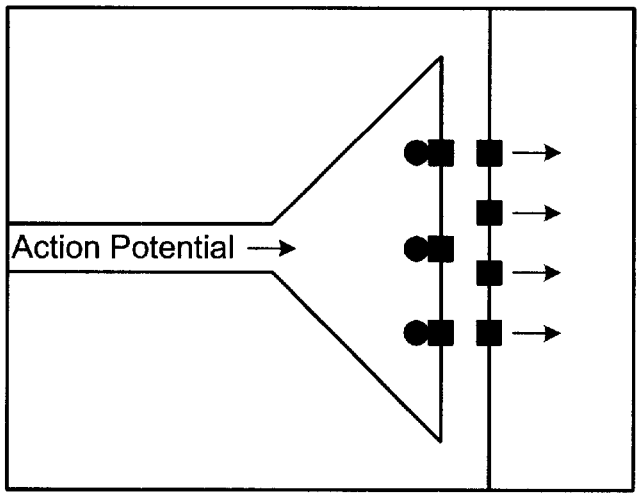
Figure 45C:
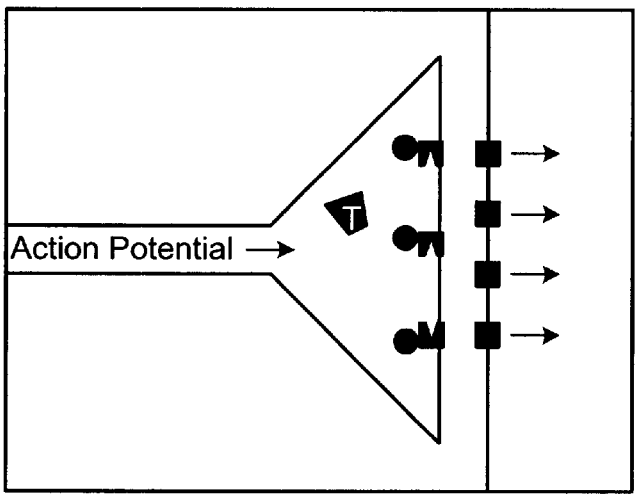

Proteases (e.g., botulinum and tetanus toxins) cleave peptide bonds at specific sequence sites on the proteins that "dock" neurotransmitter secretory vesicles to their cellular release sites (FIGS. 45A, 45B). When one or more of these proteins is degraded in this fashion, secretion is blocked and paralysis results (FIG. 45C). It is known that relatively low molecular weight peptides (~15–35 amino acids) based on the normal protein substrates of the botulinum toxins can be rapidly cleaved in solution by a toxin in a manner similar to the full-length protein. Such experiments have been described by Schmidt, J. J.; Stafford, R. G.; Bostian, K. A. "Type A botulinum neurotoxin proteolytic activity: development of competitive inhibitors and implications for substrate specificity at the $S_1'$ binding subsite" *FEBS Lett.*, 1998, 435, 61–64 and Shone, C. C.; Roberts, A. K. "Peptide substrate specificity and properties of the zinc-endopeptidase activity of botulinum type B neurotoxin" *Eur. J. Biochem.*, 1994, 225, 263–270, both of which are incorporated herein by reference as if set forth herein. It has also been demonstrated that these peptide substrates can retain high levels of activity for both botulinum and tetanus toxins even when chemically modified by amino acid substitutions and fluorescence labeling (See also Soleihac, J.-M.; Cornille, F.; Martin, L.; Lenoir, C.; Fournie-Zaluski, M.-C.; Roques, B. P. "A sensitive and rapid fluorescence-based assay for determination of tetanus toxin peptidase activity" *Anal. Biochem.*, 1996, 241, 120–127 and Adler, M.; Nicholson, J. D.; Hackley, B. E., Jr. "Efficacy of a novel metalloprotease inhibitor on botulinum neurotoxin B activity" *FEBS Lett.*, 1998, 429, 234–238 both of which are incorporated herein by reference).

For newly discovered proteases, or proteases of which the protease recognition sequence is not known, a suitable amino acid sequence for use as the protease binding site may be determined experimentally. The synthesis of libraries of peptides and the use of these libraries to determine a protease binding sequence for a particular protease is described in U.S. Pat. No. 5,834,318 which is incorporated herein by reference. Generally, combinatorial libraries composed of between about 2 to about 20 amino acids may be synthesized. These libraries may be used to screen for an interaction with the protease. Analysis of the sequences that bind to the protease may be used to determine potential binding sequences for use as a receptor for the protease.

The interaction of the receptor with a protease may be indicated by an indicator molecule coupled to the receptor or the polymeric resin. In one embodiment, the indicator may be a chromophore or a fluorophore. A fluorophore is a molecule that absorbs light at a characteristic wavelength and then re-emits the light most typically at a characteristic different wavelength. Fluorophores include, but are not limited to rhodamine and rhodamine derivatives, fluorescein and fluorescein derivatives, coumarins and chelators with the lanthanide ion series. A chromophore is a molecule which absorbs light at a characteristic wavelength, but does not re-emit light.

In one embodiment, a peptide containing the cleavage sequence is immobilized through a covalent or strong non-covalent bond to an addressable site on a sensor array. In one embodiment, this may be accomplished by coupling the peptide to a polymeric resin, as described above. The polymeric resin may be positioned in a cavity of a sensor array, such as the sensor arrays described above. In some embodiments, different peptides containing different cleavage sequences for the various proteases may be immobilized at different array positions. A sample containing one or more proteases may be applied to the array, and peptide cleavage may occur at specific array addresses, depending on the presence of particular proteases. Alternatively, different peptides containing different cleavage sequences may be coupled to a single polymeric bead. In this manner, a single bead may be used to analyze multiple proteases.

Figure 62A:
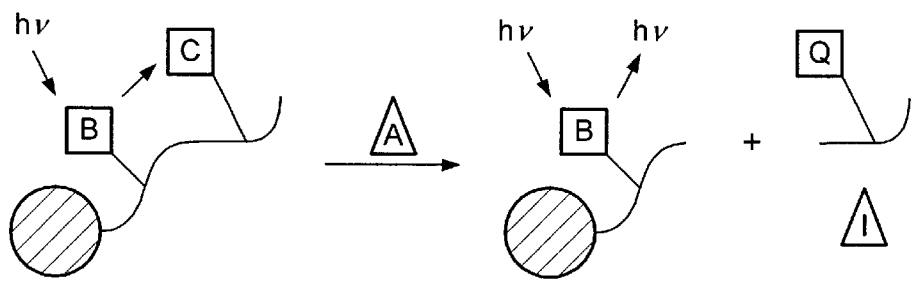
FIGS. 62A–D depict various sensing protocols for receptor-indicator-polymeric resin particles in which a cleavage reaction occurs.

A variety of signaling mechanisms for the above described cleavage reactions may be used. In an embodiment, a fluorescent dye and a fluorescence quencher may be coupled to the biopolymer on opposite sides of the cleavage site. The fluorescent dye and the fluorescence quencher may be positioned within the Förster energy transfer radius. The Förster energy transfer radius is defined as the maximum distance between two molecules in which at least a portion of the fluorescence energy emitted from one of the molecules is quenched by the other molecule. Förster energy transfer has been described above. Before cleavage, little or no fluorescence may be generated by virtue of the molecular quencher. After cleavage, the dye and quencher are no longer maintained in proximity of one another, and fluorescence may be detected (FIG. 62A). The use of fluorescence quenching is described in U.S. Pat. No. 6,037,137 which is incorporated herein by reference. Further examples of this energy transfer are described in the following papers, all of which are incorporated herein by reference: James, T. D.; Samandumara, K. R. A.; Iguchi, R.; Shinkai, S. *J. Am. Chem. Soc.* 1995, 117, 8982. Murukami, H.; Nagasaki, T.; Hamachi, I.; Shinkai, S. *Tetrahedron Lett.*, 34, 6273. Shinkai, S.; Tsukagohsi, K.; Ishikawa, Y.; Kunitake, T. *J. Chem. Soc. Chem. Commun.* 1991, 1039. Kondo, K.; Shiomi, Y.; Saisho, M.; Harada, T.; Shinkai, S. *Tetrahedron.* 1992, 48, 8239. Shiomi, Y.; Kondo, K.; Saisho, M.; Harada, T.; Tsukagoshi, K.; Shinkai, S. *Supramol. Chem.* 1993, 2, 11. Shiomi, Y.; Saisho, M.; Tsukagoshi, K.; Shinkai, S. *J. Chem. Soc. Perkin Trans 1 1993, 2111.* Deng, G.; James, T. D.; Shinkai, S. *J. Am. Chem. Soc.* 1994, 116, 4567. James, T. D.; Harada, T.; Shinkai, S. *J. Chem. Soc. Chem. Commun.* 1993, 857. James, T. D.; Murata, K.; Harada, T.; Ueda, K.; Shinkai, S. *Chem. Lett.* 1994, 273. Ludwig, R.; Harada, T.; Ueda, K.; James, T.D.; Shinkai, S. *J. Chem. Soc. Perkin Trans* 2. 1994, 4, 497. Sandanayake, K. R. A. S.; Shinkai, S. *J. Chem. Soc., Chem. Commun.* 1994, 1083. Nagasaki, T.; Shinmori, H.; Shinkai, S. *Tetrahedron Lett.* 1994, 2201. Murakami, H.; Nagasaki, T.; Hamachi, I.; Shinkai, S. *J. Chem. Soc. Perkin Trans* 2. 1994, 975. Nakashima, K.; Shinkai, S. *Chem. Lett.* 1994, 1267. Sandanayake, K. R. A. S.; Nakashima, K.; Shinkai, S. *J. Chem. Soc.* 1994, 1621. James, T. D.; Sandanayake, K. R. A. S.; Shinkai, S. *J. Chem. Soc., Chem. Commun.* 1994, 477. James, T. D.; Sandanayake, K. R. A. S.; *Angew. Chem., Int. Ed. Eng.* 1994, 33, 2207. James, T. D.; Sandanayake, K. R. A. S.; Shinkai, S. *Nature*, 1995, 374, 345.

The fluorophores may be linked to the peptide receptor by any of a number of means well known to those of skill in the art. In an embodiment, the fluorophore may be linked directly from a reactive site on the fluorophore to a reactive group on the peptide such as a terminal amino or carboxyl group, or to a reactive group on an amino acid side chain such as a sulfur, an amino, a hydroxyl, or a carboxyl moiety. Many fluorophores normally contain suitable reactive sites. Alternatively, the fluorophores may be derivatized to provide reactive sites for linkage to another molecule. Fluorophores derivatized with functional groups for coupling to a second molecule are commercially available from a variety of manufacturers. The derivatization may be by a simple substitution of a group on the fluorophore itself, or may be by conjugation to a linker. Various linkers are well known to those of skill in the art and are discussed below.

The fluorogenic protease indicators may be linked to a solid support directly through the fluorophores or through the peptide backbone comprising the indicator. In embodiments where the indicator is linked to the solid support through the peptide backbone, the peptide backbone may comprise an additional peptide spacer. The spacer may be present at either the amino or carboxyl terminus of the peptide backbone and may vary from about 1 to about 50 amino acids, preferably from 1 to about 20 and more preferably from 1 to about 10 amino acids in length. The amino acid composition of the peptide spacer is not critical as the spacer just serves to separate the active components of the molecule from the substrate thereby preventing undesired interactions. However, the amino acid composition of the spacer may be selected to provide amino acids (e.g. a cysteine or a lysine) having side chains to which a linker or the solid support itself, is easily coupled. Alternatively the linker or the solid support itself may be attached to the amino terminus of or the carboxyl terminus.

In an embodiment, the peptide spacer may be joined to the solid support by a linker. The term "linker", as used herein, refers to a molecule that may be used to link a peptide to another molecule, (e.g. a solid support, fluorophore, etc.). A linker is a hetero or homobifunctional molecule that provides a first reactive site capable of forming a covalent linkage with the peptide and a second reactive site capable of forming a covalent linkage with a reactive group on the solid support. Linkers as use din these embodiments are the same as the previously described linkers.

Figure 62B:
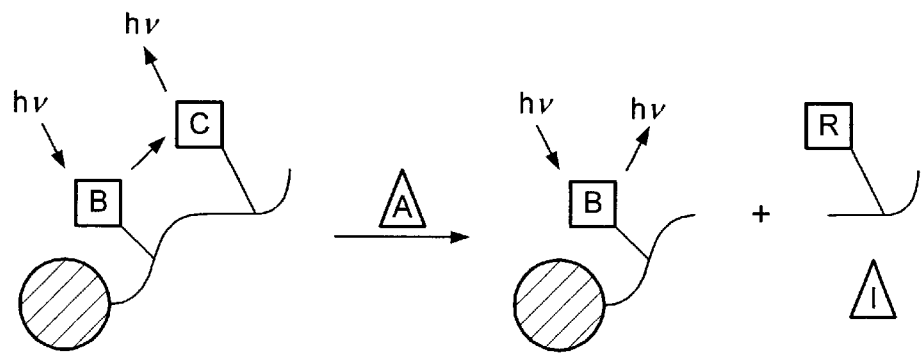

In an embodiment, a first fluorescent dye and a second fluorescent dye may be coupled to the biopolymer on opposite sides of the cleavage site. Before cleavage, a FRET (fluorescence resonance energy transfer) signal may be observed as a long wavelength emission. After cleavage, the change in the relative positions of the two dyes may cause a loss of the FRET signal and an increase in fluorescence from the shorter-wavelength dye (FIG. 62B). Examples of solution phase FRET have been described in Förster, Th. "Transfer Mechanisms of Electronic Excitation:, *Discuss. Faraday Soc.*, 1959,.27, 7; Khanna, P. L., Ullman, E. F. "4',5'-Dimethoxyl-6-carboxyfluorescein: A novel dipole-dipole coupled fluorescence energy transfer acceptor useful for fluorescence immunoassays", *Anal. Biochem.* 1980, 108, 156; and Morrison, L.E. "Time resolved Detection of Energy Transfer: Theory and Application to Immunoassays", *Anal. Biochem.* 1998, 174, 101, all of which are incorporated herein by reference.

Figure 62C:
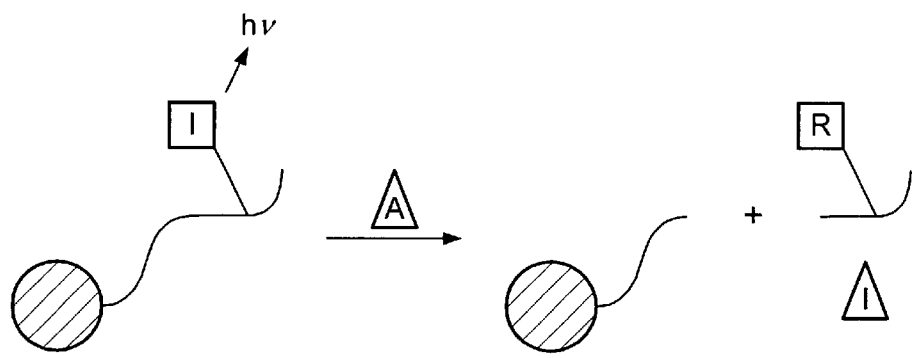

In another embodiment, a single fluorescent dye may be coupled to the peptide on the opposite side of the cleavage site to the polymeric resin. Before cleavage, the dye is fluorescent, but is spatially confined to the attachment site. After cleavage, the peptide fragment containing the dye may diffuse from the attachment site (e.g., to positions elsewhere in the cavity) where it may be measured with a spatially sensitive detection approach, such as confocal microscopy (FIG. 62C). Alternatively, the solution in the cavities may be flushed from the system. A reduction in the fluorescence of the particle would indicate the presence of the analyte (e.g., a protease).

In another embodiment, a single indicator (e.g., a chromophore or a fluorophore) may be coupled to the peptide receptor on the side of the cleavage site that remains on the polymeric resin or to the polymeric resin at a location proximate to the receptor. Before cleavage the indicator may produce a signal that reflects the microevironment determined by the interaction of the receptor with the indicator. Hydrogen bonding or ionic substituents on the indicator involved in analyte binding have the capacity to change the electron density and/or rigidity of the indicator, thereby changing observable spectroscopic properties such as fluorescence quantum yield, maximum excitation wavelength, or maximum emission wavelength for fluorophores or absorption spectra for chromophores. When the peptide receptor is cleaved, the local pH and dielectric constants of the beads change, and the indicator may respond in a predictable fashion. An advantage to this approach is that it does not require the dissociation of a preloaded fluorescent ligand (limited in response time by $k_{off}$). Furthermore, several different indicators may be used with the same receptor. Different beads may have the same receptors but different indicators, allowing for multiple testing for the presence of proteases. Alternatively, a single polymeric resin may include multiple dyes along with a single receptor. The interaction of each of these dyes with the receptor may be monitored to determine the presence of the analyte.

Nucleases represent a number of families of enzymes that catalytically hydrolyze the phosphodiester bonds of nucleic acids. Nucleases may be classified according to the nucleic acid that they are specific for. Ribonucleases ("RNases") are specific for ribonucleic acids while deoxyribonucleases ("DNases") are specific for deoxyribonucleic acids. Some enzymes will hydrolyze both ribonucleic acids and deoxyribonucleic acids. Nucleases may also be classified according to their point of attack upon the nucleic acid. Nucleases that attack the polymer at either the 3' terminus or the 5' terminus are known as exonucleases. Nucleases that attack the nucleic acid within the chain are called endonucleases.

Restriction enzymes recognize short polynucleotide sequences and cleave double-stranded nucleic acids at specific sites within or adjacent to these sequences. Approximately 3,000 restriction enzymes, recognizing over 230 different nucleic acid sequences, are known. They have been found mostly in bacteria, but have also been isolated from viruses, archaea and eukaryotes. Because many of these restriction enzymes are only found in a particular organism, nucleic acids may be used as a receptor to determine if a particular organism is present in a sample by analyzing for restriction enzymes. Restriction endonucleases specifically bind to nucleic acids only at a specific recognition sequence that varies among restriction endonucleases. Since restriction enzymes only cut nucleic acids in the vicinity of the recognition sequence, a receptor may be designed that includes the recognition sequence for the nuclease being investigated.

Most nucleases bind to and act on double stranded deoxyribonucleic acid ("DNA"). Restriction endonucleases are typically symmetrical dimers. Each monomeric unit binds to one strand of DNA and recognizes the first half the DNA recognition sequence. Each monomer also typically cuts one strand of DNA. Together, the dimer recognizes a palindromic DNA sequence and cuts both strands of DNA symmetrically about the central point in the palindromic sequence. Typically, each monomer of the restriction endonucleases needs at least two specific nucleotides that it recognizes, though in a few cases a restriction endonuclease monomer only needs to bind to one specific nucleotide and two others with less specificity. This means that restriction endonucleases may recognize a sequence of 4 nucleotides at a minimum, and generally recognize sequences that contain an even number of nucleotides (since the same sites are recognized by each monomer. Restriction endonucleases are known that recognize 4, 6, or 8 nucleotides, with only a few 8-cutters known. Some restriction endonucleases bind to recognition sequences that have an odd number of nucleotides (typically this is 5 or 7) with the central nucleotide specifically recognized or with some or strict specificity for a central base pair. The origin and sequence specificity of hundreds of restriction endonucleases are known and can be found from catalogs available from New England Biolabs, Boston, Mass.; Life Technologies, Rockville, Md.; Promega Scientific, Madison, Wis., Rouche Molecular Biochemicals, Indianapolis, Ind.

In one embodiment, the presence of a nuclease may be detected by the use of a polynucleotide coupled to a polymeric resin. For the detection of nucleases, the polynucleotide may be a double stranded deoxyribonucleic acid or a ribonucleic acid. Methods for synthesizing and/or attaching a polynucleotide to a polymeric resin are described, for example, in U.S. Pat. No. 5,843,655 which is incorporated herein by reference. "Polynucleotides" are herein defined as chains of nucleotides. The nucleotides are linked to each other by phosphodiester bonds. "Deoxyribonucleic acid" is composed of deoxyribonucleotide residues, while "Riboriucleic acid" is composed of ribonucleotide residues.

The term "nuclease binding site" as used herein refers to a polynucleotide sequence that may be recognized and cleaved by a nuclease. The nuclease binding site contains a phosphodiester bond that is cleaved by the nuclease and the polynucleotide residues joined by this phosphodiester bond are said to form the cleavage site.

For newly discovered nucleases, or nucleases of which the nuclease recognition sequence is not known, a suitable polynucleotide sequence for use as the nuclease binding site may be determined experimentally. Generally, combinatorial libraries of polynucleotides composed of between about 2 to about 20 nucleotides may be synthesized. The synthesis of such libraries is described, for example, in U.S. Pat. No. 5,843,655 which is incorporated herein by reference. These libraries may be used to screen for an interaction with the nuclease. Analysis of the sequences that bind to the nuclease may be used to determine potential binding sequences for use as a receptor for the nuclease.

The interaction of the receptor with a nuclease may be indicated by an indicator molecule coupled to the receptor or the polymeric resin. In one embodiment, the indicator may be a chromophore or a fluorophore.

In one embodiment, a polynucleotide containing the nuclease binding sequence is immobilized through a covalent or strong non-covalent bond to an addressable site on a sensor array. In one embodiment, this may be accomplished by coupling or synthesizing the polynucleotide on a polymeric resin, as described above. The polymeric resin may be positioned in a cavity of a sensor array, such as the sensor arrays described above. In some embodiments, different polynucleotides containing different cleavage sequences for the various nucleases may be immobilized at different array positions. A sample containing one or more nucleases may be applied to the array, and polynucleotide cleavage may occur at specific array addresses, depending on the presence of particular nucleases. Alternatively, different polynucleotides containing different cleavage sequences may be coupled to a single polymeric bead. In this manner, a single bead may be used to analyze multiple nucleases.

A variety of signaling mechanisms for the above described cleavage reactions may be used. In an embodiment, a fluorescent dye and a fluorescence quencher may be coupled to the polynucleotide on opposite sides of the cleavage site. The fluorescent dye and the fluorescence quencher may be positioned within the Förster energy transfer radius. Before cleavage, little or no fluorescence may be generated by virtue of the molecular quencher. After cleavage, the dye and quencher are no longer maintained in proximity of one another, and fluorescence may be detected (FIG. 62A).

The fluorophores may be linked to the polynucleotide receptor by any of a number of means well known to those of skill in the art. Examples of methods of attaching fluorophores and dyes to polynucleotides are described in U.S. Pat. Nos. 4,855,225; 5,188,934, and 5,366,860 all of which are incorporated herein by reference.

In another embodiment, a first fluorescent dye and a second fluorescent dye may be coupled to the polynucleotide receptor on opposite sides of the cleavage site. Before cleavage, a FRET (fluorescence resonance energy transfer) signal may be observed as a long wavelength emission. After cleavage, the change in the relative positions of the two dyes may cause a loss of the FRET signal and an increase in fluorescence from the shorter-wavelength dye (FIG. 62B).

In another embodiment, a single fluorescent dye may be coupled to the polynucleotide receptor on the opposite side of the cleavage site to the polymeric resin. Before cleavage, the dye is fluorescent, but is spatially confined to the attachment site. After cleavage, the nucleic acid fragment containing the dye may diffuse from the attachment site (e.g., to positions elsewhere in the cavity) where it may be measured with a spatially sensitive detection approach, such as confocal microscopy (FIG. 62C). Alternatively, the solution in the cavities may be flushed from the system. A reduction in the fluorescence of the particle would indicate the presence of the analyte (e.g., a nuclease).

Figure 62D:
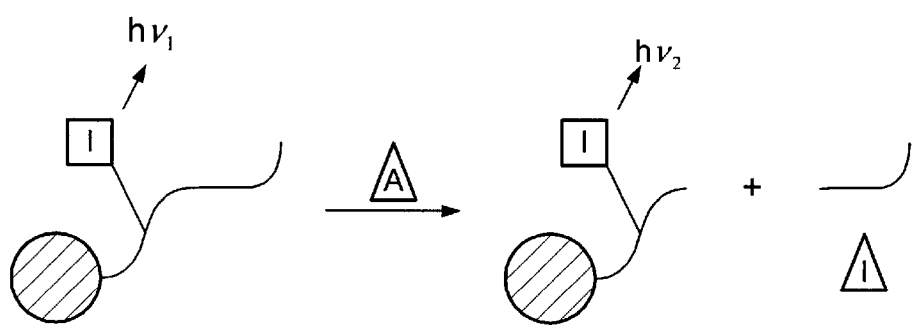

In another embodiment, depicted in FIG. 62D, a single indicator (e.g., a chromophore or a fluorophore) may be coupled to the polynucleotide receptor on the side of the cleavage site that remains on the polymeric resin or to the polymeric resin at a location proximate to the polynucleotide receptor. Before cleavage the indicator may produce a signal that reflects the microevironment determined by the interaction of the receptor with the indicator. Hydrogen bonding or ionic substituents on the indicator involved in analyte binding have the capacity to change the electron density and/or rigidity of the indicator, thereby changing observable spectroscopic properties such as fluorescence quantum yield, maximum excitation wavelength, or maximum emission wavelength for fluorophores or absorption spectra for chromophores. When the polynucleotide receptor is cleaved, the local pH and dielectric constants of the beads change, and the indicator may respond in a predictable fashion. An advantage to this approach is that it does not require the dissociation of a preloaded fluorescent ligand (limited in response time by $k_{off}$). Furthermore, several different indicators may be used with the same receptor. Different beads may have the same receptors but different indicators, allowing for multiple testing for the presence of nucleases. Alternatively, a single polymeric resin may include multiple dyes along with a single receptor. The interaction of each of these dyes with the receptor may be monitored to determine the presence of the analyte.

In another embodiment, polynucleotide receptors may be used to determine the presence of other types of analytes. It some instances, polynucleotide receptors will bind to small organic molecules. These small organic molecules may disrupt the action of nucleases upon the polynucleotide receptor. Typically, the small molecules will occupy the preferred binding site of the nuclease, inhibiting the action of the nuclease on the polynucleotide. Thus the presence of a small organic molecule, which is known to bind to a specific polynucleotide, may be detected by the observation of reduced nuclease activity at the specific polynucleotide. An analogous methodology may be applied to a peptide-protease reaction.

In another embodiment, oligosaccharides may also be used to determine the presence of analytes. In a system similar to those described above for peptides and polynucleotides, oligosaccharides may be coupled to a polymeric resin. In the presence of oligosaccharide cleaving agents (e.g., enzymes such as amylase, an enzyme that cleaves a long saccharide polymer and disaccharide cleaving enzymes such as invertase, β-galactosidase, and lactase, to name a few) the oligosaccharide may be cleaved. The cleavage of the oligosaccharide may be used to generate a signal. Methods for synthesizing and/or attaching oligosaccharides to a polymeric resin are described, for example, in U.S. Pat. Nos. 5,278,303 and 5,616,698 which are incorporated herein by reference.

In another embodiment, an analyte may cause a change to a biopolymer, but not necessarily cleavage of the biopolymer, when the analyte interacts with the biopolymer. The induced change may cause a detectable signal to be generated. Typically, the binding or association ability of an indicator molecule with a biopolymer is dependent upon the structure of the biopolymer. If the structure of the biopolymer is altered, the association of an indicator molecule may be significantly altered. Such a change may be accompanied by a change in the signal produced by the indicator. For biopolymers many different types of enzymes may induce a variety of structural changes to the biopolymer which may alter the binding site of an associated indicator molecule. Such changes may occur without cleavage of the biopolymer.

Alternatively, an indicator and a biopolymer may be coupled to a polymeric bead. The biopolymer may undergo a chemical reaction in the presence of an analyte. This chemical reaction may also induce a change in the chemical structure of the indicator. The change in the chemical structure of the indicator may lead to a detectable change in the optical properties of the particle, signaling the presence of the analyte.

In one example, NAD and glucose may be coupled to a polymeric bead. This system may be used to detect the presence of an carbohydrate modifying enzyme. For example, the system may be used to detect the presence of glucose dehydrogenase. In the presence of glucose dehydrogenase, glucose may be consumed, and in the process would convert the coupled NAD into NADH. NADH has both different UV absorbance and different fluorescence properties from NAD. These differences may be used to signal the presence of glucose dehydrogenase in a fluid sample. Many other types of enzymes may be detected in a similar manner.

Figure 63:
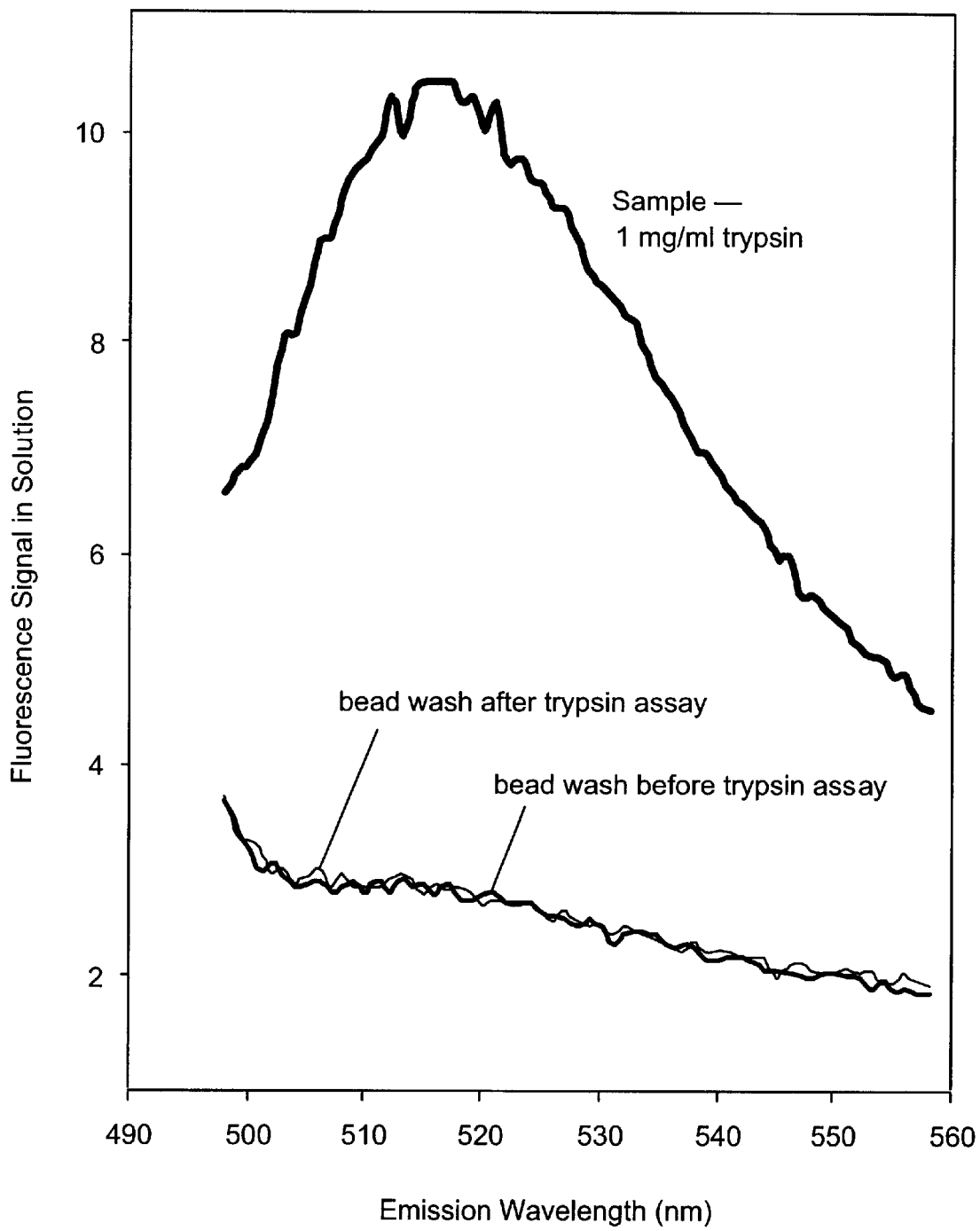
FIG. 63 depicts a plot of the fluorescence signal of a chemically sensitive particle in the presence of trypsin.

In an example, the protease trypsin was analyzed using an immobilized "sacrificial receptor" that is cleaved by trypsin, an event that results in modulation of a fluorescence signal. In an embodiment of a protease assay, a peptide that may be cleaved between two amino acids by the enzyme trypsin was immobilized. This immobilization was accomplished by first conjugating many streptavidin molecules to aldehyde-activated 6% agarose beads using a reductive amination procedure. A biotin chemical group attached to the amino-terminus of the peptide was strongly bound by the immobilized streptavidin molecules, thereby immobilizing the peptide chains. A fluorescein group was attached to the carboxyl-terminus of the peptide, thereby making the bead highly fluorescent. Importantly, the immobilized peptide contains a cleavage site recognized by trypsin between the biotin attachment site and the fluorescein, so that exposure of the bead to trypsin analyte causes release of fluorescent peptide fragments from the bead. This release may be visualized either as a decrease in the fluorescence at the bead, or by an increase in the fluorescence of the surrounding solution (see FIG. 63).

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system for detecting an analyte in a fluid comprising:
a light source;
a sensor array, the sensor array comprising:
    a supporting member comprising at least one cavity formed within the supporting member; and
    a top cover layer, wherein the top cover layer is coupled to a top surface of the supporting member such that a particle is contained within the cavity by the top cover layer;
the particle positioned within the cavity, wherein the particle comprises a receptor coupled to a polymeric resin, and an indicator coupled to the polymeric resin, and wherein the indicator is configured to produce a signal when the receptor interacts with the analyte during use;
a detector, the detector being configured to detect the signal produced by the interaction of the analyte with the particle during use;
wherein the light source and detector are positioned such that light passes from the light source, to the particle, and onto the detector during use.

2. The system of claim 1, wherein the system further comprises a plurality of particles positioned within a plurality of cavities, and wherein the system is configured to substantially simultaneously detect a plurality of analytes in the fluid.

3. The system of claim 1, wherein the system further comprises a plurality of particles positioned within the cavity.

4. The system of claim 1, wherein the light source comprises a light emitting diode.

5. The system of claim 1, wherein the light source comprises a white light source.

6. The system of claim 1, wherein the sensor array further comprises a bottom layer, wherein the bottom layer is positioned below a bottom surface of the supporting member, and wherein the bottom layer is positioned such that the particle is substantially contained within the cavity by the bottom layer and the top cover layer.

7. The system of claim 6, wherein the bottom layer and the top cover layer are substantially transparent to light produced by the light source.

8. The system of claim 1, wherein the sensor array further comprises a bottom layer, wherein the bottom layer is coupled to a bottom surface of the supporting member, and wherein both the bottom layer is coupled to the supporting member such that the particle is substantially contained within the cavity by bottom layer and the top cover layer.

9. The system of claim 8, wherein the bottom layer and the top cover layer are substantially transparent to light produced by the light source.

10. The system of claim 1, wherein the sensor array further comprises a bottom layer coupled to the supporting member, and wherein the supporting member comprises silicon, and wherein the bottom layer comprises silicon nitride.

11. The system of claim 1, wherein the sensor array further comprises a sensing cavity formed on a bottom surface of the sensor array.

12. The system of claim 1, wherein the supporting member is formed from a plastic material, and wherein the top cover layer is configured to allow the fluid to pass through the top cover layer to the particle, and wherein both the supporting member and the top cover layer are substantially transparent to light produced by the light source.

13. The system of claim 1, further comprising a fluid delivery system coupled to the supporting member.

14. The system of claim 1, wherein the detector comprises a charge-coupled device.

15. The system of claim 1, wherein the detector comprises an ultraviolet detector.

16. The system of claim 1, wherein the detector comprises a fluorescence detector.

17. The system of claim 1, wherein the detector comprises a semiconductor based photodetector, and wherein the detector is coupled to the sensor array.

18. The system of claim 1, wherein the particle ranges from about 0.05 micron to about 500 microns.

19. The system of claim 1, wherein a volume of the particle changes when contacted with the fluid.

20. The system of claim 1, wherein the polymeric resin comprises polystyrene-polyethylene glycol-divinyl benzene.

21. The system of claim 1, wherein the receptor comprises a polynucleotide.

22. The system of claim 1, wherein the receptor comprises a peptide.

23. The system of claim 1, wherein the receptor comprises a compound of the general formula:

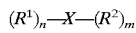

wherein X comprises carbocyclic systems or $C_1$–$C_{10}$ alkanes, n is an integer of at least 1, m is an integer of at least 1; and wherein each of $R^1$ independently represents —$(CH_2)_y$—$NR^3$—$C(NR^4)$—$NR^5$, —$(CH_2)_y$—$NR^6R^7$, —$(CH_2)_y$—NH—Y, —$(CH_2)_y$—O—Z;

where y is an integer of at least 1;

where $R^3$, $R^4$, and $R^5$ independently represent hydrogen, alkyl, aryl, alkyl carbonyl of 1 to 10 carbon atoms, or alkoxy carbonyl of 1 to 10 carbon atoms, or $R^4$ and $R^5$ together represent a cycloalkyl group;

where $R^6$ represents hydrogen, alkyl, aryl, alkyl carbonyl of 1 to 10 carbon atoms, or alkoxy carbonyl of 1 to 10 carbon atoms;

where $R^7$ represents alkyl, aryl, alkyl carbonyl of 1 to 10 carbon atoms, or alkoxy carbonyl of 1 to 10 carbon atoms;

where $R^6$ and $R^7$ together represent a cycloalkyl group;

where Y is a peptide, or hydrogen and where Z is a polynucleotide, an oligosaccharide or hydrogen; and wherein each of $R^2$ independently represents hydrogen, alkyl, alkenyl, alkynyl, phenyl, phenylalkyl, arylalkyl, aryl, or together with another $R^2$ group represent a carbocyclic ring.

24. The system of claim 1, wherein the receptor comprises a compound of the general formula:

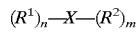

wherein X comprises carbocyclic systems or $C_1$–$C_{10}$ alkanes, n is an integer of at least 1, m is an integer of at least 1; and wherein each of $R^1$ independently represents —$(CH_2)_y$—NH—Y;

where y is an integer of at least 1;

where $R^3$, $R^4$, and $R^5$ independently represent hydrogen, alkyl, aryl, alkyl carbonyl of 1 to 10 carbon atoms, or alkoxy carbonyl of 1 to 10 carbon atoms, or $R^4$ and $R^5$ together represent a cycloalkyl group;

where $R^6$ represents hydrogen, alkyl, aryl, alkyl carbonyl of 1 to 10 carbon atoms, or alkoxy carbonyl of 1 to 10 carbon atoms;

where $R^7$ represents alkyd, aryl, alkyl carbonyl of 1 to 10 carbon atoms, or alkoxy carbonyl of 1 to 10 carbon atoms;

where $R^6$ and $R^7$ together represent a cycloalkyl group;

where Y is a peptide or hydrogen; and wherein each of $R^2$ independently represents hydrogen, alkyl, alkenyl, alkynyl, phenyl, phenylalkyl, arylalkyl, aryl, or together with another $R^2$ group represent a carbocyclic ring.

25. The system of claim 1, wherein the receptor comprises a compound of the general formula:

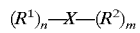

wherein X comprises carbocyclic systems or $C_1$–$C_{10}$ alkanes, n is an integer of at least 1, m is an integer of at least 1; and wherein each of $R^1$ independently represents —$(CH_2)_y$—O—Z;

where y is an integer of at least 1;

where $R^3$, $R^4$, and $R^5$ independently represent hydrogen, alkyl, aryl, alkyl carbonyl of 1 to 10 carbon atoms, or alkoxy carbonyl of 1 to 10 carbon atoms, or $R^4$ and $R^5$ together represent a cycloalkyl group;

where $R^6$ represents hydrogen, alkyl, aryl, alkyl carbonyl of 1 to 10 carbon atoms, or alkoxy carbonyl of 1 to 10 carbon atoms;

where $R^7$ represents alkyl, aryl, alkyl carbonyl of 1 to 10 carbon atoms, or alkoxy carbonyl of 1 to 10 carbon atoms;

where $R^6$ and $R^7$ together represent a cycloalkyl group;

and where Z is a polynucleotide or hydrogen;

wherein each of $R^2$ independently represents hydrogen, alkyl, alkenyl, alkynyl, phenyl, phenylalkyl, arylalkyl, aryl, or together with another $R^2$ group represent a carbocyclic ring.

26. The system of claim 1, wherein the receptor comprises a compound of the general formula:

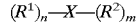

wherein X comprises carbocyclic systems or $C_1$–$C_{10}$ alkanes, n is an integer of at least 1, m is an integer of at least 1; and wherein each of $R^1$ independently represents —$(CH_2)_y$—O—Z;

where y is an integer of at least 1;

where $R^3$, $R^4$, and $R^5$ independently represent hydrogen, alkyl, aryl, alkyl carbonyl of 1 to 10 carbon atoms, or alkoxy carbonyl of 1 to 10 carbon atoms, or $R^4$ and $R^5$ together represent a cycloallkyl group;

where $R^6$ represents hydrogen, alkyl, aryl, alkyl carbonyl of 1 to 10 carbon atoms, or alkoxy carbonyl of 1 to 10 carbon atoms;

where $R^7$ represents alkyl, aryl, alkyl carbonyl of 1 to 10 carbon atoms, or alkoxy carbonyl of 1 to 10 carbon atoms;

where $R^6$ and $R^7$ together represent a cycloalkyl group; and where Z is a oligosaccharide or hydrogen;

wherein each of $R^2$ independently represents hydrogen, alkyl, alkenyl, alkynyl, phenyl, phenylalkyl, arylalkyl, aryl, or together with another $R^2$ group represent a carbocyclic ring.

27. The system of claim 1, wherein the receptor comprises an enzyme.

28. The system of claim 1, wherein the receptor comprises a peptide mimetic.

29. The system of claim 1, wherein the receptor is coupled to the polymeric resin by a linker.

30. The system of claim 1, wherein the receptor is coupled to the polymeric resin by a first linker and wherein the indicator is coupled to the polymeric resin by a second linker.

31. The system of claim 1, wherein the receptor is coupled to the polymeric resin by a first linker and wherein the indicator is coupled to the polymeric resin by a second linker, and wherein the particle further comprises an additional indicator coupled to the polymeric resin by a third linker, wherein the interaction of the receptor with the analyte causes the indicator and the additional indicator to interact such that the signal is produced.

32. The system of claim 1, wherein the receptor is coupled to the polymeric resin by a first linker and wherein the indicator is coupled to the receptor.

33. The system of claim 1, wherein the receptor is coupled to the polymeric resin by a first linker and wherein the indicator is coupled to the receptor, and wherein the particle further comprises an additional indicator coupled to the receptor, wherein the interaction of the receptor with the analyte causes the indicator and the additional indicator to interact such that the signal is produced.

34. The system of claim 1, wherein the receptor is coupled to the polymeric resin by a first, linker and wherein the indicatoy is coupled to the receptor by a second linker.

35. The system of claim 1, wherein the receptor is coupled to the polymeric resin by a first linker and wherein the indicator is coupled to the receptor by a second linker, and wherein the particle further comprises an additional indicator coupled to the receptor, wherein the interaction of the receptor with the analyte causes the indicator and the additional indicator to interact such that the signal is produced.

36. The system of claim 1, wherein the receptor is coupled to the polymeric resin by a first linker and wherein the indicator is, coupled to the first linker.

37. The system of claim 1, wherein the receptor is coupled to the polymeric resin by a first linker, and wherein the indicator is coupled to the first linker by a second linker.

38. The system of claim 1, wherein the receptor is coupled to the polymeric resin by a first linker, and wherein the indicator is coupled to the first linker by a second linker, and wherein the particle further comprises an additional indicator coupled to the receptor, wherein the interaction of the receptor with the analyte causes the indicator and the additional indicator to interact such that the signal is produced.

39. The system of claim 1, wherein the receptor is coupled to the polymeric resin by a first linker, and wherein the indicator is coupled to the first linker by a second linker, and wherein the particle further comprises an additional indicator coupled to the first linker by a third linker, wherein the interaction of the receptor with the analyte causes the indicator and the additional indicator to interact such that the signal is produced.

40. The system of claim 1, wherein the indicator interacts with the receptor in the absence of an analyte.

41. The system of claim 1, wherein the particle further comprises an additional indicator coupled to the polymeric resin, and wherein the indicator is a first fluorescent dye and wherein the additional indicator is a second fluorescent dye, and wherein the indicator and the additional indicator produce a fluorescence resonance energy transfer signal, and wherein the interaction of the analyte with the receptor causes the distance between the indicator and the additional indicator to become altered such that the fluorescence resonance energy transfer signal is altered.

42. The system of claim 1, wherein the particle further comprises an additional indicator coupled to the polymeric resin, wherein the indicator is a fluorescent dye and wherein the additional indicator is a fluorescence quencher, and wherein the indicator and the additional indicator are positioned such that the fluorescence of the indicator is at least partially quenched by the additional indicator, and wherein the interaction of the analyte with the receptor causes the distance between the indicator and the additional indicator to become altered such that the absorbance of the fluorescence of the indicator by the additional indicator is altered.

43. The system of claim 1, wherein the particle ranges from about 0.05 micron to about 500 microns.

44. The system of claim 1, wherein the polymeric resin comprises polystyrene-polyethylene glycol-divinyl benzene.

45. The system of claim 1, wherein the system further comprises a plurality of particles positioned within a plurality of cavities, and wherein the plurality of particles produce a detectable pattern in the presence of the analyte.

* * * * *

UNITED STATES PATENT AND TRADEMARK OFFICE
CERTIFICATE OF CORRECTION

PATENT NO.    : 6,589,779 B1
DATED         : July 8, 2003
INVENTOR(S)   : McDevitt et al.

It is certified that error appears in the above-identified patent and that said Letters Patent is hereby corrected as shown below:

Column 81,
Line 45, please delete "first, linker" and substitute therefor -- first linker --.
Line 46, please delete "indicatoy" and substitute therefor -- indicator --.

Signed and Sealed this

Twenty-first Day of December, 2004

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,589,779 B1 | Page 1 of 1 |
| APPLICATION NO. | : 09/616482 | |
| DATED | : July 8, 2003 | |
| INVENTOR(S) | : John T. McDevitt et al. | |

It is certified that error appears in the above-identified patent and that said Letters Patent is hereby corrected as shown below:

In the specification,

Delete the paragraph at column 1, lines 19-23 and replace with --This invention was made with Government support under Grant No. 1R01GM57306-01 awarded by the National Institutes of Health. The Government has certain rights in the invention.-- therefor.

Signed and Sealed this
Fourteenth Day of April, 2015

Michelle K. Lee
*Director of the United States Patent and Trademark Office*